US012662547B2

(12) United States Patent
Chen et al.

(10) Patent No.: US 12,662,547 B2
(45) Date of Patent: Jun. 23, 2026

(54) ANTI-CD93 CONSTRUCTS AND USES THEREOF

(71) Applicant: DYNAMICURE BIOTECHNOLOGY LLC, Cambridge, MA (US)

(72) Inventors: Zirong Chen, Saugus, MA (US); Roxann Guerrette, Cambridge, MA (US); Gregory Jones, Cambridge, MA (US); Shigeru Komaba, Cambridge, MA (US); Jian Li, Cambridge, MA (US); Angela Norton, Reading, MA (US); Lihua Wu, Boston, MA (US); Zhinan Xia, Waltham, MA (US)

(73) Assignee: Dynamicure Biotechnology LLC, Waltham, MA (US)

( * ) Notice: Subject to any disclaimer, the term of this patent is extended or adjusted under 35 U.S.C. 154(b) by 762 days.

(21) Appl. No.: 18/008,089

(22) PCT Filed: Jun. 2, 2021

(86) PCT No.: PCT/US2021/035542
§ 371 (c)(1),
(2) Date: Dec. 2, 2022

(87) PCT Pub. No.: WO2021/247769
PCT Pub. Date: Dec. 9, 2021

(65) Prior Publication Data
US 2023/0235075 A1     Jul. 27, 2023

Related U.S. Application Data

(60) Provisional application No. 63/084,474, filed on Sep. 28, 2020, provisional application No. 63/058,359, filed on Jul. 29, 2020, provisional application No. 63/033,755, filed on Jun. 2, 2020.

(51) Int. Cl.
| | |
|---|---|
| *C07K 16/28* | (2006.01) |
| *A61P 17/00* | (2006.01) |
| *A61P 35/00* | (2006.01) |
| *A61K 39/00* | (2006.01) |

(52) U.S. Cl.
CPC .......... *C07K 16/2896* (2013.01); *A61P 17/00* (2018.01); *A61P 35/00* (2018.01); *C07K 16/2818* (2013.01); *C07K 16/2827* (2013.01); *A61K 2039/505* (2013.01); *C07K 2317/24* (2013.01); *C07K 2317/33* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly |
| 5,500,362 | A | 3/1996 | Robinson |
| 5,624,821 | A | 4/1997 | Winter |
| 5,648,260 | A | 7/1997 | Winter |
| 5,750,373 | A | 5/1998 | Garrard |
| 5,770,429 | A | 6/1998 | Longberg |
| 5,821,337 | A | 10/1998 | Carter |
| 6,075,181 | A | 6/2000 | Kucherlapati |
| 6,150,584 | A | 11/2000 | Kucherlapati |
| 6,194,551 | B1 | 2/2001 | Idusogie |
| 6,602,684 | B1 | 8/2003 | Umana et al. |
| 6,737,056 | B1 | 5/2004 | Presta |
| 6,982,321 | B2 | 1/2006 | Winter |
| 7,041,870 | B2 | 5/2006 | Tomizuka |
| 7,087,409 | B2 | 8/2006 | Barbas |
| 7,189,826 | B2 | 3/2007 | Rodman |
| 7,332,581 | B2 | 2/2008 | Presta |
| 7,371,826 | B2 | 5/2008 | Presta |
| 7,371,849 | B2 | 5/2008 | Honda et al. |
| 7,521,541 | B2 | 4/2009 | Eigenbrot |
| 7,527,791 | B2 | 5/2009 | Adams |
| 8,313,913 | B2 | 11/2012 | Nakamura |
| 8,575,317 | B2 | 11/2013 | Kuramochi et al. |
| 8,679,491 | B2 | 3/2014 | Hanai |
| 8,754,287 | B2 | 6/2014 | Macdonald |
| 8,945,862 | B2 | 2/2015 | Wu et al. |

(Continued)

FOREIGN PATENT DOCUMENTS

| | | |
|---|---|---|
| EP | 2392352 A2 | 12/2011 |
| WO | 198704462 A1 | 7/1987 |

(Continued)

OTHER PUBLICATIONS

How is Alzheimer's Disease Treated?, Sep. 12, 2023, NIH-National Institute on Aging, https://www.nia.nih.gov/health/alzheimers-treatment/how-alzheimers-disease-treated. (Year: 2023) (Year: 2023).*
HIV Overview, HIV Treatment: The Basics, Sep. 4, 2024, NIH, https://hivinfo.nih.gov/understanding-hiv/fact-sheets/hiv-and-aids-basics. (Year: 2024) (Year: 2024).*
Abhinandan, K.R. et al. (Aug. 2008, e-pub. Jul. 9, 2008). "Analysis and Improvements to Kabat and Structurally Correct Numbering of Antibody Variable Domains," Molecular Immunology 45(14):3832-3839.
Adolf-Bryfogle, J. et al. (2015, e-pub. Nov. 11, 2014). "PylgClassify: A Database of Antibody CDR Structural Classifications," Nucleic Acids Res. 43:D432-D438.

(Continued)

*Primary Examiner* — Nelson B Moseley, II
*Assistant Examiner* — James Ryland Melchoir
(74) *Attorney, Agent, or Firm* — MORRISON & FOERSTER LLP

(57) ABSTRACT

The present application provides anti-CD93 constructs that bind to CD93 (e.g., anti-CD93 antibodies), nucleic acid molecules encoding an amino acid sequence of the anti-CD93, vectors comprising the nucleic acid molecules, host cells containing the vectors, methods of preparing the anti-CD93 construct, pharmaceutical compositions containing the anti-CD93 construct, and methods of using the anti-CD93 construct or compositions.

25 Claims, 50 Drawing Sheets

Specification includes a Sequence Listing.

(56) References Cited

U.S. PATENT DOCUMENTS

| | | | |
|---|---|---|---|
| 8,993,343 B2 * | 3/2015 | Park | A61P 43/00 |
| | | | 436/501 |
| 2002/0164328 A1 | 11/2002 | Shinkawa et al. | |
| 2003/0115614 A1 | 6/2003 | Kanda et al. | |
| 2003/0157108 A1 | 8/2003 | Presta | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2004/0259150 A1 | 12/2004 | Nakamura | |
| 2005/0014934 A1 | 1/2005 | Hinton et al. | |
| 2005/0031613 A1 | 2/2005 | Nakamura | |
| 2005/0079574 A1 | 4/2005 | Bond | |
| 2005/0119455 A1 | 6/2005 | Fuh et al. | |
| 2005/0123546 A1 | 6/2005 | Umana et al. | |
| 2005/0216958 A1 | 9/2005 | Yamane et al. | |
| 2005/0266000 A1 | 12/2005 | Bond et al. | |
| 2005/0272916 A1 | 12/2005 | Hanai | |
| 2006/0270045 A1 | 11/2006 | Cregg | |
| 2007/0061900 A1 | 3/2007 | Murphy et al. | |
| 2007/0071675 A1 | 3/2007 | Wu et al. | |
| 2007/0117126 A1 | 5/2007 | Sidhu et al. | |
| 2007/0134759 A1 | 6/2007 | Nishiya | |
| 2007/0160598 A1 | 7/2007 | Dennis et al. | |
| 2007/0237764 A1 | 10/2007 | Birtalan et al. | |
| 2007/0292936 A1 | 12/2007 | Barthelemy et al. | |
| 2008/0241884 A1 | 10/2008 | Shitara | |
| 2009/0002360 A1 | 1/2009 | Chen et al. | |
| 2009/0203078 A1 | 8/2009 | Ogawa | |
| 2009/0307787 A1 | 12/2009 | Grosveld et al. | |
| 2010/0122358 A1 | 5/2010 | Brueggemann | |
| 2012/0039911 A1 | 2/2012 | Park et al. | |
| 2015/0289489 A1 | 10/2015 | MacDonald et al. | |
| 2019/0062427 A1 * | 2/2019 | Rosenthal | C07K 16/2803 |
| 2019/0389960 A1 | 12/2019 | Ghebrehiwet et al. | |
| 2020/0115454 A1 | 4/2020 | Chen et al. | |
| 2023/0322935 A1 | 10/2023 | Chen et al. | |
| 2023/0365705 A1 | 11/2023 | Chen et al. | |

FOREIGN PATENT DOCUMENTS

| | | |
|---|---|---|
| WO | 199429351 A2 | 12/1994 |
| WO | 199634103 A1 | 10/1996 |
| WO | 199704801 A1 | 2/1997 |
| WO | 199730087 A1 | 8/1997 |
| WO | 199858964 A1 | 12/1998 |
| WO | 199922764 A1 | 5/1999 |
| WO | 199951642 A1 | 10/1999 |
| WO | 199954440 A1 | 10/1999 |
| WO | 200061739 A1 | 10/2000 |
| WO | 2001029246 A1 | 4/2001 |
| WO | 01/77342 A1 | 10/2001 |
| WO | 200231140 A1 | 4/2002 |
| WO | 2003011878 A2 | 2/2003 |
| WO | 2003048731 A2 | 6/2003 |
| WO | 2003084570 A1 | 10/2003 |
| WO | 2003085107 A1 | 10/2003 |
| WO | 2003085119 A1 | 10/2003 |
| WO | 2004049794 A2 | 6/2004 |
| WO | 2004056312 A2 | 7/2004 |
| WO | 2005035586 A1 | 4/2005 |
| WO | 2005035778 A1 | 4/2005 |
| WO | 2005053742 A1 | 6/2005 |
| WO | 2005100402 A1 | 10/2005 |
| WO | 2006029879 A2 | 3/2006 |
| WO | 2008077546 A1 | 7/2008 |
| WO | 2008100328 A2 | 8/2008 |
| WO | 2015/166073 A1 | 11/2015 |
| WO | 2016/090327 A2 | 6/2016 |
| WO | 2018020222 A2 | 2/2018 |
| WO | 2018133837 A1 | 7/2018 |
| WO | 2018133842 A1 | 7/2018 |
| WO | 2019/232449 A1 | 12/2019 |
| WO | 2019227490 A1 | 12/2019 |
| WO | 2019228514 A1 | 12/2019 |
| WO | 2020/018413 A1 | 1/2020 |
| WO | 2020019232 A1 | 1/2020 |
| WO | 2021062128 A1 | 4/2021 |
| WO | 2021247769 A1 | 12/2021 |
| WO | 2022026763 A1 | 2/2022 |
| WO | 2022067262 A1 | 3/2022 |

OTHER PUBLICATIONS

Al-Lazikani, B. et al. (1997). "Standard Conformations for the Canonical Structures of Immunoglobulins," J. Mol. Biol. 273:927-948.

Almagro, J.C. et al. (Jan. 1, 2008). "Humanization of Antibodies," Frontiers in Bioscience 13:1619-1633.

Baca, M. et al. (Apr. 18, 1997). "Antibody Humanization Using Monovalent Phage Display," J. Biol. Chem. 272(16):10678-10684.

Boerner, P. et al. (Jul. 1, 1991). "Production of Antigen-Specific Human Monoclonal Antibodies from In Vitro-Primed Human Splenocytes," J. Immunol. 147(1):86-95.

Brodeur, B.R. et al. (1987). "Mouse-Human Myeloma Partners for the Production Monoclonal Antibody Production of Heterohybridomas," Chapter 4 in Techniques and Applications, Marcel Dekker, Inc., New York, pp. 51-63.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Burton, D.R. (1985). "Immunoglobulin G: Functional Sites," Molec. Immunol. 22(3):161-206.

Capel, P.J. et al. (Feb. 1994). "Heterogeneity of Human IgG Fc Receptors," Immunomethods 4(1):25-34.

Carter, P. et al. (May 1992). "Humanization of an Anti-p185HER2 Antibody for Human Cancer Therapy," Proc. Natl. Acad. Sci. USA 89:4285-4289.

Cheadle, C. et al. (Jan. 1992). "Cloning and Expression of the Variable Regions of Mouse Myeloma Protein Mopc315 in E. Coli: Recovery of Active Fv Fragments," Molecular Immunology 29(1):21-30.

Chothia, C. et al. (Aug. 20, 1987). "Canonical Structures for the Hypervariable Regions of Immunoglobulins," J. Mol. Biol. 196(4):901-917.

Chothia, C. et al. (Dec. 21/28, 1989). "Conformations of Immunoglobulin Hypervariable Regions," Nature 342 (6252):877-883.

Chothia, C. et al. (Dec. 5, 1985). "Domain Association in Immunoglobulin Molecules. The Packing of Variable Domains," J. Mol. Biol. 186(3):651-663.

Chowdhury, P.S. (2008). "Engineering Hot Spots for Affinity Enhancement of Antibodies," Methods Mol. Biol. 207:179-196.

Clackson, T. et al. (Aug. 15, 1991) "Making Antibody Fragments Using Phage Display Libraries," Nature 352:624-628.

Clynes, R. et al. (Jan. 1998). "Fc Receptors Are Required in Passive and Active Immunity to Melanoma," Proc. Natl. Acad. Sci. USA 95:652-656.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Cragg, M.S. et al. (Apr. 1, 2004, e-pub. Oct. 9, 2003). "Antibody Specificity Controls in Vivo Effector Mechanisms of Anti-CD20 Reagents," Blood 103(7):2738-2743, 7 pages.

Cragg, M.S. et al. (Feb. 1, 2003). "Complement-Mediated Lysis by Anti-CD20 Mab Correlates With Segregation Into Lipid Rafts," Blood 101(3):1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

Dall'Acqua, W. et al. (1998). "Contribution of Domain Interface Residues to the Stability of Antibody CH3 Domain Homodimers," Biochemistry 37(26):9266-9273.

Dall'Acqua, W.F. et al. (2005). "Antibody Humanization by Framework Shuffling," Methods 36:43-60.

Darëon, M. (1997). "Fc Receptor Biology," Ann. Rev. Immunol. 15:203-234.

(56)                    References Cited

OTHER PUBLICATIONS

De Haas, M. et al. (Oct. 1995). "Fcγ Receptors of Phagocytes," J. Lab. Clin. Med. 126(4):330-341.
Duncan, A.R. et al. (Apr. 21, 1988). "The Binding Site for C1q on IgG," Nature 322:738-740.
Edgar, R.C. (2004, e-pub. Mar. 19, 2004). "MUSCLE: Multiple Sequence Alignment With High Accuracy and High Throughput," Nucleic Acids Research 32(5):1792-1797.
Edgar, R.C. (Aug. 19, 2004, e-pub. Mar. 19, 2004). "MUSCLE: A Multiple Sequence Alignment Method with Reduced Time and Space Complexity," BMC Bioinformatics 5(1):113, 19 pages.
Ehrenmann, F. et al. (Jan. 2010, e-pub. Nov. 9, 2009). "IMGT/3Dstructure-DB and IMGT/DomainGapAlign: A Database and a Tool for Immunoglobulins or Antibodies, T Cell Receptors, MHC, IgSF and MhcSF," Nucleic Acids Res. 38:D301-D307.
Endo, Y. et al. (2003). "High-Throughput, Genome-Scale Protein Production Method Based on the Wheat Germ Cell-Free Expression System," Biotechnol. Adv. 21:695-713.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Gazzano-Santoro, H. et al. (1997). "A Non-Radioactive Complement-Dependent Cytotoxicity Assay for Anti-CD20 Monoclonal Antibody," J. Immunol. Methods 202:163-171.
Goding, J.W. (1983). "Production of Monoclonal Antibodies," Chapter 3 in Monoclonal Antibodies: Principles and Practice, Academic Press, pp. 59-103, 27 pages.
Griffiths, A.D. et al. (1993). "Human Anti-Self Antibodies with High Specificity from Phage Display Libraries," EMBO J. 12(2):725-734.
Guyer, R.L. et al. (Aug. 1976). "Immunoglobulin Binding by Mouse Intestinal Epithelial Cell Receptors," J. Immunol. 117(2):587-593.
Hellstrom, I. et al. (Mar. 1985). "Strong Antitumor Activities of IgG3 Antibodies to a Human Melanoma-Associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Holash, J. et al. (Aug. 20, 2002, e-pub. Aug. 12, 2002). "VEGF-Trap: A VEGF Blocker with Potent Antitumor Effects," PNAS 99(17):11393-11398.
Honegger, A. et al. (Jun. 8, 2001). "Yet Another Numbering Scheme for Immunoglobulin Variable Domains: An Automatic Modeling and Analysis Tool," J. Mol. Biol. 309:657-670.
Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.
Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability, issued Dec. 6, 2022, for PCT Application No. PCT/US2021/035542, filed Jun. 2, 2021, 9 pages.
International Preliminary Report on Patentability, issued Jan. 31, 2023, for PCT Application No. PCT/US2021/043784, filed Jul. 29, 2021, 8 pages.
International Preliminary Report on Patentability, issued Mar. 28, 2023, for PCT Application No. PCT/US2021/052446, filed Sep. 28, 2021, 9 pages.
International Search Report and Written Opinion, mailed Jan. 3, 2022, for PCT Application No. PCT/US2021/043784, filed Jul. 29, 2021, 16 pages.
International Search Report and Written Opinion, mailed Mar. 3, 2022, for PCT Application No. PCT/US2021/052446, filed Sep. 28, 2021, 19 pages.

International Search Report and Written Opinion, mailed Nov. 18, 2021, for PCT Application No. PCT/US2021/035542, filed Jun. 2, 2021, 12 pages.
Jansen, F.K. et al. (1982). "Immunotoxins: Hybrid Molecules Combining High Specificity and Potent Cytotoxicity," Immunol. Rev. 62:185-216.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th ed., Public Health Service, National Institutes of Health, Bethesda, MD. TOC, 21 pages.
Kabat, E.A. et al. (Oct. 10, 1977). "Unusual Distributions of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR Grafting—A New Approach to Antibody Humanization," Methods 36:25-34.
Killen, J.A. et al. (Nov. 1, 1984). "Specific Killing of Lymphocytes That Cause Experimental Autoimmune Myasthenia Gravis by Ricin Toxin-Acetylcholine Receptor Conjugates," J. Immunol. 133(5):2549-2553.
Kim, J-K. et al. (1994). "Localization of the Site of the Murine IgGI Molecule That is Involved in Binding to the Murine Intestinal Fc Receptor," Eur. J. Immunol. 24:2429-2434.
Klimka, A. et al. (2000). "Human Anti-CD30 Recombinant Antibodies by Guided Phage Antibody Selection Using Cell Panning," Br. J. Cancer 83(2):252-260.
Kozbor, D. et al. (Dec. 1984). "A Human Hybrid Myeloma for Production of Human Monoclonal Antibodies," J. Immunol. 133(6):3001-3005.
Köhler, G. et al. (Aug. 7, 1975). "Continuous Cultures of Fused Cells Secreting Antibody of Predefined Specificity," Nature 256:495-497.
Lee, C.V. et al. (2004). "Bivalent Antibody Phage Display Mimics Natural Immunoglobulin," Journal of Immunological Methods 284:119-132.
Lee, C.V. et al. (2004). "High-Affinity Human Antibodies From Phage-Displayed Synthetic Fab Libraries With a Single Framework Scaffold," J. Mol. Biol. 340:1073-1093.
LeFranc, M.P. et al. (Jan. 2003). "IMGT Unique Numbering for Immunoglobulin and T Cell Receptor Variable Domains and Ig Superfamily V-Like Domains," Dev. Comp. Immunol. 27(1):55-77.
Li, J. et al. (Mar. 7, 2006). "Human Antibodies for Immunotherapy Development Generated via a Human B Cell Hybridoma Technology," Proc. Natl. Acad. Sci. USA 103(10):3557-3562.
Lonberg, N. (2008, e-pub. Jul. 21, 2008). "Fully Human Antibodies From Transgenic Mouse and Phage Display Platforms," Curr. Opin. Immunol. 20:450-459.
Maccallum, R.M. et al. (1996). "Antibody-Antigen Interactions: Contact Analysis and Binding Site Topography," J. Mol. Biol. 262:732-745.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
Mccafferty, J. et al. (Dec. 6, 1990). "Phage Antibodies: Filamentous Phage Displaying Antibody Variable Domains," Nature 348:552-554.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

(56) References Cited

OTHER PUBLICATIONS

Munson, P.J. et al. (1980). "Ligand: A Versatile Computerized Approach for Characterization of Ligand-Binding Systems," Anal. Biochem. 107:220-239.
Ni, J. (Oct. 23, 2006). "Research Progress and Future Perspectives in Antibodmics and Antibodomic Drugs," J. General Review 26(4):265-268, 3 pages.
Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5):1239-1249.
Orlandini, M. et al. (May 15, 2014, e-pub. Apr. 7, 2014). "The Characterization of a Novel Monoclonal Antibody Against CD93 Unveils a New Antiangiogenic Target," Oncotarget 5(9):2750-2760.
Osbourn, J. et al. (2005). "From Rodent Reagents to Human Therapeutics Using Antibody Guided Selection," Methods 36:61-68.
Padlan, E.A. (1991). "A Possible Procedure for Reducing the Immunogenicity of Antibody Variable Domains While Preserving Their Ligand-Binding Properties," Mol. Immunol. 28(4/5):489-498.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Plückthun, A. (1992). "Mono- and Bivalent Antibody Fragments Producted in Escherichia coli: Engineering, Folding and Antigen Binding," Immunol. Revs. 130:151-188.
Plückthun, A. (1994). "Antibodies from Escherichia coli," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Presta, L.G. et al. (Sep. 1, 1993). "Humanization of an Antibody Directed Against IgE," J. Immunol. 151 (5):2623-2632.
Queen, C. et al. (Dec. 1989). "A Humanized Antibody That Binds to the Interleukin 2 Receptor," Proc. Natl Acad. Sci. USA 86:10029-10033.
Raag, R. et al. (Jan. 1995). "Single-chain Fvs," The FASEB Journal 9:73-80.
Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.
Ravetch, J.V. et al. (1991). "Fc Receptors," Annu. Rev. Immunol. 9:457-492.
Remington's Pharmaceutical Sciences. (1980). 16th edition, Osol, A. Ed, pp. 1-2, (Table of Contents Only).
Retter I. et al. (Jan. 1, 2005). "VBASE2, An Integrative V Gene Database,". Nucleic Acids Res. 33:D671-D674. (Database issue), 4 pages.
Riechmann, L. et al. (Mar. 24, 1988). "Reshaping Human Antibodies for Therapy," Nature 33(6162):323-327.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Running Deer, J. et al. (May-Jun. 2004, e-pub. Mar. 10, 2004). "High-Level Expression of Proteins in Mammalian Cells Using Transcription Regulatory Sequences From the Chinese Hamster EF-1Alpha Gene," Biotechnol. Prog. 20(3):880-889.
Sambrook, J. et al. (2001). Molecular Cloning: A Laboratory Manual Cold Spring Harbor Laboratory Press, Cold Spring Harbor, N.Y., 3rd ed., 1 page, Table of Contents.
Scheraga, H. A. (1992). "Predicting Three-Dimensional Structures of Oligopeptides," Rev. Computational Chem. 3:73-142.
SEER Program Coding and Staging Manual 2016, 204 pages.

Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol. Chem. 276(9):6591-6604.
Sidhu, S.S. et al. (2004). "Phage-Displayed Antibody Libraries of Synthetic Heavy Chain Complementarity Determining Regions," J. Mol. Biol. 338(2):299-310.
Sims, M.J. et al. (Aug. 15, 1993). "A Humanized CD18 Antibody Can Block Function Without Cell Destruction," J. Immunol. 151(4):2296-2308.
Sitaraman, K. et al. (2009). "High-Throughput Protein Expression Using Cell-Free System," Methods Mol. Biol. 498:229-244.
Skerra, A. (1993) "Bacterial Expression of Immunoglobulin Fragments," Current Opinion in Immunology 5:256-262.
Song, W. et al. (Jun. 8, 2018). "Synergistic and Low Adverse Effect Cancer Immunotherapy by Immunogenic Chemotherapy and Locally Expressed PD-L1 Trap," Nat Commun. 9(1):2237, 11 pages.
Spirin, A.S. (Oct. 2004). "High-Throughput Cell-Free Systems for Synthesis of Functionally Active Proteins," Trends Biotechnol. 22(10):538-545.
U.S. Appl. No. 18/018,568, filed Jan. 29, 2023, for Chen et al. (Copy not submitted herewith pursuant to the waiver of 37 C.F.R. § 1.98(a)(2)(iii) issued by the Office on Sep. 21, 2004).
U.S. Appl. No. 18/028,170, filed Mar. 23, 2023, for Chen et al. (Copy not submitted herewith pursuant to the waiver of 37 C.F.R. § 1.98(a)(2)(iii) issued by the Office on Sep. 21, 2004).
Van Dijk, M.A. et al. (2001). "Human Antibodies as Next Generation Therapeutics," Curr. Opin. Pharmacol 5:368-374.
Vitetta, E.S. et al. (Nov. 20, 1987). "Redesigning Nature's Poisons to Create Anti-Tumor Reagents," Science 238:1098-1104.
Vollmers, H.P. et al. (2005). "Death by Stress: Natural IgM-Induced Apoptosis," Methods and Findings in Experimental and Clinical Pharmacology 27(3):185-191.
Vollmers, H.P. et al. (2005). "The "Early Birds": Natural IgM Antibodies and Immune Surveillance," Histology and Histopathology, 20(3):927-937.
Waterhouse, P. et al. (1993). "Combinatorial Infection and In Vivo Recombination: A Strategy for Making Large Phage Antibody Repertoires," Nucleic Acids Research 21(9):2265-2266.
Winter, G. et al. (1994). "Making Antibodies by Phage Display Technology," Ann. Rev. Immunol. 12:433-455.
Wright, A. et al. (Jan. 1997). "Effect of Glycosylation on Antibody Function: Implications for Genetic Engineering," Trends Biotech. 15:26-32.
Yamane-Ohnuki, N. et al. (Sep. 5, 2004, e-pub Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering 87(5):614-622.
Anonymous (Sep. 12, 2023). "How is Alzheimer's Disease Treated?" NIA.NIH.gov, 7 pages.
Anonymous (Sep. 4, 2024). "HIV Overview: HIV and AIDS: The Basics," Dept. of Health and Human Services, 4 pages.
Badri, H. et al. (2016, e-pub. Jun. 21, 2015). "Optimization of Radiation Dosing Schedules for Proneural Glioblastoma," J Math Biol. 72(5):1301-1336, 36 pages.
Baylot, V. et al. (2017). "TCTP Has a Crucial Role in the Different Stages of Prostate Cancer Malignant Progression," Chapter 13 in TCTP/tpt1-Remodeling Signaling From Stem Cell to Disease, Telerman, A. et al. eds., Springer International Publishing: Cham, Switzerland, pp. 255-261.
Colman, P.M. (1994). "Effects of Amino Acid Sequence Changes on Antibody-Antigen Interactions," Research in Immunology 145(1):33-36.
Dimberg, A. (Dec. 2014). "The Glioblastoma Vasculature as a Target for Cancer Therapy," Biochemical Society Transaction 42(6):1647-1652.
Frankel, A.E. et al. (Aug. 2000). "Characterization of Diphtheria Fusion Proteins Targeted to the Human Interleukin-3 Receptor," Protein Eng. 13(8):575-581. Abstract Only, 1 page.
Galvagni, F. et al. (Dec. 2017). "Dissecting the CD93-Multimerin 2 Interaction Involved in Cell Adhesion and Migration of the Activated Endothelium," Matrix Biology 64:112-127.

(56)                    References Cited

OTHER PUBLICATIONS

Higashi, K. et al. (2007). "Impairment of Angiogenic Activity in the Serum From Patients with Coronary Aneurysms Due to Kawasaki Disease," Circ. J. 71:1052-1059.

Mariuzza, R.A. et al. (1987). "The Structural Basis of Antigen-Antibody Recognition," Annu. Rev. Biophys. Chem. 16:139-159.

Mulligan, P.R. et al. (2014). "Vascular Anomalies: Classification, Imaging Characteristics and Implications for Interventional Radiology Treatment Approaches," Br. J. Radiol. 87:20130392, 18 pages.

Rudikoff, S. et al. (Mar. 1982). "Single Amino Acid Substation Altering Antigen-Binding Specificity," Proc. Natl. Acad. Sci. USA 78:1979-1983.

Shen, J. et al. (Apr. 21, 2006, e-pub. Feb. 15, 2006). "Single Variable Domain-IgG Fusion: A Novel Recombinant Approach to Fc Domain-Containing Bispecific Antibodies," J. of Biological Chemistry 281(16):10706-10714.

Singer, M. et al. (1998). Genes and Genomes, Moscow, Mir. 1:63-64. With English Abstract, 6 pages.

Torres, M. et al. (2008). "The Immunoglobulin Constant Region Contributes to Affinity and Specificity," Trends in Immunology 29(2):91-97.

Beckman, R.A. et al. (2007, e-pub. Dec. 11, 2006). "Antibody Constructs in Cancer Therapy: Protein Engineering Strategies to Improve Exposure in Solid Tumors," Am. Can. Society 109:170-179.

Fujimori, K. et al. (1990). "A Modeling Analysis of Monoclonal Antibody Percolation Through Tumors: A Binding-Site Barrier," J. Nuc. Med. 31:1191-1198.

Huang, C.-J. et al. (2010, e-pub. Apr. 27, 2010). "Recombinant Immunotherapeutics: Current State and Perspectives Regarding the Feasibility and Market," Appl. Microbiol. Biotechnol. 87:401-410.

Rudnick, S.I. et al. (2009). "Affinity and Avidity in Antibody-Based Tumor Targeting," Can. Biotherp. & Radiopharm. 24(2):155-162.

Thurber, G.M. et al. (2008, e-pub. Apr. 24, 2008). "Antibody Tumor Penetration: Transport Opposed by Systemic and Antigen-Mediated Clearance,". Adv. Drug Deliv. Rev. 60:1421-1434.

Altshuler, E.P. et al. (2010). "Production of Recombinant Antibodies and Methods for Increasing Their Affinity", Advances in Biological Chemistry 50:203-258.

Greenlee, M.C. (2009). "Detection and Characterization of Soluble CD93 Released During Inflammation," Inflamm. Res. 58(12):909-919. Abstract Only. 2 pages.

Shakhidzhanov, S.S. et al. (2019). "A Modern View on the Complement System," Pediatric Hematology/Oncology and Immunopathology 18(3):130-144. English Abstract, 15 pages.

Strawbridge, R.J. et al. (2016). "Soluble CD93 is Involved in Metabolic Dysregulation but Does Not Influence Carotid Intima-Media Thickness," Diabetes 65(10):2888-2899.

* cited by examiner

FIG. 4C

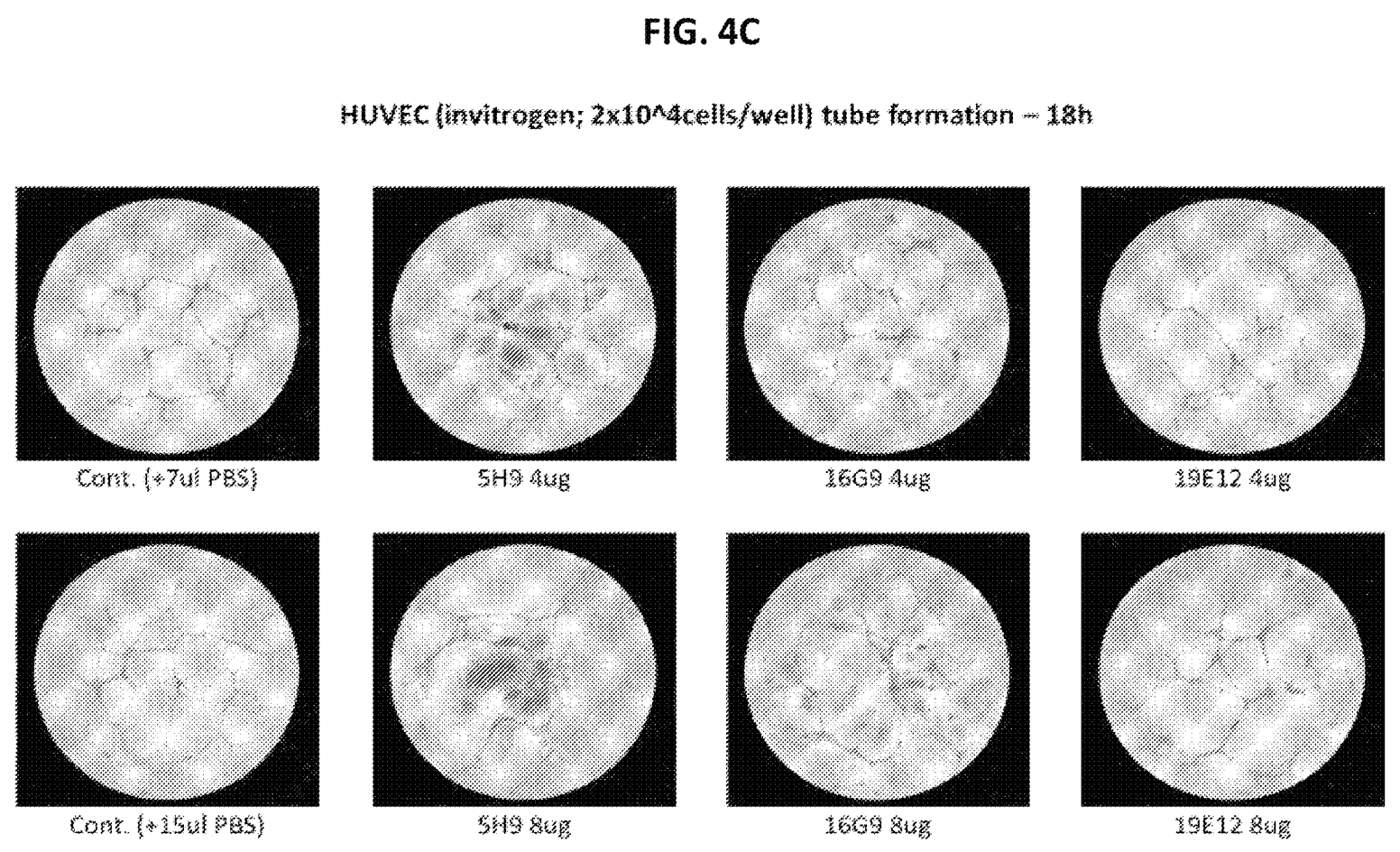

HUVEC (invitrogen; 2x10^4cells/well) tube formation ~ 18h

Cont. (+7ul PBS)    5H9 4ug    16G9 4ug    19E12 4ug

Cont. (+15ul PBS)    5H9 8ug    16G9 8ug    19E12 8ug

FIG. 4E    HUVEC (invitrogen; 2x10^4cells/well) tube formation – 18h

Cont.          Avastin-IL-10 (12ug/well)          10B1 (12ug/well)

Epitope binning in anti-CD93 hybridoma sups

|  |  | CDRL1 | CDRL2 |
|---|---|---|---|
| 19E12_VL | 1 | QAVVTQ-ESALTTSPGETVTLTCRSSTGAVTTS---NSANWVQEKPDHLFTGLIGGTNNR | |
| 19B5_VL | 1 | DIVLTQSPATLSVTPGDSVSLSCKASQSI-----KNYLHWYQQRSHESPRLLIKFASQS | |
| 5H9_VL | 1 | DIVMTQAAFSNPVTLGTSASISCSSSKSLLHSN-GVTYLYWYLQRPGQSPQLLIYRMSN | |
| 17A7_VL | 1 | DIVMTQAAFSNPVTLGTSASISCSSTKSLLHSS-GITYLYWYLQRPGQSPQLLIYRMSN | |
| 17B10_VL | 1 | DIVMTQAAFSNPVTLGTSASISCRPSKSLLHSN-GITYLYWYLQKPGQSPQLLIYQMSN | |
| 16A1_VL | 1 | DIVMTQSPSSLAMSIGQEVTMSCKSSKSLLNSHKQKNCLAWYQQKPGQSPRLLIYFACTR | |
| 17G11_VL | 1 | SIVMTQTPKFLLVSAGDRVTITCKASQSV-----SNDVAWYQQKPGQSPRLLIYYASNR | |
| 10B1_VL | 1 | DIVMTQSQKFMSTSTGDRVSVTCKASQNV-----GTNVAWYQQKPGQSPKALIYSASYR | |
| 20C7_VL | 1 | DIVMTQSHKFMSTSVGDRVSITCKASQDV-----STNVAWYQQKPGQSPKLLIHSASYR | |
| 17E6_VL | 1 | DIVMTQSHKFMSTSVGDRVSTTCKASQDV-----STAVWYQQKPGQSPKLLIYSASYR | |
| 16B6_VL | 1 | DIRMTQSPSSMYASLGERVTITCKASQDIK-----SYLSWYQQKPWKSPKTLIYYATNL | |
| 12H4_VL | 1 | QIVLTQSPAIMSASPGEKVTITCSASSSV------SLIYWFQQKPGTSPMLWIYSTSN | |
| 16E4_VL | 1 | DIVLTQSPASLAVSLGQRATISCKASQSVDYAG--DSYMNWYQQKPGQPPKLLIYAASN | |
| 16G9_VL | 1 | DIVLTQSPASLAVSLGQRATISCKASQSVSTSS--YSYMHWYQQKPGQPPKLLIKYASNL | |

|  |  | CDRL3 |
|---|---|---|
| 19E12_VL | 57 | AEGVPARFSGSLIGDKAALTITGAQTEDEAIYPCALWYNNHFVFGGGTKLTVL |
| 19B5_VL | 55 | ISDIPSRFSGSGSTDFTLSINSIETEDFGMYFCQQSNSWPLTFGAGTKLELK |
| 5H9_VL | 60 | ASGVPDRFSGSGSGTDFTLRISEVEAEDVGIYYCAQMLERFTFGSGTKLEIK |
| 17A7_VL | 60 | ASGVPDRFSGSGSGTDFTLRISRVEAEDVGVYYCAQMLERFTFGSGTKLEIK |
| 17B10_VL | 60 | ASGVPDRFSSSGSGTDFTLRISRVEAEDVGVYYCAQNLELPWTFGGGTKLEIK |
| 16A1_VL | 61 | ESGVPDRFIGSGSGTDFTLTISSVQAEDLAYYFCQHCNTPLTFGAGTKLELK |
| 17G11_VL | 55 | YTSVPDRFTGSGYGTDFTFTISTVQAEDLAVYFCQQDYS-SYTFGGGTKLEIK |
| 10B1_VL | 55 | FIGVPDRFTGSGSGTDFTLTITNVQSEDLAEYFCQYNRWITFGSGTKLEIK |
| 20C7_VL | 55 | YTSVPDRFTGRGSGTDFTFTISSVQAEDLAVYYCQHYSTPFTFGSGTKLEIK |
| 17E6_VL | 55 | YTSVPDRFTGSGSGTDFTFTIPSVQAEDLAVYYCQHYSTPFTFGSGTKLEIK |
| 16B6_VL | 55 | ADGVPSRFSGSGSGQDYSLTISSLGSDDTATYYCLQHVESPWTFGGGTKLEIK |
| 12H4_VL | 54 | ASSVPARFSGSGSGTSYSLTISRMEAEDAATYYCQQRSGYPFTFGGGTKLEIK |
| 16E4_VL | 59 | ESGIPARFSGSGSGTDFTLNIBPVEEEDAATYYCQTNEDPRTFGGGTKLEIK |
| 16G9_VL | 59 | ESGVPARFSGSGSGTDFTLNIHPVEEEDTATYYCQHSWEIPFTFGGGTKLEIK |

FIG. 8A

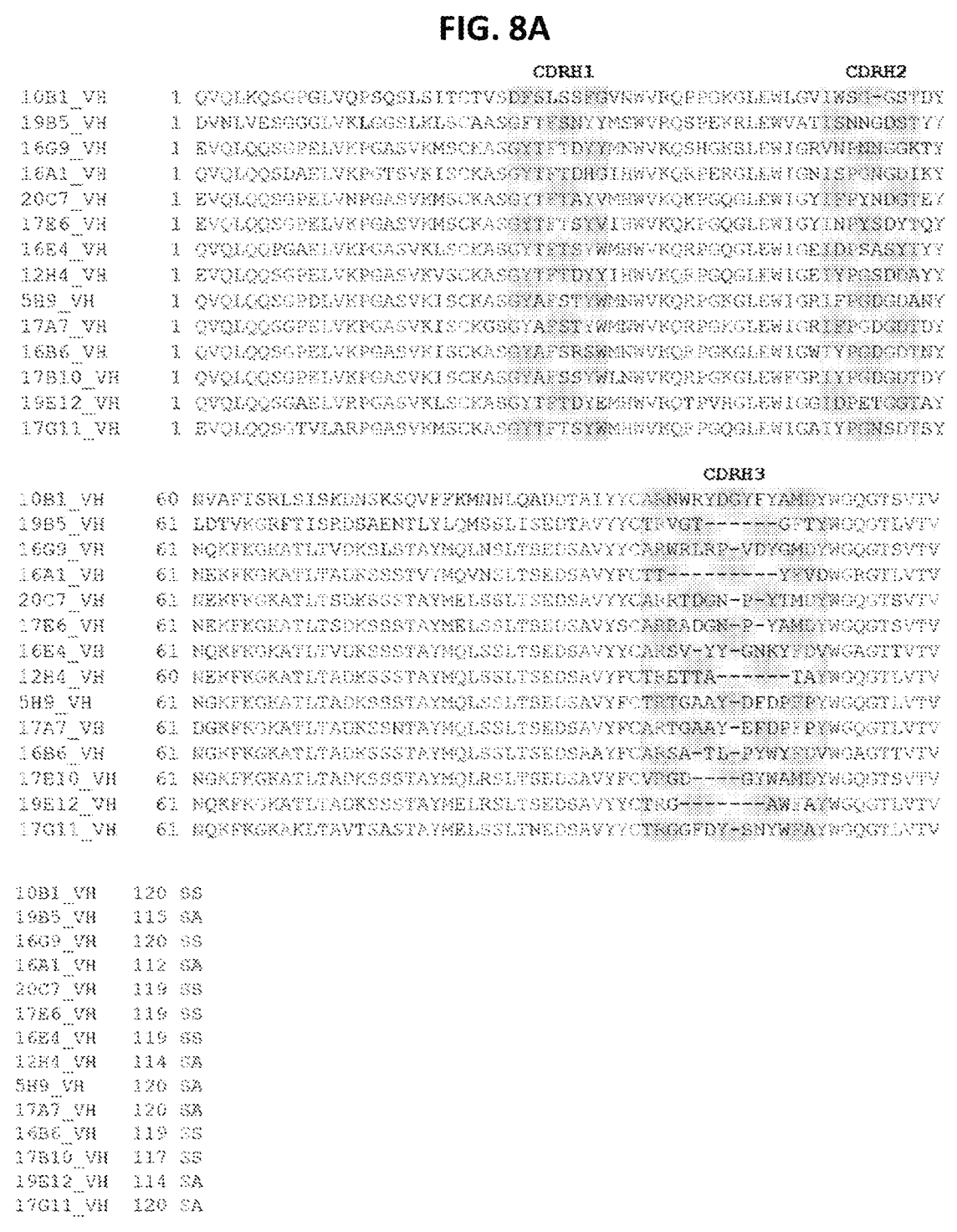

|  |  | CDRH1 | CDRH2 |
|---|---|---|---|
| 10B1_VH | 1 | QVQLKQSGPGLVQPSQSLSITCTVSDFSLSSSVKWVRQPPGKGLEWLGVIWS--SSFDY |
| 19B5_VH | 1 | DVNLVESGGGLVKLGGSLKLSCAASGFTFSHYYMSWVRQSPEKRLEWVATISNNGDSTYY |
| 16G9_VH | 1 | EVQLQQSGPELVKPGASVKMSCKASGYTFTDFYNWVKQSHGKSLEWIGRVNPNNGGKTY |
| 16A1_VH | 1 | QVQLQQSDAELVKPGTSVKISCKASGYTFTDHSIRWVKQRPERGLEWIGNISPNGDIKY |
| 20C7_VH | 1 | EVQLQQSGPELVNPGASVKMSCKASGYTFTAYVMSWVKQKPGQGLEWIGYIFPYNDSTEY |
| 17B6_VH | 1 | EVQLQQSGPELVKPGASVKMSCKASGYTFTSYMIRWVKQKPGQGLEWIGYINPYSDYTQY |
| 16E4_VH | 1 | QVQLQQPGAELVKPGASVKLSCKASGYTFTSYWMHWVKQRPGQGLEWIGEIDPSASYTYY |
| 12H4_VH | 1 | EVQLQQSGPELVKPGASVKVSCKASGYTFTDYYIHWVKQSPGQGLEWIGEIYPGSDFAYY |
| 5H9_VH | 1 | QVQLQQSGPDLVKPGASVKISCKASGYAFSTYWMNWVKQRPGKGLEWIGRIFPNDGDANY |
| 17A7_VH | 1 | QVQLQQSGPELVKPGASVKISCKGSGYAFSTYWMHWVKQRPGKGLEWIGRIFPGDDSTDY |
| 16B6_VH | 1 | QVQLQQSGPELVKPGASVKISCKASGYAFSRSWMNWVKQPPGKGLEWIGWIYPGDGDTNY |
| 17B10_VH | 1 | QVQLQQSGPELVKPGASVKISCKASGYAFSSYWLNWVKQRPGKGLEWFGRIYPGDGDTDY |
| 19E12_VH | 1 | QVQLQQSGAELVRPGASVKLSCKASGYTFTDYEMHWVRQTPVRGLEWIGGIDPETGGTAY |
| 17G11_VH | 1 | EVQLQQSGTVLARPGASVKMSCKASGYTFTSYWMHWVKQPPGQGLEWIGAIYPGNSDTSY |

|  |  | CDRH3 |
|---|---|---|
| 10B1_VH | 60 | SVAFISRLSISKDNSKSQVFFKMNNLQADDTAIYYCARNWRYDSYFYAMDYWGQGTSVTV |
| 19B5_VH | 61 | LDTVKGRFTISRDSAENTLYLQMSSLISEDTAVYYCTRVQT-----GFYWGQGTLVTV |
| 16G9_VH | 61 | NQKFKGKATLTVDKSLSTAYMQLNSLTSEDSAVYYCAPWKLRP-VDYGMDYWGQGTSVTV |
| 16A1_VH | 61 | NEKFKGKATLFADKSSSTVMQVNSLTSEDSAVYFCTT-------YFVDNGBGTLVTV |
| 20C7_VH | 61 | NEKFKGKATLTSDKSGSTAYMELSSLTSEDSAVYYCARRTDGN-P-YTMDYWGQGTSVTV |
| 17B6_VH | 61 | NEKFKGKATLTSDKSSSTAYMELSSLTSEDSAVYSCARBADGN-P-YAMDYWGQGTSVTV |
| 16E4_VH | 61 | NQKFKGKATLTVDKSSSTAYMQLSSLTSEDSAVYYCARSV-YY-GNKYFDVWGAGTTVTV |
| 12H4_VH | 60 | NEKFKGKATLTADKSSSTAYMQLSSLTSEDSAVYFCTRETTA-----TAYWGQGTLVTV |
| 5H9_VH | 61 | NGKFKGKATLTADKSSSTAYMQLSSLTSEDSAVYFCTRTGAAY-DFDFPYWGQGTLVTV |
| 17A7_VH | 61 | DGRFKGKATLTADKSNTAYMQLSSLTSEDSAVYFCARTQAAY-EFDFPYWGQGTLVTV |
| 16B6_VH | 61 | NGRFKGKATLTADKSSSTAYMQLSSLTSEDSAAYFCARSA-TL-DYWYFDVWGAGTTVTV |
| 17B10_VH | 61 | NGKFKGKATLTADKSSSTAYMQLRSLPSEDSAVYFCVTGD----GYNAMDYWGQGTSVTV |
| 19E12_VH | 61 | NQKFKGKATLTADKSSSTAYMELRSLTSEDSAVYYCTRG-------AWFAYWGQGTLVTV |
| 17G11_VH | 61 | NQKFKGKAKLTAVTSASTAYMELSSLTNEDSAVYYCTRDGFDY-SNYWAYWGQGTLVTV |

| 10B1_VH | 120 | SS |
|---|---|---|
| 19B5_VH | 119 | SA |
| 16G9_VH | 120 | SS |
| 16A1_VH | 112 | SA |
| 20C7_VH | 119 | SS |
| 17B6_VH | 119 | SS |
| 16E4_VH | 119 | SS |
| 12H4_VH | 114 | SA |
| 5H9_VH | 120 | SA |
| 17A7_VH | 120 | SA |
| 16B6_VH | 119 | SS |
| 17B10_VH | 117 | SS |
| 19E12_VH | 114 | SA |
| 17G11_VH | 120 | SA |

FIG. 8B

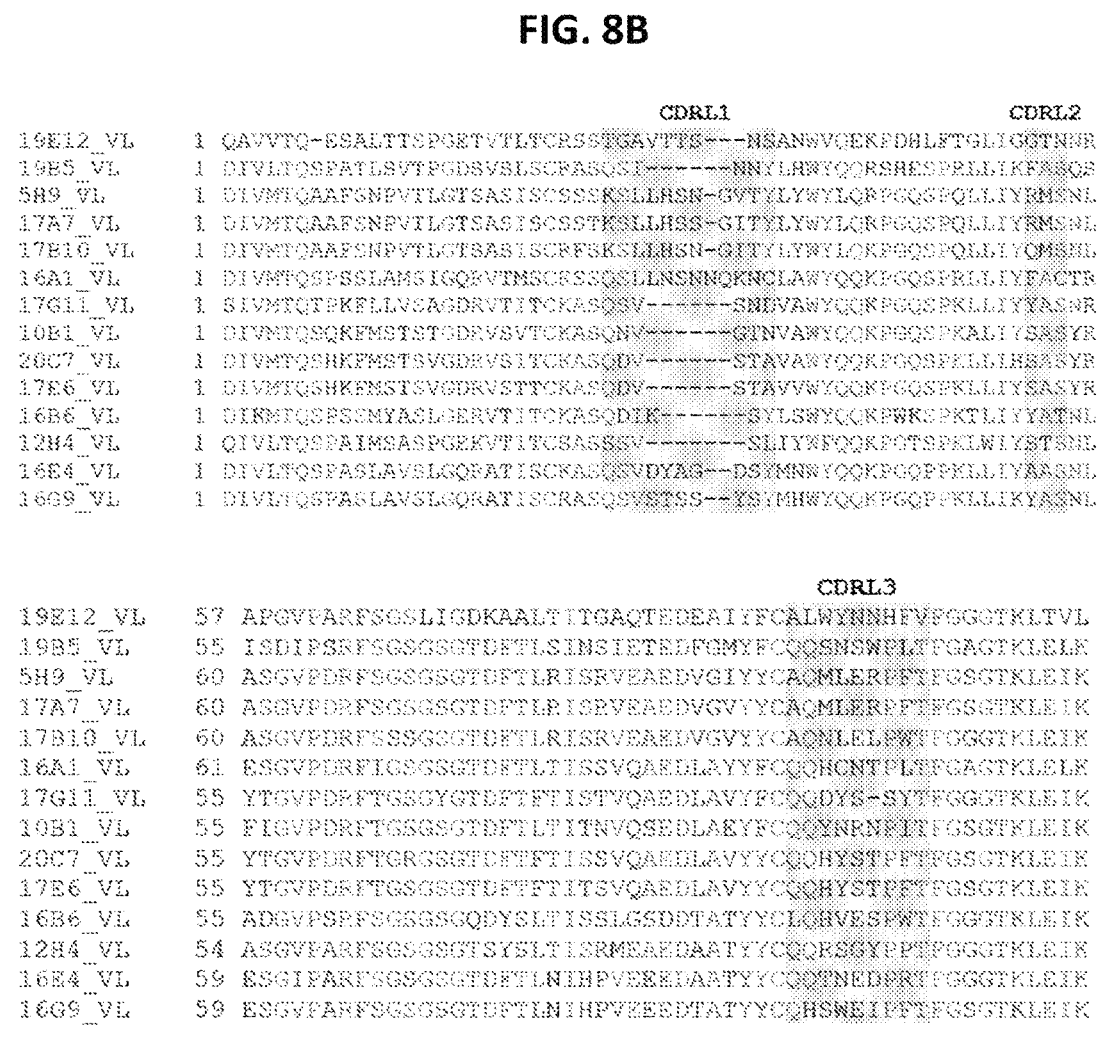

```
                                         CDRL1                        CDRL2
19E12_VL   1  QAVVTQ-ESALTTSPGETVTLTCRSSTGAVTTS---NSANWVQEKPDHLFTGLIGGTNNR
19B5_VL    1  DIVLTQSPATLSVTPGDSVSLSCRASQSI------NNYLAWYQQRSHESPRLLIKFSSQS
5H9_VL     1  DIVMTQAAFSNPVTLGTSASISCSSSKSLLRSN-GVTYLYWYLQRPGQSPQLLIYRMSNL
17A7_VL    1  DIVMTQAAFSNPVTLGTSASISCSSTKSLLRSS-GITYLYWYLQRPGQSPQLLIYRMSNL
17B10_VL   1  DIVMTQAAFSNPVTLGTSASISCRFSKSLLRSN-GITYLYWYLQKPGQSPQLLIYQMSNL
16A1_VL    1  DIVMTQSPSSLAMSIGQSVTMSCSSSQSLLNSNNQKNCLAWYQQKPGQSPRLLIYFACTR
17G11_VL   1  SIVMTQTPKFLLVSAGDRVTITCKASQSV------SMIVAWYQQKPGQSPKLLIYYASNR
10B1_VL    1  DIVMTQSQKFMSTSTDRVSVTCKASQNV------QINVAWYQQKPGQSPKALIYSASYR
20C7_VL    1  DIVMTQSHKFMSTSVGDRVSITCKASQDV------STAVAWYQQKPGQSPRLLIHSASYR
17E6_VL    1  DIVMTQSHKFMSTSVGDRVSTTCKASQDV------STAVWYQQKPGQSPKLLIYSASYR
16B6_VL    1  DIRMTQSPSCMYASLGERVTITCKASQDIK-----SYLSWYQQKPWKSPKTLIYYRSNL
12H4_VL    1  QIVLTQSPAIMSASPGEKVTITCSASSSV------SLIYNFQQKPCTSPKLWIYSTSNL
16E4_VL    1  DIVLTQSPASLAVSLGQRATISCKASNVDYAS--DSYMNWYQQKPGQPPKLLIYAASNL
16G9_VL    1  DIVLTQSPASLAVSLGQRATISCRASQSVSTSS--YSYMHWYQQKPGQPPKLLIKYASNL

CDRL3
19E12_VL   57 APGVPARFSGSLIGDKAALTITGAQTEDEAIYFCALWYNNHFVFGGGTKLTVL
19B5_VL    55 ISDIPSRFSGSGSGTDFTLSIMSIETELFGMYFCQQSMSNPLSTGAGTKLELK
5H9_VL     60 ASGVPDRFSGSGSGTDFTLRISRVEAEDVGIYYCAQMLERPFTFGSGTKLEIK
17A7_VL    60 ASGVPDRFSGSGSGTDFTLRISRVEAEDVGVYYCAQMLERPFTFGSGTKLEIK
17B10_VL   60 ASGVPDRFSSSGGGTDFTLRISRVEAEDVGVYYCAQNLELPWTFGGGTKLEIK
16A1_VL    61 ESGVPDRFICSGSGTDFTLTISSVQAEDLAYYFCQQHCNTPLSFGAGTKLELK
17G11_VL   55 YTGVPDRFTGSGYGTDFTFTISTVQAEDLAVYFCQQDYS-SYTFGGGTKLEIK
10B1_VL    55 FIGVPDRFTGSGSGTDFTLTITNVQSEDLAEYFCQYNRNIITFGSGTKLEIK
20C7_VL    55 YTGVPDRFTGSGSGTDFTFTISSVQAEDLAVYYCQOHYSTPFTFGSGTKLEIK
17E6_VL    55 YTGVPDRFTGSGSGTDFTFTITSVQAEDLAVYYCQOHYSTPFTFGSGTKLEIK
16B6_VL    55 ADGVPSPFSGSGSGQDYSLTISSLGSDDTATYYCLQHVESPWTFGGTTKLEIK
12H4_VL    54 ASGVPARFSGSGSGTSYSLTISRMEAEDAATYYCQQRSGYPPTFGGGTKLEIK
16E4_VL    59 ESGIPARFSGSGSGTDFTLNIHPVEEEIAATYYCQQTNEDPRTFGGGTKLEIK
16G9_VL    59 ESGVPARFSGSGSGTDFTLNIHPVEEEDTATYYCHSNEIPPTFGSGTKLEIK
```

Test the binding affinity of anti-CD93 mAbs by Octet

| Sample IDc | KD (M) | ka (1/Ms) | kdis (1/s) | Rmax | kobs (1/s) |
|---|---|---|---|---|---|
| 10B1-mIgG1 | 9.04E-10 | 1.28E+05 | 1.16E-04 | 0.598 | 4.27E-02 |
| 7F3 | 1.26E-09 | 3.81E+05 | 4.78E-04 | 0.3437 | 1.27E-01 |

Anti-Penta-HIS(HIS1K) biosensor

Test the new anti-CD93 mAb binding to human CD93 expressing cells 0.1 ug/ml
MMRN2$^{495-674}$ 0.5 ug/ml
MMRN2$^{495-674}$

Blocking assay of anti-hCD93 on hCD93/hMMRN2 in CHO-hCD93 cells

FACS analysis of the blocking effect of 7F3 antibody on IGFBP7 binding to CHO-CD93 cells

17B10 (humanized, mouse IgG1, H3L3)

stained with caleinAM 30min
counted by eye
HUVEC tubule assay

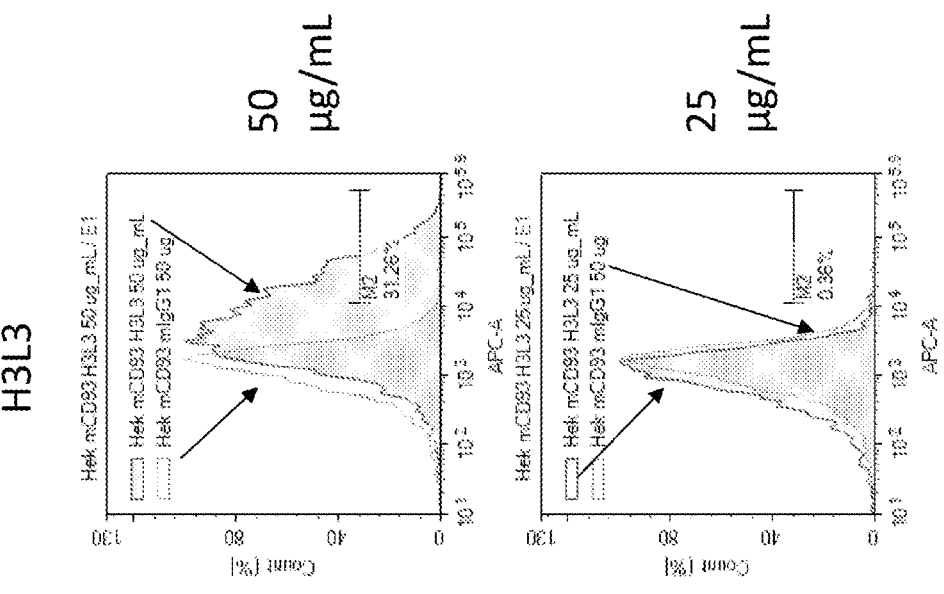
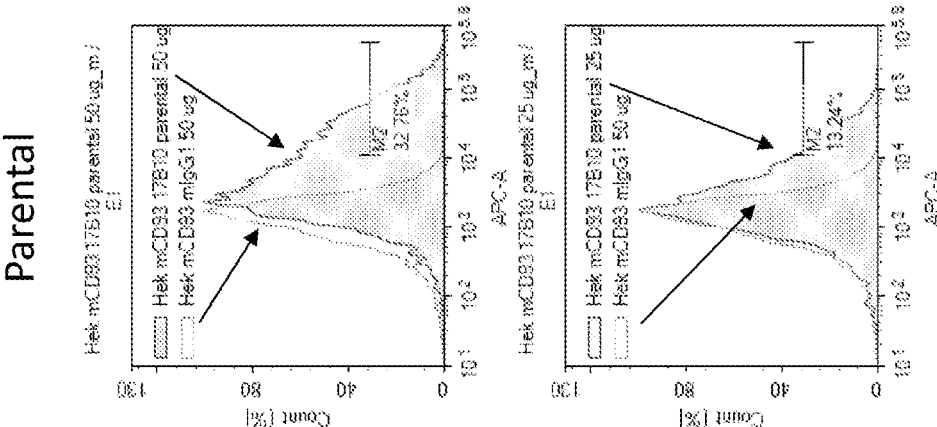
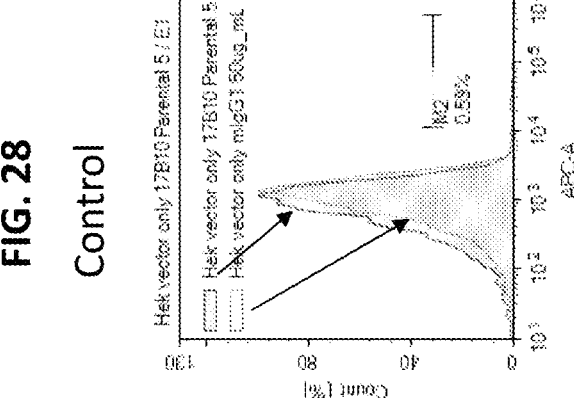
FIG. 28

SDS-PAGE analysis of humanized 16E4 and humanized 7F3

Humanized 16E4: h16E4
Humanized 7F3: h7F3

1. Marker
2. 16E4-Hyb.
3. h16E4
4. h16E4-40°C for 2w
5. h16E4- 40°C for 4w
6. h7F3
7. h7F3-40°C for 2w
8. h7F3-40°C for 4w 4-12% SDS-PAGE (reducing)

4-12% SDS-PAGE (non-reducing)

FACS analysis of h16E4 binding to CHO-hCD93 cells h16E4-0 (EC50: 388pM)
h16E4-2w (EC50: 274pM)
h16E4-4w (EC50: 312pM)

FACS analysis of h7F3 binding to HUVEC cells h7F3-hIgG1 (EC50: 1.34 nM)
h7F3-hIgG1-2w (EC50: 1.17 nM)
h7F3-hIgG1-4w (EC50: 1.12 nMM)

FIG. 41 Kinetic characterization of 16E4 and 7F3 binding to hCD93

| Sample ID | KD (M) | KD Error | ka (1/Ms) | ka Error | kdis (1/s) | kdis Error |
|-----------|--------|----------|-----------|----------|------------|------------|
| 16E4-hIgG1 | 1.35E-10 | 3.51E-11 | 2.17E+05 | 1.53E+03 | 2.93E-05 | 7.59E-06 |
| 7F3-hIgG1 | 5.88E-10 | 3.54E-11 | 5.70E+05 | 1.09E+04 | 3.35E-04 | 1.91E-05 |
| h7F3 | 4.72E-10 | 3.19E-11 | 6.81E+05 | 1.43E+04 | 3.21E-04 | 2.07E-05 |
| h7F3-2w | 4.95E-10 | 3.23E-11 | 7.20E+05 | 1.60E+04 | 3.56E-04 | 2.19E-05 |
| h7F3-4w | 4.87E-10 | 2.83E-11 | 7.93E+05 | 1.70E+04 | 3.86E-04 | 2.09E-05 |

2 weeks at 40°C 4 weeks at 40°C

Kinetic characterization of h16E4 binding to hCD93

| Sample ID | KD (M) | KD Error | ka (1/Ms) | ka Error | kdis (1/s) | kdis Error |
|-----------|--------|----------|-----------|----------|------------|------------|
| h16E4 | 4.16E-10 | 2.55E-11 | 249400 | 1490 | 1.04E-04 | 6.34E-06 |
| h16E4-2w | 2.04E-11 | 2.66E-11 | 248600 | 1549 | 5.08E-06 | 6.62E-06 |
| h16E4-4w | 1.12E-10 | 2.47E-11 | 288600 | 1994 | 3.24E-05 | 7.13E-06 |

FIG. 43

Summary of 16E4 and 7F3 binding affinity by Octet

| Ab | ELISA (hCD93) | Octet (hCD93) | FACS (CHO-hCD93 cells) |
|---|---|---|---|
| 16E4-Hyb. | 112 pM | 334 pM | 590 pM |
| 16E4-hIgG1 | 41 pM | 135 pM | 240 pM |
| h16E4 | 33 pM | 416 pM | 388 pM |
| h16E4-2w | 49 pM | 20.4 pM | 274 pM |
| h16E4-4w | 51 pM | 112 pM | 312 pM |
| | | | |
| 7F3-Hyb. | 66.7 pM | 493 pM | 210 pM |
| 7F3-hIgG1 | 41 pM | 588 pM | 400 pM |
| h7F3 | 42.7 pM | 472 pM | 175 pM |
| h7F3-2w | 41.3 pM | 495 pM | 194 pM |
| h7F3-4w | 40.7 pM | 487 pM | 195 pM |

(2 weeks at 40°C — h16E4-2w)
(4 weeks at 40°C — h16E4-4w)
(2 weeks at 40°C — h7F3-2w)
(4 weeks at 40°C — h7F3-4w)

| Ab | FACS (HUVEC cells) | FACS (KG1a cells) |
|---|---|---|
| 16E4-Hyb. | 200 pM | |
| 16E4-hIgG1 | | |
| h16E4 | | 131 pM |
| h16E4-2w | | 113 pM |
| h16E4-4w | | 115 pM |
| | | |
| 7F3-Hyb. | 2.94 nM | |
| 7F3-hIgG1 | | |
| h7F3 | 1.34 nM | 24 pM |
| h7F3-2w | 1.17 nM | 21 pM |
| h7F3-4w | 1.12 nM | 19 pM |

(2 weeks at 40°C — h16E4-2w)
(4 weeks at 40°C — h16E4-4w)
(2 weeks at 40°C — h7F3-2w)
(4 weeks at 40°C — h7F3-4w)

FACS analysis of h7F3 blocking hMMRN2 binding to CHO-hCD93 cells h7F3-0w (IC50: 173 pM)
h7F3-2w (IC50: 133 pM)
h7F3-4w (IC50: 153 pM)

MMRN2 blocking assay in CHO-hCD93 cells h16E4 (IC50: 225 nM)
h7F3 (IC50: 133 pM )

FACS analysis of h7F3 blocking hIGFBP7-His binding to HUVEC cells

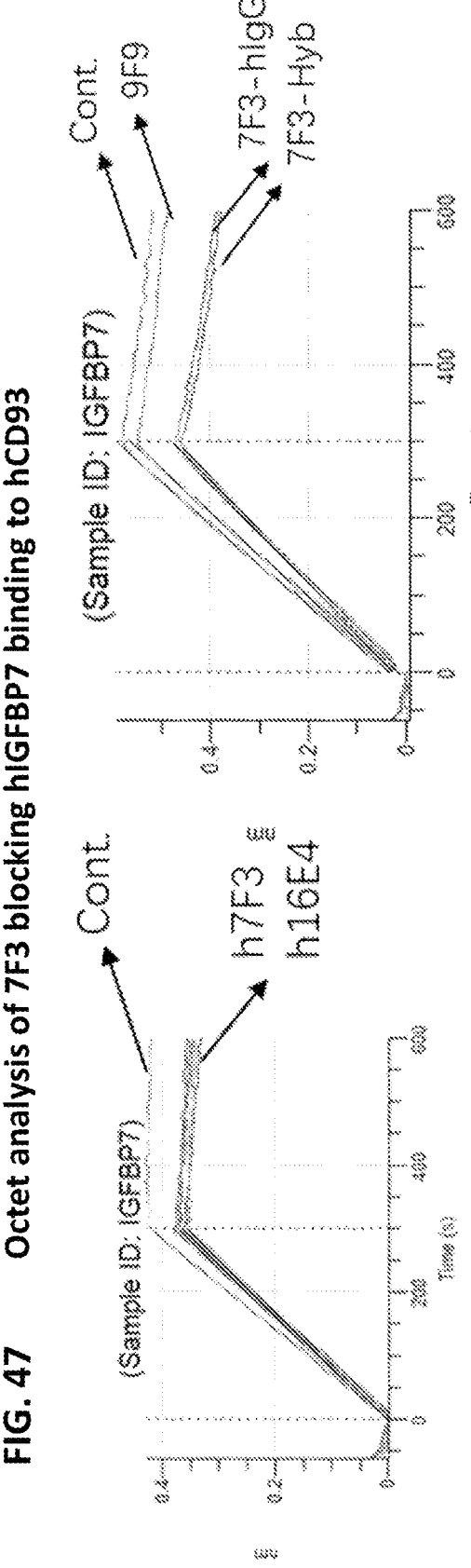
FIG. 47    Octet analysis of 7F3 blocking hIGFBP7 binding to hCD93
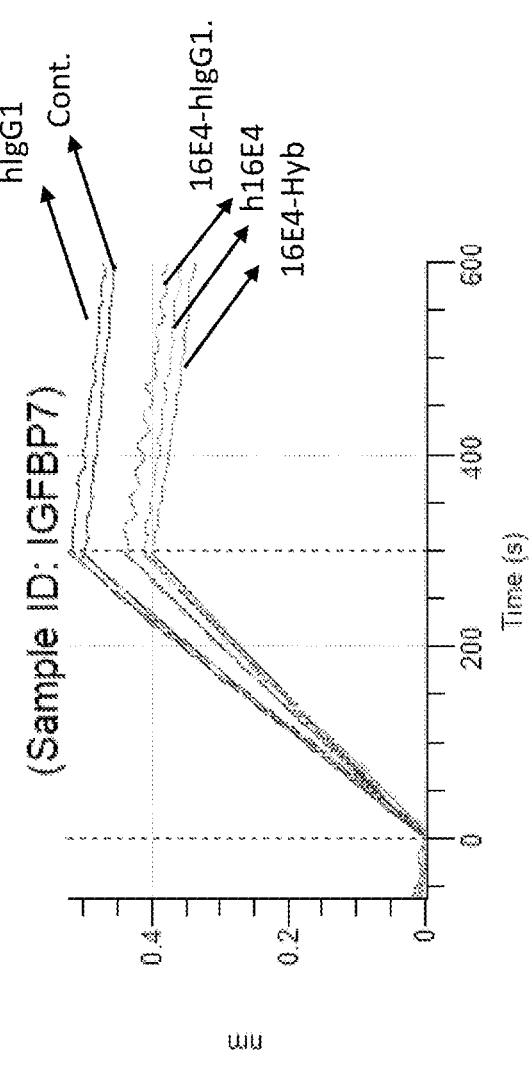
FIG. 48    Octet analysis of 16E4 blocking hIGFBP7 binding to hCD93

HUVEC tube formation assay h7F3 h16E4 hIgG1

Cont. (PBS)

FIG. 51

Summary of properties of 16E4, 7F3, 16A1, and 17B10

| Clone Name | Isotype | hCD93 Binding | Cyno Cross | Mouse Cross | Whole cell binding (CHO-hCD93) | Whole cell binding (HEK293-mCD93) | IGFBP7 Blocking (FACS) | MMRN2 Blocking (FACS) | HUVEC Tube inhibition | Tumor animal model |
|---|---|---|---|---|---|---|---|---|---|---|
| 16E4 | IgG1 | +++ | +++ | - | +++ | - | + | - | + | |
| 7F3 | IgG1 | +++ | +++ | - | +++ | - | + | + | + | |
| 16A1 | IgG1 | +++ | +++ | +++ | ++ | + | - | - | + | + (B16, KPC) |
| 17B10 | IgG1 | +++ | +++ | +++ | +++ | + | - | - | + | + (B16) |

SEQUENCE LISTING

<160> NUMBER OF SEQ ID NOS: 422

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Ser Phe Gly Val Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Val Ile Trp Ser Gly Gly Ser Thr Asp Tyr Asn Val Ala Phe Ile Ser
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

```
Asn Trp Arg Tyr Asp Gly Tyr Phe Tyr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Lys Ala Ser Gln Asn Val Gly Thr Asn Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ser Ala Ser Tyr Arg Phe Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Tyr Asn Arg Asn Pro Ile Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Asp Phe Ser Leu Ser Ser Phe Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Ile Trp Ser Gly Gly Ser Thr
1               5

<210> SEQ ID NO 9
<211> LENGTH: 15
<212> TYPE: PRT
<213> ORGANISM: Artificial Sequence
<220> FEATURE:
<223> OTHER INFORMATION: Synthetic Construct

<400> SEQUENCE: 9

Ala Arg Asn Trp Arg Tyr Asp Gly Tyr Phe Tyr Ala Met Asp Tyr
```

-continued

```
1               5                    10                   15
```

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Gln Asn Val Gly Thr Asn
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic Construct

<400> SEQUENCE: 11

Ser Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Gln Tyr Asn Arg Asn Pro Ile Thr
1               5

<210> SEQ ID NO 13
<211> LENGTH: 121
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Lys Gln Ser Gly Pro Gly Leu Val Gln Pro Ser Gln
1               5                    10                   15

Ser Leu Ser Ile Thr Cys Thr Val Ser Asp Phe Ser Leu Ser Ser Phe
                20                  25                   30

Gly Val Asn Trp Val Arg Gln Pro Pro Gly Lys Gly Leu Glu Trp Leu
            35                  40                   45

Gly Val Ile Trp Ser Gly Gly Ser Thr Asp Tyr Asn Val Ala Phe Ile
        50                  55                  60

Ser Arg Leu Ser Ile Ser Lys Asp Asn Ser Lys Ser Gln Val Phe Phe
65                  70                  75                  80

Lys Met Asn Asn Leu Gln Ala Asp Asp Thr Ala Ile Tyr Tyr Cys Ala
                85                  90                  95

Arg Asn Trp Arg Tyr Asp Gly Tyr Phe Tyr Ala Met Asp Tyr Trp Gly
            100                 105                 110

Gln Gly Thr Ser Val Thr Val Ser Ser
            115                 120

<210> SEQ ID NO 14
<211> LENGTH: 107
<212> TYPE: PRT

-continued

```
<213> ORGANISM: Artificial Sequence
<220> FEATURE:
<223> OTHER INFORMATION: Synthetic Construct

<400> SEQUENCE: 14

Asp Ile Val Met Thr Gln Ser Gln Lys Phe Met Ser Thr Ser Thr Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Phe Ile Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Arg Asn Pro Ile
                85                  90                  95

Thr Phe Gly Ser Gly Thr Lys Leu Glu Ile Lys
            100                 105

<210> SEQ ID NO 15
<211> LENGTH: 364
<212> TYPE: DNA
<213> ORGANISM: Artificial Sequence
<220> FEATURE:
<223> OTHER INFORMATION: Synthetic Construct

<400> SEQUENCE: 15
caggtgcagc tgaagcagtc aggacctggc ctagtgcagc cctcacagag cctgtccatc      60
acctgcacag tctctgattt ctcattatct agctttggtg taaactgggt tcgccagcct     120
ccaggaaagg gtctggagtg gctgggggtg atatggagtg gtggaagtac agactataat     180
gtagctttca tatccagact gagcatcagc aaggacaact ccaagagcca gttttctttt     240
aaaatgaaca atctgcaagc tgatgacaca gccatatact actgtgccag aaattggagg     300
tatgatggtt acttctatgc tatggactac tggggtcaag gaacctcagt caccgtctcc     360
tcag                                                                   364

<210> SEQ ID NO 16
<211> LENGTH: 322
<212> TYPE: DNA
<213> ORGANISM: Artificial Sequence
<220> FEATURE:
<223> OTHER INFORMATION: Synthetic Construct

<400> SEQUENCE: 16
gacattgtga tgacccagtc tcaaaaattc atgtccacat caacaggaga cagggtcagc      60
gtcacctgca aggccagtca gaatgtgggt actaatgtag cctggtatca acagaaacca     120
ggacagtctc ctaaagcact gatttactcg gcatcatacc gattcattgg agtccctgat     180
cgcttcacag gcagtggatc tgggacagat ttcactctca ccatcaccaa tgtgcagtct     240
gaagacttgg cagagtattt ctgtcagcaa tataacagaa atcctatcac gttcggctcg     300
gggacaaagt tggaaataaa ac                                              322

<210> SEQ ID NO 17
<211> LENGTH: 5
<212> TYPE: PRT
<213> ORGANISM: Artificial Sequence
<220> FEATURE:
```

<223> OTHER INFORMATION: Synthetic Construct

<400> SEQUENCE: 17

Ser Tyr Trp Met His
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Glu Ile Asp Pro Ser Ala Ser Tyr Thr Tyr Tyr Asn Gln Lys Phe Lys
1               5                   10                  15

Gly

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Ser Val Tyr Tyr Gly Asn Lys Tyr Phe Asp Val
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Lys Ala Ser Gln Ser Val Asp Tyr Ala Gly Asp Ser Tyr Met Asn
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Ala Ala Ser Asn Leu Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Thr Asn Glu Asp Pro Arg Thr
1               5

<210> SEQ ID NO 23
<211> LENGTH: 8
<212> TYPE: PRT
<213> ORGANISM: Artificial Sequence -continued
<220> FEATURE:
<223> OTHER INFORMATION: Synthetic Construct

<400> SEQUENCE: 23

Gly Tyr Thr Phe Thr Ser Tyr Trp
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Ile Asp Pro Ser Ala Ser Tyr Thr
1               5

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Ala Arg Ser Val Tyr Tyr Gly Asn Lys Tyr Phe Asp Val
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Gln Ser Val Asp Tyr Ala Gly Asp Ser Tyr
1               5                   10

<210> SEQ ID NO 27
<211> LENGTH: 3
<212> TYPE: PRT
<213> ORGANISM: Artificial Sequence
<220> FEATURE:
<223> OTHER INFORMATION: Synthetic Construct

<400> SEQUENCE: 27

Ala Ala Ser
1

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gln Gln Thr Asn Glu Asp Pro Arg Thr
1               5

<210> SEQ ID NO 29
<211> LENGTH: 120
<212> TYPE: PRT
<213> ORGANISM: Artificial Sequence
<220> FEATURE:

<223> OTHER INFORMATION: Synthetic Construct

<400> SEQUENCE: 29

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Ala Ser Tyr Thr Tyr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Val Tyr Tyr Gly Asn Lys Tyr Phe Asp Val Trp Gly Ala
            100                 105                 110

Gly Thr Thr Val Thr Val Ser Ser
        115                 120
```

<210> SEQ ID NO 30
<211> LENGTH: 111
<212> TYPE: PRT
<213> ORGANISM: Artificial Sequence
<220> FEATURE:
<223> OTHER INFORMATION: Synthetic Construct

<400> SEQUENCE: 30

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Ala
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Asn
                85                  90                  95

Glu Asp Pro Arg Thr Phe Gly Gly Gly Thr Lys Leu Glu Ile Lys
            100                 105                 110
```

<210> SEQ ID NO 31
<211> LENGTH: 360
<212> TYPE: DNA
<213> ORGANISM: Artificial Sequence
<220> FEATURE:
<223> OTHER INFORMATION: Synthetic Construct

<400> SEQUENCE: 31

```
caggtccagc ttcagcagcc tgggggctgaa ctggtgaagc ctgggggcttc agtgaagctg      60 tcctgcaagg cttctggata caccttcact agctactgga tgcactgggt gaagcagagg     120
cctggacaag gccttgagtg gatcggagag attgatcctt ctgctagtta tacttactac     180
aatcaaaagt tcaagggcaa ggccacattg actgtagaca atcctccag cacagcctac      240 atgcaactca gcagcctgac atctgaggac tctgcggtct attactgtgc aagatcggtc     300
```

```
tactatggta acaagtattt cgatgtctgg ggcgcaggga ccacggtcac cgtctcctca     360

<210> SEQ ID NO 32
<211> LENGTH: 334
<212> TYPE: DNA
<213> ORGANISM: Artificial Sequence
<220> FEATURE:
<223> OTHER INFORMATION: Synthetic Construct

<400> SEQUENCE: 32
gacattgtgc tgacccaatc tccagcttct ttggctgtgt ctctagggca gagggccacc      60
atctcctgca aggccagcca aagtgttgat tatgccggtg atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaactaatga ggatcctcgg     300
acgttcggtg gaggcaccaa gctggaaatc aaac                                 334

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Thr Tyr Trp Met Asn
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Arg Ile Phe Pro Gly Asp Gly Asp Ala Asn Tyr Asn Gly Lys Phe Lys
1               5                   10                  15

Gly

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

Thr Gly Ala Ala Tyr Asp Phe Asp Pro Phe Pro Tyr
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Synthetic Construct

<400> SEQUENCE: 36

Ser Ser Ser Lys Ser Leu Leu His Ser Asn Gly Val Thr Tyr Leu Tyr
1               5                   10                  15
```

-continued

```
<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Arg Met Ser Asn Leu Ala Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Ala Gln Met Leu Glu Arg Pro Phe Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Construct

<400> SEQUENCE: 39

Gly Tyr Ala Phe Ser Thr Tyr Trp
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Ile Phe Pro Gly Asp Gly Asp Ala
1               5

<210> SEQ ID NO 41
<211> LENGTH: 14
<212> TYPE: PRT
<213> ORGANISM: Artificial Sequence
<220> FEATURE:
<223> OTHER INFORMATION: Synthetic Construct

<400> SEQUENCE: 41

Thr Arg Thr Gly Ala Ala Tyr Asp Phe Asp Pro Phe Pro Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Lys Ser Leu Leu His Ser Asn Gly Val Thr Tyr
1               5                   10

<210> SEQ ID NO 43
```

```
<211> LENGTH: 3
<212> TYPE: PRT
<213> ORGANISM: Artificial Sequence
<220> FEATURE:
<223> OTHER INFORMATION: Synthetic Construct

<400> SEQUENCE: 43

Arg Met Ser
1

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Ala Gln Met Leu Glu Arg Pro Phe Thr
1               5

<210> SEQ ID NO 45
<211> LENGTH: 121
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Gln Gln Ser Gly Pro Asp Leu Val Lys Pro Gly Ala
1               5                   10                  15

Ser Val Lys Ile Ser Cys Lys Ala Ser Gly Tyr Ala Phe Ser Thr Tyr
            20                  25                  30

Trp Met Asn Trp Val Lys Gln Arg Pro Gly Lys Gly Leu Glu Trp Ile
        35                  40                  45

Gly Arg Ile Phe Pro Gly Asp Gly Asp Ala Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Thr Gly Ala Ala Tyr Asp Phe Asp Pro Phe Pro Tyr Trp Gly
            100                 105                 110

Gln Gly Thr Leu Val Thr Val Ser Ala
        115                 120

<210> SEQ ID NO 46
<211> LENGTH: 112
<212> TYPE: PRT
<213> ORGANISM: Artificial Sequence
<220> FEATURE:
<223> OTHER INFORMATION: Synthetic Construct

<400> SEQUENCE: 46

Asp Ile Val Met Thr Gln Ala Ala Phe Ser Asn Pro Val Thr Leu Gly
1               5                   10                  15

Thr Ser Ala Ser Ile Ser Cys Ser Ser Ser Lys Ser Leu Leu His Ser
            20                  25                  30

Asn Gly Val Thr Tyr Leu Tyr Trp Tyr Leu Gln Arg Pro Gly Gln Ser
        35                  40                  45

Pro Gln Leu Leu Ile Tyr Arg Met Ser Asn Leu Ala Ser Gly Val Pro
    50                  55                  60
```

-continued

```
Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Ala Gln Met
                85                  90                  95

Leu Glu Arg Pro Phe Thr Phe Gly Ser Gly Thr Lys Leu Glu Ile Lys
            100                 105                 110
```

```
<210> SEQ ID NO 47
<211> LENGTH: 364
<212> TYPE: DNA
<213> ORGANISM: Artificial Sequence
<220> FEATURE:
<223> OTHER INFORMATION: Synthetic Construct

<400> SEQUENCE: 47
caggttcagc tgcagcagtc tggacctgac ctggtgaagc ctggggcctc agtgaagatt      60
tcctgcaaag cttctggcta cgcattcagt acctactgga tgaactgggt gaagcagagg     120
cctggaaagg gtcttgagtg gattggacgg attttcctg gagatggaga tgctaactac     180
aatgggaagt tcaagggcaa ggccacactg actgcagaca atcctccag cacagcctac     240 atgcaactca gcagcctgac atctgaggac tctgcggtct acttctgtac aagaactggg     300
gccgcctatg atttcgaccc ttttccttac tggggccaag ggactctggt cactgtctct     360
gcag                                                                    364
```

```
<210> SEQ ID NO 48
<211> LENGTH: 337
<212> TYPE: DNA
<213> ORGANISM: Artificial Sequence
<220> FEATURE:
<223> OTHER INFORMATION: Synthetic Construct

<400> SEQUENCE: 48
gatattgtga tgacgcaggc tgcattctcc aatccagtca ctcttggaac atcagcttcc      60
atctcttgca gttctagtaa gagtctccta catagtaatg gcgtcactta tttgtattgg     120
tatctgcaga ggccaggcca gtctcctcag ctcctgatat atcggatgtc caaccttgcc     180
tcaggagtcc cagacaggtt cagtggcagt gggtcaggaa ctgatttcac actgagaatc     240
agcagagtgg aggctgagga tgtgggtatt tattactgtg ctcaaatgct agaacgccca     300
ttcacgttcg gctcggggac aaagttggaa ataaaac                              337
```

```
<210> SEQ ID NO 49
<211> LENGTH: 5
<212> TYPE: PRT
<213> ORGANISM: Artificial Sequence
<220> FEATURE:
<223> OTHER INFORMATION: Synthetic Construct

<400> SEQUENCE: 49

Asp Tyr Tyr Met Asn
1               5
```

```
<210> SEQ ID NO 50
<211> LENGTH: 17
<212> TYPE: PRT
<213> ORGANISM: Artificial Sequence
<220> FEATURE:
<223> OTHER INFORMATION: Synthetic Construct

<400> SEQUENCE: 50
```

```
Arg Val Asn Pro Asn Asn Gly Gly Lys Thr Tyr Asn Gln Lys Phe Lys
1               5                   10                  15

Gly
```

```
<210> SEQ ID NO 51
<211> LENGTH: 12
<212> TYPE: PRT
<213> ORGANISM: Artificial Sequence
<220> FEATURE:
<223> OTHER INFORMATION: Synthetic Construct

<400> SEQUENCE: 51

Trp Arg Leu Arg Pro Val Asp Tyr Gly Met Asp Tyr
1               5                   10
```

```
<210> SEQ ID NO 52
<211> LENGTH: 15
<212> TYPE: PRT
<213> ORGANISM: Artificial Sequence
<220> FEATURE:
<223> OTHER INFORMATION: Synthetic Construct

<400> SEQUENCE: 52

Arg Ala Ser Gln Ser Val Ser Thr Ser Ser Tyr Ser Tyr Met His
1               5                   10                  15
```

```
<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Tyr Ala Ser Asn Leu Glu Ser
1               5
```

```
<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

Gln His Ser Trp Glu Ile Pro Phe Thr
1               5
```

```
<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Gly Tyr Thr Phe Thr Asp Tyr Tyr
1               5
```

```
<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56
```

Val Asn Pro Asn Asn Gly Gly Lys
1               5

<210> SEQ ID NO 57
<211> LENGTH: 14
<212> TYPE: PRT
<213> ORGANISM: Artificial Sequence
<220> FEATURE:
<223> OTHER INFORMATION: Synthetic Construct

<400> SEQUENCE: 57

Ala Arg Trp Arg Leu Arg Pro Val Asp Tyr Gly Met Asp Tyr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Gln Ser Val Ser Thr Ser Ser Tyr Ser Tyr
1               5                   10

<210> SEQ ID NO 59
<211> LENGTH: 3
<212> TYPE: PRT
<213> ORGANISM: Artificial Sequence
<220> FEATURE:
<223> OTHER INFORMATION: Synthetic Construct

<400> SEQUENCE: 59

Tyr Ala Ser
1

<210> SEQ ID NO 60
<211> LENGTH: 9
<212> TYPE: PRT
<213> ORGANISM: Artificial Sequence
<220> FEATURE:
<223> OTHER INFORMATION: Synthetic Construct

<400> SEQUENCE: 60

Gln His Ser Trp Glu Ile Pro Phe Thr
1               5

<210> SEQ ID NO 61
<211> LENGTH: 121
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Asn Asn Gly Gly Lys Thr Tyr Asn Gln Lys Phe
    50                  55                  60

Lys Gly Lys Ala Thr Leu Thr Val Asp Lys Ser Leu Ser Thr Ala Tyr

```
65                   70                  75                  80

Met Gln Leu Asn Ser Leu Thr Ser Glu Asp Ser Ala Val Tyr Tyr Cys
                    85                  90                  95

Ala Arg Trp Arg Leu Arg Pro Val Asp Tyr Gly Met Asp Tyr Trp Gly
            100                 105                 110

Gln Gly Thr Ser Val Thr Val Ser Ser
        115                 120
```

```
<210> SEQ ID NO 62
<211> LENGTH: 111
<212> TYPE: PRT
<213> ORGANISM: Artificial Sequence
<220> FEATURE:
<223> OTHER INFORMATION: Synthetic Construct

<400> SEQUENCE: 62

Asp Ile Val Leu Thr Gln Ser Pro Ala Ser Leu Ala Val Ser Leu Gly
1               5                  10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                    85                  90                  95

Glu Ile Pro Phe Thr Phe Gly Ser Gly Thr Lys Leu Glu Ile Lys
            100                 105                 110
```

```
<210> SEQ ID NO 63
<211> LENGTH: 364
<212> TYPE: DNA
<213> ORGANISM: Artificial Sequence
<220> FEATURE:
<223> OTHER INFORMATION: Synthetic Construct

<400> SEQUENCE: 63
gaggtccagc tgcaacagtc tggacctgag ctggtgaagc ctgggggcttc agtgaagatg      60 tcctgtaagg cttctggata cacattcact gactactaca tgaactgggt gaagcagagt     120
catggaaaga gtcttgagtg gattggacgt gttaatccta caatggtgg taaaacctac     180 aaccagaagt tcaagggcaa ggccacattg acagtagaca atccctcag cacagcctac     240 atgcagctca acagcctgac atctgaggac tctgcggtct attactgtgc aagatggagg     300
ctacggcccg ttgactatgg tatggactac tggggtcaag gaacctcagt caccgtctcc     360
tcag                                                                    364
```

```
<210> SEQ ID NO 64
<211> LENGTH: 334
<212> TYPE: DNA
<213> ORGANISM: Artificial Sequence
<220> FEATURE:
<223> OTHER INFORMATION: Synthetic Construct

<400> SEQUENCE: 64
gacattgtgc tgacacagtc tcctgcttcc ttggctgtat ctctggggca gagggccacc      60
atctcatgca gggccagcca aagtgtcagt acatctagct atagttatat gcactggtac     120
```

-continued

```
caacagaaac caggacagcc acccaaactc ctcatcaagt atgcatccaa cctagaatct    180
ggggtccctg ccaggttcag tggcagtggg tctgggacag acttcaccct caacatccat    240
cctgtggagg aggaggatac tgcaacatat tactgtcagc acagttggga gattccattc    300
acgttcggct cggggacaaa gttggaaata aaac                                334

<210> SEQ ID NO 65
<211> LENGTH: 5
<212> TYPE: PRT
<213> ORGANISM: Artificial Sequence
<220> FEATURE:
<223> OTHER INFORMATION: Synthetic Construct

<400> SEQUENCE: 65

Asp Tyr Glu Met His
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

Gly Ile Asp Pro Glu Thr Gly Gly Thr Ala Tyr Asn Gln Lys Phe Lys
1               5                   10                  15

Gly

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct

<400> SEQUENCE: 67

Gly Ala Trp Phe Ala Tyr
1               5

<210> SEQ ID NO 68
<211> LENGTH: 14
<212> TYPE: PRT
<213> ORGANISM: Artificial Sequence
<220> FEATURE:
<223> OTHER INFORMATION: Synthetic Construct

<400> SEQUENCE: 68

Arg Ser Ser Thr Gly Ala Val Thr Thr Ser Asn Ser Ala Asn
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Gly Thr Asn Asn Arg Ala Pro
1               5

<210> SEQ ID NO 70
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 70

Ala Leu Trp Tyr Asn Asn His Phe Val
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic Construct

<400> SEQUENCE: 71

Gly Tyr Thr Phe Thr Asp Tyr Glu
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Construct

<400> SEQUENCE: 72

Ile Asp Pro Glu Thr Gly Gly Thr
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Construct

<400> SEQUENCE: 73

Thr Arg Gly Ala Trp Phe Ala Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Construct

<400> SEQUENCE: 74

Thr Gly Ala Val Thr Thr Ser Asn Ser
1               5

<210> SEQ ID NO 75
<211> LENGTH: 3
<212> TYPE: PRT
<213> ORGANISM: Artificial Sequence
<220> FEATURE:
<223> OTHER INFORMATION: Synthetic Construct

<400> SEQUENCE: 75

Gly Thr Asn
1

<210> SEQ ID NO 76
<211> LENGTH: 9
<212> TYPE: PRT
```

-continued

```
<213> ORGANISM: Artificial Sequence
<220> FEATURE:
<223> OTHER INFORMATION: Synthetic Construct

<400> SEQUENCE: 76

Ala Leu Trp Tyr Asn Asn His Phe Val
1               5

<210> SEQ ID NO 77
<211> LENGTH: 115
<212> TYPE: PRT
<213> ORGANISM: Artificial Sequence
<220> FEATURE:
<223> OTHER INFORMATION: Synthetic Construct

<400> SEQUENCE: 77

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Arg Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Gly Ala Trp Phe Ala Tyr Trp Gly Gln Gly Thr Leu Val Thr
            100                 105                 110

Val Ser Ala
        115

<210> SEQ ID NO 78
<211> LENGTH: 109
<212> TYPE: PRT
<213> ORGANISM: Artificial Sequence
<220> FEATURE:
<223> OTHER INFORMATION: Synthetic Construct

<400> SEQUENCE: 78

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Ser Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                85                  90                  95

His Phe Val Phe Gly Gly Gly Thr Lys Leu Thr Val Leu
            100                 105

<210> SEQ ID NO 79
<211> LENGTH: 346
<212> TYPE: DNA
<213> ORGANISM: Artificial Sequence
```

<220> FEATURE:
<223> OTHER INFORMATION: Synthetic Construct

<400> SEQUENCE: 79
caggttcaat tgcagcagtc tggggctgag ctggtgaggc ctggggcttc agtgaagctg      60
tcctgcaagg cttcgggcta tacatttact gactatgaaa tgcactgggt gaggcagaca     120
cctgtgcatg gcctggaatg gattggaggt attgatcctg aaactggtgg tactgcctac     180
aatcagaagt tcaagggcaa ggccacactg actgcagaca atcctccag cacagcctac      240 atggagctcc gcagcctgac atctgaggac tctgccgtct attactgtac acgagggcc      300 tggtttgctt actggggcca agggactctg gtcactgtct ctgcag                    346

<210> SEQ ID NO 80
<211> LENGTH: 328
<212> TYPE: DNA
<213> ORGANISM: Artificial Sequence
<220> FEATURE:
<223> OTHER INFORMATION: Synthetic Construct

<400> SEQUENCE: 80
caggctgttg tgactcagga atctgcactc accacatcac ctggtgaaac agtcacactc      60
acttgtcgct caagtactgg ggctgttaca actagtaact ctgccaactg ggtccaagaa     120
aaaccagatc atttattcac tggtctaatc ggtggtacca acaaccgagc tccaggtgtt     180
cctgccagat tctcaggctc cctgattgga gacaaggctg ccctcaccat cacagggca     240 cagactgagg atgaggcaat atatttctgt gctctatggt acaacaacca tttcgtgttc     300
ggtggaggca ccaaactgac tgtcctag                                        328

<210> SEQ ID NO 81
<211> LENGTH: 5
<212> TYPE: PRT
<213> ORGANISM: Artificial Sequence
<220> FEATURE:
<223> OTHER INFORMATION: Synthetic Construct

<400> SEQUENCE: 81

Ser Tyr Trp Met His
1               5

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct

<400> SEQUENCE: 82

Ala Ile Tyr Pro Gly Asn Ser Asp Thr Ser Tyr Asn Gln Lys Phe Lys
1               5                   10                  15

Gly

<210> SEQ ID NO 83
<211> LENGTH: 12
<212> TYPE: PRT
<213> ORGANISM: Artificial Sequence
<220> FEATURE:
<223> OTHER INFORMATION: Synthetic Construct

<400> SEQUENCE: 83

Gly Gly Phe Asp Tyr Ser Asn Tyr Trp Phe Ala Tyr
1               5                   10

```
<210> SEQ ID NO 84
<211> LENGTH: 11
<212> TYPE: PRT
<213> ORGANISM: Artificial Sequence
<220> FEATURE:
<223> OTHER INFORMATION: Synthetic Construct

<400> SEQUENCE: 84

Lys Ala Ser Gln Ser Val Ser Asn Asp Val Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct

<400> SEQUENCE: 85

Tyr Ala Ser Asn Arg Tyr Thr
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic Construct

<400> SEQUENCE: 86

Gln Gln Asp Tyr Ser Ser Tyr Thr
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct

<400> SEQUENCE: 87

Gly Tyr Thr Phe Thr Ser Tyr Trp
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Ile Tyr Pro Gly Asn Ser Asp Thr
1               5

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

Thr Arg Gly Gly Phe Asp Tyr Ser Asn Tyr Trp Phe Ala Tyr
1               5                   10
```

-continued

<210> SEQ ID NO 90
<211> LENGTH: 6
<212> TYPE: PRT
<213> ORGANISM: Artificial Sequence
<220> FEATURE:
<223> OTHER INFORMATION: Synthetic Construct

<400> SEQUENCE: 90

Gln Ser Val Ser Asn Asp
1               5

<210> SEQ ID NO 91
<211> LENGTH: 3
<212> TYPE: PRT
<213> ORGANISM: Artificial Sequence
<220> FEATURE:
<223> OTHER INFORMATION: Synthetic Construct

<400> SEQUENCE: 91

Tyr Ala Ser
1

<210> SEQ ID NO 92
<211> LENGTH: 8
<212> TYPE: PRT
<213> ORGANISM: Artificial Sequence
<220> FEATURE:
<223> OTHER INFORMATION: Synthetic Construct

<400> SEQUENCE: 92

Gln Gln Asp Tyr Ser Ser Tyr Thr
1               5

<210> SEQ ID NO 93
<211> LENGTH: 121
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Gly Phe Asp Tyr Ser Asn Tyr Trp Phe Ala Tyr Trp Gly
            100                 105                 110

Gln Gly Thr Leu Val Thr Val Ser Ala
        115                 120

<210> SEQ ID NO 94
<211> LENGTH: 106
<212> TYPE: PRT
<213> ORGANISM: Artificial Sequence
<220> FEATURE:

<223> OTHER INFORMATION: Synthetic Construct

<400> SEQUENCE: 94

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Tyr Thr
                85                  90                  95

Phe Gly Gly Gly Thr Lys Leu Glu Ile Lys
            100                 105
```

<210> SEQ ID NO 95
<211> LENGTH: 363
<212> TYPE: DNA
<213> ORGANISM: Artificial Sequence
<220> FEATURE:
<223> OTHER INFORMATION: Synthetic Construct

<400> SEQUENCE: 95

```
gaggttcagc tccagcagtc tgggactgtg ctggcaaggc ctggggcttc agtgaagatg     60
tcctgcaagg cttctggcta cacctttacc agctactgga tgcactgggt aaaacagagg    120
cctggacagg gtctggaatg gattggcgct atttatcctg gaaatagtga tactagctac    180
aaccagaagt tcaagggcaa ggccaaactg actgcagtca catctgccag cactgcctac    240
atggagctca gcagcctgac aaatgaggac tctgcggtct attactgtac aagaggagga    300
tttgactata gtaactactg gtttgcttac tggggccaag gactctggt cactgtctct    360 gca                                                                  363
```

<210> SEQ ID NO 96
<211> LENGTH: 319
<212> TYPE: DNA
<213> ORGANISM: Artificial Sequence
<220> FEATURE:
<223> OTHER INFORMATION: Synthetic Construct

<400> SEQUENCE: 96

```
agtattgtga tgacccagac tcccaaattc ctgcttgtat cagcaggaga cagggttacc     60
ataacctgca aggccagtca gagtgtgagt aatgatgtag cttggtacca acagaagcca    120
gggcagtctc ctaaactgct gatatactat gcatccaatc gctacactgg agtccctgat    180
cgcttcactg gcagtggata tgggacggat ttcactttca ccatcagcac tgtgcaggct    240
gaagacctgg cagtttattt ctgtcagcag gattatagct cgtacacgtt cggagggggg    300
accaagctgg aaataaaac                                                 319
```

<210> SEQ ID NO 97
<211> LENGTH: 5
<212> TYPE: PRT
<213> ORGANISM: Artificial Sequence
<220> FEATURE:
<223> OTHER INFORMATION: Synthetic Construct -continued

```
<400> SEQUENCE: 97

Arg Ser Trp Met Asn
1               5

<210> SEQ ID NO 98
<211> LENGTH: 17
<212> TYPE: PRT
<213> ORGANISM: Artificial Sequence
<220> FEATURE:
<223> OTHER INFORMATION: Synthetic Construct

<400> SEQUENCE: 98

Trp Ile Tyr Pro Gly Asp Gly Asp Thr Asn Tyr Asn Gly Lys Phe Lys
1               5                   10                  15

Gly

<210> SEQ ID NO 99
<211> LENGTH: 11
<212> TYPE: PRT
<213> ORGANISM: Artificial Sequence
<220> FEATURE:
<223> OTHER INFORMATION: Synthetic Construct

<400> SEQUENCE: 99

Ser Ala Thr Leu Pro Tyr Trp Tyr Phe Asp Val
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic Construct

<400> SEQUENCE: 100

Lys Ala Ser Gln Asp Ile Lys Ser Tyr Leu Ser
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 101

Tyr Ala Thr Asn Leu Ala Asp
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Construct

<400> SEQUENCE: 102

Leu Gln His Val Glu Ser Pro Trp Thr
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 103

Gly Tyr Ala Phe Ser Arg Ser Trp
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic Construct

<400> SEQUENCE: 104

Ile Tyr Pro Gly Asp Gly Asp Thr
1               5

<210> SEQ ID NO 105
<211> LENGTH: 13
<212> TYPE: PRT
<213> ORGANISM: Artificial Sequence
<220> FEATURE:
<223> OTHER INFORMATION: Synthetic Construct

<400> SEQUENCE: 105

Ala Arg Ser Ala Thr Leu Pro Tyr Trp Tyr Phe Asp Val
1               5                   10

<210> SEQ ID NO 106
<211> LENGTH: 6
<212> TYPE: PRT
<213> ORGANISM: Artificial Sequence
<220> FEATURE:
<223> OTHER INFORMATION: Synthetic Construct

<400> SEQUENCE: 106

Gln Asp Ile Lys Ser Tyr
1               5

<210> SEQ ID NO 107
<211> LENGTH: 3
<212> TYPE: PRT
<213> ORGANISM: Artificial Sequence
<220> FEATURE:
<223> OTHER INFORMATION: Synthetic Construct

<400> SEQUENCE: 107

Tyr Ala Thr
1

<210> SEQ ID NO 108
<211> LENGTH: 9
<212> TYPE: PRT
<213> ORGANISM: Artificial Sequence
<220> FEATURE:
<223> OTHER INFORMATION: Synthetic Construct

<400> SEQUENCE: 108

Leu Gln His Val Glu Ser Pro Trp Thr
1               5

<210> SEQ ID NO 109
<211> LENGTH: 120
<212> TYPE: PRT
<213> ORGANISM: Artificial Sequence
<220> FEATURE:
<223> OTHER INFORMATION: Synthetic Construct

<400> SEQUENCE: 109

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Lys Gly Leu Glu Trp Ile
        35                  40                  45

Gly Trp Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Ala Tyr Phe Cys
            85                  90                  95

Ala Arg Ser Ala Thr Leu Pro Tyr Trp Tyr Phe Asp Val Trp Gly Ala
            100                 105                 110

Gly Thr Thr Val Thr Val Ser Ser
        115                 120

<210> SEQ ID NO 110
<211> LENGTH: 107
<212> TYPE: PRT
<213> ORGANISM: Artificial Sequence
<220> FEATURE:
<223> OTHER INFORMATION: Synthetic Construct

<400> SEQUENCE: 110

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Asn Leu Ala Asp Gly Val Pro Ser Arg Phe Ser Gly
    50                  55                  60

Ser Gly Ser Gly Gln Asp Tyr Ser Leu Thr Ile Ser Ser Leu Gly Ser
65                  70                  75                  80

Asp Asp Thr Ala Thr Tyr Tyr Cys Leu Gln His Val Glu Ser Pro Trp
            85                  90                  95

Thr Phe Gly Gly Gly Thr Lys Leu Glu Ile Lys
        100                 105

<210> SEQ ID NO 111
<211> LENGTH: 361
<212> TYPE: DNA
<213> ORGANISM: Artificial Sequence
<220> FEATURE:
<223> OTHER INFORMATION: Synthetic Construct

<400> SEQUENCE: 111
caggtccagc tgcagcagtc tggacctgag ctggtgaagc ctggggcctc agtgaagatt      60
tcctgcaaag cttctggcta tgcattcagt cgctcctgga tgaactgggt aaagcagagg     120
cctggaaagg gtcttgagtg gattggatgg atttatcctg gagatggtga tactaactac     180
aatggaaagt tcaagggcaa ggccacactg actgcagaca atcctcaag cacagcctac      240 atgcagctca gcagcctgac atctgaggac tctgcggcct atttctgtgc aaggtcggct     300
accctacctt actggtactt cgatgtctgg ggcgcaggga ccacggtcac cgtctcctca     360
g                                                                                361

<210> SEQ ID NO 112
<211> LENGTH: 322
<212> TYPE: DNA
<213> ORGANISM: Artificial Sequence
<220> FEATURE:
<223> OTHER INFORMATION: Synthetic Construct

<400> SEQUENCE: 112
gacatcaaga tgacccagtc tccatcctcc atgtatgcat cgctgggaga gagagtcact      60
atcacttgca aggcgagtca ggacattaaa agctatttaa gttggtacca gcagaaacca     120
tggaaatctc ctaagaccct gatctattat gcaacaaact tggcagatgg ggtcccatca     180
agattcagtg gcagtggatc tgggcaggat tattctctaa ccatcagcag cctgggggtct    240 gacgatacag caacttatta ctgtctacag catgttgaga gcccgtggac gttcggtgga     300
ggcaccaagc tggaaatcaa ac                                             322

<210> SEQ ID NO 113
<211> LENGTH: 5
<212> TYPE: PRT
<213> ORGANISM: Artificial Sequence
<220> FEATURE:
<223> OTHER INFORMATION: Synthetic Construct

<400> SEQUENCE: 113

Ala Tyr Val Met His
1               5

<210> SEQ ID NO 114
<211> LENGTH: 17
<212> TYPE: PRT
<213> ORGANISM: Artificial Sequence
<220> FEATURE:
<223> OTHER INFORMATION: Synthetic Construct

<400> SEQUENCE: 114

Tyr Ile Phe Pro Tyr Asn Asp Gly Thr Glu Tyr Asn Glu Lys Phe Lys
1               5                   10                  15

Gly

<210> SEQ ID NO 115
<211> LENGTH: 11
<212> TYPE: PRT
<213> ORGANISM: Artificial Sequence
<220> FEATURE:
<223> OTHER INFORMATION: Synthetic Construct

<400> SEQUENCE: 115

Arg Thr Asp Gly Asn Pro Tyr Thr Met Asp Tyr
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic Construct

<400> SEQUENCE: 116

Lys Ala Ser Gln Asp Val Ser Thr Ala Val Ala
1               5                   10

```
<210> SEQ ID NO 117
<211> LENGTH: 7
<212> TYPE: PRT
<213> ORGANISM: Artificial Sequence
<220> FEATURE:
<223> OTHER INFORMATION: Synthetic Construct

<400> SEQUENCE: 117

Ser Ala Ser Tyr Arg Tyr Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct

<400> SEQUENCE: 118

Gln Gln His Tyr Ser Thr Pro Phe Thr
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic Construct

<400> SEQUENCE: 119

Gly Tyr Thr Phe Thr Ala Tyr Val
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic Construct

<400> SEQUENCE: 120

Ile Phe Pro Tyr Asn Asp Gly Thr
1               5

<210> SEQ ID NO 121
<211> LENGTH: 13
<212> TYPE: PRT
<213> ORGANISM: Artificial Sequence
<220> FEATURE:
<223> OTHER INFORMATION: Synthetic Construct

<400> SEQUENCE: 121

Ala Arg Arg Thr Asp Gly Asn Pro Tyr Thr Met Asp Tyr
1               5                   10

<210> SEQ ID NO 122
<211> LENGTH: 6
<212> TYPE: PRT
<213> ORGANISM: Artificial Sequence
<220> FEATURE:
<223> OTHER INFORMATION: Synthetic Construct

<400> SEQUENCE: 122

Gln Asp Val Ser Thr Ala
1               5

<210> SEQ ID NO 123
```

```
<211> LENGTH: 3
<212> TYPE: PRT
<213> ORGANISM: Artificial Sequence
<220> FEATURE:
<223> OTHER INFORMATION: Synthetic Construct

<400> SEQUENCE: 123

Ser Ala Ser
1

<210> SEQ ID NO 124
<211> LENGTH: 9
<212> TYPE: PRT
<213> ORGANISM: Artificial Sequence
<220> FEATURE:
<223> OTHER INFORMATION: Synthetic Construct

<400> SEQUENCE: 124

Gln Gln His Tyr Ser Ser Pro Phe Thr
1               5

<210> SEQ ID NO 125
<211> LENGTH: 120
<212> TYPE: PRT
<213> ORGANISM: Artificial Sequence
<220> FEATURE:
<223> OTHER INFORMATION: Synthetic Construct

<400> SEQUENCE: 125

Glu Val Gln Leu Gln Gln Ser Gly Pro Glu Leu Val Asn Pro Gly Ala
1               5                   10                  15

Ser Val Lys Met Ser Cys Lys Ala Ser Gly Tyr Thr Phe Thr Ala Tyr
            20                  25                  30

Val Met His Trp Val Lys Gln Lys Pro Gly Gln Gly Leu Glu Trp Ile
        35                  40                  45

Gly Tyr Ile Phe Pro Tyr Asn Asp Gly Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Thr Asp Gly Asn Pro Tyr Thr Met Asp Tyr Trp Gly Gln
            100                 105                 110

Gly Thr Ser Val Thr Val Ser Ser
        115                 120

<210> SEQ ID NO 126
<211> LENGTH: 107
<212> TYPE: PRT
<213> ORGANISM: Artificial Sequence
<220> FEATURE:
<223> OTHER INFORMATION: Synthetic Construct

<400> SEQUENCE: 126

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

His Ser Ala Ser Tyr Arg Tyr Thr Gly Val Pro Asp Arg Phe Thr Gly
    50                  55                  60
```

```
Arg Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Phe
                85                  90                  95

Thr Phe Gly Ser Gly Thr Lys Leu Glu Ile Lys
            100                 105
```

```
<210> SEQ ID NO 127
<211> LENGTH: 361
<212> TYPE: DNA
<213> ORGANISM: Artificial Sequence
<220> FEATURE:
<223> OTHER INFORMATION: Synthetic Construct

<400> SEQUENCE: 127
gaggtccagc tgcagcagtc tggacctgag ttggtaaatc ctggggcttc agtgaagatg      60
tcctgcaagg cttctggata cacattcact gcctatgtta tgcactgggt gaaacagaag     120
cctgggcagg gccttgagtg gattggatat attttccctt acaatgatgg tactgagtac     180
aatgagaagt tcaaaggcaa ggccacactg acttcagaca aatcctccag cacagcctac     240
atggagctca gcagcctgac ctctgaggac tctgcggtct attactgtgc aaggaggaca     300
gatggtaacc cctatactat ggactattgg ggtcaaggaa cctcagtcac cgtctcctca     360
g                                                                     361
```

```
<210> SEQ ID NO 128
<211> LENGTH: 322
<212> TYPE: DNA
<213> ORGANISM: Artificial Sequence
<220> FEATURE:
<223> OTHER INFORMATION: Synthetic Construct

<400> SEQUENCE: 128
gacattgtga tgacccagtc tcacaaattc atgtccacat cagtaggaga cagggtcagc      60
atcacctgca aggccagtca ggatgtgagt actgctgtag cctggtatca acagaaacca     120
ggacaatctc ctaaactact gattcattcg gcatcctacc ggtacactgg agtccctgat     180
cgcttcactg gcagaggatc tgggacggat ttcactttca ccatcagcag tgtgcaggct     240
gaagacctgg cagtttatta ctgtcagcaa cattatagta ctccattcac gttcggctcg     300
gggacaaagt tggaaataaa ac                                              322
```

```
<210> SEQ ID NO 129
<211> LENGTH: 5
<212> TYPE: PRT
<213> ORGANISM: Artificial Sequence
<220> FEATURE:
<223> OTHER INFORMATION: Synthetic Construct

<400> SEQUENCE: 129

Asp Tyr Tyr Ile His
1               5
```

```
<210> SEQ ID NO 130
<211> LENGTH: 17
<212> TYPE: PRT
<213> ORGANISM: Artificial Sequence
<220> FEATURE:
<223> OTHER INFORMATION: Synthetic Construct

<400> SEQUENCE: 130
```

-continued

```
Glu Ile Tyr Pro Gly Ser Asp Asp Ala Tyr Tyr Asn Glu Lys Phe Lys
1               5                   10                  15

Gly

<210> SEQ ID NO 131
<211> LENGTH: 7
<212> TYPE: PRT
<213> ORGANISM: Artificial Sequence
<220> FEATURE:
<223> OTHER INFORMATION: Synthetic Construct

<400> SEQUENCE: 131

Glu Thr Thr Ala Thr Ala Tyr
1               5

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct

<400> SEQUENCE: 132

Ser Ala Ser Ser Ser Val Ser Leu Ile Tyr
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Synthetic Construct

<400> SEQUENCE: 133

Ser Thr Ser Asn Leu Ala Ser
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Construct

<400> SEQUENCE: 134

Gln Gln Arg Ser Gly Tyr Pro Pro Thr
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic Construct

<400> SEQUENCE: 135

Gly Tyr Thr Phe Thr Asp Tyr Tyr
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic Construct

<400> SEQUENCE: 136
```

```
Ile Tyr Pro Gly Ser Asp Asp Ala
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic Construct

<400> SEQUENCE: 137

Thr Arg Glu Thr Thr Ala Thr Ala Tyr
1               5

<210> SEQ ID NO 138
<211> LENGTH: 5
<212> TYPE: PRT
<213> ORGANISM: Artificial Sequence
<220> FEATURE:
<223> OTHER INFORMATION: Synthetic Construct

<400> SEQUENCE: 138

Ser Ser Val Ser Leu
1               5

<210> SEQ ID NO 139
<211> LENGTH: 3
<212> TYPE: PRT
<213> ORGANISM: Artificial Sequence
<220> FEATURE:
<223> OTHER INFORMATION: Synthetic Construct

<400> SEQUENCE: 139

Ser Thr Ser
1

<210> SEQ ID NO 140
<211> LENGTH: 9
<212> TYPE: PRT
<213> ORGANISM: Artificial Sequence
<220> FEATURE:
<223> OTHER INFORMATION: Synthetic Construct

<400> SEQUENCE: 140

Gln Gln Arg Ser Gly Tyr Pro Pro Thr
1               5

<210> SEQ ID NO 141
<211> LENGTH: 116
<212> TYPE: PRT
<213> ORGANISM: Artificial Sequence
<220> FEATURE:
<223> OTHER INFORMATION: Synthetic Construct

<400> SEQUENCE: 141

Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Glu Ile Tyr Pro Gly Ser Asp Asp Ala Tyr Tyr Asn Glu Lys Phe
    50                  55                  60

Lys Gly Lys Ala Thr Leu Thr Ala Asp Lys Ser Ser Ser Thr Ala Tyr
```

```
65              70              75              80

Met Gln Leu Ser Ser Leu Thr Ser Glu Asp Ser Ala Val Tyr Phe Cys
                85              90              95

Thr Arg Glu Thr Thr Ala Thr Ala Tyr Trp Gly Gln Gly Thr Leu Val
            100             105             110

Thr Val Ser Ala
        115

<210> SEQ ID NO 142
<211> LENGTH: 106
<212> TYPE: PRT
<213> ORGANISM: Artificial Sequence
<220> FEATURE:
<223> OTHER INFORMATION: Synthetic Construct

<400> SEQUENCE: 142

Gln Ile Val Leu Thr Gln Ser Pro Ala Ile Met Ser Ala Ser Pro Gly
1               5               10              15

Glu Lys Val Thr Ile Thr Cys Ser Ala Ser Ser Ser Val Ser Leu Ile
            20              25              30

Tyr Trp Phe Gln Gln Lys Pro Gly Thr Ser Pro Lys Leu Trp Ile Tyr
        35              40              45

Ser Thr Ser Asn Leu Ala Ser Gly Val Pro Ala Arg Phe Ser Gly Ser
    50              55              60

Gly Ser Gly Thr Ser Tyr Ser Leu Thr Ile Ser Arg Met Glu Ala Glu
65              70              75              80

Asp Ala Ala Thr Tyr Tyr Cys Gln Gln Arg Ser Gly Tyr Pro Pro Thr
                85              90              95

Phe Gly Gly Gly Thr Lys Leu Glu Ile Lys
            100             105

<210> SEQ ID NO 143
<211> LENGTH: 351
<212> TYPE: DNA
<213> ORGANISM: Artificial Sequence
<220> FEATURE:
<223> OTHER INFORMATION: Synthetic Construct

<400> SEQUENCE: 143
ctgaggtcca gctgcagcag tctggacctg agctggttaa gcctggggct tcagtgaagg      60
tatcctgcaa ggcctctgga tacacattca ctgactacta tatacactgg gtgaagcaga     120
ggcctgggca gggccttgag tggattggag agatttatcc tggaagtgat gatgcttact     180
acaatgagaa attcaagggc aaggccacac tgactgcaga caaatcctcc agcacagcct     240
acatgcagct cagcagcctg acatctgagg actctgcagt ctatttctgt acaagagaga     300
ctacggctac ggcttactgg ggccaaggga ctctggtcac tgtctctgca g             351

<210> SEQ ID NO 144
<211> LENGTH: 319
<212> TYPE: DNA
<213> ORGANISM: Artificial Sequence
<220> FEATURE:
<223> OTHER INFORMATION: Synthetic Construct

<400> SEQUENCE: 144
caaattgttc tcacccagtc tccagcaatc atgtctgcat ctccagggga gaaggtcacc      60
ataacctgca gtgccagctc aagtgtaagt ctcatttact ggttccagca gaagccaggc     120
acttctccca aactctggat ttatagcaca tccaacctgg cttctggagt ccctgctcgc     180
```

-continued

```
ttcagtggca gtggatctgg gacctcttac tctctcacaa tcagccgaat ggaggctgaa      240
gatgctgcca cttattactg ccagcaaagg agtggttacc cacccacgtt cggagggggg      300
accaagctgg aaataaaac                                                    319
```

<210> SEQ ID NO 145
<211> LENGTH: 5
<212> TYPE: PRT
<213> ORGANISM: Artificial Sequence
<220> FEATURE:
<223> OTHER INFORMATION: Synthetic Construct

<400> SEQUENCE: 145

Asp His Gly Ile His
1               5

<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Asn Ile Ser Pro Gly Asn Gly Asp Ile Lys Tyr Asn Glu Lys Phe Lys
1               5               10              15

Gly

<210> SEQ ID NO 147
<211> LENGTH: 4
<212> TYPE: PRT
<213> ORGANISM: Artificial Sequence
<220> FEATURE:
<223> OTHER INFORMATION: Synthetic Construct

<400> SEQUENCE: 147

Tyr Phe Val Asp
1

<210> SEQ ID NO 148
<211> LENGTH: 17
<212> TYPE: PRT
<213> ORGANISM: Artificial Sequence
<220> FEATURE:
<223> OTHER INFORMATION: Synthetic Construct

<400> SEQUENCE: 148

Lys Ser Ser Gln Ser Leu Leu Asn Ser Asn Asn Gln Lys Asn Cys Leu
1               5               10              15

Ala

<210> SEQ ID NO 149
<211> LENGTH: 7
<212> TYPE: PRT
<213> ORGANISM: Artificial Sequence
<220> FEATURE:
<223> OTHER INFORMATION: Synthetic Construct

<400> SEQUENCE: 149

Phe Ala Cys Thr Arg Glu Ser
1               5

<210> SEQ ID NO 150
<211> LENGTH: 9

-continued

```
<212> TYPE: PRT
<213> ORGANISM: Artificial Sequence
<220> FEATURE:
<223> OTHER INFORMATION: Synthetic Construct

<400> SEQUENCE: 150

Gln Gln His Cys Asn Thr Pro Leu Thr
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic Construct

<400> SEQUENCE: 151

Gly Tyr Thr Phe Thr Asp His Gly
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic Construct

<400> SEQUENCE: 152

Ile Ser Pro Gly Asn Gly Asp Ile
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic Construct

<400> SEQUENCE: 153

Thr Thr Tyr Phe Val Asp
1               5

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct

<400> SEQUENCE: 154

Gln Ser Leu Leu Asn Ser Asn Asn Gln Lys Asn Cys
1               5                   10

<210> SEQ ID NO 155
<211> LENGTH: 3
<212> TYPE: PRT
<213> ORGANISM: Artificial Sequence
<220> FEATURE:
<223> OTHER INFORMATION: Synthetic Construct

<400> SEQUENCE: 155

Phe Ala Cys
1

<210> SEQ ID NO 156
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 156

Gln Gln His Cys Asn Thr Pro Leu Thr
1               5

<210> SEQ ID NO 157
<211> LENGTH: 113
<212> TYPE: PRT
<213> ORGANISM: Artificial Sequence
<220> FEATURE:
<223> OTHER INFORMATION: Synthetic Construct

<400> SEQUENCE: 157

Gln Val Gln Leu Gln Gln Ser Asp Ala Glu Leu Val Lys Pro Gly Thr
1               5                   10                  15

Ser Val Lys Ile Ser Cys Lys Ala Ser Gly Tyr Thr Phe Thr Asp His
            20                  25                  30

Gly Ile His Trp Val Lys Gln Arg Pro Glu Arg Gly Leu Glu Trp Ile
        35                  40                  45

Gly Asn Ile Ser Pro Gly Asn Gly Asp Ile Lys Tyr Asn Glu Lys Phe
    50                  55                  60

Lys Gly Lys Ala Thr Leu Thr Ala Asp Lys Ser Ser Ser Thr Val Tyr
65                  70                  75                  80

Met Gln Val Asn Ser Leu Thr Ser Glu Asp Ser Ala Val Tyr Phe Cys
                85                  90                  95

Thr Thr Tyr Phe Val Asp Trp Gly Arg Gly Thr Leu Val Thr Val Ser
            100                 105                 110

Ala

<210> SEQ ID NO 158
<211> LENGTH: 113
<212> TYPE: PRT
<213> ORGANISM: Artificial Sequence
<220> FEATURE:
<223> OTHER INFORMATION: Synthetic Construct

<400> SEQUENCE: 158

Asp Ile Val Met Thr Gln Ser Pro Ser Ser Leu Ala Met Ser Ile Gly
1               5                   10                  15

Gln Arg Val Thr Met Ser Cys Lys Ser Ser Gln Ser Leu Leu Asn Ser
            20                  25                  30

Asn Asn Gln Lys Asn Cys Leu Ala Trp Tyr Gln Gln Lys Pro Gly Gln
        35                  40                  45

Ser Pro Arg Leu Leu Ile Tyr Phe Ala Cys Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Tyr Tyr Phe Cys Gln Gln
                85                  90                  95

His Cys Asn Thr Pro Leu Thr Phe Gly Ala Gly Thr Lys Leu Glu Leu
            100                 105                 110

Lys

<210> SEQ ID NO 159
<211> LENGTH: 340
<212> TYPE: DNA

<213> ORGANISM: Artificial Sequence
<220> FEATURE:
<223> OTHER INFORMATION: Synthetic Construct

<400> SEQUENCE: 159
caggttcagc tgcaacagtc tgacgctgag ttggtgaaac ctgggacttc agtgaagata      60
tcctgcaagg cttctggcta caccttcact gaccatggta ttcactgggt gaaacagagg     120
cctgaacggg gcctggaatg gattggaaat atttctcccg gaaatggtga tattaagtat     180
aatgagaagt tcaagggcaa ggccacgctg actgcagaca atcctccag cactgtctac      240 atgcaggtca acagcctgac atctgaggat tctgcagtgt atttctgtac aacctatttt     300
gttgactggg gccggggggac tctggtcact gtctctgcag                          340

<210> SEQ ID NO 160
<211> LENGTH: 340
<212> TYPE: DNA
<213> ORGANISM: Artificial Sequence
<220> FEATURE:
<223> OTHER INFORMATION: Synthetic Construct

<400> SEQUENCE: 160
gacattgtga tgacacagtc tccatcctcc ctggctatgt caattggaca gagggtcact      60
atgagctgca gtccagtca gagccttta aatagtaaca atcaaaagaa ctgtttggcc      120
tggtaccagc agaaaccagg acagtctcct agacttctga tttactttgc atgtactagg     180
gaatcggggg tccctgatcg cttcattggc agtggatctg ggacagattt caccccttacc    240 atcagcagtg tgcaggctga agacctggca tattacttct gtcagcaaca ttgtaacact     300
ccgctcacgt tcggtgctgg gaccaagctg gagctgaaac                          340

<210> SEQ ID NO 161
<211> LENGTH: 5
<212> TYPE: PRT
<213> ORGANISM: Artificial Sequence
<220> FEATURE:
<223> OTHER INFORMATION: Synthetic Construct

<400> SEQUENCE: 161

Thr Tyr Trp Met Asn
1               5

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Arg Ile Phe Pro Gly Asp Gly Asp Thr Asp Tyr Asp Gly Lys Phe Lys
1               5                   10                  15

Gly

<210> SEQ ID NO 163
<211> LENGTH: 12
<212> TYPE: PRT
<213> ORGANISM: Artificial Sequence
<220> FEATURE:
<223> OTHER INFORMATION: Synthetic Construct

<400> SEQUENCE: 163

Thr Gly Ala Ala Tyr Glu Phe Asp Pro Phe Pro Tyr

-continued

```
1               5                    10
```

```
<210> SEQ ID NO 164
<211> LENGTH: 16
<212> TYPE: PRT
<213> ORGANISM: Artificial Sequence
<220> FEATURE:
<223> OTHER INFORMATION: Synthetic Construct

<400> SEQUENCE: 164

Ser Ser Thr Lys Ser Leu Leu His Ser Ser Gly Ile Thr Tyr Leu Tyr
1               5                    10                  15

<210> SEQ ID NO 165
<211> LENGTH: 7
<212> TYPE: PRT
<213> ORGANISM: Artificial Sequence
<220> FEATURE:
<223> OTHER INFORMATION: Synthetic Construct

<400> SEQUENCE: 165

Arg Met Ser Asn Leu Ala Ser
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Ala Gln Met Leu Glu Arg Pro Phe Thr
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic Construct

<400> SEQUENCE: 167

Gly Tyr Ala Phe Ser Thr Tyr Trp
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Ile Phe Pro Gly Asp Gly Asp Thr
1               5

<210> SEQ ID NO 169
<211> LENGTH: 14
<212> TYPE: PRT
<213> ORGANISM: Artificial Sequence
<220> FEATURE:
<223> OTHER INFORMATION: Synthetic Construct

<400> SEQUENCE: 169

Ala Arg Thr Gly Ala Ala Tyr Glu Phe Asp Pro Phe Pro Tyr
1               5                    10
```

```
<210> SEQ ID NO 170
<211> LENGTH: 11
<212> TYPE: PRT
<213> ORGANISM: Artificial Sequence
<220> FEATURE:
<223> OTHER INFORMATION: Synthetic Construct

<400> SEQUENCE: 170

Lys Ser Leu Leu His Ser Ser Gly Ile Thr Tyr
1               5                   10

<210> SEQ ID NO 171
<211> LENGTH: 3
<212> TYPE: PRT
<213> ORGANISM: Artificial Sequence
<220> FEATURE:
<223> OTHER INFORMATION: Synthetic Construct

<400> SEQUENCE: 171

Arg Met Ser
1

<210> SEQ ID NO 172
<211> LENGTH: 9
<212> TYPE: PRT
<213> ORGANISM: Artificial Sequence
<220> FEATURE:
<223> OTHER INFORMATION: Synthetic Construct

<400> SEQUENCE: 172

Ala Gln Met Leu Glu Arg Pro Phe Thr
1               5

<210> SEQ ID NO 173
<211> LENGTH: 121
<212> TYPE: PRT
<213> ORGANISM: Artificial Sequence
<220> FEATURE:
<223> OTHER INFORMATION: Synthetic Construct

<400> SEQUENCE: 173

Gln Val Gln Leu Gln Gln Ser Gly Pro Glu Leu Val Lys Pro Gly Ala
1               5                   10                  15

Ser Val Lys Ile Ser Cys Lys Gly Ser Gly Tyr Ala Phe Ser Thr Tyr
            20                  25                  30

Trp Met Asn Trp Val Lys Gln Arg Pro Gly Lys Gly Leu Glu Trp Ile
        35                  40                  45

Gly Arg Ile Phe Pro Gly Asp Gly Asp Thr Asp Tyr Asp Gly Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Thr Gly Ala Ala Tyr Glu Phe Asp Pro Phe Pro Tyr Trp Gly
            100                 105                 110

Gln Gly Thr Leu Val Thr Val Ser Ala
        115                 120

<210> SEQ ID NO 174
<211> LENGTH: 112
<212> TYPE: PRT
<213> ORGANISM: Artificial Sequence
```

-continued

<220> FEATURE:
<223> OTHER INFORMATION: Synthetic Construct

<400> SEQUENCE: 174

```
Asp Ile Val Met Thr Gln Ala Ala Phe Ser Asn Pro Val Thr Leu Gly
1               5                   10                  15

Thr Ser Ala Ser Ile Ser Cys Ser Ser Thr Lys Ser Leu Leu His Ser
            20                  25                  30

Ser Gly Ile Thr Tyr Leu Tyr Trp Tyr Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Leu Glu Arg Pro Phe Thr Phe Gly Ser Gly Thr Lys Leu Glu Ile Lys
            100                 105                 110
```

<210> SEQ ID NO 175
<211> LENGTH: 364
<212> TYPE: DNA
<213> ORGANISM: Artificial Sequence
<220> FEATURE:
<223> OTHER INFORMATION: Synthetic Construct
<400> SEQUENCE: 175

```
caggttcagc tgcagcagtc tggacctgag ctggtgaagc ctgggggcctc agtgaagatt      60 tcctgcaaag gttctggcta cgcattcagt acctactgga tgaactgggt gaagcagagg     120
cctggaaagg gtcttgagtg gattggacgg attttttcctg gagatggaga tacagattac     180
gatgggaagt tcaagggcaa ggccacactg actgcagaca atcctccaa cacagcctac      240 atgcaactca gcagcctgac atctgaagac tctgcggtct acttctgtgc aagaactggg     300
gccgcctatg aattcgaccc tttttccttac tggggccaag ggactctggt cactgtctct     360
gcag                                                                    364
```

<210> SEQ ID NO 176
<211> LENGTH: 337
<212> TYPE: DNA
<213> ORGANISM: Artificial Sequence
<220> FEATURE:
<223> OTHER INFORMATION: Synthetic Construct
<400> SEQUENCE: 176

```
gatattgtga tgacgcaggc tgcattctcc aatccagtca ctcttggaac atcagcttcc      60
atctcttgca gttctactaa gagtctccta catagtagcg gcatcactta tctgtattgg     120
tatctgcaga ggccaggcca gtctcctcag ctcctgatat atcggatgtc caaccttgcc     180
tcaggagtcc cagacaggtt cagtggcagt gggtcaggaa ctgatttcac actgagaatc     240
agcagagtgg aggctgagga tgtgggtgtt tattactgtg ctcaaatgct agaacgccca     300
ttcacgttcg gctcggggac aaagttggaa ataaaac                               337
```

<210> SEQ ID NO 177
<211> LENGTH: 5
<212> TYPE: PRT
<213> ORGANISM: Artificial Sequence
<220> FEATURE:
<223> OTHER INFORMATION: Synthetic Construct

<400> SEQUENCE: 177

Ser Tyr Trp Leu Asn
1               5

<210> SEQ ID NO 178
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Arg Ile Tyr Pro Gly Asp Gly Asp Thr Asp Tyr Asn Gly Lys Phe Lys
1               5                   10                  15

Gly

<210> SEQ ID NO 179
<211> LENGTH: 9
<212> TYPE: PRT
<213> ORGANISM: Artificial Sequence
<220> FEATURE:
<223> OTHER INFORMATION: Synthetic Construct

<400> SEQUENCE: 179

Gly Asp Gly Tyr Trp Ala Met Asp Tyr
1               5

<210> SEQ ID NO 180
<211> LENGTH: 16
<212> TYPE: PRT
<213> ORGANISM: Artificial Sequence
<220> FEATURE:
<223> OTHER INFORMATION: Synthetic Construct

<400> SEQUENCE: 180

Arg Phe Ser Lys Ser Leu Leu His Ser Asn Gly Ile Thr Tyr Leu Tyr
1               5                   10                  15

<210> SEQ ID NO 181
<211> LENGTH: 7
<212> TYPE: PRT
<213> ORGANISM: Artificial Sequence
<220> FEATURE:
<223> OTHER INFORMATION: Synthetic Construct

<400> SEQUENCE: 181

Gln Met Ser Asn Leu Ala Ser
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Construct

<400> SEQUENCE: 182

Ala Gln Asn Leu Glu Leu Pro Trp Thr
1               5

<210> SEQ ID NO 183
<211> LENGTH: 8
<212> TYPE: PRT
<213> ORGANISM: Artificial Sequence
<220> FEATURE:

<223> OTHER INFORMATION: Synthetic Construct

<400> SEQUENCE: 183

Gly Tyr Ala Phe Ser Ser Tyr Trp
1               5

<210> SEQ ID NO 184
<211> LENGTH: 8
<212> TYPE: PRT
<213> ORGANISM: Artificial Sequence
<220> FEATURE:
<223> OTHER INFORMATION: Synthetic Construct

<400> SEQUENCE: 184

Ile Tyr Pro Gly Asp Gly Asp Thr
1               5

<210> SEQ ID NO 185
<211> LENGTH: 11
<212> TYPE: PRT
<213> ORGANISM: Artificial Sequence
<220> FEATURE:
<223> OTHER INFORMATION: Synthetic Construct

<400> SEQUENCE: 185

Val Arg Gly Asp Gly Tyr Trp Ala Met Asp Tyr
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Synthetic Construct

<400> SEQUENCE: 186

Lys Ser Leu Leu His Ser Asn Gly Ile Thr Tyr
1               5                   10

<210> SEQ ID NO 187
<211> LENGTH: 3
<212> TYPE: PRT
<213> ORGANISM: Artificial Sequence
<220> FEATURE:
<223> OTHER INFORMATION: Synthetic Construct

<400> SEQUENCE: 187

Gln Met Ser
1

<210> SEQ ID NO 188
<211> LENGTH: 9
<212> TYPE: PRT
<213> ORGANISM: Artificial Sequence
<220> FEATURE:
<223> OTHER INFORMATION: Synthetic Construct

<400> SEQUENCE: 188

Ala Gln Asn Leu Glu Leu Pro Trp Thr
1               5

<210> SEQ ID NO 189
<211> LENGTH: 118
<212> TYPE: PRT
<213> ORGANISM: Artificial Sequence
<220> FEATURE:
<223> OTHER INFORMATION: Synthetic Construct

<400> SEQUENCE: 189

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Tyr
                20                  25                  30

Trp Leu Asn Trp Val Lys Gln Arg Pro Gly Lys Gly Leu Glu Trp Phe
            35                  40                  45

Gly Arg Ile Tyr Pro Gly Asp Gly Asp Thr Asp Tyr Asn Gly Lys Phe
            50                  55                  60

Lys Gly Lys Ala Thr Leu Thr Ala Asp Lys Ser Ser Ser Thr Ala Tyr
65                  70                  75                  80

Met Gln Leu Arg Ser Leu Thr Ser Glu Asp Ser Ala Val Tyr Phe Cys
                85                  90                  95

Val Arg Gly Asp Gly Tyr Trp Ala Met Asp Tyr Trp Gly Gln Gly Thr
                100                 105                 110

Ser Val Thr Val Ser Ser
            115
```

<210> SEQ ID NO 190
<211> LENGTH: 112
<212> TYPE: PRT
<213> ORGANISM: Artificial Sequence
<220> FEATURE:
<223> OTHER INFORMATION: Synthetic Construct

<400> SEQUENCE: 190

```
Asp Ile Val Met Thr Gln Ala Ala Phe Ser Asn Pro Val Thr Leu Gly
1               5                   10                  15

Thr Ser Ala Ser Ile Ser Cys Arg Phe Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110
```

<210> SEQ ID NO 191
<211> LENGTH: 355
<212> TYPE: DNA
<213> ORGANISM: Artificial Sequence
<220> FEATURE:
<223> OTHER INFORMATION: Synthetic Construct

<400> SEQUENCE: 191

```
caggttcagc tgcagcagtc tggacctgag ctggtgaagc ctggggcctc ggtgaagatt      60
tcctgcaaag cttctggcta cgcattcagt agctactggc tgaactgggt gaagcagagg     120
cctggaaagg gtcttgagtg gtttggacgg atttatcctg gagatggaga tactgactac     180
aatgggaagt tcaagggcaa ggccacactg actgcagaca atcctccag cacagcctac      240 atgcaactca gaagcctgac atctgaggac tctgcggtct acttctgtgt aagaggtgat     300
ggttactggg ctatggacta ctggggtcaa ggaacctcag tcaccgtctc ctcag         355
```

-continued

```
<210> SEQ ID NO 192
<211> LENGTH: 337
<212> TYPE: DNA
<213> ORGANISM: Artificial Sequence
<220> FEATURE:
<223> OTHER INFORMATION: Synthetic Construct

<400> SEQUENCE: 192
gatattgtga tgacgcaggc tgcattctcc aatccagtca ctcttggaac atcagcttcc      60
atctcctgca ggtttagtaa gagtctccta catagtaatg gcatcactta tttgtattgg     120
tatctgcaga agccaggcca gtctcctcag ctcctgattt atcagatgtc caaccttgcc     180
tcaggagtcc cagacaggtt cagtagcagt gggtcaggaa ctgatttcac actgagaatc     240
agcagagtgg aggctgagga tgtgggtgtt tattactgtg ctcaaaatct agaacttccg     300
tggacgttcg gtggaggcac caagctggaa atcaaac                              337

<210> SEQ ID NO 193
<211> LENGTH: 5
<212> TYPE: PRT
<213> ORGANISM: Artificial Sequence
<220> FEATURE:
<223> OTHER INFORMATION: Synthetic Construct

<400> SEQUENCE: 193

Asn Tyr Tyr Met Ser
1               5

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct

<400> SEQUENCE: 194

Thr Ile Ser Asn Asn Gly Asp Ser Thr Tyr Tyr Leu Asp Thr Val Lys
1               5                   10                  15

Gly

<210> SEQ ID NO 195
<211> LENGTH: 7
<212> TYPE: PRT
<213> ORGANISM: Artificial Sequence
<220> FEATURE:
<223> OTHER INFORMATION: Synthetic Construct

<400> SEQUENCE: 195

Val Gly Thr Gly Phe Thr Tyr
1               5

<210> SEQ ID NO 196
<211> LENGTH: 11
<212> TYPE: PRT
<213> ORGANISM: Artificial Sequence
<220> FEATURE:
<223> OTHER INFORMATION: Synthetic Construct

<400> SEQUENCE: 196

Arg Ala Ser Gln Ser Ile Asn Asn Tyr Leu His
1               5                   10

<210> SEQ ID NO 197
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 197

Phe Ala Ser Gln Ser Ile Ser
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic Construct

<400> SEQUENCE: 198

Gln Gln Ser Asn Ser Trp Pro Leu Thr
1               5

<210> SEQ ID NO 199
<211> LENGTH: 8
<212> TYPE: PRT
<213> ORGANISM: Artificial Sequence
<220> FEATURE:
<223> OTHER INFORMATION: Synthetic Construct

<400> SEQUENCE: 199

Gly Phe Thr Phe Ser Asn Tyr Tyr
1               5

<210> SEQ ID NO 200
<211> LENGTH: 8
<212> TYPE: PRT
<213> ORGANISM: Artificial Sequence
<220> FEATURE:
<223> OTHER INFORMATION: Synthetic Construct

<400> SEQUENCE: 200

Ile Ser Asn Asn Gly Asp Ser Thr
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic Construct

<400> SEQUENCE: 201

Thr Arg Val Gly Thr Gly Phe Thr Tyr
1               5

<210> SEQ ID NO 202
<211> LENGTH: 6
<212> TYPE: PRT
<213> ORGANISM: Artificial Sequence
<220> FEATURE:
<223> OTHER INFORMATION: Synthetic Construct

<400> SEQUENCE: 202

Gln Ser Ile Asn Asn Tyr
1               5

<210> SEQ ID NO 203
<211> LENGTH: 3
```

```
<212> TYPE: PRT
<213> ORGANISM: Artificial Sequence
<220> FEATURE:
<223> OTHER INFORMATION: Synthetic Construct

<400> SEQUENCE: 203

Phe Ala Ser
1

<210> SEQ ID NO 204
<211> LENGTH: 9
<212> TYPE: PRT
<213> ORGANISM: Artificial Sequence
<220> FEATURE:
<223> OTHER INFORMATION: Synthetic Construct

<400> SEQUENCE: 204

Gln Gln Ser Asn Ser Trp Pro Leu Thr
1               5

<210> SEQ ID NO 205
<211> LENGTH: 116
<212> TYPE: PRT
<213> ORGANISM: Artificial Sequence
<220> FEATURE:
<223> OTHER INFORMATION: Synthetic Construct

<400> SEQUENCE: 205

Asp Val Asn Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Ser Pro Glu Lys Arg Leu Glu Trp Val
        35                  40                  45

Ala Thr Ile Ser Asn Asn Gly Asp Ser Thr Tyr Tyr Leu Asp Thr Val
    50                  55                  60

Lys Gly Arg Phe Thr Ile Ser Arg Asp Ser Ala Glu Asn Thr Leu Tyr
65                  70                  75                  80

Leu Gln Met Ser Ser Leu Ile Ser Glu Asp Thr Ala Val Tyr Tyr Cys
                85                  90                  95

Thr Arg Val Gly Thr Gly Phe Thr Tyr Trp Gly Gln Gly Thr Leu Val
            100                 105                 110

Thr Val Ser Ala
        115

<210> SEQ ID NO 206
<211> LENGTH: 107
<212> TYPE: PRT
<213> ORGANISM: Artificial Sequence
<220> FEATURE:
<223> OTHER INFORMATION: Synthetic Construct

<400> SEQUENCE: 206

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Asn Asn Tyr
            20                  25                  30

Leu His Trp Tyr Gln Gln Arg Ser His Glu Ser Pro Arg Leu Leu Ile
        35                  40                  45

Lys Phe Ala Ser Gln Ser Ile Ser Asp Ile Pro Ser Arg Phe Ser Gly
    50                  55                  60
```

```
Ser Gly Ser Gly Thr Asp Phe Thr Leu Ser Ile Asn Ser Ile Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105
```

```
<210> SEQ ID NO 207
<211> LENGTH: 349
<212> TYPE: DNA
<213> ORGANISM: Artificial Sequence
<220> FEATURE:
<223> OTHER INFORMATION: Synthetic Construct

<400> SEQUENCE: 207
gacgtgaacc tcgtggagtc tgggggaggc ttagtgaagc ttggagggtc cctgaaactc      60
tcctgtgcag cctctggatt cactttcagt aactactaca tgtcttgggt tcgccagagt     120
ccggagaaga ggctggagtg ggtcgcaacc attagtaata tggtgatag cacctactat      180 ctagacactg tgaagggccg attcaccatc tccagagaca gtgccgagaa caccctgtac     240
ctgcaaatga gcagtctgat ttctgaggac acagccgtgt attactgtac aagagttggg     300
acggggttta cttactgggg ccaagggact ctggtcactg tctctgcag                 349
```

```
<210> SEQ ID NO 208
<211> LENGTH: 322
<212> TYPE: DNA
<213> ORGANISM: Artificial Sequence
<220> FEATURE:
<223> OTHER INFORMATION: Synthetic Construct

<400> SEQUENCE: 208
gatattgtgc taactcagtc tccagccacc ctgtctgtga ctccaggaga tagcgtcagt      60
ctttcctgca gggccagcca aagtattaac aactacctac actggtatca acaaagatca     120
catgagtctc caaggcttct catcaagttt gcttcccagt ccatctctga catcccctcc     180
aggttcagtg gcagtggatc agggacagat ttcactctca gtatcaacag tatagagact     240
gaagattttg gaatgtattt ctgtcaacag agtaacagct ggccgctcac gttcggtgct     300
gggaccaagc tggagctgaa ac                                             322
```

```
<210> SEQ ID NO 209
<211> LENGTH: 5
<212> TYPE: PRT
<213> ORGANISM: Artificial Sequence
<220> FEATURE:
<223> OTHER INFORMATION: Synthetic Construct

<400> SEQUENCE: 209

Ser Tyr Val Ile His
1               5
```

```
<210> SEQ ID NO 210
<211> LENGTH: 17
<212> TYPE: PRT
<213> ORGANISM: Artificial Sequence
<220> FEATURE:
<223> OTHER INFORMATION: Synthetic Construct

<400> SEQUENCE: 210

Tyr Ile Asn Pro Tyr Ser Asp Tyr Thr Gln Tyr Asn Glu Lys Phe Lys
1               5                   10                  15
```

-continued

Gly

<210> SEQ ID NO 211
<211> LENGTH: 11
<212> TYPE: PRT
<213> ORGANISM: Artificial Sequence
<220> FEATURE:
<223> OTHER INFORMATION: Synthetic Construct

<400> SEQUENCE: 211

Arg Ala Asp Gly Asn Pro Tyr Ala Met Asp Tyr
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Synthetic Construct

<400> SEQUENCE: 212

Lys Ala Ser Gln Asp Val Ser Thr Ala Val Val
1               5                   10

<210> SEQ ID NO 213
<211> LENGTH: 7
<212> TYPE: PRT
<213> ORGANISM: Artificial Sequence
<220> FEATURE:
<223> OTHER INFORMATION: Synthetic Construct

<400> SEQUENCE: 213

Ser Ala Ser Tyr Arg Tyr Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic Construct

<400> SEQUENCE: 214

Gln Gln His Tyr Ser Thr Pro Phe Thr
1               5

<210> SEQ ID NO 215
<211> LENGTH: 8
<212> TYPE: PRT
<213> ORGANISM: Artificial Sequence
<220> FEATURE:
<223> OTHER INFORMATION: Synthetic Construct

<400> SEQUENCE: 215

Gly Tyr Thr Phe Thr Ser Tyr Val
1               5

<210> SEQ ID NO 216
<211> LENGTH: 8
<212> TYPE: PRT
<213> ORGANISM: Artificial Sequence
<220> FEATURE:
<223> OTHER INFORMATION: Synthetic Construct

<400> SEQUENCE: 216

Ile Asn Pro Tyr Ser Asp Tyr Thr
1               5

<210> SEQ ID NO 217
<211> LENGTH: 13
<212> TYPE: PRT
<213> ORGANISM: Artificial Sequence
<220> FEATURE:
<223> OTHER INFORMATION: Synthetic Construct

<400> SEQUENCE: 217

Ala Arg Arg Ala Asp Gly Asn Pro Tyr Ala Met Asp Tyr
1               5                   10

<210> SEQ ID NO 218
<211> LENGTH: 6
<212> TYPE: PRT
<213> ORGANISM: Artificial Sequence
<220> FEATURE:
<223> OTHER INFORMATION: Synthetic Construct

<400> SEQUENCE: 218

Gln Asp Val Ser Thr Ala
1               5

<210> SEQ ID NO 219
<211> LENGTH: 3
<212> TYPE: PRT
<213> ORGANISM: Artificial Sequence
<220> FEATURE:
<223> OTHER INFORMATION: Synthetic Construct

<400> SEQUENCE: 219

Ser Ala Ser
1

<210> SEQ ID NO 220
<211> LENGTH: 9
<212> TYPE: PRT
<213> ORGANISM: Artificial Sequence
<220> FEATURE:
<223> OTHER INFORMATION: Synthetic Construct

<400> SEQUENCE: 220

Gln Gln His Tyr Ser Thr Pro Phe Thr
1               5

<210> SEQ ID NO 221
<211> LENGTH: 120
<212> TYPE: PRT
<213> ORGANISM: Artificial Sequence
<220> FEATURE:
<223> OTHER INFORMATION: Synthetic Construct

<400> SEQUENCE: 221

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Ile
        35                  40                  45

Gly Tyr Ile Asn Pro Tyr Ser Asp Tyr Thr Gln Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Ser Cys

-continued

```
                        85              90              95

Ala Arg Arg Ala Asp Gly Asn Pro Tyr Ala Met Asp Tyr Trp Gly Gln
            100             105             110

Gly Thr Ser Val Thr Val Ser Ser
        115             120

<210> SEQ ID NO 222
<211> LENGTH: 107
<212> TYPE: PRT
<213> ORGANISM: Artificial Sequence
<220> FEATURE:
<223> OTHER INFORMATION: Synthetic Construct

<400> SEQUENCE: 222

Asp Ile Val Met Thr Gln Ser His Lys Phe Met Ser Thr Ser Val Gly
1               5               10              15

Asp Arg Val Ser Thr Thr Cys Lys Ala Ser Gln Asp Val Ser Thr Ala
            20              25              30

Val Val Trp Tyr Gln Gln Lys Pro Gly Gln Ser Pro Lys Leu Leu Ile
        35              40              45

Tyr Ser Ala Ser Tyr Arg Tyr Thr Gly Val Pro Asp Arg Phe Thr Gly
    50              55              60

Ser Gly Ser Gly Thr Asp Phe Thr Phe Thr Ile Thr Ser Val Gln Ala
65              70              75              80

Glu Asp Leu Ala Val Tyr Tyr Cys Gln Gln His Tyr Ser Thr Pro Phe
                85              90              95

Thr Phe Gly Ser Gly Thr Lys Leu Glu Ile Lys
            100             105

<210> SEQ ID NO 223
<211> LENGTH: 361
<212> TYPE: DNA
<213> ORGANISM: Artificial Sequence
<220> FEATURE:
<223> OTHER INFORMATION: Synthetic Construct

<400> SEQUENCE: 223
gaggtccagc tacagcagtc tggacctgag ctggtaaagc ctggggcttc agtgaagatg      60
tcctgcaagg cttctggata cacattcact agctatgtta ttcactgggt aaagcagaag     120
cctgggcagg gccttgagtg gattggatat attaatcctt acagtgatta tactcagtac     180
aatgagaagt tcaaaggcaa ggccacactg acttcagaca aatcctccag cacagcctac     240
atggagctca gcagcctgac ctctgaggac tctgcggtct attcctgtgc aaggagggca     300
gatggtaacc cctatgctat ggactactgg ggtcaaggaa cctcagtcac cgtctcctca     360
g                                                                     361

<210> SEQ ID NO 224
<211> LENGTH: 322
<212> TYPE: DNA
<213> ORGANISM: Artificial Sequence
<220> FEATURE:
<223> OTHER INFORMATION: Synthetic Construct

<400> SEQUENCE: 224
gacattgtga tgacccagtc tcacaaattc atgtccacat cagtaggaga cagggtcagc      60
accacctgca aggccagtca ggatgtgagt actgctgtag tctggtatca acagaaacca     120
ggacaatctc ctaaactact gatttactcg gcatcctacc ggtacactgg agtccctgat     180
```

-continued

```
cgcttcactg gcagtggatc tgggacggat ttcactttca ccatcaccag tgtgcaggct        240
gaagacctgg cagtttatta ctgtcagcaa cattatagta ctccattcac gttcggctcg        300
gggacaaagt tggaaataaa ac                                                  322
```

```
<210> SEQ ID NO 225
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Can be present in repeats of any integer

<400> SEQUENCE: 225

Gly
1

<210> SEQ ID NO 226
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(16)
<223> OTHER INFORMATION: Can be present or absent

<400> SEQUENCE: 226

Gly Ser Gly Ser Gly Ser Gly Ser Gly Ser Gly Ser Gly Ser Gly Ser
1               5                   10                  15

<210> SEQ ID NO 227
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(40)
<223> OTHER INFORMATION: Can be present or absent

<400> SEQUENCE: 227

Gly Ser Gly Gly Ser Gly Ser Gly Gly Ser Gly Ser Gly Gly Ser Gly
1               5                   10                  15

Ser Gly Gly Ser Gly Ser Gly Gly Ser Gly Ser Gly Gly Ser Gly Ser
            20                  25                  30

Gly Gly Ser Gly Ser Gly Gly Ser
        35                  40

<210> SEQ ID NO 228
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(40)
<223> OTHER INFORMATION: Can be present or absent

<400> SEQUENCE: 228

Gly Gly Gly Gly Ser Gly Gly Gly Gly Ser Gly Gly Gly Gly Ser Gly
1               5                   10                  15
```

```
Gly Gly Gly Ser Gly Gly Gly Gly Ser Gly Gly Gly Gly Ser Gly Gly
            20                  25                  30

Gly Gly Ser Gly Gly Gly Gly Ser
        35                  40
```

<210> SEQ ID NO 229
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(32)
<223> OTHER INFORMATION: Can be present or absent

<400> SEQUENCE: 229

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30
```

<210> SEQ ID NO 230
<211> LENGTH: 15
<212> TYPE: PRT
<213> ORGANISM: Artificial Sequence
<220> FEATURE:
<223> OTHER INFORMATION: Synthetic Construct

<400> SEQUENCE: 230

```
Gly Gly Gly Gly Ser Gly Gly Gly Gly Ser Gly Gly Gly Gly Ser
1               5                   10                  15
```

<210> SEQ ID NO 231
<211> LENGTH: 30
<212> TYPE: PRT
<213> ORGANISM: Artificial Sequence
<220> FEATURE:
<223> OTHER INFORMATION: Synthetic Construct

<400> SEQUENCE: 231

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 232
<211> LENGTH: 60
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (16)..(60)
<223> OTHER INFORMATION: Can be present or absent

<400> SEQUENCE: 232

```
Gly Ser Thr Ser Gly Ser Gly Lys Pro Gly Ser Gly Glu Gly Ser Gly
1               5                   10                  15

Ser Thr Ser Gly Ser Gly Lys Pro Gly Ser Gly Glu Gly Ser Gly Ser
            20                  25                  30

Thr Ser Gly Ser Gly Lys Pro Gly Ser Gly Glu Gly Ser Gly Ser Thr
        35                  40                  45
```

-continued

```
Ser Gly Ser Gly Lys Pro Gly Ser Gly Glu Gly Ser
    50                  55                  60

<210> SEQ ID NO 233
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9, 10
<223> OTHER INFORMATION: Xaa = AN or TD
<220> FEATURE:
<221> NAME/KEY: VARIANT
<222> LOCATION: 12
<223> OTHER INFORMATION: Xaa = N or D

<400> SEQUENCE: 233

Arg Ile Phe Pro Gly Asp Gly Asp Xaa Xaa Tyr Xaa Gly Lys Phe Lys
1               5                   10                  15

Gly

<210> SEQ ID NO 234
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = D or E

<400> SEQUENCE: 234

Thr Gly Ala Ala Tyr Xaa Phe Asp Pro Phe Pro Tyr
1               5                   10

<210> SEQ ID NO 235
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = S or T
<220> FEATURE:
<221> NAME/KEY: VARIANT
<222> LOCATION: 10
<223> OTHER INFORMATION: Xaa = N or S
<220> FEATURE:
<221> NAME/KEY: VARIANT
<222> LOCATION: 12
<223> OTHER INFORMATION: Xaa = V or I

<400> SEQUENCE: 235

Ser Ser Xaa Lys Ser Leu Leu His Ser Xaa Gly Xaa Thr Tyr Leu Tyr
1               5                   10                  15

<210> SEQ ID NO 236
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S or T
```

```
<220> FEATURE:
<221> NAME/KEY: VARIANT
<222> LOCATION: 4
<223> OTHER INFORMATION: Xaa = L or M

<400> SEQUENCE: 236

Xaa Tyr Trp Xaa Asn
1               5

<210> SEQ ID NO 237
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Y or F
<220> FEATURE:
<221> NAME/KEY: VARIANT
<222> LOCATION: 9, 10
<223> OTHER INFORMATION: Xaa = AN or TD
<220> FEATURE:
<221> NAME/KEY: VARIANT
<222> LOCATION: 12
<223> OTHER INFORMATION: Xaa = N or D

<400> SEQUENCE: 237

Arg Ile Xaa Pro Gly Asp Gly Asp Xaa Xaa Tyr Xaa Gly Lys Phe Lys
1               5                   10                  15

Gly

<210> SEQ ID NO 238
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3
<223> OTHER INFORMATION: Xaa = SSS, SST, or RFS
<220> FEATURE:
<221> NAME/KEY: VARIANT
<222> LOCATION: 10
<223> OTHER INFORMATION: Xaa = N or S
<220> FEATURE:
<221> NAME/KEY: VARIANT
<222> LOCATION: 12
<223> OTHER INFORMATION: Xaa = V or I

<400> SEQUENCE: 238

Xaa Xaa Xaa Lys Ser Leu Leu His Ser Xaa Gly Xaa Thr Tyr Leu Tyr
1               5                   10                  15

<210> SEQ ID NO 239
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = R or Q

<400> SEQUENCE: 239

Xaa Met Ser Asn Leu Ala Ser
1               5
```

```
<210> SEQ ID NO 240
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = M or N
<220> FEATURE:
<221> NAME/KEY: VARIANT
<222> LOCATION: 6
<223> OTHER INFORMATION: Xaa = R or L
<220> FEATURE:
<221> NAME/KEY: VARIANT
<222> LOCATION: 8
<223> OTHER INFORMATION: Xaa = F or W

<400> SEQUENCE: 240

Ala Gln Xaa Leu Glu Xaa Pro Xaa Thr
1               5

<210> SEQ ID NO 241
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A or S
<220> FEATURE:
<221> NAME/KEY: VARIANT
<222> LOCATION: 4
<223> OTHER INFORMATION: Xaa = M or I

<400> SEQUENCE: 241

Xaa Tyr Val Xaa His
1               5

<210> SEQ ID NO 242
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = F or N
<220> FEATURE:
<221> NAME/KEY: VARIANT
<222> LOCATION: 6
<223> OTHER INFORMATION: Xaa = N or S
<220> FEATURE:
<221> NAME/KEY: VARIANT
<222> LOCATION: 8
<223> OTHER INFORMATION: Xaa = G or Y
<220> FEATURE:
<221> NAME/KEY: VARIANT
<222> LOCATION: 10
<223> OTHER INFORMATION: Xaa = E or Q

<400> SEQUENCE: 242

Tyr Ile Xaa Pro Tyr Xaa Asp Xaa Thr Xaa Tyr Asn Glu Lys Phe Lys
1               5                   10                  15

Gly

<210> SEQ ID NO 243
```

```
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 8
<223> OTHER INFORMATION: Xaa = T or A

<400> SEQUENCE: 243

Arg Xaa Asp Gly Asn Pro Tyr Xaa Met Asp Tyr
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: Xaa = A or V

<400> SEQUENCE: 244

Lys Ala Ser Gln Asp Val Ser Thr Ala Val Xaa
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = N or D
<220> FEATURE:
<221> NAME/KEY: VARIANT
<222> LOCATION: 7
<223> OTHER INFORMATION: Xaa = G or S
<220> FEATURE:
<221> NAME/KEY: VARIANT
<222> LOCATION: 9
<223> OTHER INFORMATION: Xaa = N or A
<220> FEATURE:
<221> NAME/KEY: VARIANT
<222> LOCATION: 11
<223> OTHER INFORMATION: Xaa = A or V

<400> SEQUENCE: 245

Lys Ala Ser Gln Xaa Val Xaa Thr Xaa Val Xaa
1               5                   10

<210> SEQ ID NO 246
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7
<223> OTHER INFORMATION: Xaa = FI or YT

<400> SEQUENCE: 246

Ser Ala Ser Tyr Arg Xaa Xaa
1               5
```

```
<210> SEQ ID NO 247
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 4, 5, 6
<223> OTHER INFORMATION: Xaa = YNRN or HYST
<220> FEATURE:
<221> NAME/KEY: VARIANT
<222> LOCATION: 8
<223> OTHER INFORMATION: Xaa = I or F

<400> SEQUENCE: 247

Gln Gln Xaa Xaa Xaa Xaa Pro Xaa Thr
1               5

<210> SEQ ID NO 248
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = K or R
<220> FEATURE:
<221> NAME/KEY: VARIANT
<222> LOCATION: 7, 8, 9, 10, 11
<223> OTHER INFORMATION: Xaa = DYAGD or STSSY
<220> FEATURE:
<221> NAME/KEY: VARIANT
<222> LOCATION: 15
<223> OTHER INFORMATION: Xaa = N or H

<400> SEQUENCE: 248

Xaa Ala Ser Gln Ser Val Xaa Xaa Xaa Xaa Xaa Ser Tyr Met Xaa
1               5                   10                  15

<210> SEQ ID NO 249
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A or Y

<400> SEQUENCE: 249

Xaa Ala Ser Asn Leu Glu Ser
1               5

<210> SEQ ID NO 250
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 5, 6
<223> OTHER INFORMATION: Xaa = QTNED or HSWEI
<220> FEATURE:
<221> NAME/KEY: VARIANT
<222> LOCATION: 8
<223> OTHER INFORMATION: Xaa = R or F

<400> SEQUENCE: 250
```

-continued

```
Gln Xaa Xaa Xaa Xaa Xaa Pro Xaa Thr
1               5

<210> SEQ ID NO 251
<211> LENGTH: 5
<212> TYPE: PRT
<213> ORGANISM: Artificial Sequence
<220> FEATURE:
<223> OTHER INFORMATION: Synthetic Construct

<400> SEQUENCE: 251

Asp Thr Tyr Met Tyr
1               5

<210> SEQ ID NO 252
<211> LENGTH: 17
<212> TYPE: PRT
<213> ORGANISM: Artificial Sequence
<220> FEATURE:
<223> OTHER INFORMATION: Synthetic Construct

<400> SEQUENCE: 252

Arg Ile Asp Pro Ala Asn Asp Asn Thr Lys Tyr Ala Gln Lys Phe Gln
1               5                   10                  15

Gly

<210> SEQ ID NO 253
<211> LENGTH: 10
<212> TYPE: PRT
<213> ORGANISM: Artificial Sequence
<220> FEATURE:
<223> OTHER INFORMATION: Synthetic Construct

<400> SEQUENCE: 253

Ala Lys Asn Leu Leu Asn Tyr Phe Asp Tyr
1               5                   10

<210> SEQ ID NO 254
<211> LENGTH: 11
<212> TYPE: PRT
<213> ORGANISM: Artificial Sequence
<220> FEATURE:
<223> OTHER INFORMATION: Synthetic Construct

<400> SEQUENCE: 254

Arg Ala Ser Gln Glu Ile Ser Gly Tyr Leu Ser
1               5                   10

<210> SEQ ID NO 255
<211> LENGTH: 7
<212> TYPE: PRT
<213> ORGANISM: Artificial Sequence
<220> FEATURE:
<223> OTHER INFORMATION: Synthetic Construct

<400> SEQUENCE: 255

Ala Thr Ser Thr Leu Gln Ser
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic Construct
```

-continued

```
<400> SEQUENCE: 256

Leu Gln Tyr Ala Ile Tyr Pro Leu Thr
1               5

<210> SEQ ID NO 257
<211> LENGTH: 8
<212> TYPE: PRT
<213> ORGANISM: Artificial Sequence
<220> FEATURE:
<223> OTHER INFORMATION: Synthetic Construct

<400> SEQUENCE: 257

Gly Phe Thr Phe Ser Ser Tyr Thr
1               5

<210> SEQ ID NO 258
<211> LENGTH: 8
<212> TYPE: PRT
<213> ORGANISM: Artificial Sequence
<220> FEATURE:
<223> OTHER INFORMATION: Synthetic Construct

<400> SEQUENCE: 258

Ile Ser His Gly Gly Gly Asp Thr
1               5

<210> SEQ ID NO 259
<211> LENGTH: 16
<212> TYPE: PRT
<213> ORGANISM: Artificial Sequence
<220> FEATURE:
<223> OTHER INFORMATION: Synthetic Construct

<400> SEQUENCE: 259

Ala Arg His Ser Gly Tyr Glu Arg Gly Tyr Tyr Tyr Val Met Asp Tyr
1               5                   10                  15

<210> SEQ ID NO 260
<211> LENGTH: 10
<212> TYPE: PRT
<213> ORGANISM: Artificial Sequence
<220> FEATURE:
<223> OTHER INFORMATION: Synthetic Construct

<400> SEQUENCE: 260

Glu Ser Val Asp Tyr Tyr Gly Phe Ser Phe
1               5                   10

<210> SEQ ID NO 261
<211> LENGTH: 3
<212> TYPE: PRT
<213> ORGANISM: Artificial Sequence
<220> FEATURE:
<223> OTHER INFORMATION: Synthetic Construct

<400> SEQUENCE: 261

Ala Ala Ser
1

<210> SEQ ID NO 262
<211> LENGTH: 8
<212> TYPE: PRT
<213> ORGANISM: Artificial Sequence
<220> FEATURE:
<223> OTHER INFORMATION: Synthetic Construct

<400> SEQUENCE: 262
```

-continued

```
Gln Gln Ser Lys Glu Val Pro Trp
1               5

<210> SEQ ID NO 263
<211> LENGTH: 8
<212> TYPE: PRT
<213> ORGANISM: Artificial Sequence
<220> FEATURE:
<223> OTHER INFORMATION: Synthetic Construct

<400> SEQUENCE: 263

Gly Tyr Thr Phe Thr Ser Tyr Thr
1               5

<210> SEQ ID NO 264
<211> LENGTH: 8
<212> TYPE: PRT
<213> ORGANISM: Artificial Sequence
<220> FEATURE:
<223> OTHER INFORMATION: Synthetic Construct

<400> SEQUENCE: 264

Ile Asn Pro Thr Thr Gly Tyr Thr
1               5

<210> SEQ ID NO 265
<211> LENGTH: 10
<212> TYPE: PRT
<213> ORGANISM: Artificial Sequence
<220> FEATURE:
<223> OTHER INFORMATION: Synthetic Construct

<400> SEQUENCE: 265

Ala Arg Asp Asp Ala Tyr Tyr Ser Gly Tyr
1               5                   10

<210> SEQ ID NO 266
<211> LENGTH: 7
<212> TYPE: PRT
<213> ORGANISM: Artificial Sequence
<220> FEATURE:
<223> OTHER INFORMATION: Synthetic Construct

<400> SEQUENCE: 266

Glu Asn Ile Tyr Ser Asn Leu
1               5

<210> SEQ ID NO 267
<211> LENGTH: 3
<212> TYPE: PRT
<213> ORGANISM: Artificial Sequence
<220> FEATURE:
<223> OTHER INFORMATION: Synthetic Construct

<400> SEQUENCE: 267

Ala Ala Lys
1

<210> SEQ ID NO 268
<211> LENGTH: 9
<212> TYPE: PRT
<213> ORGANISM: Artificial Sequence
<220> FEATURE:
<223> OTHER INFORMATION: Synthetic Construct

<400> SEQUENCE: 268
```

Gln His Phe Trp Gly Thr Pro Trp Thr
1               5

<210> SEQ ID NO 269
<211> LENGTH: 8
<212> TYPE: PRT
<213> ORGANISM: Artificial Sequence
<220> FEATURE:
<223> OTHER INFORMATION: Synthetic Construct

<400> SEQUENCE: 269

Gly Phe Ala Phe Ser Ser Tyr Asp
1               5

<210> SEQ ID NO 270
<211> LENGTH: 8
<212> TYPE: PRT
<213> ORGANISM: Artificial Sequence
<220> FEATURE:
<223> OTHER INFORMATION: Synthetic Construct

<400> SEQUENCE: 270

Ile Thr Ile Gly Gly Gly Thr Thr
1               5

<210> SEQ ID NO 271
<211> LENGTH: 12
<212> TYPE: PRT
<213> ORGANISM: Artificial Sequence
<220> FEATURE:
<223> OTHER INFORMATION: Synthetic Construct

<400> SEQUENCE: 271

Ala Arg His Arg Tyr Asp Tyr Phe Ala Met Asp Asn
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Synthetic Construct

<400> SEQUENCE: 272

Glu Asn Val Asp Asn Tyr Gly Ile Asn Phe
1               5                   10

<210> SEQ ID NO 273
<211> LENGTH: 3
<212> TYPE: PRT
<213> ORGANISM: Artificial Sequence
<220> FEATURE:
<223> OTHER INFORMATION: Synthetic Construct

<400> SEQUENCE: 273

Val Ser Ser
1

<210> SEQ ID NO 274
<211> LENGTH: 8
<212> TYPE: PRT
<213> ORGANISM: Artificial Sequence
<220> FEATURE:
<223> OTHER INFORMATION: Synthetic Construct

<400> SEQUENCE: 274

Gln Gln Ser Lys Asp Val Pro Trp

-continued

```
1               5

<210> SEQ ID NO 275
<211> LENGTH: 135
<212> TYPE: PRT
<213> ORGANISM: Mus musculus

<400> SEQUENCE: 275

Ser Gln Val Gln Leu Gln Gln Ser Gly Ala Glu Leu Ala Arg Pro Gly
1               5                   10                  15

Ala Ser Val Lys Met Ser Cys Lys Ala Ser Gly Tyr Thr Phe Thr Ser
                20                  25                  30

Tyr Thr Met His Trp Val Lys Gln Arg Pro Gly Gln Gly Leu Glu Trp
            35                  40                  45

Ile Gly Tyr Ile Asn Pro Thr Thr Gly Tyr Thr Asn Tyr Asn Gln Lys
        50                  55                  60

Phe Lys Asp Lys Ala Asn Pro Thr Thr Gly Tyr Thr Asn Tyr Asn Gln
65                  70                  75                  80

Lys Phe Lys Asp Lys Ala Thr Leu Thr Ala Asp Lys Ser Ser Ser Thr
                85                  90                  95

Ala Tyr Met Gln Leu Ser Ser Leu Thr Ser Glu Asp Ser Ala Val Tyr
                100                 105                 110

Tyr Cys Ala Arg Asp Asp Ala Tyr Tyr Ser Gly Tyr Trp Gly Gln Gly
            115                 120                 125

Thr Thr Leu Thr Val Ser Ser
        130                 135

<210> SEQ ID NO 276
<211> LENGTH: 108
<212> TYPE: PRT
<213> ORGANISM: Mus musculus

<400> SEQUENCE: 276

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
                20                  25                  30

Leu Ala Trp Tyr Arg Gln Lys Gln Gly Lys Ser Pro Gln Leu Leu Val
            35                  40                  45

Tyr Ala Ala Lys Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys Arg
                100                 105

<210> SEQ ID NO 277
<211> LENGTH: 140
<212> TYPE: PRT
<213> ORGANISM: Mus musculus

<400> SEQUENCE: 277

Val Gln Leu Val Glu Ser Gly Gly Gly Leu Val Lys Pro Gly Gly Ser
1               5                   10                  15

Leu Lys Leu Ser Cys Ala Ala Ser Gly Phe Ala Phe Ser Ser Tyr Asp
                20                  25                  30
```

```
Met Ser Trp Val Arg Gln Thr Pro Glu Lys Arg Leu Val Trp Val Ala
        35              40              45

Tyr Ile Thr Ile Gly Gly Gly Thr Thr Tyr Tyr Ser Asp Thr Val Lys
    50              55              60

Arg Leu Val Trp Val Ala Tyr Ile Thr Ile Gly Gly Gly Thr Thr Tyr
65              70              75              80

Tyr Ser Asp Thr Val Lys Gly Arg Phe Thr Ile Ser Arg Asp Asn Ala
            85              90              95

Lys Asn Thr Leu Tyr Leu Gln Met Ser Ser Leu Lys Ser Glu Asp Thr
            100             105             110

Ala Met Tyr Tyr Cys Ala Arg His Arg Tyr Asp Tyr Phe Ala Met Asp
        115             120             125

Asn Trp Gly His Gly Thr Ser Val Thr Val Ser Ser
    130             135             140
```

<210> SEQ ID NO 278
<211> LENGTH: 112
<212> TYPE: PRT
<213> ORGANISM: Mus musculus

<400> SEQUENCE: 278

```
Asp Ile Val Leu Thr Gln Ser Pro Ala Ser Leu Ala Val Ser Leu Glu
1               5               10              15

His Arg Ala Thr Ile Ser Cys Gln Ala Ser Glu Asn Val Asp Asn Tyr
            20              25              30

Gly Ile Asn Phe Met Asn Trp Phe Gln His Lys Pro Ala Gln Pro Pro
        35              40              45

Gln Leu Leu Ile Tyr Val Ser Ser Asn Leu Gly Ser Gly Val Pro Ala
    50              55              60

Lys Phe Ser Gly Ser Gly Ser Gly Thr Asp Phe Ser Leu Asn Ile His
65              70              75              80

Pro Met Glu Glu Asp Asp Thr Ala Met Tyr Phe Cys Gln Gln Ser Lys
            85              90              95

Asp Val Pro Trp Thr Phe Ser Gly Gly Thr Lys Leu Glu Ile Lys Arg
            100             105             110
```

<210> SEQ ID NO 279
<211> LENGTH: 123
<212> TYPE: PRT
<213> ORGANISM: Mus musculus

<400> SEQUENCE: 279

```
Glu Val Lys Leu Val Glu Ser Gly Gly Gly Leu Val Gln Pro Gly Gly
1               5               10              15

Ser Leu Lys Leu Ser Cys Ala Ala Ser Gly Phe Thr Phe Ser Ser Tyr
            20              25              30

Thr Met Ser Trp Ile Arg Gln Thr Pro Glu Lys Arg Leu Glu Trp Val
        35              40              45

Ala Tyr Ile Ser His Gly Gly Gly Asp Thr Tyr Tyr Pro Asp Thr Val
    50              55              60

Lys Gly Arg Phe Thr Ile Ser Arg Asp Asn Ala Lys Asn Thr Leu Tyr
65              70              75              80

Leu Gln Met Ser Ser Leu Lys Ser Glu Asp Thr Ala Met Tyr Tyr Cys
            85              90              95

Ala Arg His Ser Gly Tyr Glu Arg Gly Tyr Tyr Tyr Val Met Asp Tyr
            100             105             110
```

-continued

```
Trp Gly Gln Gly Thr Ser Val Thr Val Ser Ser
        115                 120

<210> SEQ ID NO 280
<211> LENGTH: 111
<212> TYPE: PRT
<213> ORGANISM: Mus musculus

<400> SEQUENCE: 280

Asp Ile Val Leu Thr Gln Phe Pro Thr Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Phe Ser Phe Ile Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Gly Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 281
<211> LENGTH: 119
<212> TYPE: PRT
<213> ORGANISM: Artificial Sequence
<220> FEATURE:
<223> OTHER INFORMATION: Synthetic Construct

<400> SEQUENCE: 281

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser
        115

<210> SEQ ID NO 282
<211> LENGTH: 119
<212> TYPE: PRT
<213> ORGANISM: Artificial Sequence
<220> FEATURE:
<223> OTHER INFORMATION: Synthetic Construct

<400> SEQUENCE: 282

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Phe Asn Ile Lys Asp Thr
        20                  25                  30

Tyr Met Tyr Trp Val Arg Gln Ala Pro Gly Gln Gly Leu Glu Trp Ile
        35                  40                  45

Gly Arg Ile Asp Pro Ala Asn Asp Asn Thr Lys Tyr Ala Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser
        115

<210> SEQ ID NO 283
<211> LENGTH: 119
<212> TYPE: PRT
<213> ORGANISM: Artificial Sequence
<220> FEATURE:
<223> OTHER INFORMATION: Synthetic Construct

<400> SEQUENCE: 283

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
        20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser
        115

<210> SEQ ID NO 284
<211> LENGTH: 108
<212> TYPE: PRT
<213> ORGANISM: Artificial Sequence
<220> FEATURE:
<223> OTHER INFORMATION: Synthetic Construct

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
        20                  25                  30

Leu Ser Trp Tyr Gln Gln Lys Pro Gly Lys Ala Pro Lys Arg Leu Ile
        35                  40                  45

Tyr Ala Thr Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro

-continued

```
65               70               75               80

Glu Asp Phe Ala Thr Tyr Tyr Cys Leu Gln Tyr Ala Ile Tyr Pro Leu
                85               90               95

Thr Phe Gly Gln Gly Thr Lys Leu Glu Ile Lys Arg
            100               105

<210> SEQ ID NO 285
<211> LENGTH: 108
<212> TYPE: PRT
<213> ORGANISM: Artificial Sequence
<220> FEATURE:
<223> OTHER INFORMATION: Synthetic Construct

<400> SEQUENCE: 285

Asp Ile Gln Met Thr Gln Ser Pro Ser Ser Leu Ser Ala Ser Val Gly
1               5                10               15

Asp Arg Val Thr Ile Thr Cys Arg Ala Ser Gln Glu Ile Ser Gly Tyr
            20               25               30

Leu Ser Trp Leu Gln Gln Lys Pro Gly Lys Ala Pro Lys Arg Leu Ile
        35               40               45

Tyr Ala Thr Ser Thr Leu Gln Ser Gly Val Pro Ser Arg Phe Ser Gly
    50               55               60

Ser Arg Ser Gly Thr Asp Tyr Thr Leu Thr Ile Ser Ser Leu Gln Pro
65               70               75               80

Glu Asp Phe Ala Thr Tyr Tyr Cys Leu Gln Tyr Ala Ile Tyr Pro Leu
                85               90               95

Thr Phe Gly Gln Gly Thr Lys Leu Glu Ile Lys Arg
            100               105

<210> SEQ ID NO 286
<211> LENGTH: 108
<212> TYPE: PRT
<213> ORGANISM: Artificial Sequence
<220> FEATURE:
<223> OTHER INFORMATION: Synthetic Construct

<400> SEQUENCE: 286

Asp Ile Gln Met Thr Gln Ser Pro Ser Ser Leu Ser Ala Ser Val Gly
1               5                10               15

Asp Arg Val Thr Ile Thr Cys Arg Ala Ser Gln Glu Ile Ser Gly Tyr
            20               25               30

Leu Ser Trp Tyr Gln Gln Lys Pro Gly Lys Ala Pro Lys Arg Leu Ile
        35               40               45

Tyr Ala Thr Ser Thr Leu Asp Ser Gly Val Pro Ser Arg Phe Ser Gly
    50               55               60

Ser Arg Ser Gly Ser Asp Tyr Thr Leu Thr Ile Ser Ser Leu Gln Pro
65               70               75               80

Glu Asp Phe Ala Thr Tyr Tyr Cys Leu Gln Tyr Ala Ile Tyr Pro Leu
                85               90               95

Thr Phe Gly Gln Gly Thr Lys Leu Glu Ile Lys Arg
            100               105

<210> SEQ ID NO 287
<211> LENGTH: 120
<212> TYPE: PRT
<213> ORGANISM: Artificial Sequence
<220> FEATURE:
<223> OTHER INFORMATION: Synthetic Construct

<400> SEQUENCE: 287
```

-continued

```
Gln Val Gln Leu Gln Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val Tyr Gly Leu Glu Trp Ile
        35                  40                  45

Gly Gly Ile Asp Pro Glu Thr Gly Asp Thr Ala Tyr Asn Gln Asn Phe
    50                  55                  60

Lys Gly Lys Ala Thr Leu Thr Ala Asp Lys Ser Ser Ser Ala Ala Tyr
65                  70                  75                  80

Met Glu Leu Arg Ser Leu Thr Ser Glu Asp Ser Ala Val Tyr Tyr Cys
                85                  90                  95

Thr Asn Tyr Gly Asn Leu Tyr Tyr Tyr Ala Met Asp Tyr Trp Gly Gln
            100                 105                 110

Gly Thr Ser Val Thr Val Ser Ser
        115                 120

<210> SEQ ID NO 288
<211> LENGTH: 108
<212> TYPE: PRT
<213> ORGANISM: Artificial Sequence
<220> FEATURE:
<223> OTHER INFORMATION: Synthetic Construct

<400> SEQUENCE: 288

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Phe Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ser Gly Thr Lys Leu Glu Ile Lys
            100                 105

<210> SEQ ID NO 289
<211> LENGTH: 5
<212> TYPE: PRT
<213> ORGANISM: Artificial Sequence
<220> FEATURE:
<223> OTHER INFORMATION: Synthetic Construct

<400> SEQUENCE: 289

Asp Tyr Glu Met His
1               5

<210> SEQ ID NO 290
<211> LENGTH: 17
<212> TYPE: PRT
<213> ORGANISM: Artificial Sequence
<220> FEATURE:
<223> OTHER INFORMATION: Synthetic Construct

<400> SEQUENCE: 290
```

```
Gly Ile Asp Pro Glu Thr Gly Asp Thr Ala Tyr Asn Gln Asn Phe Lys
1               5                   10                  15

Gly

<210> SEQ ID NO 291
<211> LENGTH: 11
<212> TYPE: PRT
<213> ORGANISM: Artificial Sequence
<220> FEATURE:
<223> OTHER INFORMATION: Synthetic Construct

<400> SEQUENCE: 291

Tyr Gly Asn Leu Tyr Tyr Tyr Ala Met Asp Tyr
1               5                   10

<210> SEQ ID NO 292
<211> LENGTH: 12
<212> TYPE: PRT
<213> ORGANISM: Artificial Sequence
<220> FEATURE:
<223> OTHER INFORMATION: Synthetic Construct

<400> SEQUENCE: 292

Arg Ala Ser Ser Ser Val Ser Ser Ser Tyr Leu His
1               5                   10

<210> SEQ ID NO 293
<211> LENGTH: 7
<212> TYPE: PRT
<213> ORGANISM: Artificial Sequence
<220> FEATURE:
<223> OTHER INFORMATION: Synthetic Construct

<400> SEQUENCE: 293

Ser Thr Ser Asn Leu Ala Phe
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic Construct

<400> SEQUENCE: 294

Gln Gln Tyr Ser Gly Tyr Pro Leu Thr
1               5

<210> SEQ ID NO 295
<211> LENGTH: 8
<212> TYPE: PRT
<213> ORGANISM: Artificial Sequence
<220> FEATURE:
<223> OTHER INFORMATION: Synthetic Construct

<400> SEQUENCE: 295

Gly Tyr Thr Phe Thr Asp Tyr Glu
1               5

<210> SEQ ID NO 296
<211> LENGTH: 8
<212> TYPE: PRT
<213> ORGANISM: Artificial Sequence
<220> FEATURE:
<223> OTHER INFORMATION: Synthetic Construct

<400> SEQUENCE: 296
```

```
Ile Asp Pro Glu Thr Gly Asp Thr
1               5

<210> SEQ ID NO 297
<211> LENGTH: 13
<212> TYPE: PRT
<213> ORGANISM: Artificial Sequence
<220> FEATURE:
<223> OTHER INFORMATION: Synthetic Construct

<400> SEQUENCE: 297

Thr Asn Tyr Gly Asn Leu Tyr Tyr Tyr Ala Met Asp Tyr
1               5                   10

<210> SEQ ID NO 298
<211> LENGTH: 7
<212> TYPE: PRT
<213> ORGANISM: Artificial Sequence
<220> FEATURE:
<223> OTHER INFORMATION: Synthetic Construct

<400> SEQUENCE: 298

Ser Ser Val Ser Ser Ser Tyr
1               5

<210> SEQ ID NO 299
<211> LENGTH: 3
<212> TYPE: PRT
<213> ORGANISM: Artificial Sequence
<220> FEATURE:
<223> OTHER INFORMATION: Synthetic Construct

<400> SEQUENCE: 299

Ser Thr Ser
1

<210> SEQ ID NO 300
<211> LENGTH: 9
<212> TYPE: PRT
<213> ORGANISM: Artificial Sequence
<220> FEATURE:
<223> OTHER INFORMATION: Synthetic Construct

<400> SEQUENCE: 300

Gln Gln Tyr Ser Gly Tyr Pro Leu Thr
1               5

<210> SEQ ID NO 301
<211> LENGTH: 15
<212> TYPE: PRT
<213> ORGANISM: Artificial Sequence
<220> FEATURE:
<223> OTHER INFORMATION: Synthetic Construct

<400> SEQUENCE: 301

Lys Ala Ser Gln Ser Val Asp Tyr Ala Gly Asp Ser Tyr Leu Asn
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Synthetic Construct

<400> SEQUENCE: 302
```

```
Arg Ala Ser Gln Ser Val Asp Tyr Ala Gly Asp Ser Tyr Met Asn
1               5                   10                  15
```

<210> SEQ ID NO 303
<211> LENGTH: 15
<212> TYPE: PRT
<213> ORGANISM: Artificial Sequence
<220> FEATURE:
<223> OTHER INFORMATION: Synthetic Construct

<400> SEQUENCE: 303

```
Arg Ala Ser Gln Ser Val Asp Tyr Ala Gly Asp Ser Tyr Leu Ala
1               5                   10                  15
```

<210> SEQ ID NO 304
<211> LENGTH: 5
<212> TYPE: PRT
<213> ORGANISM: Artificial Sequence
<220> FEATURE:
<223> OTHER INFORMATION: Synthetic Construct

<400> SEQUENCE: 304

```
Ser Tyr Trp Ile His
1               5
```

<210> SEQ ID NO 305
<211> LENGTH: 17
<212> TYPE: PRT
<213> ORGANISM: Artificial Sequence
<220> FEATURE:
<223> OTHER INFORMATION: Synthetic Construct

<400> SEQUENCE: 305

```
Glu Ile Glu Pro Ser Ala Ser Tyr Thr Tyr Tyr Asn Gln Lys Phe Lys
1               5                   10                  15

Gly
```

<210> SEQ ID NO 306
<211> LENGTH: 15
<212> TYPE: PRT
<213> ORGANISM: Artificial Sequence
<220> FEATURE:
<223> OTHER INFORMATION: Synthetic Construct

<400> SEQUENCE: 306

```
Arg Ala Ser Gln Ser Val Asp Tyr Ala Gly Asp Ser Tyr Leu Asn
1               5                   10                  15
```

<210> SEQ ID NO 307
<211> LENGTH: 120
<212> TYPE: PRT
<213> ORGANISM: Artificial Sequence
<220> FEATURE:
<223> OTHER INFORMATION: Synthetic Construct

<400> SEQUENCE: 307

```
Gln Val Gln Leu Val Glu Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Glu Ile Asp Pro Ser Ala Ser Tyr Thr Tyr Tyr Asn Gln Lys Phe
    50                  55                  60
```

```
Lys Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Tyr Tyr Gly Asn Lys Tyr Phe Asp Val Trp Gly Pro
                100                 105                 110

Gly Thr Thr Val Thr Val Ser Ser
            115                 120
```

<210> SEQ ID NO 308
<211> LENGTH: 120
<212> TYPE: PRT
<213> ORGANISM: Artificial Sequence
<220> FEATURE:
<223> OTHER INFORMATION: Synthetic Construct

<400> SEQUENCE: 308

```
Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Glu Ile Asp Pro Ser Ala Ser Tyr Thr Tyr Tyr Asn Gln Lys Phe
        50                  55                  60

Lys Gly Arg Val Thr Met Thr Arg Asp Lys Ser Ile Ser Thr Ala Tyr
65                  70                  75                  80

Met Glu Leu Asn Ser Leu Thr Ser Asp Asp Ser Ala Val Tyr Tyr Cys
                85                  90                  95

Ala Arg Ser Val Tyr Tyr Gly Asn Lys Tyr Phe Asp Val Trp Gly Ala
                100                 105                 110

Gly Thr Thr Val Thr Val Ser Ser
            115                 120
```

<210> SEQ ID NO 309
<211> LENGTH: 120
<212> TYPE: PRT
<213> ORGANISM: Artificial Sequence
<220> FEATURE:
<223> OTHER INFORMATION: Synthetic Construct

<400> SEQUENCE: 309

```
Gln Val Gln Leu Val Gln Ser Gly Ala Glu Val Arg Lys Pro Gly Ala
1                   5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Val
            35                  40                  45

Gly Glu Ile Asp Pro Ser Ala Ser Tyr Thr Tyr Tyr Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Asp Val Tyr Tyr Cys
                85                  90                  95

Ala Arg Ser Val Tyr Tyr Gly Asn Lys Tyr Phe Asp Val Trp Gly Gln
                100                 105                 110

Gly Thr Thr Val Thr Val Ser Ser
            115                 120
```

```
<210> SEQ ID NO 310
<211> LENGTH: 120
<212> TYPE: PRT
<213> ORGANISM: Artificial Sequence
<220> FEATURE:
<223> OTHER INFORMATION: Synthetic Construct

<400> SEQUENCE: 310

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
        35                  40                  45

Gly Glu Ile Asp Pro Ser Ala Ser Tyr Thr Tyr Tyr Asn Gln Lys Phe
    50                  55                  60

Lys Gly Arg Val Thr Met Thr Arg Asp Lys Ser Ser Ser Thr Val Tyr
65                  70                  75                  80

Met Glu Leu Ser Ser Leu Thr Ser Glu Asp Ser Ala Val Tyr Tyr Cys
                85                  90                  95

Ala Arg Ser Val Tyr Tyr Gly Asn Lys Tyr Phe Asp Val Trp Gly Ala
                100                 105                 110

Gly Thr Thr Val Thr Val Ser Ser
        115                 120

<210> SEQ ID NO 311
<211> LENGTH: 120
<212> TYPE: PRT
<213> ORGANISM: Artificial Sequence
<220> FEATURE:
<223> OTHER INFORMATION: Synthetic Construct

<400> SEQUENCE: 311

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Ser Tyr
                20                  25                  30

Trp Ile His Trp Val Arg Gln Ala Pro Gly Gln Gly Leu Glu Trp Ile
        35                  40                  45

Gly Glu Ile Glu Pro Ser Ala Ser Tyr Thr Tyr Tyr Asn Gln Lys Phe
    50                  55                  60

Lys Gly Arg Val Thr Met Thr Arg Asp Lys Ser Ser Ser Thr Val Tyr
65                  70                  75                  80

Met Glu Leu Ser Ser Leu Thr Ser Glu Asp Ser Ala Val Tyr Tyr Cys
                85                  90                  95

Ala Arg Ser Val Tyr Tyr Gly Asn Lys Tyr Phe Asp Val Trp Gly Ala
                100                 105                 110

Gly Thr Thr Val Thr Val Ser Ser
        115                 120

<210> SEQ ID NO 312
<211> LENGTH: 120
<212> TYPE: PRT
<213> ORGANISM: Artificial Sequence
<220> FEATURE:
<223> OTHER INFORMATION: Synthetic Construct

<400> SEQUENCE: 312
```

-continued

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Glu Ile Asp Pro Ser Ala Ser Tyr Thr Tyr Tyr Asn Gln Lys Phe
        50                  55                  60

Lys Gly Arg Val Thr Met Thr Arg Asp Lys Ser Thr Ser Thr Val Tyr
65                  70                  75                  80

Met Gln Leu Ser Ser Leu Thr Ser Glu Asp Thr Ala Val Tyr Tyr Cys
                85                  90                  95

Ala Arg Ser Val Tyr Tyr Gly Asn Lys Tyr Phe Asp Val Trp Gly Ala
            100                 105                 110

Gly Thr Thr Val Thr Val Ser Ser
            115                 120
```

<210> SEQ ID NO 313
<211> LENGTH: 111
<212> TYPE: PRT
<213> ORGANISM: Artificial Sequence
<220> FEATURE:
<223> OTHER INFORMATION: Synthetic Construct

<400> SEQUENCE: 313

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Ala
                20                  25                  30

Gly Asp Ser Tyr Leu Asn Trp Tyr Gln Gln Lys Pro Gly Gln Pro Pro
            35                  40                  45

Lys Leu Leu Ile Tyr Ala Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Asn
                85                  90                  95

Glu Asp Pro Arg Thr Phe Gly Gly Gly Thr Lys Val Glu Ile Lys
            100                 105                 110
```

<210> SEQ ID NO 314
<211> LENGTH: 111
<212> TYPE: PRT
<213> ORGANISM: Artificial Sequence
<220> FEATURE:
<223> OTHER INFORMATION: Synthetic Construct

<400> SEQUENCE: 314

```
Asp Ile Val Leu Thr Gln Ser Pro Ser Ser Leu Ser Ala Ser Val Gly
1               5                   10                  15

Gln Arg Val Thr Ile Thr Cys Arg Ala Ser Gln Ser Val Asp Tyr Ala
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
        50                  55                  60

Arg Phe Ser Gly Ser Gly Ser Gly Thr Asp Phe Thr Leu Thr Val Ser
65                  70                  75                  80
```

```
Ser Leu Glu Asp Glu Asp Phe Ala Thr Tyr Tyr Cys Gln Gln Thr Asn
                85                  90                  95

Glu Asp Pro Arg Thr Phe Gly Gly Gly Thr Lys Val Glu Ile Lys
            100                 105                 110

<210> SEQ ID NO 315
<211> LENGTH: 111
<212> TYPE: PRT
<213> ORGANISM: Artificial Sequence
<220> FEATURE:
<223> OTHER INFORMATION: Synthetic Construct

<400> SEQUENCE: 315

Glu Ile Val Leu Thr Gln Ser Pro Ala Thr Leu Ser Leu Ser Pro Gly
1               5                   10                  15

Gln Arg Ala Thr Leu Ser Cys Arg Ala Ser Gln Ser Val Asp Tyr Ala
            20                  25                  30

Gly Asp Ser Tyr Leu Ala Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Arg
65                  70                  75                  80

Pro Leu Glu Glu Glu Asp Ala Ala Val Tyr Tyr Cys Gln Gln Thr Asn
                85                  90                  95

Glu Asp Pro Arg Thr Phe Gly Gly Gly Thr Lys Leu Glu Ile Lys
            100                 105                 110

<210> SEQ ID NO 316
<211> LENGTH: 111
<212> TYPE: PRT
<213> ORGANISM: Artificial Sequence
<220> FEATURE:
<223> OTHER INFORMATION: Synthetic Construct

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Ala
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Asp Glu Asp Phe Ala Thr Tyr Tyr Cys Gln Gln Thr Asn
                85                  90                  95

Glu Asp Pro Arg Thr Phe Gly Gly Gly Thr Lys Leu Glu Ile Lys
            100                 105                 110

<210> SEQ ID NO 317
<211> LENGTH: 111
<212> TYPE: PRT
<213> ORGANISM: Artificial Sequence
<220> FEATURE:
<223> OTHER INFORMATION: Synthetic Construct

<400> SEQUENCE: 317
```

```
Asp Ile Val Leu Thr Gln Ser Pro Ser Ser Leu Ser Ala Ser Val Gly
1               5                   10                  15

Gln Arg Val Thr Ile Thr Cys Arg Ala Ser Gln Ser Val Asp Tyr Ala
            20                  25                  30

Gly Asp Ser Tyr Leu Asn Trp Tyr Gln Gln Lys Pro Gly Lys Ala Pro
        35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Glu Asp Glu Asp Phe Ala Thr Tyr Tyr Cys Gln Gln Thr Asn
                85                  90                  95

Glu Asp Pro Arg Thr Phe Gly Gly Gly Thr Lys Leu Glu Ile Lys
            100                 105                 110
```

<210> SEQ ID NO 318
<211> LENGTH: 111
<212> TYPE: PRT
<213> ORGANISM: Artificial Sequence
<220> FEATURE:
<223> OTHER INFORMATION: Synthetic Construct

<400> SEQUENCE: 318

```
Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Ser Val Asp Tyr Ala
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Asn
                85                  90                  95

Glu Asp Pro Arg Thr Phe Gly Gly Gly Thr Lys Leu Glu Ile Lys
            100                 105                 110
```

<210> SEQ ID NO 319
<211> LENGTH: 120
<212> TYPE: PRT
<213> ORGANISM: Artificial Sequence
<220> FEATURE:
<223> OTHER INFORMATION: Synthetic Construct

<400> SEQUENCE: 319

```
Gln Val Gln Leu Val Gln Ser Gly Ala Glu Met Val Lys Pro Gly Ala
1               5                   10                  15

Ser Val Lys Ile Ser Cys Lys Ala Ser Gly Tyr Thr Phe Thr Asp Tyr
            20                  25                  30

Glu Met His Trp Val Arg Gln Thr Pro Val Tyr Gly Leu Glu Trp Ile
        35                  40                  45

Gly Gly Ile Asp Pro Glu Thr Gly Asp Thr Ala Tyr Asn Gln Asn Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95
```

```
Thr Asn Tyr Gly Asn Leu Tyr Tyr Tyr Ala Met Asp Tyr Trp Gly Gln
            100                 105                 110

Gly Thr Leu Val Thr Val Ser Ser
        115                 120

<210> SEQ ID NO 320
<211> LENGTH: 120
<212> TYPE: PRT
<213> ORGANISM: Artificial Sequence
<220> FEATURE:
<223> OTHER INFORMATION: Synthetic Construct

<400> SEQUENCE: 320

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Thr Pro Val Tyr Gly Leu Glu Trp Met
        35                  40                  45

Gly Gly Ile Asp Pro Glu Thr Gly Asp Thr Ala Tyr Asn Gln Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Asn Tyr Gly Asn Leu Tyr Tyr Tyr Ala Met Asp Tyr Trp Gly Gln
            100                 105                 110

Gly Thr Thr Val Thr Val Ser Ser
        115                 120

<210> SEQ ID NO 321
<211> LENGTH: 120
<212> TYPE: PRT
<213> ORGANISM: Artificial Sequence
<220> FEATURE:
<223> OTHER INFORMATION: Synthetic Construct

<400> SEQUENCE: 321

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Gly Ile Asp Pro Glu Thr Gly Asp Thr Ala Tyr Asn Gln Asn Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Thr Ser Asp Asp Thr Ala Val Tyr Tyr Cys
                85                  90                  95

Thr Asn Tyr Gly Asn Leu Tyr Tyr Tyr Ala Met Asp Tyr Trp Gly Gln
            100                 105                 110

Gly Thr Ser Val Thr Val Ser Ser
        115                 120

<210> SEQ ID NO 322
<211> LENGTH: 108
<212> TYPE: PRT
```

-continued

```
<213> ORGANISM: Artificial Sequence
<220> FEATURE:
<223> OTHER INFORMATION: Synthetic Construct

<400> SEQUENCE: 322

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Ser Gly Ala Ser Pro Arg Leu Leu
        35                  40                  45

Ile Tyr Ser Thr Ser Asn Leu Ala Phe Gly Ile Pro Ala Arg Phe Ser
    50                  55                  60

Gly Ser Gly Ser Gly Thr Asp Tyr Thr Leu Thr Ile Ser Ser Leu Glu
65                  70                  75                  80

Ala Glu Asp Val Ala Val Tyr Tyr Cys Gln Gln Tyr Ser Gly Tyr Pro
                85                  90                  95

Leu Thr Phe Gly Gly Gly Thr Lys Val Glu Ile Lys
            100                 105

<210> SEQ ID NO 323
<211> LENGTH: 108
<212> TYPE: PRT
<213> ORGANISM: Artificial Sequence
<220> FEATURE:
<223> OTHER INFORMATION: Synthetic Construct

<400> SEQUENCE: 323

Glu Ile Val Met Thr Gln Ser Pro Ala Thr Leu Ser Val Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Ser Gly Ala Ser Pro Arg Leu Trp
        35                  40                  45

Ile Tyr Ser Thr Ser Asn Leu Ala Phe Gly Ile Pro Ala Arg Phe Ser
    50                  55                  60

Gly Ser Gly Ser Gly Thr Glu Tyr Thr Leu Thr Ile Ser Ser Leu Gln
65                  70                  75                  80

Ser Glu Asp Phe Ala Ala Tyr Tyr Cys Gln Gln Tyr Ser Gly Tyr Pro
                85                  90                  95

Leu Thr Phe Gly Gly Gly Thr Lys Val Glu Ile Lys
            100                 105

<210> SEQ ID NO 324
<211> LENGTH: 108
<212> TYPE: PRT
<213> ORGANISM: Artificial Sequence
<220> FEATURE:
<223> OTHER INFORMATION: Synthetic Construct

<400> SEQUENCE: 324

Glu Ile Val Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Phe Gly Val Pro Ser Arg Phe Ser
    50                  55                  60
```

```
Gly Ser Gly Ser Gly Thr Ser Tyr Thr Phe Thr Ile Ser Ser Leu Gln
65                  70                  75                  80

Pro Glu Asp Ile Ala Thr Tyr Tyr Cys Gln Gln Tyr Ser Gly Tyr Pro
                85                  90                  95

Leu Thr Phe Gly Ser Gly Thr Lys Leu Glu Ile Lys
            100                 105

<210> SEQ ID NO 325
<211> LENGTH: 203
<212> TYPE: PRT
<213> ORGANISM: Artificial Sequence
<220> FEATURE:
<223> OTHER INFORMATION: Synthetic Construct

<400> SEQUENCE: 325

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His
        195                 200

<210> SEQ ID NO 326
<211> LENGTH: 10
<212> TYPE: PRT
<213> ORGANISM: Artificial Sequence
<220> FEATURE:
<223> OTHER INFORMATION: Synthetic Construct

<400> SEQUENCE: 326

Gly Tyr Thr Phe Thr Asn Tyr Gly Met Asn
1               5                   10

<210> SEQ ID NO 327
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 327

Trp Ile Asn Thr Tyr Thr Gly Glu Pro Thr Tyr Ala Ala Asp Phe Lys
1               5                   10                  15

Arg

<210> SEQ ID NO 328
<211> LENGTH: 14
<212> TYPE: PRT
<213> ORGANISM: Artificial Sequence
<220> FEATURE:
<223> OTHER INFORMATION: Synthetic Construct

<400> SEQUENCE: 328

Tyr Pro His Tyr Tyr Gly Ser Ser His Trp Tyr Phe Asp Val
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Synthetic Construct

<400> SEQUENCE: 329

Ser Ala Ser Gln Asp Ile Ser Asn Tyr Leu Asn
1               5                   10

<210> SEQ ID NO 330
<211> LENGTH: 7
<212> TYPE: PRT
<213> ORGANISM: Artificial Sequence
<220> FEATURE:
<223> OTHER INFORMATION: Synthetic Construct

<400> SEQUENCE: 330

Phe Thr Ser Ser Leu His Ser
1               5

<210> SEQ ID NO 331
<211> LENGTH: 9
<212> TYPE: PRT
<213> ORGANISM: Artificial Sequence
<220> FEATURE:
<223> OTHER INFORMATION: Synthetic Construct

<400> SEQUENCE: 331

Gln Gln Tyr Ser Thr Val Pro Trp Thr
1               5

<210> SEQ ID NO 332
<211> LENGTH: 5
<212> TYPE: PRT
<213> ORGANISM: Artificial Sequence
<220> FEATURE:
<223> OTHER INFORMATION: Synthetic Construct

<400> SEQUENCE: 332

Ser Tyr Ser Met Asn
1               5

<210> SEQ ID NO 333
<211> LENGTH: 17
<212> TYPE: PRT
<213> ORGANISM: Artificial Sequence
<220> FEATURE:

<223> OTHER INFORMATION: Synthetic Construct

<400> SEQUENCE: 333

Ser Ile Ser Ser Ser Ser Ser Tyr Ile Tyr Tyr Ala Asp Ser Val Lys
1               5                   10                  15

Gly

<210> SEQ ID NO 334
<211> LENGTH: 7
<212> TYPE: PRT
<213> ORGANISM: Artificial Sequence
<220> FEATURE:
<223> OTHER INFORMATION: Synthetic Construct

<400> SEQUENCE: 334

Val Thr Asp Ala Phe Asp Ile
1               5

<210> SEQ ID NO 335
<211> LENGTH: 11
<212> TYPE: PRT
<213> ORGANISM: Artificial Sequence
<220> FEATURE:
<223> OTHER INFORMATION: Synthetic Construct

<400> SEQUENCE: 335

Arg Ala Ser Gln Gly Ile Asp Asn Trp Leu Gly
1               5                   10

<210> SEQ ID NO 336
<211> LENGTH: 7
<212> TYPE: PRT
<213> ORGANISM: Artificial Sequence
<220> FEATURE:
<223> OTHER INFORMATION: Synthetic Construct

<400> SEQUENCE: 336

Asp Ala Ser Asn Leu Asp Thr
1               5

<210> SEQ ID NO 337
<211> LENGTH: 9
<212> TYPE: PRT
<213> ORGANISM: Artificial Sequence
<220> FEATURE:
<223> OTHER INFORMATION: Synthetic Construct

<400> SEQUENCE: 337

Gln Gln Ala Lys Ala Phe Pro Pro Thr
1               5

<210> SEQ ID NO 338
<211> LENGTH: 7
<212> TYPE: PRT
<213> ORGANISM: Artificial Sequence
<220> FEATURE:
<223> OTHER INFORMATION: Synthetic Construct

<400> SEQUENCE: 338

Gly Ser Asp Lys Thr His Thr
1               5

<210> SEQ ID NO 339
<211> LENGTH: 98
<212> TYPE: PRT
<213> ORGANISM: Artificial Sequence -continued

```
<220> FEATURE:
<223> OTHER INFORMATION: Synthetic Construct

<400> SEQUENCE: 339

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 340
<211> LENGTH: 232
<212> TYPE: PRT
<213> ORGANISM: Artificial Sequence
<220> FEATURE:
<223> OTHER INFORMATION: Synthetic Construct

<400> SEQUENCE: 340

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

<210> SEQ ID NO 341
<211> LENGTH: 107
<212> TYPE: PRT
<213> ORGANISM: Homo sapiens

<400> SEQUENCE: 341

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 342
<211> LENGTH: 660
<212> TYPE: PRT
<213> ORGANISM: Artificial Sequence
<220> FEATURE:
<223> OTHER INFORMATION: Synthetic Construct

<400> SEQUENCE: 342

Gln Val Gln Leu Gln Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val Tyr Gly Leu Glu Trp Ile
        35                  40                  45

Gly Gly Ile Asp Pro Glu Thr Gly Asp Thr Ala Tyr Asn Gln Asn Phe
    50                  55                  60

Lys Gly Lys Ala Thr Leu Thr Ala Asp Lys Ser Ser Ser Ala Ala Tyr
65                  70                  75                  80

Met Glu Leu Arg Ser Leu Thr Ser Glu Asp Ser Ala Val Tyr Tyr Cys
                85                  90                  95

Thr Asn Tyr Gly Asn Leu Tyr Tyr Tyr Ala Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

-continued

```
Pro Ser Asn Thr Lys Val Asp Lys Lys Val Glu Pro Lys Ser Cys Asp
    210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
            355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
    435             440             445

Gly Lys Gly Ser Asp Lys Thr His Thr Ser Asp Thr Gly Arg Pro Phe
    450             455             460

Val Glu Met Tyr Ser Glu Ile Pro Glu Ile Ile His Met Thr Glu Gly
465             470             475             480

Arg Glu Leu Val Ile Pro Cys Arg Val Thr Ser Pro Asn Ile Thr Val
            485             490             495

Thr Leu Lys Lys Phe Pro Leu Asp Thr Leu Ile Pro Asp Gly Lys Arg
            500             505             510

Ile Ile Trp Asp Ser Arg Lys Gly Phe Ile Ile Ser Asn Ala Thr Tyr
            515             520             525

Lys Glu Ile Gly Leu Leu Thr Cys Glu Ala Thr Val Asn Gly His Leu
    530             535             540

Tyr Lys Thr Asn Tyr Leu Thr His Arg Gln Thr Asn Thr Ile Ile Asp
545             550             555             560

Val Val Leu Ser Pro Ser His Gly Ile Glu Leu Ser Val Gly Glu Lys
            565             570             575

Leu Val Leu Asn Cys Thr Ala Arg Thr Glu Leu Asn Val Gly Ile Asp
            580             585             590

Phe Asn Trp Glu Tyr Pro Ser Ser Lys His Gln His Lys Lys Leu Val
            595             600             605

Asn Arg Asp Leu Lys Thr Gln Ser Gly Ser Glu Met Lys Lys Phe Leu
    610             615             620

Ser Thr Leu Thr Ile Asp Gly Val Thr Arg Ser Asp Gln Gly Leu Tyr
```

-continued

```
625              630              635              640

Thr Cys Ala Ala Ser Ser Gly Leu Met Thr Lys Lys Asn Ser Thr Phe
                645              650              655

Val Arg Val His
        660
```

<210> SEQ ID NO 343
<211> LENGTH: 215
<212> TYPE: PRT
<213> ORGANISM: Artificial Sequence
<220> FEATURE:
<223> OTHER INFORMATION: Synthetic Construct

<400> SEQUENCE: 343

```
Glu Asn Val Leu Thr Gln Ser Pro Ala Ile Met Ser Ala Ser Pro Gly
1               5               10              15

Glu Lys Val Thr Met Thr Cys Arg Ala Ser Ser Ser Val Ser Ser Ser
                20              25              30

Tyr Leu His Trp Tyr Gln Gln Lys Ser Gly Ala Ser Pro Lys Leu Trp
        35              40              45

Ile Tyr Ser Thr Ser Asn Leu Ala Phe Gly Val Pro Ala Arg Phe Ser
        50              55              60

Gly Ser Gly Ser Gly Thr Ser Tyr Ser Leu Thr Ile Ser Ser Val Glu
65              70              75              80

Ala Glu Asp Ala Ala Thr Tyr Tyr Cys Gln Gln Tyr Ser Gly Tyr Pro
                85              90              95

Leu Thr Phe Gly Ser Gly Thr Lys Leu Glu Ile Lys Arg Thr Val Ala
                100             105             110

Ala Pro Ser Val Phe Ile Phe Pro Pro Ser Asp Glu Gln Leu Lys Ser
        115             120             125

Gly Thr Ala Ser Val Val Cys Leu Leu Asn Asn Phe Tyr Pro Arg Glu
        130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
                165             170             175

Ser Ser Thr Leu Thr Leu Ser Lys Ala Asp Tyr Glu Lys His Lys Val
                180             185             190

Tyr Ala Cys Glu Val Thr His Gln Gly Leu Ser Ser Pro Val Thr Lys
        195             200             205

Ser Phe Asn Arg Gly Glu Cys
    210             215
```

<210> SEQ ID NO 344
<211> LENGTH: 19
<212> TYPE: PRT
<213> ORGANISM: Artificial Sequence
<220> FEATURE:
<223> OTHER INFORMATION: Synthetic Construct

<400> SEQUENCE: 344

```
Met Gly Trp Thr Leu Val Phe Leu Phe Leu Leu Ser Val Thr Ala Gly
1               5               10              15

Val His Ser
```

<210> SEQ ID NO 345
<211> LENGTH: 20
<212> TYPE: PRT

-continued

<213> ORGANISM: Artificial Sequence
<220> FEATURE:
<223> OTHER INFORMATION: Synthetic Construct
<400> SEQUENCE: 345

Met Val Ser Ser Ala Gln Phe Leu Gly Leu Leu Leu Leu Cys Phe Gln
1               5                   10                  15

Gly Thr Arg Cys
            20

<210> SEQ ID NO 346
<211> LENGTH: 19
<212> TYPE: PRT
<213> ORGANISM: Artificial Sequence
<220> FEATURE:
<223> OTHER INFORMATION: Synthetic Construct
<400> SEQUENCE: 346

Met Gly Trp Ser Cys Ile Ile Leu Phe Leu Val Ala Thr Ala Thr Gly
1               5                   10                  15

Val His Ser

<210> SEQ ID NO 347
<211> LENGTH: 118
<212> TYPE: PRT
<213> ORGANISM: Artificial Sequence
<220> FEATURE:
<223> OTHER INFORMATION: Synthetic Construct
<400> SEQUENCE: 347

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Tyr
            20                  25                  30

Trp Leu Asn Trp Val Arg Gln Ala Pro Gly Gln Gly Leu Glu Trp Phe
        35                  40                  45

Gly Arg Ile Tyr Pro Gly Asp Gly Asp Thr Asp Tyr Asn Gly Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Val Arg Gly Asp Gly Tyr Trp Ala Met Asp Tyr Trp Gly Gln Gly Thr
            100                 105                 110

Thr Val Thr Val Ser Ser
        115

<210> SEQ ID NO 348
<211> LENGTH: 118
<212> TYPE: PRT
<213> ORGANISM: Artificial Sequence
<220> FEATURE:
<223> OTHER INFORMATION: Synthetic Construct
<400> SEQUENCE: 348

Gln Val Gln Leu Val Gln Ser Gly Ala Glu Val Val Lys Ser Gly Ala
1               5                   10                  15

Ser Val Lys Val Ser Cys Lys Ala Ser Gly Tyr Ala Phe Ser Ser Tyr
            20                  25                  30

Trp Leu Asn Trp Val Arg Gln Ala Pro Gly Gln Gly Leu Glu Trp Phe
        35                  40                  45

```
Gly Arg Ile Tyr Pro Gly Asp Gly Asp Thr Asp Tyr Asn Gly Lys Phe
    50                  55                  60

Lys Gly Arg Val Thr Leu Ile Arg Asp Thr Ser Thr Ser Thr Val Tyr
65                  70                  75                  80

Met Glu Leu Thr Ser Leu Thr Ser Glu Asp Thr Ala Val Tyr Tyr Cys
                85                  90                  95

Val Arg Gly Asp Gly Tyr Trp Ala Met Asp Tyr Trp Gly Gln Gly Thr
            100                 105                 110

Leu Val Thr Val Ser Ser
        115
```

<210> SEQ ID NO 349
<211> LENGTH: 118
<212> TYPE: PRT
<213> ORGANISM: Artificial Sequence
<220> FEATURE:
<223> OTHER INFORMATION: Synthetic Construct

<400> SEQUENCE: 349

```
Gln Val Gln Leu Val Gln Ser Gly Pro Glu Val Lys Lys Pro Gly Glu
1               5                   10                  15

Ser Leu Lys Ile Ser Cys Lys Ala Ser Gly Tyr Ala Phe Ser Ser Tyr
                20                  25                  30

Trp Leu Asn Trp Val Arg Gln Met Pro Gly Lys Gly Leu Glu Trp Met
            35                  40                  45

Gly Arg Ile Tyr Pro Gly Asp Gly Asp Thr Asp Tyr Asn Gly Lys Phe
    50                  55                  60

Lys Gly Gln Val Thr Ile Ser Ala Asp Lys Ser Ser Gly Thr Ala Tyr
65                  70                  75                  80

Leu Gln Leu Ser Ser Leu Lys Ala Ser Asp Thr Ala Val Tyr Phe Cys
                85                  90                  95

Val Arg Gly Asp Gly Tyr Trp Ala Met Asp Tyr Trp Gly Gln Gly Thr
            100                 105                 110

Leu Val Thr Val Ser Ser
        115
```

<210> SEQ ID NO 350
<211> LENGTH: 112
<212> TYPE: PRT
<213> ORGANISM: Artificial Sequence
<220> FEATURE:
<223> OTHER INFORMATION: Synthetic Construct

<400> SEQUENCE: 350

```
Asp Ile Val Met Thr Gln Ser Pro Leu Ser Leu Pro Val Thr Pro Gly
1               5                   10                  15

Glu Pro Ala Ser Ile Ser Cys Arg Phe Ser Gln Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
```

-continued

```
                100              105              110
```

```
<210> SEQ ID NO 351
<211> LENGTH: 112
<212> TYPE: PRT
<213> ORGANISM: Artificial Sequence
<220> FEATURE:
<223> OTHER INFORMATION: Synthetic Construct

<400> SEQUENCE: 351

Asp Ile Val Met Thr Gln Thr Pro Leu Ser Leu Pro Val Thr Pro Gly
1               5                   10                  15

Glu Pro Ala Ser Ile Ser Cys Arg Phe Ser Gln Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Thr Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

<210> SEQ ID NO 352
<211> LENGTH: 112
<212> TYPE: PRT
<213> ORGANISM: Artificial Sequence
<220> FEATURE:
<223> OTHER INFORMATION: Synthetic Construct

<400> SEQUENCE: 352

Asp Ile Val Met Thr Gln Ser Pro Asp Ser Leu Ala Val Ser Leu Gly
1               5                   10                  15

Glu Arg Ala Thr Ile Asn Cys Arg Phe Ser Lys Ser Leu Leu His Ser
            20                  25                  30

Asn Gly Ile Thr Tyr Leu Tyr Trp Tyr Gln Gln Lys Pro Gly Gln Pro
        35                  40                  45

Pro Lys Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

<210> SEQ ID NO 353
<211> LENGTH: 16
<212> TYPE: PRT
<213> ORGANISM: Artificial Sequence
<220> FEATURE:
<223> OTHER INFORMATION: Synthetic Construct

<400> SEQUENCE: 353

Arg Phe Ser Gln Ser Leu Leu His Ser Asn Gly Ile Thr Tyr Leu Tyr
1               5                   10                  15

<210> SEQ ID NO 354
```

-continued

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 354

Thr Met Ser Asn Leu Ala Ser
1               5

<210> SEQ ID NO 355
<211> LENGTH: 17
<212> TYPE: PRT
<213> ORGANISM: Artificial Sequence
<220> FEATURE:
<223> OTHER INFORMATION: Synthetic Construct

<400> SEQUENCE: 355

Lys Ser Ser Gln Ser Leu Leu Asn Ser Asn Asn Gln Lys Asn Tyr Leu
1               5                   10                  15

Ala

<210> SEQ ID NO 356
<211> LENGTH: 7
<212> TYPE: PRT
<213> ORGANISM: Artificial Sequence
<220> FEATURE:
<223> OTHER INFORMATION: Synthetic Construct

<400> SEQUENCE: 356

Phe Ala Ser Thr Arg Glu Ser
1               5

<210> SEQ ID NO 357
<211> LENGTH: 9
<212> TYPE: PRT
<213> ORGANISM: Artificial Sequence
<220> FEATURE:
<223> OTHER INFORMATION: Synthetic Construct

<400> SEQUENCE: 357

Gln Gln His Tyr Asn Thr Pro Leu Thr
1               5

<210> SEQ ID NO 358
<211> LENGTH: 17
<212> TYPE: PRT
<213> ORGANISM: Artificial Sequence
<220> FEATURE:
<223> OTHER INFORMATION: Synthetic Construct

<400> SEQUENCE: 358

Lys Ser Ser Gln Ser Leu Leu Asn Ser Asn Asn Gln Lys Asn Ser Leu
1               5                   10                  15

Ala

<210> SEQ ID NO 359
<211> LENGTH: 9
<212> TYPE: PRT
<213> ORGANISM: Artificial Sequence
<220> FEATURE:
<223> OTHER INFORMATION: Synthetic Construct

<400> SEQUENCE: 359

Gln Gln His Ser Asn Thr Pro Leu Thr
1               5
```

<210> SEQ ID NO 360
<211> LENGTH: 113
<212> TYPE: PRT
<213> ORGANISM: Artificial Sequence
<220> FEATURE:
<223> OTHER INFORMATION: Synthetic Construct

<400> SEQUENCE: 360

Glu Val Gln Leu Val Gln Ser Gly Ala Glu Val Lys Lys Pro Gly Thr
1               5                   10                  15

Thr Val Lys Ile Ala Cys Lys Val Ser Gly Tyr Thr Phe Thr Asp His
            20                  25                  30

Gly Ile His Trp Val Gln Gln Ala Pro Gly Lys Gly Leu Glu Trp Met
        35                  40                  45

Gly Asn Ile Ser Pro Gly Asn Gly Asp Ile Lys Tyr Asn Glu Lys Phe
    50                  55                  60

Lys Gly Arg Val Thr Leu Thr Ala Asp Lys Ser Ser Asp Thr Ala Tyr
65                  70                  75                  80

Met Glu Leu Asn Thr Leu Arg Ser Glu Asp Thr Ala Ile Tyr Phe Cys
                85                  90                  95

Thr Thr Tyr Phe Val Asp Trp Gly Arg Gly Thr Leu Val Thr Val Ser
            100                 105                 110

Ser

<210> SEQ ID NO 361
<211> LENGTH: 113
<212> TYPE: PRT
<213> ORGANISM: Artificial Sequence
<220> FEATURE:
<223> OTHER INFORMATION: Synthetic Construct

<400> SEQUENCE: 361

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Gly Ile His Trp Val Arg Gln Ala Pro Gly Arg Gly Leu Glu Trp Leu
        35                  40                  45

Gly Asn Ile Ser Pro Gly Asn Gly Asp Ile Lys Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Phe Cys
                85                  90                  95

Thr Thr Tyr Phe Val Asp Trp Gly Arg Gly Thr Leu Val Thr Val Ser
            100                 105                 110

Ser

<210> SEQ ID NO 362
<211> LENGTH: 113
<212> TYPE: PRT
<213> ORGANISM: Artificial Sequence
<220> FEATURE:
<223> OTHER INFORMATION: Synthetic Construct

<400> SEQUENCE: 362

Gln Val Gln Leu Leu Glu Ser Gly Ala Glu Ala Lys Lys Pro Gly Ala
1               5                   10                  15

-continued

```
Ser Val Lys Leu Ser Cys Lys Ala Ser Gly Tyr Thr Phe Thr Asp His
            20                  25                  30

Gly Ile His Trp Val His Gln Ala Pro Gly Gln Arg Leu Glu Trp Ile
            35                  40                  45

Gly Asn Ile Ser Pro Gly Asn Gly Asp Ile Lys Tyr Asn Glu Lys Phe
        50                  55                  60

Lys Gly Arg Val Thr Ile Thr Val Asp Lys Ser Ala Ser Thr Ala Tyr
65                  70                  75                  80

Met Glu Val Ser Ser Leu Arg Ser Glu Asp Thr Ala Val Tyr Phe Cys
                85                  90                  95

Thr Thr Tyr Phe Val Asp Trp Gly Arg Gly Thr Leu Val Thr Val Ser
            100                 105                 110

Ser
```

<210> SEQ ID NO 363
<211> LENGTH: 113
<212> TYPE: PRT
<213> ORGANISM: Artificial Sequence
<220> FEATURE:
<223> OTHER INFORMATION: Synthetic Construct

<400> SEQUENCE: 363

```
Asp Ile Val Met Thr Gln Ser Pro Ser Ser Leu Ala Val Ser Leu Gly
1               5                   10                  15

Glu Arg Ala Thr Leu Asn Cys Lys Ser Ser Gln Ser Leu Leu Asn Ser
            20                  25                  30

Asn Asn Gln Lys Asn Tyr Leu Ala Trp Tyr Gln Gln Lys Pro Gly Gln
            35                  40                  45

Pro Pro Lys Leu Leu Ile Tyr Phe Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Tyr Tyr Phe Cys Gln Gln
                85                  90                  95

His Tyr Asn Thr Pro Leu Thr Phe Gly Gln Gly Thr Lys Leu Glu Ile
            100                 105                 110

Lys
```

<210> SEQ ID NO 364
<211> LENGTH: 113
<212> TYPE: PRT
<213> ORGANISM: Artificial Sequence
<220> FEATURE:
<223> OTHER INFORMATION: Synthetic Construct

<400> SEQUENCE: 364

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Asn Asn Gln Lys Asn Ser Leu Ala Trp Tyr Gln Gln Lys Pro Gly Gln
            35                  40                  45

Ser Pro Lys Leu Leu Ile Tyr Phe Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80
```

-continued

Ile Ser Ser Leu Gln Ala Glu Asp Val Ala Tyr Tyr Phe Cys Gln Gln
                85                  90                  95

His Ser Asn Thr Pro Leu Thr Phe Gly Gly Gly Thr Lys Val Glu Ile
        100                 105                 110

Lys

<210> SEQ ID NO 365
<211> LENGTH: 113
<212> TYPE: PRT
<213> ORGANISM: Artificial Sequence
<220> FEATURE:
<223> OTHER INFORMATION: Synthetic Construct

<400> SEQUENCE: 365

Glu Ile Val Met Thr Gln Ser Pro Ala Thr Leu Ser Val Ser Pro Gly
1               5                   10                  15

Glu Arg Ala Thr Leu Ser Cys Lys Ser Ser Gln Ser Leu Leu Asn Ser
                20                  25                  30

Asn Asn Gln Lys Asn Cys Leu Ala Trp Tyr Gln Gln Lys Pro Gly Gln
        35                  40                  45

Ala Pro Arg Leu Leu Ile Tyr Phe Ala Ser Thr Arg Glu Ser Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Tyr Tyr Phe Cys Gln Gln
                85                  90                  95

His Cys Asn Thr Pro Leu Thr Phe Gly Gly Gly Thr Lys Val Glu Ile
        100                 105                 110

Lys

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

```
<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382
```

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393
<211> LENGTH: 121
<212> TYPE: PRT
<213> ORGANISM: Artificial Sequence
<220> FEATURE:
<223> OTHER INFORMATION: Synthetic Construct -continued

<400> SEQUENCE: 393

```
Gln Val Gln Leu Lys Gln Ser Gly Pro Gly Leu Val Gln Pro Ser Gln
1               5                   10                  15

Ser Leu Ser Ile Thr Cys Thr Val Ser Asp Phe Ser Leu Ser Ser Phe
                20                  25                  30

Gly Val Asn Trp Val Arg Gln Pro Pro Gly Lys Gly Leu Glu Trp Leu
            35                  40                  45

Gly Val Ile Trp Ser Gly Gly Ser Thr Asp Tyr Asn Val Ala Phe Ile
        50                  55                  60

Ser Arg Leu Ser Ile Ser Lys Asp Asn Ser Lys Ser Gln Val Phe Phe
65                  70                  75                  80

Lys Met Asn Asn Leu Gln Ala Asp Asp Thr Ala Ile Tyr Tyr Cys Ala
                85                  90                  95

Arg Asn Trp Arg Tyr Asp Gly Tyr Phe Tyr Ala Met Asp Tyr Trp Gly
                100                 105                 110

Gln Gly Thr Ser Val Thr Val Ser Ser
            115                 120
```

<210> SEQ ID NO 394
<211> LENGTH: 116
<212> TYPE: PRT
<213> ORGANISM: Artificial Sequence
<220> FEATURE:
<223> OTHER INFORMATION: Synthetic Construct

<400> SEQUENCE: 394

```
Asp Val Asn Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Asn Tyr
                20                  25                  30

Tyr Met Ser Trp Val Arg Gln Ser Pro Glu Lys Arg Leu Glu Trp Val
            35                  40                  45

Ala Thr Ile Ser Asn Asn Gly Asp Ser Thr Tyr Tyr Leu Asp Thr Val
        50                  55                  60

Lys Gly Arg Phe Thr Ile Ser Arg Asp Ser Ala Glu Asn Thr Leu Tyr
65                  70                  75                  80

Leu Gln Met Ser Ser Leu Ile Ser Glu Asp Thr Ala Val Tyr Tyr Cys
                85                  90                  95

Thr Arg Val Gly Thr Gly Phe Thr Tyr Trp Gly Gln Gly Thr Leu Val
                100                 105                 110

Thr Val Ser Ala
        115
```

<210> SEQ ID NO 395
<211> LENGTH: 121
<212> TYPE: PRT
<213> ORGANISM: Artificial Sequence
<220> FEATURE:
<223> OTHER INFORMATION: Synthetic Construct

<400> SEQUENCE: 395

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45
```

-continued

```
Gly Arg Val Asn Pro Asn Asn Gly Gly Lys Thr Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Arg Leu Arg Pro Val Asp Tyr Gly Met Asp Tyr Trp Gly
            100                 105                 110

Gln Gly Thr Ser Val Thr Val Ser Ser
        115                 120
```

<210> SEQ ID NO 396
<211> LENGTH: 113
<212> TYPE: PRT
<213> ORGANISM: Artificial Sequence
<220> FEATURE:
<223> OTHER INFORMATION: Synthetic Construct

<400> SEQUENCE: 396

```
Gln Val Gln Leu Gln Gln Ser Asp Ala Glu Leu Val Lys Pro Gly Thr
1               5                   10                  15

Ser Val Lys Ile Ser Cys Lys Ala Ser Gly Tyr Thr Phe Thr Asp His
                20                  25                  30

Gly Ile His Trp Val Lys Gln Arg Pro Glu Arg Gly Leu Glu Trp Ile
            35                  40                  45

Gly Asn Ile Ser Pro Gly Asn Gly Asp Ile Lys Tyr Asn Glu Lys Phe
    50                  55                  60

Lys Gly Lys Ala Thr Leu Thr Ala Asp Lys Ser Ser Ser Thr Val Tyr
65                  70                  75                  80

Met Gln Val Asn Ser Leu Thr Ser Glu Asp Ser Ala Val Tyr Phe Cys
                85                  90                  95

Thr Thr Tyr Phe Val Asp Trp Gly Arg Gly Thr Leu Val Thr Val Ser
            100                 105                 110

Ala
```

<210> SEQ ID NO 397
<211> LENGTH: 120
<212> TYPE: PRT
<213> ORGANISM: Artificial Sequence
<220> FEATURE:
<223> OTHER INFORMATION: Synthetic Construct

<400> SEQUENCE: 397

```
Glu Val Gln Leu Gln Gln Ser Gly Pro Glu Leu Val Asn Pro Gly Ala
1               5                   10                  15

Ser Val Lys Met Ser Cys Lys Ala Ser Gly Tyr Thr Phe Thr Ala Tyr
                20                  25                  30

Val Met His Trp Val Lys Gln Lys Pro Gly Gln Gly Leu Glu Trp Ile
            35                  40                  45

Gly Tyr Ile Phe Pro Tyr Asn Asp Gly Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Thr Asp Gly Asn Pro Tyr Thr Met Asp Tyr Trp Gly Gln
            100                 105                 110
```

-continued

```
Gly Thr Ser Val Thr Val Ser Ser
        115             120

<210> SEQ ID NO 398
<211> LENGTH: 120
<212> TYPE: PRT
<213> ORGANISM: Artificial Sequence
<220> FEATURE:
<223> OTHER INFORMATION: Synthetic Construct

<400> SEQUENCE: 398

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Ile
        35                  40                  45

Gly Tyr Ile Asn Pro Tyr Ser Asp Tyr Thr Gln Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Ser Cys
                85                  90                  95

Ala Arg Arg Ala Asp Gly Asn Pro Tyr Ala Met Asp Tyr Trp Gly Gln
            100                 105                 110

Gly Thr Ser Val Thr Val Ser Ser
        115             120

<210> SEQ ID NO 399
<211> LENGTH: 120
<212> TYPE: PRT
<213> ORGANISM: Artificial Sequence
<220> FEATURE:
<223> OTHER INFORMATION: Synthetic Construct

<400> SEQUENCE: 399

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Ala Ser Tyr Thr Tyr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Val Tyr Tyr Gly Asn Lys Tyr Phe Asp Val Trp Gly Ala
            100                 105                 110

Gly Thr Thr Val Thr Val Ser Ser
        115             120

<210> SEQ ID NO 400
<211> LENGTH: 116
<212> TYPE: PRT
<213> ORGANISM: Artificial Sequence
<220> FEATURE:
<223> OTHER INFORMATION: Synthetic Construct
```

-continued

<400> SEQUENCE: 400

```
Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Glu Ile Tyr Pro Gly Ser Asp Asp Ala Tyr Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Glu Thr Thr Ala Thr Ala Tyr Trp Gly Gln Gly Thr Leu Val
            100                 105                 110

Thr Val Ser Ala
        115
```

<210> SEQ ID NO 401
<211> LENGTH: 121
<212> TYPE: PRT
<213> ORGANISM: Artificial Sequence
<220> FEATURE:
<223> OTHER INFORMATION: Synthetic Construct

<400> SEQUENCE: 401

```
Gln Val Gln Leu Gln Gln Ser Gly Pro Asp Leu Val Lys Pro Gly Ala
1               5                   10                  15

Ser Val Lys Ile Ser Cys Lys Ala Ser Gly Tyr Ala Phe Ser Thr Tyr
            20                  25                  30

Trp Met Asn Trp Val Lys Gln Arg Pro Gly Lys Gly Leu Glu Trp Ile
        35                  40                  45

Gly Arg Ile Phe Pro Gly Asp Gly Asp Ala Asn Tyr Asn Gly Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Thr Gly Ala Ala Tyr Asp Phe Asp Pro Phe Pro Tyr Trp Gly
            100                 105                 110

Gln Gly Thr Leu Val Thr Val Ser Ala
        115                 120
```

<210> SEQ ID NO 402
<211> LENGTH: 121
<212> TYPE: PRT
<213> ORGANISM: Artificial Sequence
<220> FEATURE:
<223> OTHER INFORMATION: Synthetic Construct

<400> SEQUENCE: 402

```
Gln Val Gln Leu Gln Gln Ser Gly Pro Glu Leu Val Lys Pro Gly Ala
1               5                   10                  15

Ser Val Lys Ile Ser Cys Lys Gly Ser Gly Tyr Ala Phe Ser Thr Tyr
            20                  25                  30

Trp Met Asn Trp Val Lys Gln Arg Pro Gly Lys Gly Leu Glu Trp Ile
        35                  40                  45
```

-continued

```
Gly Arg Ile Phe Pro Gly Asp Gly Asp Thr Asp Tyr Asp Gly Lys Phe
    50                  55                  60

Lys Gly Lys Ala Thr Leu Thr Ala Asp Lys Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Thr Gly Ala Ala Tyr Glu Phe Asp Pro Phe Pro Tyr Trp Gly
                100                 105                 110

Gln Gly Thr Leu Val Thr Val Ser Ala
        115                 120

<210> SEQ ID NO 403
<211> LENGTH: 120
<212> TYPE: PRT
<213> ORGANISM: Artificial Sequence
<220> FEATURE:
<223> OTHER INFORMATION: Synthetic Construct

<400> SEQUENCE: 403

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Arg Ser
                20                  25                  30

Trp Met Asn Trp Val Lys Gln Arg Pro Gly Lys Gly Leu Glu Trp Ile
            35                  40                  45

Gly Trp Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Ala Tyr Phe Cys
                85                  90                  95

Ala Arg Ser Ala Thr Leu Pro Tyr Trp Tyr Phe Asp Val Trp Gly Ala
                100                 105                 110

Gly Thr Thr Val Thr Val Ser Ser
        115                 120

<210> SEQ ID NO 404
<211> LENGTH: 118
<212> TYPE: PRT
<213> ORGANISM: Artificial Sequence
<220> FEATURE:
<223> OTHER INFORMATION: Synthetic Construct

<400> SEQUENCE: 404

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Tyr
                20                  25                  30

Trp Leu Asn Trp Val Lys Gln Arg Pro Gly Lys Gly Leu Glu Trp Phe
            35                  40                  45

Gly Arg Ile Tyr Pro Gly Asp Gly Asp Thr Asp Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Arg Ser Leu Thr Ser Glu Asp Ser Ala Val Tyr Phe Cys
                85                  90                  95

Val Arg Gly Asp Gly Tyr Trp Ala Met Asp Tyr Trp Gly Gln Gly Thr
```

```
        100                 105                 110

Ser Val Thr Val Ser Ser
        115

<210> SEQ ID NO 405
<211> LENGTH: 115
<212> TYPE: PRT
<213> ORGANISM: Artificial Sequence
<220> FEATURE:
<223> OTHER INFORMATION: Synthetic Construct

<400> SEQUENCE: 405

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Arg Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Gly Ala Trp Phe Ala Tyr Trp Gly Gln Gly Thr Leu Val Thr
            100                 105                 110

Val Ser Ala
        115

<210> SEQ ID NO 406
<211> LENGTH: 121
<212> TYPE: PRT
<213> ORGANISM: Artificial Sequence
<220> FEATURE:
<223> OTHER INFORMATION: Synthetic Construct

<400> SEQUENCE: 406

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Gly Phe Asp Tyr Ser Asn Tyr Trp Phe Ala Tyr Trp Gly
            100                 105                 110

Gln Gly Thr Leu Val Thr Val Ser Ala
        115                 120

<210> SEQ ID NO 407
<211> LENGTH: 109
<212> TYPE: PRT
<213> ORGANISM: Artificial Sequence
<220> FEATURE:
```

-continued

<223> OTHER INFORMATION: Synthetic Construct

<400> SEQUENCE: 407

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Ser Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                85                  90                  95

His Phe Val Phe Gly Gly Gly Thr Lys Leu Thr Val Leu
            100                 105
```

<210> SEQ ID NO 408
<211> LENGTH: 107
<212> TYPE: PRT
<213> ORGANISM: Artificial Sequence
<220> FEATURE:
<223> OTHER INFORMATION: Synthetic Construct

<400> SEQUENCE: 408

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Asn Asn Tyr
            20                  25                  30

Leu His Trp Tyr Gln Gln Arg Ser His Glu Ser Pro Arg Leu Leu Ile
        35                  40                  45

Lys Phe Ala Ser Gln Ser Ile Ser Asp Ile Pro Ser Arg Phe Ser Gly
    50                  55                  60

Ser Gly Ser Gly Thr Asp Phe Thr Leu Ser Ile Asn Ser Ile Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105
```

<210> SEQ ID NO 409
<211> LENGTH: 112
<212> TYPE: PRT
<213> ORGANISM: Artificial Sequence
<220> FEATURE:
<223> OTHER INFORMATION: Synthetic Construct

<400> SEQUENCE: 409

```
Asp Ile Val Met Thr Gln Ala Ala Phe Ser Asn Pro Val Thr Leu Gly
1               5                   10                  15

Thr Ser Ala Ser Ile Ser Cys Ser Ser Ser Lys Ser Leu Leu His Ser
            20                  25                  30

Asn Gly Val Thr Tyr Leu Tyr Trp Tyr Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
```

-continued

```
65                  70                  75                  80

Ser Arg Val Glu Ala Glu Asp Val Gly Ile Tyr Tyr Cys Ala Gln Met
                85                  90                  95

Leu Glu Arg Pro Phe Thr Phe Gly Ser Gly Thr Lys Leu Glu Ile Lys
                100                 105                 110
```

<210> SEQ ID NO 410
<211> LENGTH: 112
<212> TYPE: PRT
<213> ORGANISM: Artificial Sequence
<220> FEATURE:
<223> OTHER INFORMATION: Synthetic Construct

<400> SEQUENCE: 410

```
Asp Ile Val Met Thr Gln Ala Ala Phe Ser Asn Pro Val Thr Leu Gly
1               5                   10                  15

Thr Ser Ala Ser Ile Ser Cys Ser Ser Thr Lys Ser Leu Leu His Ser
                20                  25                  30

Ser Gly Ile Thr Tyr Leu Tyr Trp Tyr Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Leu Glu Arg Pro Phe Thr Phe Gly Ser Gly Thr Lys Leu Glu Ile Lys
                100                 105                 110
```

<210> SEQ ID NO 411
<211> LENGTH: 112
<212> TYPE: PRT
<213> ORGANISM: Artificial Sequence
<220> FEATURE:
<223> OTHER INFORMATION: Synthetic Construct

<400> SEQUENCE: 411

```
Asp Ile Val Met Thr Gln Ala Ala Phe Ser Asn Pro Val Thr Leu Gly
1               5                   10                  15

Thr Ser Ala Ser Ile Ser Cys Arg Phe Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
                100                 105                 110
```

<210> SEQ ID NO 412
<211> LENGTH: 113
<212> TYPE: PRT
<213> ORGANISM: Artificial Sequence
<220> FEATURE:
<223> OTHER INFORMATION: Synthetic Construct

<400> SEQUENCE: 412

-continued

```
Asp Ile Val Met Thr Gln Ser Pro Ser Ser Leu Ala Met Ser Ile Gly
1               5                   10                  15

Gln Arg Val Thr Met Ser Cys Lys Ser Ser Gln Ser Leu Leu Asn Ser
                20                  25                  30

Asn Asn Gln Lys Asn Cys Leu Ala Trp Tyr Gln Gln Lys Pro Gly Gln
        35                  40                  45

Ser Pro Arg Leu Leu Ile Tyr Phe Ala Cys Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Tyr Tyr Phe Cys Gln Gln
                85                  90                  95

His Cys Asn Thr Pro Leu Thr Phe Gly Ala Gly Thr Lys Leu Glu Leu
            100                 105                 110

Lys

<210> SEQ ID NO 413
<211> LENGTH: 106
<212> TYPE: PRT
<213> ORGANISM: Artificial Sequence
<220> FEATURE:
<223> OTHER INFORMATION: Synthetic Construct

<400> SEQUENCE: 413

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Tyr Thr
                85                  90                  95

Phe Gly Gly Gly Thr Lys Leu Glu Ile Lys
            100                 105

<210> SEQ ID NO 414
<211> LENGTH: 107
<212> TYPE: PRT
<213> ORGANISM: Artificial Sequence
<220> FEATURE:
<223> OTHER INFORMATION: Synthetic Construct

<400> SEQUENCE: 414

Asp Ile Val Met Thr Gln Ser Gln Lys Phe Met Ser Thr Ser Thr Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Phe Ile Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80
```

```
Glu Asp Leu Ala Glu Tyr Phe Cys Gln Gln Tyr Asn Arg Asn Pro Ile
                85                  90                  95

Thr Phe Gly Ser Gly Thr Lys Leu Glu Ile Lys
            100                 105
```

```
<210> SEQ ID NO 415
<211> LENGTH: 107
<212> TYPE: PRT
<213> ORGANISM: Artificial Sequence
<220> FEATURE:
<223> OTHER INFORMATION: Synthetic Construct

<400> SEQUENCE: 415

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

His Ser Ala Ser Tyr Arg Tyr Thr Gly Val Pro Asp Arg Phe Thr Gly
    50                  55                  60

Arg Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Phe
                85                  90                  95

Thr Phe Gly Ser Gly Thr Lys Leu Glu Ile Lys
            100                 105
```

```
<210> SEQ ID NO 416
<211> LENGTH: 107
<212> TYPE: PRT
<213> ORGANISM: Artificial Sequence
<220> FEATURE:
<223> OTHER INFORMATION: Synthetic Construct

<400> SEQUENCE: 416

Asp Ile Val Met Thr Gln Ser His Lys Phe Met Ser Thr Ser Val Gly
1               5                   10                  15

Asp Arg Val Ser Thr Thr Cys Lys Ala Ser Gln Asp Val Ser Thr Ala
            20                  25                  30

Val Val Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Thr Ser Val Gln Ala
65                  70                  75                  80

Glu Asp Leu Ala Val Tyr Tyr Cys Gln Gln His Tyr Ser Thr Pro Phe
                85                  90                  95

Thr Phe Gly Ser Gly Thr Lys Leu Glu Ile Lys
            100                 105
```

```
<210> SEQ ID NO 417
<211> LENGTH: 107
<212> TYPE: PRT
<213> ORGANISM: Artificial Sequence
<220> FEATURE:
<223> OTHER INFORMATION: Synthetic Construct

<400> SEQUENCE: 417
```

-continued

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Asn Leu Ala Asp Gly Val Pro Ser Arg Phe Ser Gly
    50                  55                  60

Ser Gly Ser Gly Gln Asp Tyr Ser Leu Thr Ile Ser Ser Leu Gly Ser
65                  70                  75                  80

Asp Asp Thr Ala Thr Tyr Tyr Cys Leu Gln His Val Glu Ser Pro Trp
                85                  90                  95

Thr Phe Gly Gly Gly Thr Lys Leu Glu Ile Lys
            100                 105
```

```
<210> SEQ ID NO 418
<211> LENGTH: 106
<212> TYPE: PRT
<213> ORGANISM: Artificial Sequence
<220> FEATURE:
<223> OTHER INFORMATION: Synthetic Construct

<400> SEQUENCE: 418
```

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Leu Ile
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Gly Tyr Pro Pro Thr
                85                  90                  95

Phe Gly Gly Gly Thr Lys Leu Glu Ile Lys
            100                 105
```

```
<210> SEQ ID NO 419
<211> LENGTH: 111
<212> TYPE: PRT
<213> ORGANISM: Artificial Sequence
<220> FEATURE:
<223> OTHER INFORMATION: Synthetic Construct

<400> SEQUENCE: 419
```

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Ala
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Asn
                85                  90                  95
```

-continued

```
Glu Asp Pro Arg Thr Phe Gly Gly Gly Thr Lys Leu Glu Ile Lys
            100                 105                 110

<210> SEQ ID NO 420
<211> LENGTH: 111
<212> TYPE: PRT
<213> ORGANISM: Artificial Sequence
<220> FEATURE:
<223> OTHER INFORMATION: Synthetic Construct

<400> SEQUENCE: 420

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Phe Thr Phe Gly Ser Gly Thr Lys Leu Glu Ile Lys
            100                 105                 110

<210> SEQ ID NO 421
<211> LENGTH: 6
<212> TYPE: PRT
<213> ORGANISM: Artificial Sequence
<220> FEATURE:
<223> OTHER INFORMATION: Synthetic Construct

<400> SEQUENCE: 421

Ser Gly Thr Ser Thr Asp
1               5

<210> SEQ ID NO 422
<211> LENGTH: 6
<212> TYPE: PRT
<213> ORGANISM: Artificial Sequence
<220> FEATURE:
<223> OTHER INFORMATION: Synthetic Construct

<400> SEQUENCE: 422

Thr Gly Thr Ser Asp Ala
1               5
```

ANTI-CD93 CONSTRUCTS AND USES THEREOF

CROSS REFERENCE TO RELATED APPLICATIONS

This application is a national stage application under 35 U.S.C. § 371 of International Application No. PCT/US2021/035542, filed internationally on Jun. 2, 2021, which claims priority to U.S. provisional application 63/033,755, filed on Jun. 2, 2020, U.S. provisional application 63/058,359, filed on Jul. 29, 2020, and U.S. provisional application 63/084,474, filed on Sep. 28, 2020, the contents of which are incorporated by reference in their entirety for all purposes.

TECHNICAL FIELD

The present disclosure relates to anti-CD93 constructs (such as anti-CD93 antibodies) and the uses thereof.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 193852000200SEQLIST.TXT, date recorded: Nov. 22, 2022, size: 189,062 bytes).

BACKGROUND OF THE APPLICATION

CD93 (Cluster of Differentiation 93) is a protein that in humans is encoded by the CD93 gene. CD93 is a C-type lectin transmembrane receptor which plays a role not only in cell-cell adhesion processes but also in host defense. CD93 was initially thought to be a receptor for C1q, but now is thought to instead be involved in intercellular adhesion and in the clearance of apoptotic cells. The intracellular cytoplasmic tail of this protein contains two highly conserved domains which may be involved in CD93 function. Indeed, the highly charged juxtamembrane domain has been found to interact with moesin, a protein known to play a role in linking transmembrane proteins to the cytoskeleton and in the remodeling of the cytoskeleton. This process appears crucial for adhesion, migration and phagocytosis.

The disclosures of all publications, patents, patent applications and published patent applications referred to herein are hereby incorporated herein by reference in their entirety.

BRIEF SUMMARY OF THE APPLICATION

The following summary is illustrative only and is not intended to be limiting in any way. That is, the following summary is provided to introduce highlights, benefits and advantages of the novel molecules and the uses thereof. Thus, the following summary is not intended to identify essential features of the claimed subject matter, nor is it intended for use in determining the scope of the claimed subject matter.

In one aspect, the present application provides an anti-CD93 construct comprising an antibody moiety comprising a heavy chain variable region ($V_H$) and a light chain variable region ($V_L$), wherein the antibody moiety competes for a binding epitope of CD93 with an antibody or antibody fragment comprising a second heavy chain variable region ($V_{H-2}$) and a second light chain variable region ($V_L$-2), wherein:

a) the $V_{H-2}$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 3, and the $V_{L-2}$ comprises the LC-CDR1 comprising the amino acid sequence of SEQ ID NO: 4, the LC-CDR2 comprising the amino acid sequence of SEQ ID NO: 5, and the LC-CDR3 comprising the amino acid sequence of SEQ ID NO: 6;

b) the $V_{H-2}$ comprises the HC-CDR1 comprising the amino acid sequence of SEQ ID NO: 17, the HC-CDR2 comprising the amino acid sequence of SEQ ID NO: 18, and the HC-CDR3 comprising the amino acid sequence of SEQ ID NO: 19, and the $V_{L-2}$ comprises the LC-CDR1 comprising the amino acid sequence of SEQ ID NO: 20, the LC-CDR2 comprising the amino acid sequence of SEQ ID NO: 21, and the LC-CDR3 comprising the amino acid sequence of SEQ ID NO: 22;

c) the $V_{H-2}$ comprises the HC-CDR1 comprising the amino acid sequence of SEQ ID NO: 33, the HC-CDR2 comprising the amino acid sequence of SEQ ID NO: 34, and the HC-CDR3 comprising the amino acid sequence of SEQ ID NO: 35, and the $V_{L-2}$ comprises the LC-CDR1 comprising the amino acid sequence of SEQ ID NO: 36, the LC-CDR2 comprising the amino acid sequence of SEQ ID NO: 37, and the LC-CDR3 comprising the amino acid sequence of SEQ ID NO: 38;

d) the $V_{H-2}$ comprises the HC-CDR1 comprising the amino acid sequence of SEQ ID NO: 49, the HC-CDR2 comprising the amino acid sequence of SEQ ID NO: 50, and the HC-CDR3 comprising the amino acid sequence of SEQ ID NO: 51, and the $V_{L-2}$ comprises the LC-CDR1 comprising the amino acid sequence of SEQ ID NO: 52, the LC-CDR2 comprising the amino acid sequence of SEQ ID NO: 53, and the LC-CDR3 comprising the amino acid sequence of SEQ ID NO: 54;

e) the $V_{H-2}$ comprises the HC-CDR1 comprising the amino acid sequence of SEQ ID NO: 65, the HC-CDR2 comprising the amino acid sequence of SEQ ID NO: 66, and the HC-CDR3 comprising the amino acid sequence of SEQ ID NO: 67, and the $V_{L-2}$ comprises the LC-CDR1 comprising the amino acid sequence of SEQ ID NO: 68, the LC-CDR2 comprising the amino acid sequence of SEQ ID NO: 69, and the LC-CDR3 comprising the amino acid sequence of SEQ ID NO: 70;

f) the $V_{H-2}$ comprises the HC-CDR1 comprising the amino acid sequence of SEQ ID NO: 81, the HC-CDR2 comprising the amino acid sequence of SEQ ID NO: 82, and the HC-CDR3 comprising the amino acid sequence of SEQ ID NO: 83, and the $V_{L-2}$ comprises the LC-CDR1 comprising the amino acid sequence of SEQ ID NO: 84, the LC-CDR2 comprising the amino acid sequence of SEQ ID NO: 85, and the LC-CDR3 comprising the amino acid sequence of SEQ ID NO: 86;

g) the $V_{H-2}$ comprises the HC-CDR1 comprising the amino acid sequence of SEQ ID NO: 97, the HC-CDR2 comprising the amino acid sequence of SEQ ID NO: 98, and the HC-CDR3 comprising the amino acid sequence of SEQ ID NO: 99, and the $V_{L-2}$ comprises the LC-CDR1 comprising the amino acid sequence of SEQ ID NO: 100, the LC-CDR2 comprising the amino acid sequence of SEQ ID NO: 101, and the LC-CDR3 comprising the amino acid sequence of SEQ ID NO: 102;

h) the $V_{H-2}$ comprises the HC-CDR1 comprising the amino acid sequence of SEQ ID NO: 113, the HC-CDR2 comprising the amino acid sequence of SEQ ID NO: 114, and the HC-CDR3 comprising the amino acid sequence of SEQ ID NO: 115, and the $V_{L-2}$ comprises the LC-CDR1 comprising the amino acid sequence of SEQ ID NO: 116, the LC-CDR2 comprising the amino acid sequence of SEQ ID NO: 117, and the LC-CDR3 comprising the amino acid sequence of SEQ ID NO: 118;

i) the $V_{H-2}$ comprises the HC-CDR1 comprising the amino acid sequence of SEQ ID NO: 129, the HC-CDR2 comprising the amino acid sequence of SEQ ID NO: 130, and the HC-CDR3 comprising the amino acid sequence of SEQ ID NO: 131, and the $V_{L-2}$ comprises the LC-CDR1 comprising the amino acid sequence of SEQ ID NO: 132, the LC-CDR2 comprising the amino acid sequence of SEQ ID NO: 133, and the LC-CDR3 comprising the amino acid sequence of SEQ ID NO: 134;

j) the $V_{H-2}$ comprises the HC-CDR1 comprising the amino acid sequence of SEQ ID NO: 145, the HC-CDR2 comprising the amino acid sequence of SEQ ID NO: 146, and the HC-CDR3 comprising the amino acid sequence of SEQ ID NO: 147, and the $V_{L-2}$ comprises the LC-CDR1 comprising the amino acid sequence of SEQ ID NO: 148, 355, or 358, the LC-CDR2 comprising the amino acid sequence of SEQ ID NO: 149 or 356, and the LC-CDR3 comprising the amino acid sequence of SEQ ID NO: 150, 357 or 359;

k) the $V_{H-2}$ comprises the HC-CDR1 comprising the amino acid sequence of SEQ ID NO: 161, the HC-CDR2 comprising the amino acid sequence of SEQ ID NO: 162, and the HC-CDR3 comprising the amino acid sequence of SEQ ID NO: 163, and the $V_{L-2}$ comprises the LC-CDR1 comprising the amino acid sequence of SEQ ID NO: 164, the LC-CDR2 comprising the amino acid sequence of SEQ ID NO: 165, and the LC-CDR3 comprising the amino acid sequence of SEQ ID NO: 166;

l) the $V_{H-2}$ comprises the HC-CDR1 comprising the amino acid sequence of SEQ ID NO: 177, the HC-CDR2 comprising the amino acid sequence of SEQ ID NO: 178, and the HC-CDR3 comprising the amino acid sequence of SEQ ID NO: 179, and the $V_{L-2}$ comprises the LC-CDR1 comprising the amino acid sequence of SEQ ID NO: 180 or 353, the LC-CDR2 comprising the amino acid sequence of SEQ ID NO: 181 or 354, and the LC-CDR3 comprising the amino acid sequence of SEQ ID NO: 182;

m) the $V_{H-2}$ comprises the HC-CDR1 comprising the amino acid sequence of SEQ ID NO: 193, the HC-CDR2 comprising the amino acid sequence of SEQ ID NO: 194, and the HC-CDR3 comprising the amino acid sequence of SEQ ID NO: 195, and the $V_{L-2}$ comprises the LC-CDR1 comprising the amino acid sequence of SEQ ID NO: 196, the LC-CDR2 comprising the amino acid sequence of SEQ ID NO: 197, and the LC-CDR3 comprising the amino acid sequence of SEQ ID NO: 198;

n) the $V_{H-2}$ comprises the HC-CDR1 comprising the amino acid sequence of SEQ ID NO: 209, the HC-CDR2 comprising the amino acid sequence of SEQ ID NO: 210, and the HC-CDR3 comprising the amino acid sequence of SEQ ID NO: 211, and the $V_{L-2}$ comprises the LC-CDR1 comprising the amino acid sequence of SEQ ID NO: 212, the LC-CDR2 comprising the amino acid sequence of SEQ ID NO: 213, and the LC-CDR3 comprising the amino acid sequence of SEQ ID NO: 214; or o) the $V_{H-2}$ comprises the HC-CDR1 comprising the amino acid sequence of SEQ ID NO: 289, the HC-CDR2 comprising the amino acid sequence of SEQ ID NO: 290, and the HC-CDR3 comprising the amino acid sequence of SEQ ID NO: 291, and the $V_{L-2}$ comprises the LC-CDR1 comprising the amino acid sequence of SEQ ID NO: 292, the LC-CDR2 comprising the amino acid sequence of SEQ ID NO: 293, and the LC-CDR3 comprising the amino acid sequence of SEQ ID NO: 294;

p) the $V_{H-2}$ comprises the HC-CDR1 comprising the amino acid sequence of SEQ ID NO: 17 or 304, the HC-CDR2 comprising the amino acid sequence of SEQ ID NO: 18 or 305, and the HC-CDR3 comprising the amino acid sequence of SEQ ID NO: 19, and the $V_{L-2}$ comprises the LC-CDR1 comprising the amino acid sequence of SEQ ID NO: 20, 301, 302, 303, or 306, the LC-CDR2 comprising the amino acid sequence of SEQ ID NO: 21, and the LC-CDR3 comprising the amino acid sequence of SEQ ID NO:22.

In some embodiments, the $V_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 17 or 304, ii) the HC-CDR2 comprising the amino acid sequence of SEQ ID NO: 18 or 305, and iii) the HC-CDR3 comprising the amino acid sequence of SEQ ID NO: 19, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 20, 301, 302, 303, or 306, ii) the LC-CDR2 comprising the amino acid sequence of SEQ ID NO: 21, and iii) the LC-CDR3 comprising the amino acid sequence of SEQ ID NO: 22, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 33, ii) the HC-CDR2 comprising the amino acid sequence of SEQ ID NO: 34, and iii) the HC-CDR3 comprising the amino acid sequence of SEQ ID NO: 35, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 36, ii) the LC-CDR2 comprising the amino acid sequence of SEQ ID NO: 37, and iii) the LC-CDR3 comprising the amino acid sequence of SEQ ID NO: 38, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 49, ii)

the HC-CDR2 comprising the amino acid sequence of SEQ ID NO: 50, and iii) the HC-CDR3 comprising the amino acid sequence of SEQ ID NO: 51, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 52, ii) the LC-CDR2 comprising the amino acid sequence of SEQ ID NO: 53, and iii) the LC-CDR3 comprising the amino acid sequence of SEQ ID NO: 54, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 65, ii) the HC-CDR2 comprising the amino acid sequence of SEQ ID NO: 66, and iii) the HC-CDR3 comprising the amino acid sequence of SEQ ID NO: 67, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 68, ii) the LC-CDR2 comprising the amino acid sequence of SEQ ID NO: 69, and iii) the LC-CDR3 comprising the amino acid sequence of SEQ ID NO: 70, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 81, ii) the HC-CDR2 comprising the amino acid sequence of SEQ ID NO: 82, and iii) the HC-CDR3 comprising the amino acid sequence of SEQ ID NO: 83, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 84, ii) the LC-CDR2 comprising the amino acid sequence of SEQ ID NO: 85, and iii) the LC-CDR3 comprising the amino acid sequence of SEQ ID NO: 86, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 97, ii) the HC-CDR2 comprising the amino acid sequence of SEQ ID NO: 98, and iii) the HC-CDR3 comprising the amino acid sequence of SEQ ID NO: 99, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 100, ii) the LC-CDR2 comprising the amino acid sequence of SEQ ID NO: 101, and iii) the LC-CDR3 comprising the amino acid sequence of SEQ ID NO: 102, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 113, ii) the HC-CDR2 comprising the amino acid sequence of SEQ ID NO: 114, and iii) the HC-CDR3 comprising the amino acid sequence of SEQ ID NO: 115, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 116, ii) the LC-CDR2 comprising the amino acid sequence of SEQ ID NO: 117, and iii) the LC-CDR3 comprising the amino acid sequence of SEQ ID NO: 118, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 129, ii) the HC-CDR2 comprising the amino acid sequence of SEQ ID NO: 130, and iii) the HC-CDR3 comprising the amino acid sequence of SEQ ID NO: 131, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 132, ii) the LC-CDR2 comprising the amino acid sequence of SEQ ID NO: 133, and iii) the LC-CDR3 comprising the amino acid sequence of SEQ ID NO: 134, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 145, ii) the HC-CDR2 comprising the amino acid sequence of SEQ ID NO: 146, and iii) the HC-CDR3 comprising the amino acid sequence of SEQ ID NO: 147, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 148, 355, or 358, ii) the LC-CDR2 comprising the amino acid sequence of SEQ ID NO: 149 or 356, and iii) the LC-CDR3 comprising the amino acid sequence of SEQ ID NO: 150, 357 or 359, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 161, ii) the HC-CDR2 comprising the amino acid sequence of SEQ ID NO: 162, and iii) the HC-CDR3 comprising the amino acid sequence of SEQ ID NO: 163, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 164, ii) the LC-CDR2 comprising the amino acid sequence of SEQ ID NO: 165, and iii) the LC-CDR3 comprising the amino acid sequence of SEQ ID NO: 166, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 177, ii) the HC-CDR2 comprising the amino acid sequence of SEQ ID NO: 178, and iii) the HC-CDR3 comprising the amino acid sequence of SEQ ID NO: 179, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 180 or 353, ii) the LC-CDR2 comprising the amino acid sequence of SEQ ID NO: 181 or 354, and iii) the LC-CDR3 comprising the amino acid sequence of SEQ ID NO: 182, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 193, ii) the HC-CDR2 comprising the amino acid sequence of SEQ ID NO: 194, and iii) the HC-CDR3 comprising the amino acid sequence of SEQ ID NO: 195, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 196, ii) the LC-CDR2 comprising the amino acid sequence of SEQ ID NO: 197, and iii) the LC-CDR3 comprising the amino acid sequence of SEQ ID NO: 198, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 209, ii) the HC-CDR2 comprising the amino acid sequence of SEQ ID NO: 210, and iii) the HC-CDR3 comprising the amino acid sequence of SEQ ID NO: 211, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 212, ii) the LC-CDR2 comprising the amino acid sequence of SEQ ID NO: 213, and iii) the LC-CDR3 comprising the amino acid sequence of SEQ ID NO: 214, or a variant thereof comprising up to 5, 4, 3, 2, or 1 amino acid substitutions in the LC-CDRs.

In some embodiments, the $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294, or a variant thereof comprising up to 5, 4, 3, 2, or 1 amino acid substitutions in the LC-CDRs.

In some embodiments, the $V_H$ comprises the HC-CDR1 comprising the amino acid sequence of SEQ ID NO: 17 or 304, the HC-CDR2 comprising the amino acid sequence of SEQ ID NO: 18 or 305, and the HC-CDR3 comprising the amino acid sequence of SEQ ID NO: 19, or a variant thereof comprising up to 5, 4, 3, 2, or 1 amino acid substitutions in the HC-CDRs; and the $V_L$ comprises the LC-CDR1 comprising the amino acid sequence of SEQ ID NO: 20, 301, 302, 303, or 306, the LC-CDR2 comprising the amino acid sequence of SEQ ID NO: 21, and the LC-CDR3 comprising the amino acid sequence of SEQ ID NO:22, or a variant thereof comprising up to 5, 4, 3, 2, or 1 amino acid substitutions in the LC-CDRs.

The present application in another aspect comprises an anti-CD93 construct comprising an antibody moiety that specifically binds to CD93, comprising:

a) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 13, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 14;

b) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 29 and 307-312, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 30, and 313-318;

c) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 45, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 46;

d) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 61, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 62;

e) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 77, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 78;

f) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 93, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 94;

g) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 109, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 110;

h) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 125, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 126;

i) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 141, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 142;

j) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 157 and 360-362, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 158, and 363-365;

k) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 173, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 174;

l) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 189 and 347-349, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 190, and 350-352;

m) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 205, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 206;

n) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 221, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 222;

o) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 287 and 319-321, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 288, and 322-324;

p) a HC-CDR1, a HC-CDR2, and a HC-CDR3, respectively comprising the amino acid sequences of a CDR1, a CDR2, and a CDR3 within a $V_H$ chain region having the sequence set forth in any one of SEQ ID NOs: 307-312, and a LC-CDR1, a LC-CDR2, and a LC-CDR3, respectively comprising the amino acid sequences of a CDR1, a CDR2, and a CDR3 within a $V_L$ chain region having the sequence set forth in any one of SEQ ID NOs: 313-318; or q) a HC-CDR1, a HC-CDR2, and a HC-CDR3, respectively comprising the amino acid sequences of a CDR1, a CDR2, and a CDR3 within a $V_H$ chain region having the sequence set forth in any one of SEQ ID NOs: 319-321, and a LC-CDR1, a LC-CDR2, and a LC-CDR3, respectively comprising the amino acid sequences of a CDR1, a CDR2, and a CDR3 within a $V_L$ chain region having the sequence set forth in any one of SEQ ID NOs: 322-324.

In some embodiments according to any of the anti-CD93 constructs described above, wherein the $V_H$ comprises an amino acid sequence of any one of SEQ ID NOs: 13, 29, 45, 61, 77, 93, 109, 125, 141, 157, 173, 189, 205, 221, 287, 307-312 and 319-321, or a variant comprising an amino acid sequence having at least about 80% (such as at least about any one of 80%, 85%, 90%, 95%, 96%, 97%, 98%, or 99%) sequence identity; and/or wherein the $V_L$ comprises an amino acid sequence of any one of SEQ ID NOs: 14, 30, 46, 62, 78, 94, 110, 126, 142, 158, 174, 190, 206, 222, 288, 313-318 and 322-324 or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 13, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 14, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of any of SEQ ID NO: 29 and 307-312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 30, and 313-318, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 45, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 46, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 61, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 62, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 77, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 78, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 93, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 94, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 109, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 110, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 126, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 141, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO:

142, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 157, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 158, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 173, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 174, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of any of SEQ ID NO: 189 and 347-349, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 190, and 350-352, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 205, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 206, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 221, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 222, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of any of SEQ ID NO: 287 and 319-321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 288, and 322-324, or a variant comprising an amino acid sequence having at least about 80% (such as at least about any one of 80%, 85%, 90%, 95%, 96%, 97%, 98%, or 99%) sequence identity.

In some embodiments according to any of the anti-CD93 constructs described above, the antibody moiety is an antibody or antigen-binding fragment thereof selected from the group consisting of a full-length antibody, a bispecific antibody, a single-chain Fv (scFv) fragment, a Fab fragment, a Fab' fragment, a F(ab')2, an Fv fragment, a disulfide stabilized Fv fragment (dsFv), a (dsFv)2, a Fv-Fc fusion, a scFv-Fc fusion, a scFv-Fv fusion, a diabody, a tribody, and a tetrabody. In some embodiments, the antibody moiety is a full-length antibody.

In some embodiments according to any of the anti-CD93 constructs described above, the antibody moiety has an Fc fragment is selected from the group consisting of Fc fragments form IgG, IgA, IgD, IgE, IgM, and combinations and hybrids thereof. In some embodiments, the Fc fragment is selected from the group consisting of Fc fragments from IgG1, IgG2, IgG3, IgG4, and combinations and hybrids thereof. In some embodiments, the Fc fragment has a reduced effector function as compared to the corresponding wildtype Fc fragment. In some embodiments, the Fc fragment has an enhanced effector function as compared to the corresponding wildtype Fc fragment. In some embodiments the Fc fragment has extended serum half-life. In some embodiments the Fc fragment has reduced serum half-life.

In some embodiments according to any of the anti-CD93 constructs described above, the antibody moiety blocks the binding of CD93 to IGFBP7 (such as human IGFBP7).

In some embodiments according to any of the anti-CD93 constructs described above, the antibody moiety blocks the binding of CD93 to MMRN2 (such as human MMRN2).

In some embodiments according to any of the anti-CD93 constructs described above, the antibody moiety blocks a) the binding of CD93 to IGFBP7 and/or b) the binding of CD93 to MMRN2.

In some embodiments according to any of the anti-CD93 constructs described above, the CD93 is a human CD93.

The present application in another aspect provides a pharmaceutical composition comprising any of the anti-CD93 constructs described above, and a pharmaceutical acceptable carrier.

The present application in another aspect provides an isolated nucleic acid encoding any of the anti-CD93 constructs described above.

The present application in another aspect provides a vector comprising any of the isolated nucleic acids described above.

The present application in another aspect provides an isolated host cell comprising any of the isolated nucleic acids or vectors described above.

The present application in another aspect provides an immunoconjugate comprising the any of the anti-CD93 constructs described above, linked to a therapeutic agent or a label.

The present application in another aspect provides a method of producing an anti-CD93 construct comprising: a) culturing the isolated host cell of claim 25 under conditions effective to express the anti-CD93 construct; and b) obtaining the expressed anti-CD93 construct from the host cell.

The present application in another aspect provides a method of treating a disease or condition in an individual, comprising administering to the individual an effective mount of any of the anti-CD93 constructs or pharmaceutical compositions described above. In some embodiments, the disease or condition is associated with an abnormal vascular structure. In some embodiments, the disease or condition is a cancer. In some embodiments, the cancer is a solid tumor. In some embodiments, the cancer comprises CD93+ endothelial cells. In some embodiments, the cancer comprises IGFBP7+ blood vessels. In some embodiments, the cancer is characterized by tumor hypoxia. In some embodiments, the cancer is a locally advanced or metastatic cancer. In some embodiments, the cancer is selected from the group consisting of a lymphoma, colon cancer, brain cancer, breast cancer, ovarian cancer, endometrial cancer, esophageal cancer, prostate cancer, cervical cancer, renal cancer, bladder cancer, gastric cancer, non-small cell lung cancer, melanoma, and pancreatic cancer. In some embodiments, the anti-CD93 construct is administered parenterally into the individual. In some embodiments, the method further comprises administering a second therapy. In some embodiments, the second therapy is selected from the group consisting of surgery, radiation, gene therapy, immunotherapy, bone marrow transplantation, stem cell transplantation, hormone therapy, targeted therapy, cryotherapy, ultrasound therapy, photodynamic therapy, and chemotherapy.

In some embodiments, the second therapy is an immunotherapy. In some embodiments, the immunotherapy comprises administering an immunomodulatory agent. In some embodiments, the immunomodulatory agent is an immune checkpoint inhibitor. In some embodiments, the immune checkpoint inhibitor comprises an anti-PD-L1 antibody or an anti-PD-1 antibody. In some embodiments, the individual is a human.

BRIEF DESCRIPTION OF THE DRAWINGS

FIGS. 4A-4F show the inhibition of HUVEC tube formation by various anti-CD93 antibodies as compared to control.

Figure 7A:
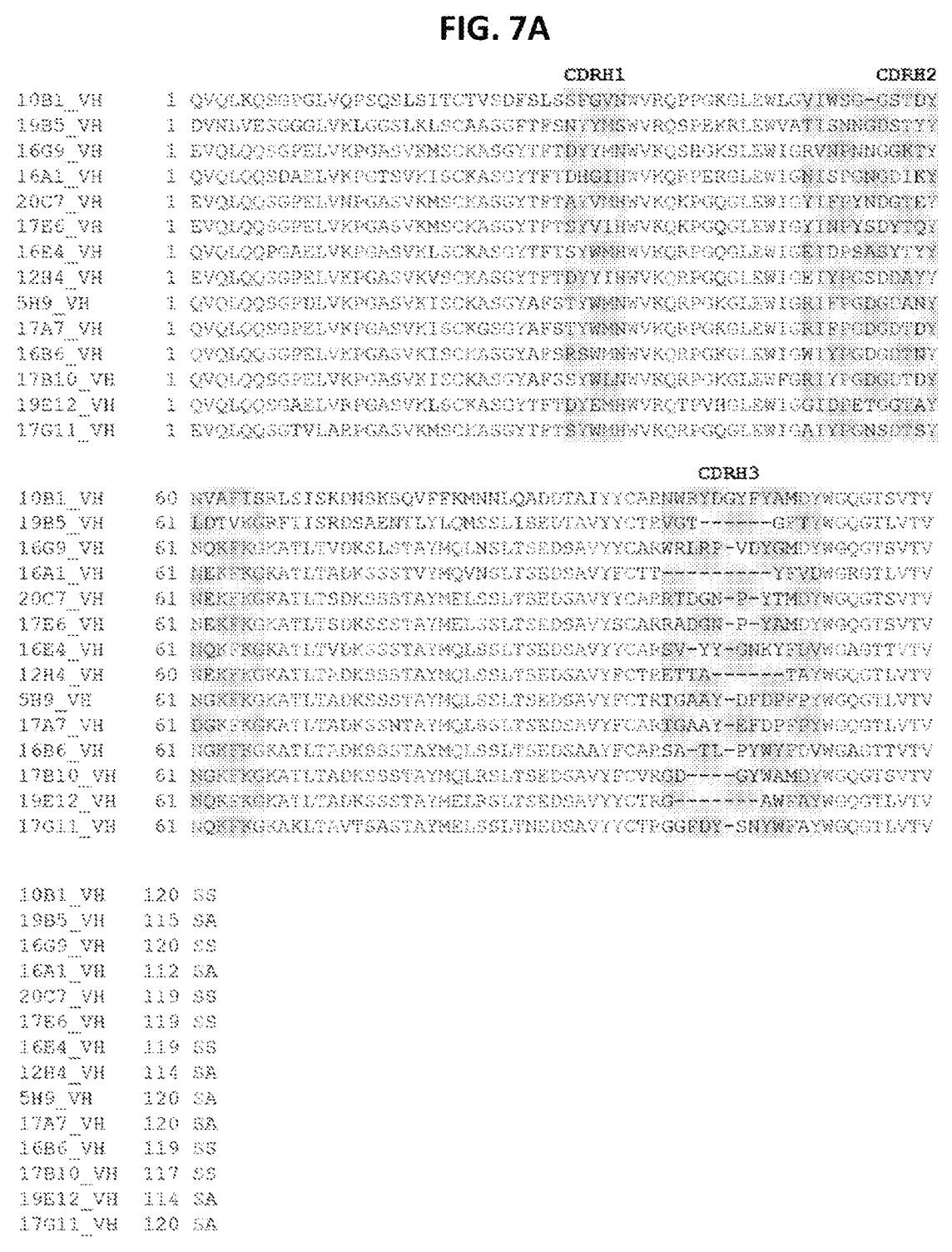

FIGS. 7A-7B show alignment of $V_H$ and $V_L$ CDRs according to Kabat numbering. From top to bottom, sequences in FIG. 7A are SEQ ID NO: 393-406, and sequences in FIG. 7B are SEQ ID NO: 407-420.

FIGS. 8A-8B show alignment of $V_H$ and $V_L$ CDRs determined by the VBASE2 tool. From top to bottom, sequences in FIG. 8A are SEQ ID NO: 393-406, and sequences in FIG. 8B are SEQ ID NO: 407-420.

FIG. 16 shows exemplary multispecific anti-CD93 constructs that also recognize VEGF.

FIGS. 23-24 show the inhibition effect of an exemplary humanized 17B10 antibody in HUVEC tube formation.

FIG. 28 shows binding of an exemplary humanized 17B10 antibody to cell surface expressing mouse CD93 HEK cells determined by fluorescence activated cell sorting (FACS) assay.

FIG. 43 shows a summary of the binding affinities of exemplary 16E4 and 7F3 antibodies to human CD93 by octet, and human CD93 expressing CHO cells, HUVEC cells, or KG1a cells measured by Flow cytometry.

FIG. 47 shows Octet analysis of the blocking effect of exemplary 7F3 or 16E4 antibodies on the binding of human IGFBP7 to human CD93.

FIG. 48 shows Octet analysis of the blocking effect of exemplary 16E4 antibodies on the binding of human IGFBP7 to human CD93.

FIG. 51 shows a summary of properties of exemplary anti-CD93 antibodies.

DETAILED DESCRIPTION OF THE APPLICATION

Figure 1:
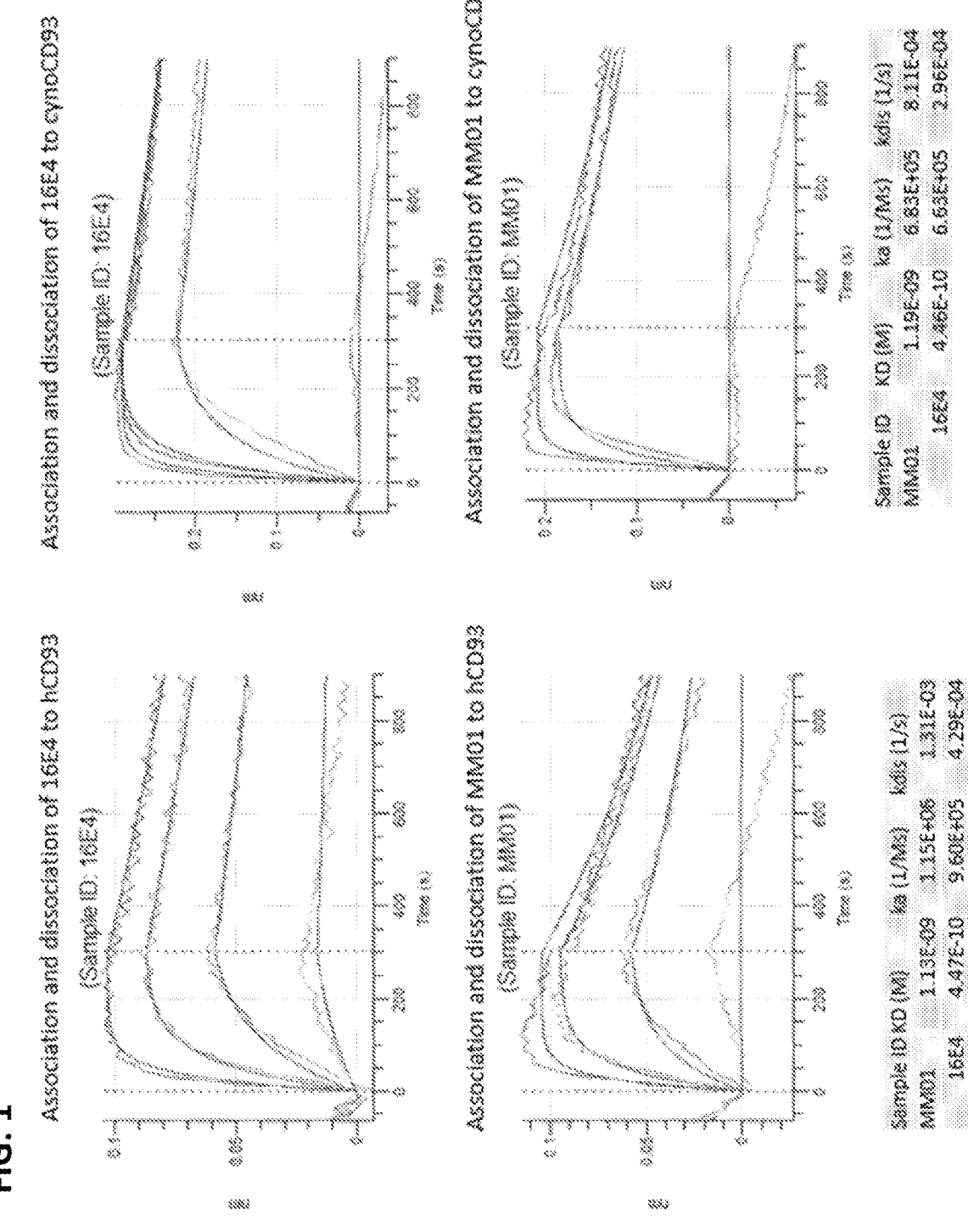
FIG. 1 shows binding affinity of 16E4 and MM01 against human or cynomolgus CD93.

The present application provides novel anti-CD93 constructs that specifically bind to CD93 (such as anti-CD93 monoclonal or multispecific antibodies), methods of preparing the anti-CD93 constructs, methods of using the constructs (e.g., methods of treating a disease or condition).

Anti-CD93 antibodies (e.g., anti-CD93 antibodies that block interaction between CD93 and IGFBP7) may effectively treat a tumor or cancer, block abnormal tumor vascular angiogenesis, normalize immature and leaky tumor blood vessel, promote functional vascular network in a tumor, promote vascular maturation, promote a favorable tumor microenvironment, increase immune cell infiltration in a tumor, increase tumor perfusion, reduce hyperplasia in a tumor, sensitize tumor to a second therapy, and/or facilitating delivery of a second agent. See e.g., WO2021062128A1, the disclosure of which is herein incorporated by reference in its entirety. In some embodiments, the anti-CD93 construct described herein reduces the size of a tumor. In some embodiments, the anti-CD93 construct described herein promotes immune cell infiltration in a tumor. In some embodiments, the anti-CD93 construct described herein promotes vascular maturation in a tumor. In some embodiments, the anti-CD93 construct described herein sensitizes a tumor to a second therapy or facilitates delivery of a second agent.

I. Definitions

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antibody moiety" refers to a full-length antibody or an antigen-binding fragment thereof.

A full-length antibody comprises two heavy chains and two light chains. The variable regions of the light and heavy chains are responsible for antigen binding. The variable domains of the heavy chain and light chain may be referred to as "$V_H$" and "$V_L$", respectively. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelid single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

"Fv" is the minimum antibody fragment, which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45: 3832-3839 (2008); Lefranc M. P. et al., *Dev. Comp. Immu-*

17

*nol.*, 27: 55-77 (2003); and Honegger and Plückthun, *J. Mol. Biol.*, 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above-cited references are set forth below in Table 1 as a comparison. CDR prediction algorithms and interfaces are known in the art, including, for example, Abhinandan and Martin, *Mol. Immunol.*, 45: 3832-3839 (2008); Ehrenmann F. et al., *Nucleic Acids Res.*, 38: D301-D307 (2010); and Adolf-Bryfogle J. et al., *Nucleic Acids Res.*, 43: D432-D438 (2015). The contents of the references cited in this paragraph are incorporated herein by reference in their entireties for use in the present application and for possible inclusion in one or more claims herein. In some embodiments, the CDR sequences provided herein are based on IMGT definition. For example, the CDR sequences may be determined by the VBASE2 tool (http://www.vbase2.org/vbase2.php, see also Retter I, Althaus H H, Münch R, Müller W: VBASE2, an integrative V gene database. Nucleic Acids Res. 2005 Jan. 1; 33 (Database issue): D671-4, which is incorporated herein by reference in its entirety).

TABLE 1

CDR DEFINITIONS

| | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Rabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or hypervariable region (HVR) of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the CDR residues as herein defined.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, See Jones et al., *Nature* 321:522-525 (1986); Riechmann et al., *Nature* 332:323-329 (1988); and Presta, *Curr. Op. Struct. Biol.* 2:593-596 (1992).

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence

US 12,662,547 B2

19 comparison computer program MUSCLE (Edgar, R. C., *Nucleic Acids Research* 32(5):1792-1797, 2004; Edgar, R. C., *BMC Bioinformatics* 5(1):113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two protein molecules is occupied by lysine, or if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the protein sequences SGTSTD and TGTSDA share 50% homology. Generally, a comparison is made when two sequences are aligned to give maximum homology.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

The "CH1 domain" (also referred to as "C1" of "H1" domain) usually extends from about amino acid 118 to about amino acid 215 (EU numbering system).

"Hinge region" is generally defined as a region in IgG corresponding to Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" domain) comprises the stretch of residues C-terminal to a CH2 domain in an Fc region (i.e. from about amino acid residue 341 to the C-terminal end of an antibody sequence, typically at amino acid residue 446 or 447 of an IgG).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, FcRN, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immuno-receptor tyrosine-based inhibition motif (ITIM) in its cytoplasmic domain. (See M. Daëron, *Annu. Rev. Immunol.* 15:203-234 (1997). FcRN is critical to the recycling of an antibody to the blood allowing for increased serum half-life of the antibodies. FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody or fragment thereof "competes" for binding to a target antigen with a second antibody or fragment thereof when the first antibody or fragment thereof inhibits the target antigen binding of the second antibody of fragment thereof by at least about 50% (such as at least about any one of 55%, 60%, 65%, 70%, 75%, 80%, 85%, 90%, 95%, 98% or 99%) in the presence of an equimolar concentration of the first antibody or fragment thereof, or vice versa. A high throughput process for "binning" antibodies based upon their cross-competition is described in PCT Publication No. WO 03/48731.

As used herein, the terms "specifically binds," "specifically recognizing," and "is specific for" refer to measurable and reproducible interactions, such as binding between a target and an antibody or antibody moiety, which is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant ($K_D$) of $\leq 10^{-5}$ M, $\leq 10^{-6}$ M, $\leq 10^{-7}$ M, $10^{-8}$ M, $\leq 10^{-9}$ M, $—10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-,BLI, RIA-, ECL-, IRMA-, EIA-, BIACORE™—tests and peptide scans.

As used herein, molecule A (e.g., an anti-CD93 construct as described herein) "blocks" the binding of molecule B (e.g., CD93) and molecule C (e.g., IGFBP7 or MMRN2) refers to both direct blocking and indirect blocking. For example, instead of directly blocking the binding of CD93 and IGFBP7 or MMRN2 by occupying at least a portion of the binding site on CD93 that is responsible for IGFBP7 or MMRN2 binding, an anti-CD93 construct as described herein may block the binding of CD93 and IGFBP7 or MMRN2 by altering the structure of CD93 such that CD93 and IGFBP7/MMRN2 cannot bind.

An "isolated" or "purified" antibody (or construct) is one that has been identified, separated and/or recovered from a component of its production environment (e.g., natural or recombinant). Preferably, the isolated polypeptide is free of association with all other components from its production environment.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, and may contain mutations. Mutant progeny that have the same function or biological activity as screened or selected for in the originally transformed cell are included herein.

The term "immunoconjugate" includes reference to a covalent linkage of a therapeutic agent or a detectable label to an antibody such as an antibody moiety described herein. The linkage can be direct or indirect through a linker (such as a peptide linker).

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the application contemplate any one or more of these aspects of treatment.

In the context of cancer, the term "treating" includes any or all of: inhibiting growth of cancer cells, inhibiting replication of cancer cells, lessening of overall tumor burden and ameliorating one or more symptoms associated with the disease.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to that of a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased or non-treated sample of an individual. In some examples, a reference is obtained from one or more healthy individuals who are not the individual or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing" as used herein, includes providing prophylaxis with respect to the occurrence or recurrence of a disease in an individual that may be predisposed to the disease but has not yet been diagnosed with the disease.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

The terms "subject," "individual," and "patient" are used interchangeably herein to refer to a mammal, including, but not limited to, human, bovine, horse, feline, canine, rodent, or primate. In some embodiments, the individual is a human.

An "effective amount" of an agent refers to an amount effective, at dosages and for periods of time necessary, to achieve the desired therapeutic or prophylactic result. The specific dose may vary depending on one or more of: the particular agent chosen, the dosing regimen to be followed, whether it is administered in combination with other compounds, timing of administration, the tissue to be imaged, and the physical delivery system in which it is carried.

A "therapeutically effective amount" of a substance/molecule of the application, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to an individual to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to an individual. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Anti-CD93 Constructs

The present application provides anti-CD93 constructs comprising an anti-CD93 antibody moiety that specifically binds to CD93 as described herein.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 3, and the $V_{L-2}$ comprises the LC-CDR1 comprising the amino acid sequence of SEQ ID NO: 4, the LC-CDR2 comprising the amino acid sequence of SEQ ID NO: 5, and the LC-CDR3 comprising the amino acid sequence of SEQ ID NO: 6.

In some embodiments, the $V_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 7, ii) the HC-CDR2 comprising the amino acid sequence of SEQ ID NO: 8, and iii) the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 10, ii) the LC-CDR2 comprising the amino acid sequence of SEQ ID NO: 11, and iii) the LC-CDR3 comprising the amino acid sequence of SEQ ID NO: 12, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, and the $V_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 13; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 14.

In some embodiments, the $V_H$ comprises an amino acid sequence of SEQ ID NO: 13, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 14, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 17, the HC-CDR2 comprising the amino acid sequence of SEQ ID NO: 18, and the HC-CDR3 comprising the amino acid sequence of SEQ ID NO: 19, and the $V_{L-2}$ comprises the LC-CDR1 comprising the amino acid sequence of SEQ ID NO: 20, the LC-CDR2 comprising the amino acid sequence of SEQ ID NO: 21, and the LC-CDR3 comprising the amino acid sequence of SEQ ID NO: 22.

In some embodiments, the $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 20, ii) the LC-CDR2 comprising the amino acid sequence of SEQ ID NO: 21, and iii) the LC-CDR3 comprising the amino acid sequence of SEQ ID NO: 22, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 23, ii) the HC-CDR2 comprising the amino acid sequence of SEQ ID NO: 24, and iii) the HC-CDR3 comprising the amino acid sequence of SEQ ID NO: 25, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 26, ii) the LC-CDR2 comprising the amino acid sequence of SEQ ID NO: 27, and iii) the LC-CDR3 comprising the amino acid sequence of SEQ ID NO: 28, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, and the $V_L$ comprises i) the LC-CDR1 comprising the amino acid sequence of SEQ ID NO: 20, ii) the LC-CDR2 comprising the amino acid sequence of SEQ ID NO: 21, and iii) the LC-CDR3 comprising the amino acid sequence of SEQ ID NO: 22.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 29 and 307-312; and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 30, and 313-318.

In some embodiments, the $V_H$ comprises an amino acid sequence of any of SEQ ID NO: 29 and 307-312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 30, and 313-318, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 33, the HC-CDR2 comprising the amino acid sequence of SEQ ID NO: 34, and the HC-CDR3 comprising the amino acid sequence of SEQ ID NO: 35, and the $V_{L-2}$ comprises the LC-CDR1 comprising the amino acid sequence of SEQ ID NO: 36, the LC-CDR2 comprising the amino acid sequence of SEQ ID NO: 37, and the LC-CDR3 comprising the amino acid sequence of SEQ ID NO: 38.

In some embodiments, the $V_H$ comprises i) the HC-CDR1 comprising the amino acid sequence of SEQ ID NO: 33, ii) the HC-CDR2 comprising the amino acid sequence of SEQ ID NO: 34, and iii) the HC-CDR3 comprising the amino acid sequence of SEQ ID NO: 35, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 36, ii) the LC-CDR2 comprising the amino acid sequence of SEQ ID NO: 37, and iii) the LC-CDR3 comprising the amino acid sequence of SEQ ID NO: 38, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 39, ii) the HC-CDR2 comprising the amino acid sequence of SEQ ID NO: 40, and iii) the HC-CDR3 comprising the amino acid sequence of SEQ ID NO: 41, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 42, ii) the LC-CDR2 comprising the amino acid sequence of SEQ ID NO: 43, and iii) the LC-CDR3 comprising the amino acid sequence of SEQ ID NO: 44, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 33, ii) the HC-CDR2 comprising the amino acid sequence of SEQ ID NO: 34, and iii) the HC-CDR3 comprising the amino acid sequence of SEQ ID NO: 35, and the $V_L$ comprises i) the LC-CDR1 comprising the amino acid sequence of SEQ ID NO: 36, ii) the LC-CDR2 comprising the amino acid sequence of SEQ ID NO: 37, and iii) the LC-CDR3 comprising the amino acid sequence of SEQ ID NO: 38.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 45; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 46.

In some embodiments, the $V_H$ comprises an amino acid sequence of SEQ ID NO: 45, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 46, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 49, the HC-CDR2 comprising the amino acid sequence of SEQ ID NO: 50, and the HC-CDR3 comprising the amino acid sequence of SEQ ID NO: 51, and the $V_{L-2}$ comprises the LC-CDR1 comprising the amino acid sequence of SEQ ID NO: 52, the LC-CDR2 comprising the amino acid sequence of SEQ ID NO: 53, and the LC-CDR3 comprising the amino acid sequence of SEQ ID NO: 54.

In some embodiments, the $V_H$ comprises i) the HC-CDR1 comprising the amino acid sequence of SEQ ID NO: 49, ii) the HC-CDR2 comprising the amino acid sequence of SEQ ID NO: 50, and iii) the HC-CDR3 comprising the amino acid sequence of SEQ ID NO: 51, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 52, ii) the LC-CDR2 comprising the amino acid sequence of SEQ ID NO: 53, and iii) the LC-CDR3 comprising the amino acid sequence of SEQ ID NO: 54, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 55, ii) the HC-CDR2 comprising the amino acid sequence of SEQ ID NO: 56, and iii) the HC-CDR3 comprising the amino acid sequence of SEQ ID NO: 57, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 58, ii) the LC-CDR2 comprising the amino acid sequence of SEQ ID NO: 59, and iii) the LC-CDR3 comprising the amino acid sequence of SEQ ID NO: 60, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 49, ii) the HC-CDR2 comprising the amino acid sequence of SEQ ID NO: 50, and iii) the HC-CDR3 comprising the amino acid sequence of SEQ ID NO: 51, and the $V_L$ comprises i) the LC-CDR1 comprising the amino acid sequence of SEQ ID NO: 52, ii) the LC-CDR2 comprising the amino acid sequence of SEQ ID NO: 53, and iii) the LC-CDR3 comprising the amino acid sequence of SEQ ID NO: 54.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 61; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 62.

In some embodiments, the $V_H$ comprises an amino acid sequence of SEQ ID NO: 61, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 62, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 65, the HC-CDR2 comprising the amino acid sequence of SEQ ID NO: 66, and the HC-CDR3 comprising the amino acid sequence of SEQ ID NO: 67, and the $V_{L-2}$ comprises the LC-CDR1 comprising the amino acid sequence of SEQ ID NO: 68, the LC-CDR2 comprising the amino acid sequence of SEQ ID NO: 69, and the LC-CDR3 comprising the amino acid sequence of SEQ ID NO: 70.

In some embodiments, the $V_H$ comprises i) the HC-CDR1 comprising the amino acid sequence of SEQ ID NO: 65, ii)

the HC-CDR2 comprising the amino acid sequence of SEQ ID NO: 66, and iii) the HC-CDR3 comprising the amino acid sequence of SEQ ID NO: 67, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 68, ii) the LC-CDR2 comprising the amino acid sequence of SEQ ID NO: 69, and iii) the LC-CDR3 comprising the amino acid sequence of SEQ ID NO: 70, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 71, ii) the HC-CDR2 comprising the amino acid sequence of SEQ ID NO: 72, and iii) the HC-CDR3 comprising the amino acid sequence of SEQ ID NO: 73, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 74, ii) the LC-CDR2 comprising the amino acid sequence of SEQ ID NO: 75, and iii) the LC-CDR3 comprising the amino acid sequence of SEQ ID NO: 76, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 65, ii) the HC-CDR2 comprising the amino acid sequence of SEQ ID NO: 66, and iii) the HC-CDR3 comprising the amino acid sequence of SEQ ID NO: 67, and the $V_L$ comprises i) the LC-CDR1 comprising the amino acid sequence of SEQ ID NO: 68, ii) the LC-CDR2 comprising the amino acid sequence of SEQ ID NO: 69, and iii) the LC-CDR3 comprising the amino acid sequence of SEQ ID NO: 70.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 77; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 78.

In some embodiments, the $V_H$ comprises an amino acid sequence of SEQ ID NO: 77, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 78, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 81, the HC-CDR2 comprising the amino acid sequence of SEQ ID NO: 82, and the HC-CDR3 comprising the amino acid sequence of SEQ ID NO: 83, and the $V_{L-2}$ comprises the LC-CDR1 comprising the amino acid sequence of SEQ ID NO: 84, the LC-CDR2 comprising the amino acid sequence of SEQ ID NO: 85, and the LC-CDR3 comprising the amino acid sequence of SEQ ID NO: 86.

In some embodiments, the $V_H$ comprises i) the HC-CDR1 comprising the amino acid sequence of SEQ ID NO: 81, ii) the HC-CDR2 comprising the amino acid sequence of SEQ ID NO: 82, and iii) the HC-CDR3 comprising the amino acid sequence of SEQ ID NO: 83, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 84, ii) the LC-CDR2 comprising the amino acid sequence of SEQ ID NO: 85, and iii) the LC-CDR3 comprising the amino acid sequence of SEQ ID NO: 86, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 87, ii) the HC-CDR2 comprising the amino acid sequence of SEQ ID NO: 88, and iii) the HC-CDR3 comprising the amino acid sequence of SEQ ID NO: 89, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 90, ii) the LC-CDR2 comprising the amino acid sequence of SEQ ID NO: 91, and iii) the LC-CDR3 comprising the amino acid sequence of SEQ ID NO: 92, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 81, ii) the HC-CDR2 comprising the amino acid sequence of SEQ ID NO: 82, and iii) the HC-CDR3 comprising the amino acid sequence of SEQ ID NO: 83, and the $V_L$ comprises i) the LC-CDR1 comprising the amino acid sequence of SEQ ID NO: 84, ii) the LC-CDR2 comprising the amino acid sequence of SEQ ID NO: 85, and iii) the LC-CDR3 comprising the amino acid sequence of SEQ ID NO: 86.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 93; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 94.

In some embodiments, the $V_H$ comprises an amino acid sequence of SEQ ID NO: 93, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 94, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 97, the HC-CDR2 comprising the amino acid sequence of SEQ ID NO: 98, and the HC-CDR3 comprising the amino acid sequence of SEQ ID NO: 99, and the $V_{L-2}$ comprises the LC-CDR1 comprising the amino acid sequence of SEQ ID NO: 100, the LC-CDR2 comprising the amino acid sequence of SEQ ID NO: 101, and the LC-CDR3 comprising the amino acid sequence of SEQ ID NO: 102.

In some embodiments, the $V_H$ comprises i) the HC-CDR1 comprising the amino acid sequence of SEQ ID NO: 97, ii) the HC-CDR2 comprising the amino acid sequence of SEQ ID NO: 98, and iii) the HC-CDR3 comprising the amino acid sequence of SEQ ID NO: 99, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 100, ii) the LC-CDR2 comprising the amino acid sequence of SEQ ID NO: 101, and iii) the LC-CDR3 comprising the amino acid sequence of SEQ ID NO: 102, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 103, ii) the HC-CDR2 comprising the amino acid sequence of SEQ ID NO: 104, and iii) the HC-CDR3 comprising the amino acid sequence of SEQ ID NO: 105, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 106, ii) the LC-CDR2 comprising the amino acid sequence of SEQ ID NO: 107, and iii) the LC-CDR3 comprising the amino acid sequence of SEQ ID NO: 108, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 97, ii) the HC-CDR2 comprising the amino acid sequence of SEQ ID NO: 98, and iii) the HC-CDR3 comprising the amino acid sequence of SEQ ID NO: 99, and the $V_L$ comprises i) the LC-CDR1 comprising the amino acid sequence of SEQ ID NO: 100, ii) the LC-CDR2 comprising the amino acid sequence of SEQ ID NO: 101, and iii) the LC-CDR3 comprising the amino acid sequence of SEQ ID NO: 102.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 109; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 110.

In some embodiments, the $V_H$ comprises an amino acid sequence of SEQ ID NO: 109, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 110, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 113, the HC-CDR2 comprising the amino acid sequence of SEQ ID NO: 114, and the HC-CDR3 comprising the amino acid sequence of SEQ ID NO: 115, and the $V_{L-2}$ comprises the LC-CDR1 comprising the amino acid sequence of SEQ ID NO: 116, the LC-CDR2 comprising the amino acid sequence of SEQ ID NO: 117, and the LC-CDR3 comprising the amino acid sequence of SEQ ID NO: 118.

In some embodiments, the $V_H$ comprises i) the HC-CDR1 comprising the amino acid sequence of SEQ ID NO: 113, ii) the HC-CDR2 comprising the amino acid sequence of SEQ ID NO: 114, and iii) the HC-CDR3 comprising the amino acid sequence of SEQ ID NO: 115, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 116, ii) the LC-CDR2 comprising the amino acid sequence of SEQ ID NO: 117, and iii) the LC-CDR3 comprising the amino acid sequence of SEQ ID NO: 118, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 119, ii) the HC-CDR2 comprising the amino acid sequence of SEQ ID NO: 120, and iii) the HC-CDR3 comprising the amino acid sequence of SEQ ID NO: 121, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 122, ii) the LC-CDR2 comprising the amino acid sequence of SEQ ID NO: 123, and iii) the LC-CDR3 comprising the amino acid sequence of SEQ ID NO: 124, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 113, ii) the HC-CDR2 comprising the amino acid sequence of SEQ ID NO: 114, and iii) the HC-CDR3 comprising the amino acid sequence of SEQ ID NO: 115, and the $V_L$ comprises i) the LC-CDR1 comprising the amino acid sequence of SEQ ID NO: 116, ii) the LC-CDR2 comprising the amino acid sequence of SEQ ID NO: 117, and iii) the LC-CDR3 comprising the amino acid sequence of SEQ ID NO: 118.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 125; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 126.

In some embodiments, the $V_H$ comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 126, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 129, the HC-CDR2 comprising the amino acid sequence of SEQ ID NO: 130, and the HC-CDR3 comprising the amino acid sequence of SEQ ID NO: 131, and the $V_L2$ comprises the LC-CDR1 comprising the amino acid sequence of SEQ ID NO: 132, the LC-CDR2 comprising the amino acid sequence of SEQ ID NO: 133, and the LC-CDR3 comprising the amino acid sequence of SEQ ID NO: 134.

In some embodiments, the $V_H$ comprises i) the HC-CDR1 comprising the amino acid sequence of SEQ ID NO: 129, ii) the HC-CDR2 comprising the amino acid sequence of SEQ ID NO: 130, and iii) the HC-CDR3 comprising the amino acid sequence of SEQ ID NO: 131, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 132, ii) the LC-CDR2 comprising the amino acid sequence of SEQ ID NO: 133, and iii) the LC-CDR3 comprising the amino acid sequence of SEQ ID NO: 134, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 135, ii) the HC-CDR2 comprising the amino acid sequence of SEQ ID NO: 136, and iii) the HC-CDR3 comprising the amino acid sequence of SEQ ID NO: 137, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 138, ii) the LC-CDR2 comprising the amino acid sequence of SEQ ID NO: 139, and iii) the LC-CDR3 comprising the amino acid sequence of SEQ ID NO: 140, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 129, ii) the HC-CDR2 comprising the amino acid sequence of SEQ ID NO: 130, and iii) the HC-CDR3 comprising the amino acid sequence of SEQ ID NO: 131, and the $V_L$ comprises i) the LC-CDR1 comprising the amino acid sequence of SEQ ID NO: 132, ii) the LC-CDR2 comprising the amino acid sequence of SEQ ID NO: 133, and iii) the LC-CDR3 comprising the amino acid sequence of SEQ ID NO: 134.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 141; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 142.

In some embodiments, the $V_H$ comprises an amino acid sequence of SEQ ID NO: 141, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 142, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 145, the HC-CDR2 comprising the amino acid sequence of SEQ ID NO: 146, and the HC-CDR3 comprising the amino acid sequence of SEQ ID NO: 147, and the $V_{L-2}$ comprises the LC-CDR1 comprising the amino acid sequence of SEQ ID NO: 148, 355, or 358, the LC-CDR2 comprising the amino acid sequence of SEQ ID NO: 149 or 356, and the LC-CDR3 comprising the amino acid sequence of SEQ ID NO: 150, 357 or 359.

In some embodiments, the $V_H$ comprises i) the HC-CDR1 comprising the amino acid sequence of SEQ ID NO: 145, ii) the HC-CDR2 comprising the amino acid sequence of SEQ ID NO: 146, and iii) the HC-CDR3 comprising the amino acid sequence of SEQ ID NO: 147, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 148, 355, or 358, ii) the LC-CDR2 comprising the amino acid sequence of SEQ ID NO: 149 or 356, and iii) the LC-CDR3 comprising the amino acid sequence of SEQ ID NO: 150, 357 or 359, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 151, ii) the HC-CDR2 comprising the amino acid sequence of SEQ ID NO: 152, and iii) the HC-CDR3 comprising the amino acid sequence of SEQ ID NO: 153, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 154, ii) the LC-CDR2 comprising the amino acid sequence of SEQ ID NO: 155, and iii) the LC-CDR3 comprising the amino acid sequence of SEQ ID NO: 156, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 145, ii) the HC-CDR2 comprising the amino acid sequence of SEQ ID NO: 146, and iii) the HC-CDR3 comprising the amino acid sequence of SEQ ID NO: 147, and the $V_L$ comprises i) the LC-CDR1 comprising the amino acid sequence of SEQ ID NO: 148, 355, or 358, ii) the LC-CDR2 comprising the amino acid sequence of SEQ ID NO: 149 or 356, and iii) the LC-CDR3 comprising the amino acid sequence of SEQ ID NO: 150, 357 or 359.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 157 and 360-362; and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 158, and 363-365.

In some embodiments, the $V_H$ comprises an amino acid sequence of any of SEQ ID NO: 157 and 360-362, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 158, and 363-365, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 157, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 158, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 360, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 363, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 360, or a variant comprising an amino acid sequence having at least about 80% (such as at least about any one of 80%, 85%, 90%, 95%, 96%, 97%, 98%, or 99%) sequence identity; and the $V_L$ comprises amino acid sequence of SEQ ID NO: 364, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 360, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 365, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 361, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 363, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 361, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 364, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 361, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 365, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 362, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 363, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 362, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 364, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 362, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 365, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 161, the HC-CDR2 comprising the amino acid sequence of SEQ ID NO: 162, and the HC-CDR3 comprising the amino acid sequence of SEQ ID NO: 163, and the $V_{L-2}$ comprises the LC-CDR1 comprising the amino acid sequence of SEQ ID NO: 164, the LC-CDR2 comprising the amino acid sequence of SEQ ID NO: 165, and the LC-CDR3 comprising the amino acid sequence of SEQ ID NO: 166.

In some embodiments, the $V_H$ comprises i) the HC-CDR1 comprising the amino acid sequence of SEQ ID NO: 161, ii) the HC-CDR2 comprising the amino acid sequence of SEQ ID NO: 162, and iii) the HC-CDR3 comprising the amino acid sequence of SEQ ID NO: 163, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 164, ii) the LC-CDR2 comprising the amino acid sequence of SEQ ID NO: 165, and iii) the LC-CDR3 comprising the amino acid sequence of SEQ ID NO: 166, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 167, ii) the HC-CDR2 comprising the amino acid sequence of SEQ ID NO: 168, and iii) the HC-CDR3 comprising the amino acid sequence of SEQ ID NO: 169, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 170, ii) the LC-CDR2 comprising the amino acid sequence of SEQ ID NO: 171, and iii) the LC-CDR3 comprising the amino acid sequence of SEQ ID NO: 172, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 161, ii) the HC-CDR2 comprising the amino acid sequence of SEQ ID NO: 162, and iii) the HC-CDR3 comprising the amino acid sequence of SEQ ID NO: 163, and the $V_L$ comprises i) the LC-CDR1 comprising the amino acid sequence of SEQ ID NO: 164, ii) the LC-CDR2 comprising the amino acid sequence of SEQ ID NO: 165, and iii) the LC-CDR3 comprising the amino acid sequence of SEQ ID NO: 166.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 173; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 174.

In some embodiments, the $V_H$ comprises an amino acid sequence of SEQ ID NO: 173, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 174, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 177, the HC-CDR2 comprising the amino acid sequence of SEQ ID NO: 178, and the HC-CDR3 comprising the amino acid sequence of SEQ ID NO: 179, and the $V_{L-2}$ comprises the LC-CDR1 comprising the amino acid sequence of SEQ ID NO: 180 or 353, the LC-CDR2 comprising the amino acid sequence of SEQ ID NO: 181 or 354, and the LC-CDR3 comprising the amino acid sequence of SEQ ID NO: 182.

In some embodiments, the $V_H$ comprises i) the HC-CDR1 comprising the amino acid sequence of SEQ ID NO: 177, ii) the HC-CDR2 comprising the amino acid sequence of SEQ ID NO: 178, and iii) the HC-CDR3 comprising the amino acid sequence of SEQ ID NO: 179, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 180 or 353, ii) the LC-CDR2 comprising the amino acid sequence of SEQ ID NO: 181 or 354, and iii) the LC-CDR3 comprising the amino acid sequence of SEQ ID NO: 182, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 177, ii) the HC-CDR2 comprising the amino acid sequence of SEQ ID NO: 178, and iii) the HC-CDR3 comprising the amino acid sequence of SEQ ID NO: 179, and the $V_L$ comprises i) the LC-CDR1 comprising the amino acid sequence of SEQ ID NO: 180, ii) the LC-CDR2 comprising the amino acid sequence of SEQ ID NO: 181, and iii) the LC-CDR3 comprising the amino acid sequence of SEQ ID NO: 182. In some embodiments, the $V_H$ comprises i) the HC-CDR1 comprising the amino acid sequence of SEQ ID NO: 183, ii) the HC-CDR2 comprising the amino acid sequence of SEQ ID NO: 184, and iii) the HC-CDR3 comprising the amino acid sequence of SEQ ID NO: 185, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 186, ii) the LC-CDR2 comprising the amino acid sequence of SEQ ID NO: 187, and iii) the LC-CDR3 comprising the amino acid sequence of SEQ ID NO: 188, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 177, ii) the HC-CDR2 comprising the amino acid sequence of SEQ ID NO: 178, and iii) the HC-CDR3 comprising the amino acid sequence of SEQ ID NO: 179, and the $V_L$ comprises i) the LC-CDR1 comprising the amino acid sequence of SEQ ID NO: 180 or 353, ii) the LC-CDR2 comprising the amino acid sequence of SEQ ID NO: 181 or 354, and iii) the LC-CDR3 comprising the amino acid sequence of SEQ ID NO: 182.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 189 and 347-349; and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 190, and 350-352.

In some embodiments, the $V_H$ comprises an amino acid sequence of any of SEQ ID NO: 189 and 347-349, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 190, and 350-352, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 189, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 190, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 347, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 350, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 347, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 351, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of any of SEQ ID NO: 347, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 352, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 348, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 350, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 348, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 351, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 348, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 352, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 349, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 350, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 349, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 351, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 349, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 352, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 193, the HC-CDR2 comprising the amino acid sequence of SEQ ID NO: 194, and the HC-CDR3 comprising the amino acid sequence of SEQ ID NO: 195, and the $V_{L-2}$ comprises the LC-CDR1 comprising the amino acid sequence of SEQ ID NO: 196, the LC-CDR2 comprising the amino acid sequence of SEQ ID NO: 197, and the LC-CDR3 comprising the amino acid sequence of SEQ ID NO: 198.

In some embodiments, the $V_H$ comprises i) the HC-CDR1 comprising the amino acid sequence of SEQ ID NO: 193, ii)

the HC-CDR2 comprising the amino acid sequence of SEQ ID NO: 194, and iii) the HC-CDR3 comprising the amino acid sequence of SEQ ID NO: 195, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 196, ii) the LC-CDR2 comprising the amino acid sequence of SEQ ID NO: 197, and iii) the LC-CDR3 comprising the amino acid sequence of SEQ ID NO: 198, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 199, ii) the HC-CDR2 comprising the amino acid sequence of SEQ ID NO: 200, and iii) the HC-CDR3 comprising the amino acid sequence of SEQ ID NO: 201, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 202, ii) the LC-CDR2 comprising the amino acid sequence of SEQ ID NO: 203, and iii) the LC-CDR3 comprising the amino acid sequence of SEQ ID NO: 204, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 193, ii) the HC-CDR2 comprising the amino acid sequence of SEQ ID NO: 194, and iii) the HC-CDR3 comprising the amino acid sequence of SEQ ID NO: 195, and the $V_L$ comprises i) the LC-CDR1 comprising the amino acid sequence of SEQ ID NO: 196, ii) the LC-CDR2 comprising the amino acid sequence of SEQ ID NO: 197, and iii) the LC-CDR3 comprising the amino acid sequence of SEQ ID NO: 198.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 205; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 206.

In some embodiments, the $V_H$ comprises an amino acid sequence of SEQ ID NO: 205, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 206, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 209, the HC-CDR2 comprising the amino acid sequence of SEQ ID NO: 210, and the HC-CDR3 comprising the amino acid sequence of SEQ ID NO: 211, and the $V_U2$ comprises the LC-CDR1 comprising the amino acid sequence of SEQ ID NO: 212, the LC-CDR2 comprising the amino acid sequence of SEQ ID NO: 213, and the LC-CDR3 comprising the amino acid sequence of SEQ ID NO: 214.

In some embodiments, the $V_H$ comprises i) the HC-CDR1 comprising the amino acid sequence of SEQ ID NO: 209, ii) the HC-CDR2 comprising the amino acid sequence of SEQ ID NO: 210, and iii) the HC-CDR3 comprising the amino acid sequence of SEQ ID NO: 211, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 212, ii) the LC-CDR2 comprising the amino acid sequence of SEQ ID NO: 213, and iii) the LC-CDR3 comprising the amino acid sequence of SEQ ID NO: 214, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 215, ii) the HC-CDR2 comprising the amino acid sequence of SEQ ID NO: 216, and iii) the HC-CDR3 comprising the amino acid sequence of SEQ ID NO: 217, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 218, ii) the LC-CDR2 comprising the amino acid sequence of SEQ ID NO: 219, and iii) the LC-CDR3 comprising the amino acid sequence of SEQ ID NO: 220, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 209, ii) the HC-CDR2 comprising the amino acid sequence of SEQ ID NO: 210, and iii) the HC-CDR3 comprising the amino acid sequence of SEQ ID NO: 211, and the $V_L$ comprises i) the LC-CDR1 comprising the amino acid sequence of SEQ ID NO: 212, ii) the LC-CDR2 comprising the amino acid sequence of SEQ ID NO: 213, and iii) the LC-CDR3 comprising the amino acid sequence of SEQ ID NO: 214.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 221; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 222.

In some embodiments, the $V_H$ comprises an amino acid sequence of SEQ ID NO: 221, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 222, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 289, the HC-CDR2 comprising the amino acid sequence of SEQ ID NO: 290, and the HC-CDR3 comprising the amino acid sequence of SEQ ID NO: 291, and the $V_{L-2}$ comprises the LC-CDR1 comprising the amino acid sequence of SEQ ID NO: 292, the LC-CDR2 comprising the amino acid sequence of SEQ ID NO: 293, and the LC-CDR3 comprising the amino acid sequence of SEQ ID NO: 294.

In some embodiments, the $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294, or a variant thereof comprising up to 5, 4, 3, 2, or 1 amino acid substitutions in the LC-CDRs. In some embodiments, the $V_H$ comprises i) the HC-CDR1 comprising the amino acid sequence of SEQ ID NO: 295, ii) the HC-CDR2 comprising the amino acid sequence of SEQ ID NO: 296, and iii) the HC-CDR3 comprising the amino acid sequence of SEQ ID NO: 297, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 298, ii) the LC-CDR2 comprising the amino acid sequence of SEQ ID NO: 299, and iii) the LC-CDR3 comprising the amino acid sequence of SEQ ID NO: 300, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, and the $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 287 and 319-321; and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 288, and 322-324.

In some embodiments, the $V_H$ comprises an amino acid sequence of any of SEQ ID NO: 287 and 319-321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 288, and 322-324, or a variant comprising an amino acid sequence having at least about 80% (such as at least about any one of 80%, 85%, 90%, 95%, 96%, 97%, 98%, or 99%) sequence identity.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NOs: 287, and 319-321; and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 288, and 322-324.

In some embodiments, the $V_H$ comprises an amino acid sequence of any one of SEQ ID NOs: 319-321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any one of SEQ ID NOs: 322-324, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 319, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 322, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 319, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 323, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 319, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 324, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 320, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 322, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 320, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 323, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 320, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 324, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 322, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 323, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 324, or a variant comprising an amino acid sequence having at least about 80% (such as at least about any one of 80%, 85%, 90%, 95%, 96%, 97%, 98%, or 99%) sequence identity.

In some embodiments, the anti-CD93 construct comprises an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 17 or 304, the HC-CDR2 comprising the amino acid sequence of SEQ ID NO: 18 or 305, and the HC-CDR3 comprising the amino acid sequence of SEQ ID NO: 19, and the $V_L2$ comprises the LC-CDR1 comprising the amino acid sequence of SEQ ID NO: 20, 301, 302, 303, or 306, the LC-CDR2 comprising the amino acid sequence of SEQ ID NO: 21, and the LC-CDR3 comprising the amino acid sequence of SEQ ID NO: 22.

In some embodiments, the $V_H$ comprises i) the HC-CDR1 comprising the amino acid sequence of SEQ ID NO: 17 or 304, ii) the HC-CDR2 comprising the amino acid sequence of SEQ ID NO: 18 or 305, and iii) the HC-CDR3 comprising the amino acid sequence of SEQ ID NO: 19, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 20, 301, 302, 303, or 306, ii) the LC-CDR2 comprising the amino acid sequence of SEQ ID NO: 21, and iii) the LC-CDR3 comprising the amino acid sequence of SEQ ID NO: 22, or a variant thereof comprising up to 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-CD93 $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, and the anti-CD93 $V_L$ comprises i) the LC-CDR1 comprising the amino acid sequence of SEQ ID NO: 20, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, and the anti-CD93 $V_L$ comprises i) the LC-CDR1 comprising the amino acid sequence of SEQ ID NO: 301, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, and the anti-CD93 $V_L$ comprises i) the LC-CDR1 comprising the amino acid sequence of SEQ ID NO: 302, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, and the anti-CD93 $V_L$ comprises i) the LC-CDR1 comprising the amino acid sequence of SEQ ID NO: 303, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, and the anti-CD93 $V_L$ comprises i) the LC-CDR1 comprising the amino acid sequence of SEQ ID NO: 306, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 304, ii) the HC-CDR2 comprising the amino acid sequence of SEQ ID NO: 305, and iii) the HC-CDR3 comprising the amino acid sequence of SEQ ID NO: 19, and the anti-CD93 $V_L$ comprises i) the LC-CDR1 comprising the amino acid sequence of SEQ ID NO: 20, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 304, ii) the HC-CDR2 comprising the amino acid sequence of SEQ ID NO: 305, and iii) the HC-CDR3 comprising the amino acid sequence of SEQ ID NO: 19, and the anti-CD93 $V_L$ comprises i) the LC-CDR1 comprising the amino acid sequence of SEQ ID NO: 301, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 304, ii) the HC-CDR2 comprising the amino acid sequence of SEQ ID NO: 305, and iii) the HC-CDR3 comprising the amino acid sequence of SEQ ID NO: 19, and the anti-CD93 $V_L$ comprises i) the LC-CDR1 comprising the amino acid sequence of SEQ ID NO: 302, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 304, ii) the HC-CDR2 comprising the amino acid sequence of SEQ ID NO: 305, and iii) the HC-CDR3 comprising the amino acid sequence of SEQ ID NO: 19, and the anti-CD93 $V_L$ comprises i) the LC-CDR1 comprising the amino acid sequence of SEQ ID NO: 303, ii) the LC-CDR2 comprising the amino acid sequence of SEQ ID NO: 21, and iii) the LC-CDR3 comprising the amino acid sequence of SEQ ID NO: 22.

In some embodiments, the anti-CD93 $V_H$ comprises i) the HC-CDR1 comprising the amino acid sequence of SEQ ID NO: 304, ii) the HC-CDR2 comprising the amino acid sequence of SEQ ID NO: 305, and iii) the HC-CDR3 comprising the amino acid sequence of SEQ ID NO: 19, and the anti-CD93 $V_L$ comprises i) the LC-CDR1 comprising the amino acid sequence of SEQ ID NO: 306, ii) the LC-CDR2 comprising the amino acid sequence of SEQ ID NO: 21, and iii) the LC-CDR3 comprising the amino acid sequence of SEQ ID NO: 22.

In some embodiments, the antibody moiety comprises a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NOs: 29, and 307-312; and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NOs: 30, and 313-318.

In some embodiments, the $V_H$ comprises an amino acid sequence of any one of SEQ ID NOs: 307-312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any one of SEQ ID NOs: 313-318, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 307, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 313, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 307, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 314, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 307, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 315, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 307, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 316, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 307, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 317, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 307, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 318, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 308, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 313, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 308, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 314, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 308, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 315, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 308, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 316, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 308, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 317, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 308, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 318, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 309, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 313, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 309, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 314, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 309, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 315, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 309, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 316, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 309, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 317, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 309, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 318, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 310, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 313, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 310, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 314, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 310, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 315, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 310, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 316, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 310, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 317, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 310, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 318, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 311, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 313, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 311, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 314, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 311, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 315, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 311, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 316, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 311, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 317, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 311, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 318, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 313, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 314, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 315, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 316, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 317, or a variant comprising an amino acid sequence having at least about 80% (such as at least about any one of 80%, 85%, 90%, 95%, 96%, 97%, 98%, or 99%) sequence identity.

In some embodiments, the $V_H$ comprises an amino acid sequence of SEQ ID NO: 312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 318, or a variant comprising an amino acid sequence having at least about 80% (such as at least about any one of 80%, 85%, 90%, 95%, 96%, 97%, 98%, or 99%) sequence identity.

In some embodiments, the antibody moiety comprises a heavy chain variable region ($V_H$) and a light chain variable region ($V_L$), wherein the $V_H$ comprises i) the HC-CDR1 comprising the amino acid sequence of SEQ ID NO: 33, ii) the HC-CDR2 comprising the amino acid sequence RIFPGDGDX$_1$X$_2$YX$_3$GKFKG (SEQ ID NO: 233), wherein X$_1$X$_2$ are AN or TD, and/or X$_3$ is N or D, and iii) the HC-CDR3 comprising the amino acid sequence of TGAAYX$_1$FDPFPY (SEQ ID NO: 234), wherein X$_1$ is D or E; and the $V_L$ comprises i) the LC-CDR1 comprising the amino acid sequence SSX$_1$KSLLHSX$_2$GX$_3$TYLY (SEQ ID NO: 235), wherein X$_1$ is S or T, X$_2$ is N or S, and/or X$_3$ is V or I, ii) the LC-CDR2 comprising the amino acid sequence of SEQ ID NO: 37, and iii) the LC-CDR3 comprising the amino acid sequence of SEQ ID NO: 38.

In some embodiments, the antibody moiety comprises a heavy chain variable region ($V_H$) and a light chain variable region ($V_L$), wherein the $V_H$ comprises i) the HC-CDR1 comprising the amino acid sequence X$_1$YWX$_2$N (SEQ ID NO: 236), wherein X$_1$ is S or T, and/or X$_2$ is L or M, ii) the HC-CDR2 comprising the amino acid sequence RIX$_1$PGDGDX$_2$X$_3$YX$_4$GKFKG (SEQ ID NO: 237), wherein X$_1$ is Y or F, X$_2$X$_3$ are TD or AN, and/or X$_4$ is N or D, and iii) the HC-CDR3 comprising the amino acid sequence selected from the group consisting of SEQ ID NOs: 35, 163, and 179; and the $V_L$ comprises i) the LC-CDR1 comprising the amino acid sequence of X$_1$X$_2$X$_3$KSLLHSX$_4$GX$_5$TYLY (SEQ ID NO: 238), wherein X$_1$X$_2$X$_3$ are SSS, SST, or RFS, X$_4$ is N or S, and/or X$_5$=V or I, ii) the LC-CDR2 comprising the amino acid sequence X$_1$MSNLAS (SEQ ID NO: 239), wherein X$_1$ is R or Q, and iii) the LC-CDR3 comprising the amino acid sequence AQX$_1$LEX$_2$PX$_3$T (SEQ ID NO: 240), wherein X$_1$ is M or N, X$_2$ is R or L, and/or X$_3$ is F or W. In some embodiments, the LC-CDR3 comprises the amino acid sequence selected from the group consisting of SEQ ID NOS: 38, 166, and 182.

In some embodiments, the antibody moiety comprises a heavy chain variable region ($V_H$) and a light chain variable region ($V_L$), wherein the $V_H$ comprises i) the HC-CDR1 comprising the amino acid sequence X$_1$YVX$_2$H (SEQ ID NO: 241), wherein X$_1$ is A or S, and/or X$_2$ is M or I, ii) the HC-CDR2 comprising the amino acid sequence YIX$_1$PYX$_2$DX$_3$TX$_4$YNEKFKG (SEQ ID NO: 242), wherein X$_1$ is F or N, X$_2$ is N or S, X$_3$ is G or Y, and/or X$_4$ is E or Q, and iii) the HC-CDR3 comprising the amino acid sequence RX$_1$DGNPYX$_2$MDY (SEQ ID NO: 243), wherein X$_1$ is T or A, and/or X$_2$ is T or A; and the $V_L$ comprises i) the LC-CDR1 comprising the amino acid sequence of KASQDVSTAVX$_1$ (SEQ ID NO: 244), wherein X$_1$ is A or V, ii) the LC-CDR2 comprising the amino acid sequence of SEQ ID NO: 117, and iii) the LC-CDR3 comprising the amino acid sequence of SEQ ID NO: 118. In some embodiments, the LC-CDR3 comprises the amino acid sequence set forth in SEQ ID NO: 115 or 221.

In some embodiments, the antibody moiety comprises a heavy chain variable region ($V_H$) and a light chain variable region ($V_L$), wherein the $V_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, or a variant thereof comprising up to 5, 4, 3, 2, or 1 amino acid substitutions in the HC-CDRs; and wherein the $V_L$ comprises i) the LC-CDR1 comprising the amino acid sequence of KASQX$_1$VX$_2$TX$_3$VX$_4$(SEQ ID NO: 245), wherein X$_1$ is N or D, X$_2$ is G or S, X$_3$ is N or A, and/or X$_4$ is A or V, ii) the LC-CDR2 comprising the amino acid sequence of SASYRX$_1$X$_2$ (SEQ ID NO: 246), wherein a) X$_1$ is F or Y, X$_2$ is I or T, or b) X$_1$X$_2$ are FI or YT, and iii) the LC-CDR3 comprising the amino acid sequence QQX$_1$X$_2$X$_3$X$_4$PX$_5$T (SEQ ID NO: 247), wherein X$_1$X$_2$X$_3$X$_4$ are YNRN or HYST, and/or X$_5$ and I or F. In some embodiments, the LC-CDR3 comprises the amino acid sequence set forth in SEQ ID NO: 6, 118, or 214. In some embodiments, the LC-CDR3 comprises the amino acid sequence set forth in SEQ ID NO: 6.

In some embodiments, the antibody moiety comprises a heavy chain variable region ($V_H$) and a light chain variable region ($V_L$), wherein the $V_H$ comprises i) the HC-CDR1 comprising the amino acid sequence of SEQ ID NO: 113, ii)

the HC-CDR2 comprising the amino acid sequence of SEQ ID NO: 114, and iii) the HC-CDR3 comprising the amino acid sequence of SEQ ID NO: 115, or a variant thereof comprising up to 5, 4, 3, 2, or 1 amino acid substitutions in the HC-CDRs; and wherein the $V_L$ comprises i) the LC-CDR1 comprising the amino acid sequence of KASQX$_1$VX$_2$TX$_3$VX$_4$(SEQ ID NO: 245), wherein X$_1$ is N or D, X$_2$ is G or S, X$_3$ is N or A, and/or X$_4$ is A or V, ii) the LC-CDR2 comprising the amino acid sequence of SASYRX$_1$X$_2$ (SEQ ID NO: 246), wherein a) X$_1$ is F or Y, X$_2$ is I or T, or b) X$_1$X$_2$ are FI or YT, and iii) the LC-CDR3 comprising the amino acid sequence QQX$_1$X$_2$X$_3$X$_4$PX$_5$T (SEQ ID NO: 247), wherein X$_1$X$_2$X$_3$X$_4$ are YNRN or HYST, and/or X$_5$ and I or F. In some embodiments, the LC-CDR3 comprises the amino acid sequence set forth in SEQ ID NO: 6, 118, or 214. In some embodiments, the LC-CDR3 comprises the amino acid sequence set forth in SEQ ID NO: 118.

In some embodiments, the antibody moiety comprises a heavy chain variable region ($V_H$) and a light chain variable region ($V_L$), wherein the $V_H$ comprises i) the HC-CDR1 comprising the amino acid sequence of SEQ ID NO: 209, ii) the HC-CDR2 comprising the amino acid sequence of SEQ ID NO: 210, and iii) the HC-CDR3 comprising the amino acid sequence of SEQ ID NO: 211, or a variant thereof comprising up to 5, 4, 3, 2, or 1 amino acid substitutions in the HC-CDRs; and wherein the $V_L$ comprises i) the LC-CDR1 comprising the amino acid sequence of KASQX$_1$VX$_2$TX$_3$VX$_4$(SEQ ID NO: 245), wherein X$_1$ is N or D, X$_2$ is G or S, X$_3$ is N or A, and/or X$_4$ is A or V, ii) the LC-CDR2 comprising the amino acid sequence of SASYRX$_1$X$_2$ (SEQ ID NO: 246), wherein a) X$_1$ is F or Y, X$_2$ is I or T, or b) X$_1$X$_2$ are FI or YT, and iii) the LC-CDR3 comprising the amino acid sequence QQX$_1$X$_2$X$_3$X$_4$PX$_5$T (SEQ ID NO: 247), wherein X$_1$X$_2$X$_3$X$_4$ are YNRN or HYST, and/or X$_5$ and I or F. In some embodiments, the LC-CDR3 comprises the amino acid sequence set forth in SEQ ID NO: 6, 118, or 214. In some embodiments, the LC-CDR3 comprises the amino acid sequence set forth in SEQ ID NO: 214.

In some embodiments, the antibody moiety comprises a heavy chain variable region ($V_H$) and a light chain variable region ($V_L$), wherein the $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, or a variant thereof comprising up to 5, 4, 3, 2, or 1 amino acid substitutions in the HC-CDRs; and wherein the $V_L$ comprises i) the LC-CDR1 comprising the amino acid sequence of X$_1$ASQSVX$_2$X$_3$X$_4$X$_5$X$_6$SYMX$_7$ (SEQ ID NO: 248), wherein X$_1$ is K or R, X$_2$X$_3$X$_4$X$_5$X$_6$ are DYAGD or STSSY, and/or X$_7$ is N or H, ii) the LC-CDR2 comprising the amino acid sequence of X$_1$ASNLES (SEQ ID NO: 249), wherein X$_1$ is A or Y, and iii) the LC-CDR3 comprising the amino acid sequence QX$_1$X$_2$X$_3$X$_4$X$_5$PX$_6$T (SEQ ID NO: 250), wherein X$_1$X$_2$X$_3$X$_4$X$_5$ are QTNED or HSWEI, and/or X$_6$ is R or F. In some embodiments, the LC-CDR3 comprises the amino acid sequence set forth in SEQ ID NO: 22 or 54. In some embodiments, the LC-CDR3 comprises the amino acid sequence set forth in SEQ ID NO: 22.

In some embodiments, the antibody moiety comprises a heavy chain variable region ($V_H$) and a light chain variable region ($V_L$), wherein the $V_H$ comprises i) the HC-CDR1 comprising the amino acid sequence of SEQ ID NO: 49, ii) the HC-CDR2 comprising the amino acid sequence of SEQ ID NO: 50, and iii) the HC-CDR3 comprising the amino acid sequence of SEQ ID NO: 51, or a variant thereof comprising up to 5, 4, 3, 2, or 1 amino acid substitutions in the HC-CDRs; and wherein the $V_L$ comprises i) the LC-CDR1 comprising the amino acid sequence of X$_1$ASQSVX$_2$X$_3$X$_4$X$_5$X$_6$SYMX$_7$ (SEQ ID NO: 248), wherein X$_1$ is K or R, X$_2$X$_3$X$_4$X$_5$X$_6$ are DYAGD or STSSY, and/or X$_7$ is N or H, ii) the LC-CDR2 comprising the amino acid sequence of X$_1$ASNLES (SEQ ID NO: 249), wherein X$_1$ is A or Y, and iii) the LC-CDR3 comprising the amino acid sequence QX$_1$X$_2$X$_3$X$_4$X$_5$PX$_6$T (SEQ ID NO: 250), wherein X$_1$X$_2$X$_3$X$_4$X$_5$ are QTNED or HSWEI, and/or X$_6$ is R or F. In some embodiments, the LC-CDR3 comprises the amino acid sequence set forth in SEQ ID NO: 22 or 54. In some embodiments, the LC-CDR3 comprises the amino acid sequence set forth in SEQ ID NO: 54.

In some embodiments, the construct comprises or is an antibody or antigen-binding fragment thereof selected from the group consisting of a full-length antibody, a bispecific antibody, a single-chain Fv (scFv) fragment, a Fab fragment, a Fab' fragment, a F(ab')2, an Fv fragment, a disulfide stabilized Fv fragment (dsFv), a (dsFv)$_2$, a $V_H$H, a Fv-Fc fusion, a scFv-Fc fusion, a scFv-Fv fusion, a diabody, a tribody, and a tetrabody.

In some embodiments, the anti-CD93 antibody moiety is a full-length antibody.

In some embodiments, the anti-CD93 antibody moiety is an scFv.

In some embodiments, the anti-CD93 antibody moiety described above comprises an Fc fragment of an immuno-globulin selected from the group consisting of IgG, IgA, IgD, IgE, IgM, and combinations and hybrids thereof. In some embodiments, the anti-CD93 antibody moiety or the full-length antibody described above comprises an Fc fragment of an immunoglobulin selected from the group consisting of IgG1, IgG2, IgG3, IgG4, and combinations and hybrids thereof. In some embodiments, the Fc fragment has a reduced effector function as compared to the corresponding wildtype Fc fragment. In some embodiments, the Fc fragment has an enhanced effector function as compared to the corresponding wildtype Fc fragment. In some embodiments the Fc fragment has been altered for increased serum half-life compared to the corresponding wildtype Fc fragment. In some embodiments the Fc fragment has been altered for decreased serum half life compared to the corresponding wildtype Fc fragment.

In some embodiments, the antibody moiety comprises a humanized antibody of any of the antibody moiety described herein.

In some embodiments, the anti-CD93 construct comprises or is an anti-CD93 fusion protein.

In some embodiments, the anti-CD93 construct comprises or is a multispecific anti-CD93 construct (such as a bispe-cific antibody).

In some embodiments, the anti-CD93 construct comprises or is an anti-CD93 immunoconjugate.

In some embodiments, the anti-CD93 construct blocks the binding of CD93 and IGFBP7. In some embodiments, the IGFBP7 is a human IGFBP7. In some embodiments, the binding of CD93 to IGFBP7 is at least blocked by 10%, 20%, 30%, 40%, 50%, 60%, 70%, 80%, 90% or more after a pre-incubation of the anti-CD93 antibody with CD93 or CD93-expressing cells. In some embodiments, the dose of anti-CD93 antibody and CD93 is at a ratio of about 1:10, 1:6, 1:3, 1:1.5, 1:1, 4:3, 2:1, or 5:1. In some embodiments, the binding of CD93 to IGFBP7 is at least blocked by 10%, 20%, 30%, 40%, 50%, 60%, 70%, 80%, 90% or more after a pre-incubation of the anti-CD93 antibody at a concentration of about 50 µg/ml, 25 µg/ml, 10 µg/ml, 5 µg/ml, 2 µg/ml, 1 µg/ml, 0.8 µg/ml, 0.6 µg/ml, or 0.4 µg/ml.

In some embodiments, the anti-CD93 construct blocks the binding of CD93 and MMRN2. In some embodiments, the MMRN2 is a human MMRN2. In some embodiments, the MMRN2 is a MMRN2$^{495-674}$ fragment. In some embodiments, the binding of CD93 to MMRN2 is at least blocked by 10%, 20%, 30%, 40%, 50%, 60%, 70%, 80%, 90% or more after a pre-incubation of the anti-CD93 antibody with CD93 or CD93-expressing cells. In some embodiments, the anti-CD93 construct does not block the binding of CD93 and MMRN2.

In some embodiments, the anti-CD93 construct blocks the binding of CD93 to both IGFBP7 and MMRN2.

In some embodiments, the anti-CD93 construct does not block the interaction between CD93 and IGFBP7. In some embodiments, the anti-CD93 construct does not block the interaction between CD93 and MMRN2. In some embodiments, the anti-CD93 construct does not block the interaction between either IGFBP7 or MMRN2.

In some embodiments, the CD93 is a human CD93.

a) Antibody Affinity

Binding specificity of the antibody moieties can be determined experimentally by methods known in the art. Such methods comprise, but are not limited to Western blots, ELISA-, RIA-, ECL-, IRMA-, EIA-, BLI, BIACORE™-tests, flow cytometry and peptide scans.

In some embodiments, the $K_D$ of the binding between the antibody moiety and CD93 is about $10^{-7}$ M to about $10^{-12}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-7}$ M to about $10^{-11}$ M, about $10^{-8}$ to about $10^{-11}$ M, about $10^{-9}$ M to about $10^{-11}$ M, about $10^{-7}$ M to about $10^{-10}$ M, about $10^{-8}$ M to about $10^{-10}$ M, or about $10^{-7}$ M to about $10^{-9}$ M. In some embodiments, the $K_D$ of the binding between the antibody moiety and CD93 is stronger than about any one of $10^{-7}$ M, $10^{-8}$ M, $10^{-9}$ M, $10^{-10}$ M, $10^{-11}$ M, or $10^{-12}$ M. In some embodiments, the CD93 is a human CD93.

In some embodiments, the $K_{on}$ of the binding between antibody moiety and CD93 is about $10^3$ M$^{-1}$s$^{-1}$ to about $10^8$ M$^{-1}$s$^{-1}$, about $10^3$ M$^{-1}$s$^{-1}$ to about $10^4$ M$^{-1}$s$^{-1}$, about $10^4$ M$^{-1}$s$^{-1}$ to about $10^5$ M$^{-1}$s$^{-1}$, about $10^5$ M$^{-1}$s$^{-1}$ to about $10^6$ M$^{-1}$s$^{-1}$, about $10^6$ M$^{-1}$s$^{-1}$ to about $10^7$ M$^{-1}$ s$^{-1}$, or about $10^7$ M$^{-1}$s$^{-1}$ to about $10^8$ M$^{-1}$s$^{-1}$. In some embodiments, the $K_{on}$ of the binding between the antibody moiety and CD93 is about $10^3$ M$^{-1}$s$^{-1}$ to about $10^5$ M$^{-1}$s$^{-1}$, about $10^4$ M$^{-1}$s$^{-1}$ to about $10^6$ M$^{-1}$s$^{-1}$, about $10^5$ M$^{-1}$s$^{-1}$ to about $10^7$ M$^{-1}$s$^{-1}$, about $10^6$ M$^{-1}$s$^{-1}$ to about $10^8$ M$^{-1}$s$^{-1}$, about $10^4$ M$^{-1}$s$^{-1}$ to about $10^7$ M$^{-1}$s$^{-1}$, or about $10^5$ M$^{-1}$s$^{-1}$ to about $10^8$ M$^{-1}$s$^{-1}$. In some embodiments, the $K_{on}$ of the binding between antibody moiety and CD93 is no more than about any one of $10^3$ M$^{-1}$s$^{-1}$, $10^4$ M$^{-1}$s$^{-1}$, $10^5$ M$^{-1}$s$^{-1}$, $10^6$ M$^{-1}$s$^{-1}$, $10^7$ M$^{-1}$s$^{-1}$ or $10^8$ M$^{-1}$s$^{-1}$. In some embodiments, CD93 is human CD93.

In some embodiments, the $K_{off}$ of the binding between the antibody moiety and CD93 is about 1 s$^{-1}$ to about $10^{-6}$ s$^{-1}$, about 1 s$^{-1}$ to about $10^{-2}$ s$^{-1}$, about $10^{-2}$ s$^{-1}$ to about $10^{-3}$ s$^{-1}$, about $10^{-3}$ s$^{-1}$ to about $10^{-4}$ s$^{-1}$, about $10^{-4}$ s$^{-1}$ to about $10^{-5}$ s$^{-1}$, about $10^{-5}$ s$^{-1}$ to about $10^{-6}$ s$^{-1}$, about 1 s$^{-1}$ to about $10^{-5}$ s$^{-1}$, about $10^{-2}$ s$^{-1}$ to about $10^{-6}$ s$^{-1}$, about $10^{-3}$ s$^{-1}$ to about $10^{-6}$ s$^{-1}$, about $10^{-4}$ s$^{-1}$ to about $10^{-6}$ s$^{-1}$, about $10^{-2}$ s$^{-1}$ to about $10^{-5}$ s$^{-1}$, or about $10^{-3}$ s$^{-1}$ to about $10^{-5}$ s$^{-1}$. In some embodiments, the $K_{off}$ of the binding between the antibody moiety and CD93 is at least about any one of 1 s$^{-1}$, $10^{-2}$ s$^{-1}$, $10^{-3}$ s$^{-1}$, $10^{-4}$ s$^{-1}$, $10^{-5}$ s$^{-1}$ or $10^{-6}$ s$^{-1}$. In some embodiments, CD93 is human CD93.

In some embodiments, the binding affinity of the anti-CD93 antibody moiety or anti-CD93 construct are higher (for example, has a smaller $K_D$ value) than an existing anti-CD93 antibody (e.g., anti-human CD93 antibody, e.g., MM01).

b) Chimeric or Humanized Antibodies

In some embodiments, the anti-CD93 antibody moiety is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In some embodiments, a chimeric antibody comprises a non-human variable region (e.g., a variable region derived from mouse) and a human constant region. In some embodiments, a chimeric antibody is a "class switched" antibody in which the class or subclass has been changed from that of the parent antibody. Chimeric antibodies include antigen-binding fragments thereof.

In some embodiments, the anti-CD93 antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); Framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

It is understood that the humanization of mouse derived antibodies is a common and routinely used art. It is therefore understood that a humanized format of any and all of the anti-CD93 antibodies disclosed in Sequence Table can be used in a preclinical or clinical setting. In cases where a humanized format of any of the referenced anti-CD93 antibodies or their antigen-binding regions thereof is used in such a preclinical or clinical setting, the then humanized format is expected to bear the same or similar biological activities and profiles as the original non-humanized format.

c) Human Antibodies

In some embodiments, the anti-CD93 antibody moiety is a human antibody (known as human domain antibody, or human DAb). Human antibodies can be produced using various techniques known in the art. Human antibodies are described generally in van Dijk and van de Winkel, *Curr. Opin. Pharmacol.* 5: 368-74 (2001), Lonberg, *Curr. Opin. Immunol.* 20:450-459 (2008), and Chen, *Mol. Immunol.* 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies have been described (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991)). Human antibodies generated via human B-cell hybridoma technology are also described in Li et al., *Proc. Natl Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4): 265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

d) Library-Derived Antibodies

The anti-CD93 antibody moieties described herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004). Methods for constructing single-domain antibody libraries have been described, for example, See U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

e) Substitution, Insertion, Deletion and Variants

In some embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Amino acid substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; He | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | He; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Mrg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity or molecular behavior. Another method to introduce diversity involves HVR-directed approaches, in which several HVR residues (e.g., 4-6 residues at a time) are randomized. HVR residues involved in antigen binding may be specifically identified, e.g., using alanine or histidine scanning mutagenesis or modeling. HC-CDR3 and LC-CDR3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties for the antibody.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

f) Glycosylation Variants

In some embodiments, the anti-CD93 antibody moiety is altered to increase or decrease the extent to which the construct is glycosylated. Addition or deletion of glycosylation sites to an antibody may be conveniently accomplished by altering the amino acid sequence such that one or more glycosylation sites is created or removed.

Where the antibody moiety comprises an Fc region, the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antibody moiety may be made in order to create antibody variants with certain improved properties.

In some embodiments, the anti-CD93 antibody moiety has a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4): 680-688 (2006); and WO2003/085107).

In some embodiments, the anti-CD93 antibody moiety has bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

g) Fc Region Variants

In some embodiments, the anti-CD93 antibody moiety comprises an Fc fragment.

The term "Fc region," "Fc domain," "Fc fragment" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, MD, 1991.

In some embodiments, the Fc fragment is from an immunoglobulin selected from the group consisting of IgG, IgA, IgD, IgE, IgM, and combinations and hybrids thereof. In some embodiments, the Fc fragment is from an immunoglobulin selected from the group consisting of IgG1, IgG2, IgG3, IgG4, and combinations and hybrids thereof.

In some embodiments, the Fc fragment has a reduced effector function as compared to corresponding wildtype Fc fragment (such as at least about 30%, 40%, 50%, 60%, 70%, 80%, 85%, 90%, or 95% reduced effector function as measured by the level of antibody-dependent cellular cytotoxicity (ADCC)).

In some embodiments, the Fc fragment is an IgG1 Fc fragment. In some embodiments, the IgG1 Fc fragment comprises a L234A mutation and/or a L235A mutation. In some embodiments, the Fc fragment is an IgG2 or IgG4 Fc fragment. In some embodiments, the Fc fragment is an IgG4 Fc fragment comprising a S228P, F234A, and/or a L235A mutation. In some embodiments, the Fc fragment comprises a N297A mutation. In some embodiments, the Fc fragment comprises a N297G mutation.

In some embodiments, one or more amino acid modifications may be introduced into the Fc region of the antibody moiety, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the Fc fragment possesses some but not all effector functions, which make it a desirable candidate for applications in which the half-life of the antibody moiety in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (See Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and Cyto-Tox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). In some embodiments, the Fc fragment comprises a N297A mutation. In some embodiments, the Fc fragment comprises a N297G mutation.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, the Fc fragment is an IgG1 Fc fragment. In some embodiments, the IgG1 Fc fragment comprises a L234A mutation and/or a L235A mutation. In some embodiments, the IgG1 Fc fragment comprises a L235A mutation and/or a G237A mutation. In some embodiments, the Fc fragment is an IgG2 or IgG4 Fc fragment. In some embodiments, the Fc fragment is an IgG4 Fc fragment comprising a S228P, F234A, and/or a L235A mutation.

In some embodiments, the antibody moiety comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, the antibody moiety variant comprising a variant Fc region comprising one or more amino acid substitutions which alters half-life and/or changes binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which alters binding of the Fc region to FcRn. Such Fc variants include those with substitutions at one or more of Fc region residues, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

h) Cysteine Engineered Antibody Variants

In some embodiments, it may be desirable to create cysteine engineered antibody moieties, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibody moieties may be generated as described, e.g., in U.S. Pat. No. 7,521,541.

i) Antibody Derivatives

In some embodiments, the antibody moiety described herein may be further modified to comprise additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in diagnosis under defined conditions, etc.

In some embodiments, the antibody moiety may be further modified to comprise one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine.

Multispecific Anti-CD93 Constructs

The anti-CD93 constructs in some embodiments comprise a multispecific (e.g., bispecific) anti-CD93 construct comprising an anti-CD93 antibody moiety according to any one of the anti-CD93 antibody moieties described herein, and a second binding moiety (such as a second antibody moiety) specifically recognizing a second antigen.

In some embodiments, the multispecific anti-CD93 molecule comprises an anti-CD93 antibody moiety and a second moiety (such as a second antibody moiety) specifically recognizing a second antigen.

In some embodiments, the second antigen is an immune checkpoint molecule. In some embodiments, the second antigen is PD-1 or PD-L1.

In some embodiment, the second moiety is an extracellular domain (ECD) of PD-1 or PD-L1. In some embodiments, the second moiety is a PD-L1 trap or PD-1 trap. See e.g., Nat Commun. 2018 Jun. 8; 9(1):2237.

In some embodiments, the second antigen is a tumor antigen.

In some embodiments, the second antigen is an angiogenic agent. In some embodiments, the angiogenic agent is a VEGF (e.g., a human VEGF) antibody. In some embodiments, the angiogenic agent is a VEGF receptor. In some embodiments, the angiogenic agent is a VEGFR1 (e.g., a human VEGFR1). In some embodiments, the angiogenic agent is a VEGFR2 (e.g., a human VEGFR2).

In some embodiments, the second moiety comprises an extracellular domain (ECD) of a VEGF receptor. In some embodiments, the second moiety comprises an ECD of VEGFR1 and/or VEGFR2. In some embodiments, the second moiety comprises a VEGF-trap. See e.g., Proc Natl Acad Sci USA. 2002 Aug. 20; 99(17):11393-8.

In some embodiments, the second antibody moiety and the anti-CD93 antibody moiety are fused with each other via a linker such as any of the linkers described herein with any operable form that allows the proper function of the binding moieties. In some embodiments, the linker is a GS linker. In some embodiments, the linker is selected from the group consisting of SEQ ID NOs: 225-232 and 338.

In some embodiments, the anti-CD93 construct is a multispecific (e.g., bispecific) anti-CD93 construct comprising a) an anti-CD93 antibody moiety according to any one of the anti-CD93 antibody moieties described herein; b) a second antibody moiety specifically recognizing PD-L1 (an anti-PD-L1 antibody moiety).

In some embodiments, the anti-CD93 construct is a multispecific (e.g., bispecific) anti-CD93 construct comprising a) an anti-CD93 full-length antibody comprising two heavy chains and two light chains, wherein the two heavy chains each comprises a heavy chain variable region ($V_H$) and the two light chains each comprises a light chain variable region (V), b) an anti-PD-L1 antibody moiety (such as any of the antibody moiety described herein) fused to at least one or both of the heavy chains of the anti-CD93 full-length antibody. In some embodiments, the anti-PD-L1 antibody moiety is fused to N-terminus of both heavy chains. In some embodiments, the anti-PD-L1 antibody moiety is fused to C-terminus of both heavy chains.

In some embodiments, the anti-CD93 construct is a multispecific (e.g., bispecific) anti-CD93 construct comprising a) an anti-PD-L1 antibody moiety comprising a full-length antibody comprising two heavy chains and two light chains, wherein the two heavy chains each comprises a heavy chain variable region ($V_H$) and the two light chains each comprises a light chain variable region (V), b) an anti-CD93 antibody moiety (such as any of the anti-CD93 antibody moiety described herein) fused to at least one or both of the heavy chains of the anti-PD-L1 full-length antibody. In some embodiments, the anti-CD93 antibody moiety is fused to N-terminus of both heavy chains. In some embodiments, the anti-CD93 antibody moiety is fused to C-terminus of both heavy chains.

In some embodiments, the anti-CD93 construct is a multispecific (e.g., bispecific) anti-CD93 construct comprising a) an anti-CD93 full-length antibody comprising two heavy chains and two light chains, wherein the two heavy chains each comprises a heavy chain variable region ($V_H$) and the two light chains each comprises a light chain variable region (V), b) an anti-PD-L1 antibody moiety (such as any of the antibody moiety described herein) fused to at least one or both of the light chains of the anti-CD93 full-length antibody. In some embodiments, the anti-PD-L1 antibody moiety is fused to N-terminus of both light chains. In some embodiments, the anti-PD-L1 antibody moiety is fused to C-terminus of both light chains.

In some embodiments, the anti-CD93 construct is a multispecific (e.g., bispecific) anti-CD93 construct comprising a) an anti-PD-L1 antibody moiety comprising a full-length antibody comprising two heavy chains and two light chains, wherein the two heavy chains each comprises a heavy chain variable region ($V_H$) and the two light chains each comprises a light chain variable region (V), b) an anti-CD93 antibody moiety (such as any of the antibody moiety described herein) fused to at least one or both of the light chains of the anti-PD-L1 full-length antibody. In some embodiments, the anti-CD93 antibody moiety is fused to N-terminus of both light chains. In some embodiments, the anti-CD93 antibody moiety is fused to C-terminus of both light chains.

In some embodiments, the anti-CD93 construct is a multispecific (e.g., bispecific) anti-CD93 construct comprising a) an anti-CD93 antibody moiety according to any one of the anti-CD93 antibody moieties described herein; b) a second antibody moiety specifically recognizing PD-1 (an anti-PD-1 antibody moiety).

In some embodiments, the anti-CD93 construct is a multispecific (e.g., bispecific) anti-CD93 construct comprising a) an anti-CD93 full-length antibody comprising two heavy chains and two light chains, wherein the two heavy chains each comprises a heavy chain variable region ($V_H$) and the two light chains each comprises a light chain variable region (V), b) an anti-PD-1 antibody moiety (such as any of the antibody moiety described herein) fused to at least one or both of the heavy chains of the anti-CD93 full-length antibody. In some embodiments, the anti-PD-antibody moiety is fused to N-terminus of both heavy chains. In some embodiments, the anti-PD-1 antibody moiety is fused to C-terminus of both heavy chains.

In some embodiments, the anti-CD93 construct is a multispecific (e.g., bispecific) anti-CD93 construct comprising a) an anti-PD-1 antibody moiety comprising a full-length antibody comprising two heavy chains and two light chains, wherein the two heavy chains each comprises a heavy chain variable region ($V_H$) and the two light chains each comprises a light chain variable region (V), b) an anti-CD93 antibody moiety (such as any of the anti-CD93 antibody moiety described herein) fused to at least one or both of the heavy chains of the anti-PD-1 full-length antibody. In some embodiments, the anti-CD93 antibody moiety is fused to N-terminus of both heavy chains. In some embodiments, the anti-CD93 antibody moiety is fused to C-terminus of both heavy chains.

In some embodiments, the anti-CD93 construct is a multispecific (e.g., bispecific) anti-CD93 construct comprising a) an anti-CD93 full-length antibody comprising two heavy chains and two light chains, wherein the two heavy chains each comprises a heavy chain variable region ($V_H$) and the two light chains each comprises a light chain variable region (V), b) an anti-PD-1 antibody moiety (such as any of the antibody moiety described herein) fused to at least one or both of the light chains of the anti-CD93 full-length antibody. In some embodiments, the anti-PD-1 antibody moiety is fused to N-terminus of both light chains. In some embodiments, the anti-PD-1 antibody moiety is fused to C-terminus of both light chains.

In some embodiments, the anti-CD93 construct is a multispecific (e.g., bispecific) anti-CD93 construct comprising a) an anti-PD-1 antibody moiety comprising a full-length antibody comprising two heavy chains and two light chains, wherein the two heavy chains each comprises a heavy chain variable region ($V_H$) and the two light chains each comprises a light chain variable region (V), b) an anti-CD93 antibody moiety (such as any of the antibody moiety described herein) fused to at least one or both of the light chains of the anti-PD-1 full-length antibody. In some embodiments, the anti-CD93 antibody moiety is fused to N-terminus of both light chains. In some embodiments, the anti-CD93 antibody moiety is fused to C-terminus of both light chains.

In some embodiments, the anti-CD93 construct is a multispecific (e.g., bispecific) anti-CD93 construct comprising a) an anti-CD93 antibody moiety according to any one of the anti-CD93 antibody moieties described herein; b) a second binding moiety specifically recognizing VEGF.

In some embodiments, the anti-CD93 construct is a multispecific (e.g., bispecific) anti-CD93 construct comprising a) an anti-CD93 full-length antibody comprising two heavy chains and two light chains, wherein the two heavy chains each comprises a heavy chain variable region ($V_H$) and the two light chains each comprises a light chain variable region (V), b) a second binding moiety specifically recognizing VEGF fused to at least one or both of the heavy chains of the anti-CD93 full-length antibody. In some embodiments, the second binding moiety is fused to N-terminus of both heavy chains. In some embodiments, the second binding moiety is fused to C-terminus of both heavy chains.

In some embodiments, the anti-CD93 construct is a multispecific (e.g., bispecific) anti-CD93 construct comprising a) an anti-VEGF antibody moiety comprising a full-length antibody comprising two heavy chains and two light chains, wherein the two heavy chains each comprises a heavy chain variable region ($V_H$) and the two light chains each comprises a light chain variable region (V), b) an anti-CD93 antibody moiety (such as any of the anti-CD93 antibody moiety described herein) fused to at least one or both of the heavy chains of the anti-VEGF full-length antibody. In some embodiments, the anti-CD93 antibody moiety is fused to N-terminus of both heavy chains. In some embodiments, the anti-CD93 antibody moiety is fused to C-terminus of both heavy chains.

In some embodiments, the anti-CD93 construct is a multispecific (e.g., bispecific) anti-CD93 construct comprising a) an anti-CD93 full-length antibody comprising two heavy chains and two light chains, wherein the two heavy chains each comprises a heavy chain variable region ($V_H$) and the two light chains each comprises a light chain variable region ($V_L$), b) a second binding moiety specifically recognizing VEGF fused to at least one or both of the light chains of the anti-CD93 full-length antibody. In some embodiments, the second binding moiety is fused to N-terminus of both light chains. In some embodiments, a second binding moiety specifically recognizing VEGF is fused to C-terminus of both light chains.

In some embodiments, the anti-CD93 construct is a multispecific (e.g., bispecific) anti-CD93 construct comprising a) an anti-VEGF antibody moiety comprising a full-length antibody comprising two heavy chains and two light chains, wherein the two heavy chains each comprises a heavy chain variable region ($V_H$) and the two light chains each comprises a light chain variable region ($V_L$), b) an anti-CD93 antibody moiety (such as any of the antibody moiety described herein) fused to at least one or both of the light chains of the anti-VEGF full-length antibody. In some embodiments, the anti-CD93 antibody moiety is fused to N-terminus of both light chains. In some embodiments, the anti-CD93 antibody moiety is fused to C-terminus of both light chains.

In some embodiments, there is provided an anti-CD93 construct comprising a) a full-length antibody that specifically recognizes CD93 comprising two heavy chains and two light chains, wherein the two heavy chains each comprises a heavy chain variable region ($V_H$) comprising the HC-CDR1 comprising the amino acid sequence of SEQ ID NO: 289, the HC-CDR2 comprising the amino acid sequence of SEQ ID NO: 290, and the HC-CDR3 comprising the amino acid sequence of SEQ ID NO: 291, and wherein the two light chains each comprises a light chain variable region ($V_L$) comprises the LC-CDR1 comprising the amino acid sequence of SEQ ID NO: 292, the LC-CDR2 comprising the amino acid sequence of SEQ ID NO: 293, and the LC-CDR3 comprising the amino acid sequence of SEQ ID NO: 294, and b) a VEGF binding moiety comprising the amino acid sequence of SEQ ID NO: 325, wherein the VEGF binding moiety is fused to one or both of the heavy chains of the full-length antibody. In some embodiments, the VEGF binding moiety is fused to C-terminus of both heavy chains of the full-length antibody. In some embodiments, the VEGF binding moiety is fused to the full-length antibody via a linker. In some embodiments, the linker is GS linker or selected from the group consisting of SEQ ID NOs: 225-232 and 338. In some embodiments, the linker comprises the amino acid sequence of SEQ ID NO: 338. In some embodiments, the anti-CD93 $V_H$ comprises the amino acid sequence of any one of SEQ ID NOs: 287, and 319-321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any one of SEQ ID NOs: 288, and 322-324, or a variant comprising an amino acid sequence having at least about 80% (such as at least about any one of 80%, 85%, 90%, 95%, 96%, 97%, 98%, or 99%) sequence identity. In some embodiments, the full-length antibody has an IgG1 isotype (such as a human IgG1 isotype). In some embodiments, the heavy chain comprises the amino acid sequence of SEQ ID NO: 342, or a variant comprising an amino acid sequence having at least about 80% (such as at least about any one of 80%, 85%, 90%, 95%, 96%, 97%, 98%, or 99%) sequence identity. In some embodiments, the light chain comprises the amino acid sequence of SEQ ID NO: 343, or a variant comprising an amino acid sequence having at least about 80% (such as at least about any one of 80%, 85%, 90%, 95%, 96%, 97%, 98%, or 99%) sequence identity.

In some embodiments, the anti-CD93 $V_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, or a variant thereof comprising up to 5, 4, 3, 2, or 1 amino acid substitutions in the HC-CDRs, and the anti-CD93 $V_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6, or a variant thereof comprising up to 5, 4, 3, 2, or 1 amino acid substitutions in the LC-CDRs.

In some embodiments, the anti-CD93 $V_H$ comprises i) the HC-CDR1 comprising the amino acid sequence of SEQ ID NO: 17 or 304, ii) the HC-CDR2 comprising the amino acid sequence of SEQ ID NO: 18 or 305, and iii) the HC-CDR3 comprising the amino acid sequence of SEQ ID NO: 19, or a variant thereof comprising up to 5, 4, 3, 2, or 1 amino acid substitutions in the HC-CDRs, and the anti-CD93 $V_L$ comprises i) the LC-CDR1 comprising the amino acid sequence of SEQ ID NO: 20, 301, 302, 303, or 306, ii) the LC-CDR2 comprising the amino acid sequence of SEQ ID NO: 21, and iii) the LC-CDR3 comprising the amino acid sequence of SEQ ID NO: 22, or a variant thereof comprising up to 5, 4, 3, 2, or 1 amino acid substitutions in the LC-CDRs.

In some embodiments, the anti-CD93 $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, or a variant thereof comprising up to 5, 4, 3, 2, or 1 amino acid substitutions in the HC-CDRs, and the anti-CD93 $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294, or a variant thereof comprising up to 5, 4, 3, 2, or 1 amino acid substitutions in the LC-CDRs. In some embodiments, the anti-CD93 $V_H$ comprises i) the HC-CDR1 comprising the amino acid sequence of SEQ ID NO: 295, ii) the HC-CDR2 comprising the amino acid sequence of SEQ ID NO: 296, and iii) the HC-CDR3 comprising the amino acid sequence of SEQ ID NO: 297, or a variant thereof comprising up to 5, 4, 3, 2, or 1 amino acid substitutions in the HC-CDRs, and the anti-CD93 $V_L$ comprises i) the LC-CDR1 comprising the amino acid sequence of SEQ ID NO: 298, ii) the LC-CDR2 comprising the amino acid sequence of SEQ ID NO: 299, and iii) the LC-CDR3 comprising the amino acid sequence of SEQ ID NO: 300, or a variant thereof comprising up to 5, 4, 3, 2, or 1 amino acid substitutions in the LC-CDRs.

In some embodiments, the amino acid substitutions described above are limited to "exemplary substitutions" shown in Table 2 of this application. In some embodiments, the amino acid substitutions are limited to "preferred substitutions" shown in Table 2 of this application.

Exemplary Anti-PD-L1 Antibody Moieties

Exemplary anti-PD-L1 antibody moieties include, but not are limited to those described in WO2019228514A1, WO2019227490A1 and WO2020019232A1.

In some embodiments, the anti-PD-L1 antibody moiety (such as an scFv) used in multispecific anti-CD93 constructs comprises an antibody moiety comprising a heavy chain variable region ($V_H$) and a light chain variable region ($V_L$), wherein the antibody moiety competes for a binding epitope of PD-L1 with an antibody or antibody fragment comprising a second heavy variable region ($V_{H\text{-}2}$) and a second light chain variable region ($V_L$0.2), wherein the $V_{H\text{-}2}$ comprises the HC-CDR1 comprising the amino acid sequence of SEQ ID NO: 251, the HC-CDR2 comprising the amino acid sequence of SEQ ID NO: 252, and the HC-CDR3 comprising the amino acid sequence of SEQ ID NO: 253, and the $V_L$-2 comprises the LC-CDR1 comprising the amino acid sequence of SEQ ID NO: 254, the LC-CDR2 comprising the amino acid sequence of SEQ ID NO: 255, and the LC-CDR3 comprising the amino acid sequence of SEQ ID NO: 256.

In some embodiments, the anti-PD-L1 moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 281, 282, or 283; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 284, 285, or 286.

In some embodiments, the anti-PD-L1 antibody moiety (such as an scFv) used in multispecific anti-CD93 constructs comprises a heavy chain variable region ($V_H$) and a light chain variable region ($V_L$), wherein: a) the $V_H$ comprises an HC-CDR1 comprising the amino acid sequence of SEQ ID NO: 251, an HC-CDR2 comprising the amino acid sequence of SEQ ID NO: 252, and an HC-CDR3 comprising the amino acid sequence of SEQ ID NO: 253, or a variant thereof comprising up to a total of about 5, 4, 3, 2, or 1 amino acid substitutions in the HC-CDRs; and b) the $V_L$ comprises an LC-CDR1 comprising the amino acid sequence of SEQ ID NO: 254, an LC-CDR2 comprising the amino acid sequence of any one of SEQ ID NO: 255, and an LC-CDR3 comprising the amino acid sequence of any one of SEQ ID NO: 256, or a variant thereof comprising up to a total of about 5, 4, 3, 2, or 1 amino acid substitutions in the LC-CDRs.

In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the $V_H$ comprises an amino acid sequence of SEQ ID NO: 281, 282, or 283, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 284, 285 or 286, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 281, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 284, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 282, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 285, or a variant comprising an amino acid sequence having at least about 80% (such as at least about any one of 80%, 85%, 90%, 95%, 96%, 97%, 98%, or 99%) sequence identity. In some embodiments, the $V_H$ comprises an amino acid sequence of SEQ ID NO: 283, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 286, or a variant comprising an amino acid sequence having at least about 80% (such as at least about any one of 80%, 85%, 90%, 95%, 96%, 97%, 98%, or 99%) sequence identity.

In some embodiments, the second antibody moiety and the anti-CD93 antibody moiety are fused with each other via a linker such as any of the linkers described herein with any operable form that allows the proper function of the binding moieties.

Exemplary Anti-PD-1 Antibody Moieties

Exemplary anti-PD-1 antibody moieties include, but not are limited to those described in WO2018133842 and WO2018133837.

In some embodiments, the anti-PD-1 antibody moiety (such as an scFv) used in multispecific anti-CD93 constructs comprises an antibody moiety comprising a heavy chain variable region ($V_H$) and a light chain variable region ($V_L$), wherein the antibody moiety competes for a binding epitope of PD-1 with an antibody or antibody fragment comprising a second heavy variable region ($V_{H\text{-}2}$) and a second light chain variable region ($V_L$0.2), wherein the $V_{H\text{-}2}$ comprises the HC-CDR1 comprising the amino acid sequence of SEQ ID NO: 257, the HC-CDR2 comprising the amino acid sequence of SEQ ID NO: 258, and the HC-CDR3 comprising the amino acid sequence of SEQ ID NO: 259, and the $V_L$-2 comprises the LC-CDR1 comprising the amino acid sequence of SEQ ID NO: 260, the LC-CDR2 comprising the amino acid sequence of SEQ ID NO: 261, and the LC-CDR3 comprising the amino acid sequence of SEQ ID NO: 262.

In some embodiments, the anti-PD-1 moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 275; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 276.

In some embodiments, the anti-PD-1 antibody moiety (such as an scFv) used in multispecific anti-CD93 constructs comprises a heavy chain variable region ($V_H$) and a light chain variable region ($V_L$), wherein: a) the $V_H$ comprises an HC-CDR1 comprising the amino acid sequence of SEQ ID NO: 257, an HC-CDR2 comprising the amino acid sequence of SEQ ID NO: 258, and an HC-CDR3 comprising the amino acid sequence of SEQ ID NO: 259, or a variant thereof comprising up to a total of about 5, 4, 3, 2, or 1 amino acid substitutions in the HC-CDRs; and b) the $V_L$ comprises an LC-CDR1 comprising the amino acid sequence of SEQ ID NO: 260, an LC-CDR2 comprising the amino acid sequence of any one of SEQ ID NO: 261, and an LC-CDR3 comprising the amino acid sequence of any one of SEQ ID NO: 262, or a variant thereof comprising up to a total of about 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the second antibody moiety comprises a humanized antibody moiety derived from a murine antibody comprising a heavy chain variable region ($V_H$) comprising the amino acid sequence set forth in SEQ ID NO: 275 and a light chain variable region ($V_L$) comprising the amino acid sequence forth in SEQ ID NO: 276.

In some embodiments, the anti-PD-1 antibody moiety (such as an scFv) used in multispecific anti-CD93 constructs comprises an antibody moiety comprising a heavy chain variable region ($V_H$) and a light chain variable region ($V_L$), wherein the antibody moiety competes for a binding epitope of PD-1 with an antibody or antibody fragment comprising a second heavy variable region ($V_{H-2}$) and a second light chain variable region ($V_L$0.2), wherein the $V_{H-2}$ comprises the HC-CDR1 comprising the amino acid sequence of SEQ ID NO: 263, the HC-CDR2 comprising the amino acid sequence of SEQ ID NO: 264, and the HC-CDR3 comprising the amino acid sequence of SEQ ID NO: 265, and the $V_L$2 comprises the LC-CDR1 comprising the amino acid sequence of SEQ ID NO: 266, the LC-CDR2 comprising the amino acid sequence of SEQ ID NO: 267, and the LC-CDR3 comprising the amino acid sequence of SEQ ID NO: 268.

In some embodiments, the anti-PD-1 moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 277; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 278.

In some embodiments, the anti-PD-1 antibody moiety (such as an scFv) used in multispecific anti-CD93 constructs comprises a heavy chain variable region ($V_H$) and a light chain variable region ($V_L$), wherein: a) the $V_H$ comprises an HC-CDR1 comprising the amino acid sequence of SEQ ID NO: 263, an HC-CDR2 comprising the amino acid sequence of SEQ ID NO: 264, and an HC-CDR3 comprising the amino acid sequence of SEQ ID NO: 265, or a variant thereof comprising up to a total of about 5, 4, 3, 2, or 1 amino acid substitutions in the HC-CDRs; and b) the $V_L$ comprises an LC-CDR1 comprising the amino acid sequence of SEQ ID NO: 266, an LC-CDR2 comprising the amino acid sequence of any one of SEQ ID NO: 267, and an LC-CDR3 comprising the amino acid sequence of any one of SEQ ID NO: 268, or a variant thereof comprising up to a total of about 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the anti-PD-1 antibody moiety comprises a humanized antibody moiety derived from a murine antibody comprising a heavy chain variable region ($V_H$) comprising the amino acid sequence set forth in SEQ ID NO: 277 and a light chain variable region ($V_L$) comprising the amino acid sequence forth in SEQ ID NO: 278.

In some embodiments, the anti-PD-1 antibody moiety (such as an scFv) used in multispecific anti-CD93 constructs comprises an antibody moiety comprising a heavy chain variable region ($V_H$) and a light chain variable region ($V_L$), wherein the antibody moiety competes for a binding epitope of PD-1 with an antibody or antibody fragment comprising a second heavy variable region ($V_{H-2}$) and a second light chain variable region ($V_L$0.2), wherein the $V_{H-2}$ comprises the HC-CDR1 comprising the amino acid sequence of SEQ ID NO: 269, the HC-CDR2 comprising the amino acid sequence of SEQ ID NO: 270, and the HC-CDR3 comprising the amino acid sequence of SEQ ID NO: 271, and the $V_L$2 comprises the LC-CDR1 comprising the amino acid sequence of SEQ ID NO: 272, the LC-CDR2 comprising the amino acid sequence of SEQ ID NO: 273, and the LC-CDR3 comprising the amino acid sequence of SEQ ID NO: 274.

In some embodiments, the anti-PD-1 moiety comprises a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 279; and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 280.

In some embodiments, the anti-PD-1 antibody moiety (such as an scFv) used in multispecific anti-CD93 constructs comprises a heavy chain variable region ($V_H$) and a light chain variable region ($V_L$), wherein: a) the $V_H$ comprises an HC-CDR1 comprising the amino acid sequence of SEQ ID NO: 269, an HC-CDR2 comprising the amino acid sequence of SEQ ID NO: 270, and an HC-CDR3 comprising the amino acid sequence of SEQ ID NO: 271, or a variant thereof comprising up to a total of about 5, 4, 3, 2, or 1 amino acid substitutions in the HC-CDRs; and b) the $V_L$ comprises an LC-CDR1 comprising the amino acid sequence of SEQ ID NO: 272, an LC-CDR2 comprising the amino acid sequence of any one of SEQ ID NO: 273, and an LC-CDR3 comprising the amino acid sequence of any one of SEQ ID NO: 274, or a variant thereof comprising up to a total of about 5, 4, 3, 2, or 1 amino acid substitutions in the LC-CDRs. In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, the second antibody moiety comprises a humanized antibody moiety derived from a murine antibody comprising a heavy chain variable region ($V_H$) comprising the amino acid sequence set forth in SEQ ID NO: 279 and a light chain variable region ($V_L$) comprising the amino acid sequence forth in SEQ ID NO: 280.

In some embodiments, the second antibody moiety and the anti-CD93 antibody moiety are fused with each other via a linker such as any of the linkers described herein with any operable form that allows the proper function of the binding moieties.

Exemplary Binding Moieties Specifically Recognizing VEGF

Exemplary binding moieties specifically recognizing VEGF include, but not are limited to avastin, ramucirumab, or VEGF-trap (Aflibercept), or a variant or a functional portion thereof.

In some embodiments, the binding moiety that specifically recognizes VEGF used in multispecific anti-CD93 constructs is an antibody moiety (such as an scFv) comprising an antibody moiety comprising a heavy chain variable region ($V_H$) and a light chain variable region ($V_L$), wherein the $V_H$ comprises the HC-CDR1 comprising the amino acid sequence of SEQ ID NO: 326, the HC-CDR2 comprising the amino acid sequence of SEQ ID NO: 327, and the HC-CDR3 comprising the amino acid sequence of SEQ ID NO: 328, and the $V_L$ comprises the LC-CDR1 comprising the amino acid sequence of SEQ ID NO: 329, the LC-CDR2 comprising the amino acid sequence of SEQ ID NO: 330, and the LC-CDR3 comprising the amino acid sequence of SEQ ID NO: 331.

In some embodiments, the binding moiety that specifically recognizes VEGF used in multispecific anti-CD93 constructs is an antibody moiety (such as an scFv) comprising an antibody moiety comprising a heavy chain variable region ($V_H$) and a light chain variable region ($V_L$), wherein the $V_H$ comprises the HC-CDR1 comprising the amino acid sequence of SEQ ID NO: 332, the HC-CDR2 comprising the amino acid sequence of SEQ ID NO: 333, and the HC-CDR3 comprising the amino acid sequence of SEQ ID NO: 334, and the $V_L$ comprises the LC-CDR1 comprising the amino acid sequence of SEQ ID NO: 335, the LC-CDR2 comprising the amino acid sequence of SEQ ID NO: 336, and the LC-CDR3 comprising the amino acid sequence of SEQ ID NO: 337.

In some embodiments, the binding moiety that specifically recognizes VEGF used in multispecific anti-CD93 constructs comprises the amino acid sequence of SEQ ID NO: 325.

Anti-CD93 Fusion Proteins

The anti-CD93 constructs in some embodiments comprise an anti-CD93 antibody moiety (e.g., an anti-CD93 scFv) and a second moiety.

In some embodiments, the second moiety comprises a half-life extending moiety. In some embodiments, the half-life extending moiety is an albumin binding moiety (e.g., an albumin binding antibody moiety). In some embodiments, the anti-CD93 antibody moiety and the half-life extending moiety is linked via a linker (such as any of the linkers described in the "Linkers" section).

In some embodiments, the second moiety comprises an extracellular domain of a receptor. In some embodiment, the second moiety is an extracellular domain (ECD) of PD-1 or PD-L1. In some embodiments, the second moiety is a PD-L1 trap or PD-1 trap. See e.g., Nat Commun. 2018 Jun. 8; 9(1):2237. In some embodiments, the second moiety comprises an extracellular domain (ECD) of a VEGF receptor. In some embodiments, the second moiety comprises an ECD of VEGFR1 and/or VEGFR2. In some embodiments, the second moiety comprises a VEGF-trap. See e.g., Proc Natl Acad Sci USA. 2002 Aug. 20; 99(17):11393-8.

Anti-CD93 Immunoconjugates

The present application also provides anti-CD93 immunoconjugates comprising an anti-CD93 antibody moiety (such as any of the CD93 antibody moieties described herein) and a second agent. In some embodiments, the second agent is a therapeutic agent. In some embodiments, the second agent is a label.

Linkers

In some embodiments, the anti-CD93 constructs described herein comprise one or more linkers between two moieties (e.g., the anti-CD93 antibody moiety and the half-life extending moiety, the anti-CD93 antibody moiety and the second binding moiety in the multispecific constructs described above). The length, the degree of flexibility and/or other properties of the linker(s) used in the anti-CD93 constructs may have some influence on properties, including but not limited to the affinity, specificity or avidity for one or more particular antigens or epitopes. For example, longer linkers may be selected to ensure that two adjacent domains do not sterically interfere with one another. In some embodiment, a linker (such as peptide linker) comprises flexible residues (such as glycine and serine) so that the adjacent domains are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

Peptide Linkers

The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the domains to each other can be provided by, e.g., genetic engineering. Methods for preparing fused and operatively linked bispecific single chain constructs and expressing them in mammalian cells or bacteria are well-known in the art (e.g. WO 99/54440, Ausubel, Current Protocols in Molecular Biology, Green Publishing Associates and Wiley Interscience, N. Y. 1989 and 1994 or Sambrook et al., Molecular Cloning: A Laboratory Manual, Cold Spring Harbor Laboratory Press, Cold Spring Harbor, N. Y., 2001).

The peptide linker can be a stable linker, which is not cleavable by proteases, especially by Matrix metalloproteinases (MMPs).

The linker can also be a flexible linker. Exemplary flexible linkers include glycine polymers $(G)_n$ (SEQ ID NO: 225), glycine-serine polymers (including, for example, $(GS)_n$ (SEQ ID NO: 226), $(GSGGS)_n$ (SEQ ID NO: 227), $(GGGGS)_n$ (SEQ ID NO: 228), and $(GGGS)_n$ (SEQ ID NO: 229), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (See Scheraga, Rev. Computational Chem. 11 173-142 (1992)). The ordinarily skilled artisan will recognize that design of an antibody fusion protein can include linkers that are all or partially flexible, such that the linker can include a flexible linker portion as well as one or more portions that confer less flexible structure to provide a desired antibody fusion protein structure.

Furthermore, exemplary linkers also include the amino acid sequence of such as $(GGGGS)_n$(SEQ ID NO: 228), wherein n is an integer between 1 and 8, e.g. $(GGGGS)_3$ (SEQ ID NO: 230; hereinafter referred to as "(G4S)3" or "GS3"), or $(GGGGS)_6$ (SEQ ID NO: 231; hereinafter referred to as "(G4S)6" or "GS6"). In some embodiments, the peptide linker comprises the amino acid sequence of $(GSTSGSGKPGSGEGS)_n$(SEQ ID NO: 232), wherein n is an integer between 1 and 3.

Non-Peptide Linkers

Coupling of two moieties may be accomplished by any chemical reaction that will bind the two molecules so long as both components retain their respective activities, e.g., binding to CD93 and a second agent in an anti-CD93 multispecific antibody, respectively. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents may be useful in coupling protein molecules in this context. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (See Killen and Lindstrom, Jour. Immun. 133:1335-2549 (1984); Jansen et al., Immunological Reviews 62:185-216 (1982); and Vitetta et al., Science 238:1098 (1987)).

Linkers that can be applied in the present application are described in the literature (see, for example, Ramakrishnan, S. et al., Cancer Res. 44:201-208 (1984) describing use of MBS (M-maleimidobenzoyl-N-hydroxysuccinimide ester). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. In some embodiments, the linker is a PEG containing linker.

The linkers described above contain components that have different attributes, thus may lead to bispecific antibodies with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form antibody fusion protein with increased stability. Disulfide linkages, are in general, less stable than other linkages because the disulfide linkage is cleaved in vitro, resulting in less antibody fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

III. Methods of Preparation

In some embodiments, there is provided a method of preparing an anti-CD93 construct or antibody moiety that specifically binds to CD93 and a composition such as polynucleotide, nucleic acid construct, vector, host cell, or culture medium that is produced during the preparation of the anti-CD93 construct or antibody moiety. The anti-CD93 construct or antibody moiety or composition described herein may be prepared by a number of processes as generally described below and more specifically in the Examples.

Antibody Expression and Production

The antibodies (including anti-CD93 monoclonal antibodies, anti-CD93 bispecific antibodies, and anti-CD93 antibody moieties) described herein can be prepared using any known methods in the art, including those described below and in the Examples.

Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature,* 256:495 (1975), or may be made by recombinant DNA methods (U.S. Pat. No. 4,816,567). In the hybridoma method, a mouse or other appropriate host animal, such as a hamster or a llama, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986). Also See Example 1 for immunization in Camels.

The immunizing agent will typically include the antigenic protein or a fusion variant thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice,* Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., 63-Ag8-653) available from the American Type Culture Collection, Manassas, Va. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as flow cytometry, radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA), enzyme-linked assay (ELISA), or BLI. Such techniques and assays are known in the in art. For example, binding affinity may be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, ion exchange chromatography, gel electrophoresis, dialysis, or affinity chromatography.

Monoclonal antibodies may also be made by recombinant DNA methods, such as those described in U.S. Pat. No. 4,816,567, and as described above. mRNA encoding the monoclonal antibodies is readily isolated and sequenced using conventional procedures (e.g., by using oligonucleotide probes that are capable of binding specifically to cDNA encoding the heavy and light chains of murine antibodies). The hybridoma cells serve as a preferred source of such mRNA. Once isolated, the cDNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130:151-188 (1992).

In a further embodiment, antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Nucleic Acid Molecules Encoding Antibody Moieties

In some embodiments, there is provided a polynucleotide encoding any one of the anti-CD93 constructs or antibody moieties described herein. In some embodiments, there is provided a polynucleotide prepared using any one of the methods as described herein. In some embodiments, a nucleic acid molecule comprises a polynucleotide that encodes a heavy chain or a light chain of an antibody moiety (e.g., anti-CD93 antibody moiety). In some embodiments, a nucleic acid molecule comprises both a polynucleotide that encodes a heavy chain and a polynucleotide that encodes a light chain, of an antibody moiety (e.g., anti-CD93 antibody moiety). In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody moiety (e.g., anti-CD93 antibody moiety) comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

In some embodiments, the polynucleotide is a DNA. In some embodiments, the polynucleotide is an RNA. In some embodiments, the RNA is an mRNA.

Nucleic acid molecules may be constructed using recombinant DNA techniques conventional in the art. In some embodiments, a nucleic acid molecule is an expression vector that is suitable for expression in a selected host cell.

Nucleic Add Construct

In some embodiments, there is provided a nucleic acid construct comprising any one of the polynucleotides described herein. In some embodiments, there is provided a nucleic acid construct prepared using any method described herein.

In some embodiments, the nucleic acid construct further comprises a promoter operably linked to the polynucleotide. In some embodiments, the polynucleotide corresponds to a gene, wherein the promoter is a wild-type promoter for the gene.

Vectors

In some embodiments, there is provided a vector comprising any polynucleotides that encode the heavy chains and/or light chains of any one of the antibody moieties described herein (e.g., anti-CD93 antibody moieties) or nucleic acid construct described herein. In some embodiments, there is provided a vector prepared using any method described herein. Vectors comprising polynucleotides that encode any of anti-CD93 constructs such as antibodies, scFvs, fusion proteins or other forms of constructs described herein (e.g., anti-CD93 scFv) are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

Host Cells

In some embodiments, there is provided a host cell comprising any polypeptide, nucleic acid construct and/or vector described herein. In some embodiments, there is provided a host cell prepared using any method described herein. In some embodiments, the host cell is capable of producing any of antibody moieties described herein under a fermentation condition.

In some embodiments, the antibody moieties described herein (e.g., anti-CD93 antibody moieties) may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S, DG44. Lec13 CHO cells, CHOZN® and FUT8 CHO cells; PER.C6® cells (Crucell); and NSO cells. In some embodiments, the antibody moieties described herein (e.g., anti-CD93 antibody moieties) may be expressed in yeast. See, e.g., U.S. Publication No. US 2006/0270045 A1. In some embodiments, a particular eukaryotic host cell is selected based on its ability to make desired post-translational modifications to the heavy chains and/or light chains of the antibody moiety. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

The present application also provides host cells comprising any of the polynucleotides or vectors described herein. In some embodiments, the invention provides a host cell comprising an anti-CD93 antibody. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis).

In some embodiments, the antibody moiety is produced in a cell-free system. Non-limiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Culture Medium

In some embodiments, there is provided a culture medium comprising any antibody moiety, polynucleotide, nucleic acid construct, vector, and/or host cell described herein. In some embodiments, there is provided a culture medium prepared using any method described herein.

In some embodiments, the medium comprises hypoxanthine, aminopterin, and/or thymidine (e.g., HAT medium). In some embodiments, the medium does not comprise serum. In some embodiments, the medium comprises serum. In some embodiments, the medium is a D-MEM or RPMI-1640 medium. In some embodiments, the medium is a chemically defined medium. In some embodiments, the chemically defined medium is optimized for the host cell line.

Purification of Antibody Moieties

The anti-CD93 constructs (e.g., anti-CD93 monoclonal antibodies or multispecific antibodies) may be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an anti-CD93 construct comprising an Fc fragment. Hydrophobic interactive chromatography, for example, a butyl or phenyl column, may also suitable for purifying some polypeptides such as antibodies. Ion exchange chromatography (e.g. anion exchange chromatography and/or cation exchange chromatography) may also suitable for purifying some polypeptides such as antibodies. Mixed-mode chromatography (e.g. reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

V. Methods of Treatments

Also provided here are methods of treating a disease or condition in an individual or modulating an immune response in an individual. The methods comprise administering the anti-CD93 construct described herein into individuals (e.g., mammals such as humans).

In some embodiments, there is provided a method of treating a disease or condition or modulating an immune response in an individual, comprising administering to the individual an effective amount of an anti-CD93 construct described herein. Exemplary diseases or conditions include but are not limited to age-related macular degeneration (AMD), diabetic macular edema (DME), choroidal neovascularization (CNV) and cancer.

In some embodiments, there is provided a method of treating a disease or condition (such as an AMD, DME, CNV, or cancer) in an individual, comprising administering to the individual an effective mount of the anti-CD93 construct comprising an antibody moiety comprising a heavy chain variable region (V$_H$) and a light chain variable region (V$_L$), wherein the antibody moiety competes for a binding epitope of CD93 with an antibody or antibody fragment comprising a second heavy variable region (V$_{H-2}$) and a second light chain variable region (V$_{L-2}$), wherein the V$_{H-2}$ comprises the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 3, and the V$_{L-2}$ comprises the LC-CDR1 comprising the amino acid sequence of SEQ ID NO: 4, the LC-CDR2 comprising the amino acid sequence of SEQ ID NO: 5, and the LC-CDR3 comprising the amino acid sequence of SEQ ID NO: 6. In some embodiments, the V$_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, or a variant thereof comprising up to 5, 4, 3, 2, or 1 amino acid substitutions in the HC-CDRs, and the V$_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6, or a variant thereof comprising up to 5, 4, 3, 2, or 1 amino acid substitutions in the LC-CDRs. In some embodiments, the anti-CD93 antibody moiety is a humanized antibody derived from an anti-CD93 antibody comprising a heavy chain variable region (V$_H$) and a light chain variable region (V$_L$), wherein the V$_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, and the V$_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6. In some embodiments, the V$_H$ comprises an amino acid sequence of SEQ ID NO: 13, or a variant comprising an amino acid sequence having at least about 80% (such as at least about any one of 80%, 85%, 90%, 95%, 96%, 97%, 98%, or 99%) sequence identity; and the V$_L$ comprises an amino acid sequence of SEQ ID NO: 14, or a variant comprising an amino acid sequence having at least about 80% (such as at least about any one of 80%, 85%, 90%, 95%, 96%, 97%, 98%, or 99%) sequence identity.

In some embodiments, there is provided a method of treating a disease or condition (such as an AMD, DME, CNV, or cancer) in an individual, comprising administering to the individual an effective mount of the anti-CD93 construct comprising an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 17, the HC-CDR2 comprising the amino acid sequence of SEQ ID NO: 18, and the HC-CDR3 comprising the amino acid sequence of SEQ ID NO: 19, and the $V_{L-2}$ comprises the LC-CDR1 comprising the amino acid sequence of SEQ ID NO: 20, the LC-CDR2 comprising the amino acid sequence of SEQ ID NO: 21, and the LC-CDR3 comprising the amino acid sequence of SEQ ID NO: 22. In some embodiments, the anti-CD93 $V_H$ comprises i) the HC-CDR1 comprising the amino acid sequence of SEQ ID NO: 17 or 304, ii) the HC-CDR2 comprising the amino acid sequence of SEQ ID NO: 18 or 305, and iii) the HC-CDR3 comprising the amino acid sequence of SEQ ID NO: 19, or a variant thereof comprising up to 5, 4, 3, 2, or 1 amino acid substitutions in the HC-CDRs, and the anti-CD93 $V_L$ comprises i) the LC-CDR1 comprising the amino acid sequence of SEQ ID NO: 20, 301, 302, 303, or 306, ii) the LC-CDR2 comprising the amino acid sequence of SEQ ID NO: 21, and iii) the LC-CDR3 comprising the amino acid sequence of SEQ ID NO: 22, or a variant thereof comprising up to 5, 4, 3, 2, or 1 amino acid substitutions in the LC-CDRs.

In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, and the $V_L$ comprises i) the LC-CDR1 comprising the amino acid sequence of SEQ ID NO: 20, ii) the LC-CDR2 comprising the amino acid sequence of SEQ ID NO: 21, and iii) the LC-CDR3 comprising the amino acid sequence of SEQ ID NO: 22. In some embodiments, the $V_H$ comprises an amino acid sequence of any of SEQ ID NO: 29 and 307-312, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 30, and 313-318, or a variant comprising an amino acid sequence having at least about 80% (such as at least about any one of 80%, 85%, 90%, 95%, 96%, 97%, 98%, or 99%) sequence identity.

In some embodiments, there is provided a method of treating a disease or condition (such as an AMD, DME, CNV, or cancer) in an individual, comprising administering to the individual an effective mount of the anti-CD93 construct comprising an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 33, the HC-CDR2 comprising the amino acid sequence of SEQ ID NO: 34, and the HC-CDR3 comprising the amino acid sequence of SEQ ID NO: 35, and the $V_{L-2}$ comprises the LC-CDR1 comprising the amino acid sequence of SEQ ID NO: 36, the LC-CDR2 comprising the amino acid sequence of SEQ ID NO: 37, and the LC-CDR3 comprising the amino acid sequence of SEQ ID NO: 38. In some embodiments, the $V_H$ comprises i) the HC-CDR1 comprising the amino acid sequence of SEQ ID NO: 33, ii) the HC-CDR2 comprising the amino acid sequence of SEQ ID NO: 34, and iii) the HC-CDR3 comprising the amino acid sequence of SEQ ID NO: 35, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 36, ii) the LC-CDR2 comprising the amino acid sequence of SEQ ID NO: 37, and iii) the LC-CDR3 comprising the amino acid sequence of SEQ ID NO: 38, or a variant thereof comprising up to 5, 4, 3, 2, or 1 amino acid substitutions in the LC-CDRs. In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 33, ii) the HC-CDR2 comprising the amino acid sequence of SEQ ID NO: 34, and iii) the HC-CDR3 comprising the amino acid sequence of SEQ ID NO: 35, and the $V_L$ comprises i) the LC-CDR1 comprising the amino acid sequence of SEQ ID NO: 36, ii) the LC-CDR2 comprising the amino acid sequence of SEQ ID NO: 37, and iii) the LC-CDR3 comprising the amino acid sequence of SEQ ID NO: 38. In some embodiments, the $V_H$ comprises an amino acid sequence of SEQ ID NO: 45, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 46, or a variant comprising an amino acid sequence having at least about 80% (such as at least about any one of 80%, 85%, 90%, 95%, 96%, 97%, 98%, or 99%) sequence identity.

In some embodiments, there is provided a method of treating a disease or condition (such as an AMD, DME, CNV, or cancer) in an individual, comprising administering to the individual an effective mount of the anti-CD93 construct comprising an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 65, the HC-CDR2 comprising the amino acid sequence of SEQ ID NO: 66, and the HC-CDR3 comprising the amino acid sequence of SEQ ID NO: 67, and the $V_{L-2}$ comprises the LC-CDR1 comprising the amino acid sequence of SEQ ID NO: 68, the LC-CDR2 comprising the amino acid sequence of SEQ ID NO: 69, and the LC-CDR3 comprising the amino acid sequence of SEQ ID NO: 70. In some embodiments, the $V_H$ comprises i) the HC-CDR1 comprising the amino acid sequence of SEQ ID NO: 65, ii) the HC-CDR2 comprising the amino acid sequence of SEQ ID NO: 66, and iii) the HC-CDR3 comprising the amino acid sequence of SEQ ID NO: 67, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 68, ii) the LC-CDR2 comprising the amino acid sequence of SEQ ID NO: 69, and iii) the LC-CDR3 comprising the amino acid sequence of SEQ ID NO: 70, or a variant thereof comprising up to 5, 4, 3, 2, or 1 amino acid substitutions in the LC-CDRs. In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 65, ii) the HC-CDR2 comprising the amino acid sequence of SEQ ID NO: 66, and iii) the HC-CDR3 comprising the amino acid sequence of SEQ ID NO: 67, and the $V_L$ comprises i) the LC-CDR1 comprising the amino acid sequence of SEQ ID NO: 68, ii) the LC-CDR2 comprising the amino acid sequence of SEQ ID NO: 69, and iii) the LC-CDR3 comprising the amino acid sequence of SEQ ID NO: 70. In some embodiments, the $V_H$ comprises an amino acid sequence of SEQ ID NO: 77, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 78, or a variant comprising an amino acid sequence having at least about 80% (such as at least about any one of 80%, 85%, 90%, 95%, 96%, 97%, 98%, or 99%) sequence identity.

In some embodiments, there is provided a method of treating a disease or condition (such as an AMD, DME, CNV, or cancer) in an individual, comprising administering to the individual an effective mount of the anti-CD93 construct comprising an antibody moiety comprising a heavy chain variable region ($V_H$) and a light chain variable region ($V_L$), wherein the antibody moiety competes for a binding epitope of CD93 with an antibody or antibody fragment comprising a second heavy variable region ($V_{H-2}$) and a second light chain variable region ($V_{L-2}$), wherein the $V_{H-2}$ comprises the HC-CDR1 comprising the amino acid sequence of SEQ ID NO: 289, the HC-CDR2 comprising the amino acid sequence of SEQ ID NO: 290, and the HC-CDR3 comprising the amino acid sequence of SEQ ID NO: 291, and the $V_L$2 comprises the LC-CDR1 comprising the amino acid sequence of SEQ ID NO: 292, the LC-CDR2 comprising the amino acid sequence of SEQ ID NO: 293, and the LC-CDR3 comprising the amino acid sequence of SEQ ID NO: 294. In some embodiments, the $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294, or a variant thereof comprising up to 5, 4, 3, 2, or 1 amino acid substitutions in the LC-CDRs. In some embodiments, the anti-CD93 antibody moiety is a humanized antibody derived from an anti-CD93 antibody comprising a heavy chain variable region ($V_H$) and a light chain variable region ($V_L$), wherein the $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, and the $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294. In some embodiments, the $V_H$ comprises an amino acid sequence of any of SEQ ID NO: 287 and 319-321, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of any of SEQ ID NO: 288, and 322-324, or a variant comprising an amino acid sequence having at least about 80% (such as at least about any one of 80%, 85%, 90%, 95%, 96%, 97%, 98%, or 99%) sequence identity.

In some embodiments, the amino acid substitutions described above are limited to "exemplary substitutions" shown in Table 2 of this application. In some embodiments, the amino acid substitutions are limited to "preferred substitutions" shown in Table 2 of this application.

In some embodiments, there is provided a method of treating a tumor, comprising administering to the subject any one of the anti-CD93 constructs described herein. In some embodiments, the method retards tumor growth by at least about 5%, about 10%, about 20%, about 30%, about 40%, about 50%, about 60%, about 70%, about 80%, about 90%, or more than 90%, compared to the tumor growth in the absence of the anti-CD93 constructs.

In some embodiments, there is provided a method of reducing size of a tumor in a subject, comprising administering to the subject any one of the anti-CD93 constructs described herein. In some embodiments, reducing size of a tumor refers to reducing tumor volume in a subject. In some embodiments, reducing size of a tumor refers to reducing tumor dimensions (e.g., diameter) in a subject. In some embodiments, the tumor size is reduced by at least about 2%, about 5%, about 10%, about 20%, about 30%, about 40%, about 50%, about 60%, about 70%, about 80%, about 90%, or more than about 90% compared to the size of a counterpart tumor in a subject without the administration of the anti-CD93 construct.

In some embodiments, there is provided a method of eliminating one or more tumors in a subject, comprising administering to the subject any one of the anti-CD93 constructs described herein. In some embodiments, tumor elimination occurs after about 3 days, about 1 week, about 2 weeks, about 3 weeks, about 4 weeks, about 5 weeks, about 6 weeks, about 7 weeks, about 8 weeks, or more than about 8 weeks after anti-CD93 construct.

In some embodiments, there is provided a method of promoting immune cell infiltration into tumors in a subject, comprising administering to the subject any one of the anti-CD93 constructs described herein. In some embodiments, the method increases immune cell penetration into tumors by at least about 2%, about 5%, about 10%, about 20%, about 30%, about 40%, about 50%, about 60%, about 70%, about 80%, about 90%, or more than about 90% compared to that in a subject without the administration of the anti-CD93 construct.

Disease or Condition

The methods described herein are applicable to any disease or conditions associated with an abnormal vascular structure. In some embodiments, the disease or condition is associated with neovascularization. In some embodiments, the disease or condition is a cutaneous psoriasis. In some embodiments, the disease or condition is a benign tumor. In some embodiments, the disease or condition is a cancer.

Diseases Associated with Neovascularization

In some embodiments, the disease or condition is associated with neovascularization. "Neovascularization" described herein refers to a phenomenon that a new vasculature is developed from an existing vasculature.

In some embodiments, the disease of condition is associated with neovascularization of the eye.

In some embodiments, the disease or condition is choroidal neovascularization (CNV), also known as wet AMD. Choroidal neovascularization can involve the growth of new blood vessels that originate from the choroid through a break in the Bruch membrane into the sub-retinal pigment epithelium (sub-RPE) or subretinal space, which can be a major cause of visual loss. CNV can create a sudden deterioration of central vision, noticeable within a few weeks. Other symptoms which can occur include color disturbances, and metamorphopsia (distortions in which straight lines appears wavy). Hemorrhaging of the new blood vessels can accelerate the onset of symptoms of CNV. CNV may also include the feeling of pressure behind the eye. In some embodiments, methods and pharmaceutical compositions as disclosed herein are used to treat CNV or an eye condition associated with neovascularization.

The advanced "wet" form (neovascular or exudative) of AMD is less common, but may frequently cause a rapid and often substantial loss of central vision in patients. In the wet form of AMD, choroidal neovascularization forms and develops into a network of vessels that may grow under and through the retinal pigment epithelium. As this is accompanied by leakage of plasma and/or hemorrhage into the subretinal space, there could be severe sudden loss of central vision if this occurs in the macula. The term "AMD", if not otherwise specified, can be either dry AMD or wet AMD. The present application contemplates treatment or prevention of AMD, wet AMD and/or dry AMD.

In some embodiments, the disease or condition is a macular edema following retinal vein occlusion (RVO).

In some embodiments, the disease or condition is a diabetic macular edema (DME). Diabetic macular edema (DME) is a swelling of the retina in diabetes mellitus due to leaking of fluid from blood vessels within the macula. The macula is the central portion of the retina, a small area rich in cones, the specialized nerve endings that detect color and upon which daytime vision depends. As macular edema develops, blurring occurs in the middle or just to the side of the central visual field. Visual loss from diabetic macular edema can progress over a period of months and make it impossible to focus clearly. Common symptoms of DME are blurry vision, floaters, double vision, and eventually blindness if it goes untreated. In some embodiments, methods and pharmaceutical compositions as disclosed herein are used to treat DME.

In some embodiments, the disease or condition is a retinal vein occlusion. Retinal vein occlusion is a blockage of the small veins that carry blood away from the retina. The retina is the layer of tissue at the back of the inner eye that converts light images to nerve signals and sends them to the brain. Retinal vein occlusion is most often caused by hardening of the arteries (atherosclerosis) and the formation of a blood clot. Blockage of smaller veins (branch veins or BRVO) in the retina often occurs in places where retinal arteries that have been thickened or hardened by atherosclerosis cross over and place pressure on a retinal vein. Symptoms of retinal vein occlusion can include a sudden blurring or vision loss in all or part of one eye. In some embodiments, methods and pharmaceutical compositions as disclosed herein are used to treat retinal vein occlusion.

In some embodiments, the disease or condition is a diabetic retinopathy (DR) in patients with DME.

Cancer

In some embodiments, the disease or condition described herein is a cancer. Cancers that may be treated using any of the methods described herein include any types of cancers. Types of cancers to be treated with the agent as described in this application include, but are not limited to, carcinoma, blastoma, sarcoma, benign and malignant tumors, and malignancies e.g., sarcomas, carcinomas, and melanomas. Adult tumors/cancers and pediatric tumors/cancers are also included.

In various embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to a therapy.

In some embodiments, the cancer is a solid tumor.

In some embodiments, the cancer comprises CD93+ tumor endothelial cells. In some embodiments, at least 10%, 20%, 30%, 40%, 50%, 60%, 70%, 80%, or 90% of the endothelial cells in the tumor are CD93 positive. In some embodiments, the cancer comprises at least 20%, 40%, 60%, 80%, or 100% more CD93+ endothelial cells than that of a normal tissue in the subject. In some embodiments, the cancer comprises at least 20%, 40%, 60%, 80%, or 100% more CD93+ endothelial cells than that of a corresponding organ in a subject or a group of subjects who do not have the cancer.

In some embodiments, the cancer comprises IGFBP7+ blood vessels. In some embodiments, the cancer comprises at least 20%, 40%, 60%, 80%, or 100% more IGFBP7+ blood vessels than that of a normal tissue in the subject. In some embodiments, the cancer comprises at least 20%, 40%, 60%, 80%, or 100% more IGFBP7+ blood vessels than that of a corresponding organ in a subject or a group of subjects who do not have the cancer.

In some embodiments, the cancer (e.g., a solid tumor) is characterized by tumor hypoxia. In some embodiments, the cancer is characterized by a pimonidazole positive percentage (i.e., pimonidazole positive area divided by total tumor area) of at least about 1%, 2%, 3%, 4%, or 5%.

Examples of cancers that may be treated by the methods of this application include, but are not limited to, anal cancer, astrocytoma (e.g., cerebellar and cerebral), basal cell carcinoma, bladder cancer, bone cancer, (osteosarcoma and malignant fibrous histiocytoma), brain tumor (e.g., glioma, brain stem glioma, cerebellar or cerebral astrocytoma (e.g., astrocytoma, malignant glioma, medulloblastoma, and glioblastoma), breast cancer, cervical cancer, colon cancer, brain cancer, colorectal cancer, endometrial cancer (e.g., uterine cancer), esophageal cancer, eye cancer (e.g., intraocular melanoma and retinoblastoma), gastric (stomach) cancer, gastrointestinal stromal tumor (GIST), head and neck cancer, hepatocellular (liver) cancer (e.g., hepatic carcinoma and heptoma), liver cancer, lung cancer (e.g., small cell lung cancer, non-small cell lung cancer, adenocarcinoma of the lung, and squamous carcinoma of the lung), medulloblastoma, melanoma, mesothelioma, myelodysplastic syndromes, nasopharyngeal cancer, neuroblastoma, ovarian cancer, pancreatic cancer, parathyroid cancer, cancer of the peritoneal, pituitary tumor, rectal cancer, renal cancer, renal pelvis and ureter cancer (transitional cell cancer), rhabdomyosarcoma, skin cancer (e.g., non-melanoma (e.g., squamous cell carcinoma), melanoma, and Merkel cell carcinoma), small intestine cancer, squamous cell cancer, testicular cancer, thyroid cancer, and tuberous sclerosis. Additional examples of cancers can be found in The Merck Manual of Diagnosis and Therapy, 19th Edition, § on Hematology and Oncology, published by Merck Sharp & Dohme Corp., 2011 (ISBN 978-0-911910-19-3); The Merck Manual of Diagnosis and Therapy, 20th Edition, § on Hematology and Oncology, published by Merck Sharp & Dohme Corp., 2018 (ISBN 978-0-911-91042-1) (2018 digital online edition at internet website of Merck Manuals); and SEER Program Coding and Staging Manual 2016, each of which are incorporated by reference in their entirety for all purposes.

Subject

In some embodiments, the subject is a mammal (such as a human).

In some embodiments, the subject has a tissue comprising abnormal vascular comprising CD93+ endothelial cells. In some embodiments, at least 10%, 20%, 30%, 40%, 50%, 60%, 70%, 80%, or 90% of the endothelial cells in the tissue with abnormal vascular are CD93 positive. In some embodiments, the tissue with abnormal vascular comprises at least 20%, 40%, 60%, 80%, or 100% more CD93+ endothelial cells than that of a normal tissue in the subject. In some embodiments, the tissue with abnormal vascular comprises at least 20%, 40%, 60%, 80%, or 100% more CD93+ endothelial cells than that of a corresponding organ in a subject or a group of subjects who do not have the abnormal vascular.

In some embodiments, the subject has a tissue comprising abnormal vascular comprising IGFBP7+ blood vessels. In some embodiments, the tissue comprises at least 20%, 40%, 60%, 80%, or 100% more IGFBP7+ blood vessels than that of a normal tissue in the subject. In some embodiments, the tissue comprises at least 20%, 40%, 60%, 80%, or 100% more IGFBP7+ blood vessels than that of a corresponding organ in a subject or a group of subjects who do not have the abnormal vascular.

In some embodiments, the subject is selected for treatment based upon an abnormal vascular structure. In some embodiments, the abnormal vascular structure is characterized by CD93+ endothelial cells (for example, by measuring CD93+ CD31+ cells). In some embodiments, at least 10%, 20%, 30%, 40%, 50%, 60%, 70%, 80%, or 90% of the endothelial cells in the tissue with abnormal vascular are CD93 positive. In some embodiments, the tissue with abnormal vascular comprises at least 20%, 40%, 60%, 80%, or 100% more CD93+ endothelial cells than that of a normal tissue in the subject. In some embodiments, the tissue with abnormal vascular comprises at least 20%, 40%, 60%, 80%, or 100% more CD93+ endothelial cells than that of a corresponding organ in a subject or a group of subjects who do not have the abnormal vascular.

In some embodiments, the abnormal vascular structure is characterized by an abnormal level of IGFBP7+ blood vessels. In some embodiments, the tissue comprises at least 20%, 40%, 60%, 80%, or 100% more IGFBP7+ blood vessels than that of a normal tissue in the subject. In some embodiments, the tissue comprises at least 20%, 40%, 60%, 80%, or 100% more IGFBP7+ blood vessels than that of a corresponding organ in a subject or a group of subjects who do not have the abnormal vascular.

In some embodiments, the subject has at least one prior therapy. In some embodiments, the prior therapy comprises a radiation therapy, a chemotherapy and/or an immunotherapy. In some embodiments, the subject is resistant, refractory, or recurrent to the prior therapy.

Dosing and Method of Administering the Anti-CD93 Construct

The dosing regimen of the anti-CD93 construct (such as the specific dosages and frequencies) used for treating a disease or disorder as described herein administered into the individual may vary with the particular anti-CD93 construct (such as anti-CD93 monoclonal or multispecific antibodies, such as anti-CD93 fusion proteins), the mode of administration, and the type of disease or condition being treated. In some embodiments, the type of disease or condition is a cancer. In some embodiments, the effective amount of the anti-CD93 construct (such as anti-CD93 monoclonal or multispecific antibodies) is an amount that is effective to result in an objective response (such as a partial response or a complete response). In some embodiments, the effective amount of the anti-CD93 construct (such as anti-CD93 monoclonal or multispecific antibodies) is an amount that is sufficient to result in a complete response in the individual. In some embodiments, the effective amount of the anti-CD93 construct (such as anti-CD93 monoclonal or multispecific antibodies) is an amount that is sufficient to result in a partial response in the individual. In some embodiments, the effective amount of anti-CD93 construct (such as anti-CD93 monoclonal or multispecific antibodies) is an amount that is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-CD93 construct (such as anti-CD93 monoclonal or multispecific antibodies). Responses of an individual to the treatment of the methods described herein can be determined, for example, based on RECIST levels.

In some embodiments, the effective amount of the anti-CD93 construct (such as anti-CD93 monoclonal or multispecific antibodies) is an amount that is sufficient to prolong progress-free survival of the individual. In some embodiments, the effective amount of the anti-CD93 construct (such as anti-CD93 monoclonal or multispecific antibodies) is an amount that is sufficient to prolong overall survival of the individual. In some embodiments, the effective amount of the anti-CD93 construct (such as anti-CD93 monoclonal or multispecific antibodies) is an amount that is sufficient to produce clinical benefit of more than about any of 50%, 60%, 70%, 80%, or 90% among a population of individuals treated with the anti-CD93 construct (such as anti-CD93 monoclonal or multispecific antibodies).

In some embodiments, the effective amount of the anti-CD93 construct (such as anti-CD93 monoclonal or multispecific antibodies) alone or in combination with a second, third, and/or fourth agent, is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment (e.g., receiving a placebo treatment). Standard methods can be used to measure the magnitude of this effect, such as in vitro assays with purified enzyme, cell-based assays, animal models, or human testing.

In some embodiments, the effective amount of the anti-CD93 construct (such as anti-CD93 monoclonal or multispecific antibodies) is an amount that is below the level that induces a toxicological effect (i.e., an effect above a clinically acceptable level of toxicity) or is at a level where a potential side effect can be controlled or tolerated when the composition is administered to the individual.

In some embodiments, the effective amount of the anti-CD93 construct (such as anti-CD93 monoclonal or multispecific antibodies) is an amount that is close to a maximum tolerated dose (MTD) of the composition following the same dosing regimen. In some embodiments, the effective amount of the anti-CD93 construct (such as anti-CD93 monoclonal or multispecific antibodies) is more than about any of 80%, 90%, 95%, or 98% of the MTD.

In some embodiments, the effective amount of the anti-CD93 construct (such as anti-CD93 monoclonal or multispecific antibodies) is an amount that slows or inhibits the progression of the disease or condition (for example, by at least about 5%, 10%, 15%, 20%, 30%, 40%, 50%) as compared to that of the individual not receiving the treatment. In some embodiments, the disease or condition is an autoimmune disease. In some embodiments, the disease or condition is an infection.

In some embodiments, the effective amount of the anti-CD93 construct (such as anti-CD93 monoclonal or multi-specific antibodies) is an amount that reduces the side effects (autoimmune response) of a condition (e.g., transplantation) (for example, by at least about 5%, 10%, 15%, 20%, 30%, 40%, or 50%) as compared to that of the individual not receiving the treatment.

In some embodiments of any of the above aspects, the effective amount of an anti-CD93 construct (such as anti-CD93 monoclonal or multispecific antibodies) is in the range of about 0.001 µg/kg to about 100 mg/kg of total body weight, for example, about 0.005 µg/kg to about 50 mg/kg, about 0.01 µg/kg to about 10 mg/kg, or about 0.01 µg/kg to about 1 mg/kg.

In some embodiments, the treatment comprises more than one administration of the anti-CD93 constructs (such as about two, three, four, five, six, seven, eight, night, or ten administrations of anti-CD93 constructs). In some embodiments, two administrations are carried out within about a week. In some embodiments, a second administration is carried out at least about 1, 2, 3, 4, 5, 6, or 7 days after the completion of the first administration. In some embodiments, a second administration is carried out about 1-14 days, 1-10 days, 1-7 days, 2-6 days, or 3-5 days after the completion of the first administration. In some embodiments, the anti-CD93 construct is administered about 1-3 times a week (such as about once a week, about twice a week, or about three times a week).

The anti-CD93 construct can be administered to an individual (such as human) via various routes, including, for example, intravenous, intra-arterial, intraperitoneal, intra-pulmonary, oral, inhalation, intravesicular, intramuscular, intra-tracheal, subcutaneous, intraocular, intrathecal, trans-mucosal, and transdermal. In some embodiments, the anti-CD93 construct is included in a pharmaceutical composition while administered into the individual.

In some embodiments, sustained continuous release formulation of the composition may be used. In some embodiments, the composition is administered intravenously. In some embodiments, the composition is administered intra-peritoneally. In some embodiments, the composition is administered intravenously. In some embodiments, the composition is administered intraperitoneally. In some embodiments, the composition is administered intramuscularly. In some embodiments, the composition is administered subcu-taneously. In some embodiments, the composition is administered intravenously. In some embodiments, the composition is administered orally.

Combination Therapy

This application also provides methods of administering an anti-CD93 construct into an individual for treating a disease or condition (such as cancer), wherein the method further comprises administering a second agent or therapy. In some embodiments, the second agent or therapy is a standard or commonly used agent or therapy for treating the disease or condition. In some embodiments, the second agent or therapy comprises a chemotherapeutic agent. In some embodiments, the second agent or therapy comprises a surgery. In some embodiments, the second agent or therapy comprises a radiation therapy. In some embodiments, the second agent or therapy comprises an immunotherapy. In some embodiments, the second agent or therapy comprises a cell therapy (such as a cell therapy comprising an immune cell (e.g., CAR T cell)). In some embodiments, the second agent or therapy comprises an angiogenesis inhibitor.

In some embodiments, the second agent is a chemothera-peutic agent. In some embodiments, the second agent is antimetabolite agent. In some embodiments, the antimetabo-lite agent is 5-FU.

In some embodiments, the second agent is an immune checkpoint modulator. In some embodiments, the immune checkpoint modulator is an inhibitor of an immune check-point protein selected from the group consisting of PD-L1, PD-L2, CTLA4, PD-L2, PD-1, CD47, TIGIT, GITR, TIM3, LAG3, CD27, 4-1BB, and B7H4. In some embodiments, the immune checkpoint protein is PD-1. In some embodiments, the second agent is an anti-PD-1 antibody or fragment thereof.

In some embodiments, the second therapy is an immu-notherapy. In some embodiments, the immunotherapy com-prises administering an immune cell expressing a chimeric antigen receptor. In some embodiments, the immune cell is a T cell (such as a CD4+ T cell or a CD8+ T cell). In some embodiments, the chimeric antigen receptor binds to a tumor antigen.

In some embodiments, the anti-CD93 construct is admin-istered simultaneously with the second agent or therapy. In some embodiments, the anti-CD93 construct is administered concurrently with the second agent or therapy. In some embodiments, the anti-CD93 construct is administered sequentially with the second agent or therapy. In some embodiments, the anti-CD93 construct is administered prior to the second agent or therapy. In some embodiments, the anti-CD93 construct is administered after the second agent or therapy. In some embodiments, the anti-CD93 construct is administered in the same unit dosage form as the second agent or therapy. In some embodiment, the anti-CD93 construct is administered in a different unit dosage form from the second agent or therapy. In some embodiments, the anti-CD93 construct is administered in the same unit dosage form as the second agent or therapy. In some embodiment, the anti-CD93 construct is administered in a different unit dosage form from the second agent or therapy.

VI. Compositions, Kits and Articles of Manufacture

Also provided herein are compositions (such as formula-tions) comprising any one of the anti-CD93 construct or anti-CD93 antibody moiety described herein, nucleic acid encoding the antibody moieties, vector comprising the nucleic acid encoding the antibody moieties, or host cells comprising the nucleic acid or vector.

Suitable formulations of the anti-CD93 construct described herein can be obtained by mixing the anti-CD93 construct or anti-CD93 antibody moiety having the desired degree of purity with optional pharmaceutically acceptable carriers, excipients or stabilizers (*Remington's Pharmaceu-tical Sciences* 16th edition, Osol, A. Ed. (1980)), in the form of lyophilized formulations or aqueous solutions. Accept-able carriers, excipients, or stabilizers are nontoxic to recipi-ents at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides;

proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be imaged, diagnosed, or treated herein.

The formulations to be used for in vivo administration must be sterile. This is readily accomplished by, e.g., filtration through sterile filtration membranes.

Also provided are kits comprising any one of the anti-CD93 construct or anti-CD93 antibody moiety described herein. The kits may be useful for any of the methods of modulating cell composition or treatment described herein.

In some embodiments, there is provided a kit comprising an anti-CD93 construct specifically binding to CD93.

In some embodiments, the kit further comprises a device capable of delivering the anti-CD93 construct into an individual. One type of device, for applications such as parenteral delivery, is a syringe that is used to inject the composition into the body of a subject. Inhalation devices may also be used for certain applications.

In some embodiments, the kit further comprises a therapeutic agent for treating a disease or condition, e.g., cancer, infectious disease, autoimmune disease, or transplantation.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information.

The present application thus also provides articles of manufacture. The article of manufacture can comprise a container and a label or package insert on or associated with the container. Suitable containers include vials (such as sealed vials), bottles, jars, flexible packaging, and the like. Generally, the container holds a composition, and may have a sterile access port (for example the container may be an intravenous solution bag or a vial having a stopper pierceable by a hypodermic injection needle). The label or package insert indicates that the composition is used for imaging, diagnosing, or treating a particular condition in an individual. The label or package insert will further comprise instructions for administering the composition to the individual and for imaging the individual. The label may indicate directions for reconstitution and/or use. The container holding the composition may be a multi-use vial, which allows for repeat administrations (e.g. from 2-6 administrations) of the reconstituted formulation. Package insert refers to instructions customarily included in commercial packages of diagnostic products that contain information about the indications, usage, dosage, administration, contraindications and/or warnings concerning the use of such diagnostic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the compositions and instructions for use, packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXEMPLARY EMBODIMENTS

Embodiment 1. An anti-CD93 construct comprising an antibody moiety comprising a heavy chain variable region ($V_H$) and a light chain variable region ($V_L$), wherein the antibody moiety competes for a binding epitope of CD93 with an antibody or antibody fragment comprising a second heavy chain variable region ($V_{H-2}$) and a second light chain variable region ($V_{L-2}$), wherein:

a) the $V_{H-2}$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 3, and the $V_{L-2}$ comprises the LC-CDR1 comprising the amino acid sequence of SEQ ID NO: 4, the LC-CDR2 comprising the amino acid sequence of SEQ ID NO: 5, and the LC-CDR3 comprising the amino acid sequence of SEQ ID NO: 6;

b) the $V_{H-2}$ comprises the HC-CDR1 comprising the amino acid sequence of SEQ ID NO: 17, the HC-CDR2 comprising the amino acid sequence of SEQ ID NO: 18, and the HC-CDR3 comprising the amino acid sequence of SEQ ID NO: 19, and the $V_{L-2}$ comprises the LC-CDR1 comprising the amino acid sequence of SEQ ID NO: 20, the LC-CDR2 comprising the amino acid sequence of SEQ ID NO: 21, and the LC-CDR3 comprising the amino acid sequence of SEQ ID NO: 22;

c) the $V_{H-2}$ comprises the HC-CDR1 comprising the amino acid sequence of SEQ ID NO: 33, the HC-CDR2 comprising the amino acid sequence of SEQ ID NO: 34, and the HC-CDR3 comprising the amino acid sequence of SEQ ID NO: 35, and the $V_{L-2}$ comprises the LC-CDR1 comprising the amino acid sequence of SEQ ID NO: 36, the LC-CDR2 comprising the amino acid sequence of SEQ ID NO: 37, and the LC-CDR3 comprising the amino acid sequence of SEQ ID NO: 38;

d) the $V_{H-2}$ comprises the HC-CDR1 comprising the amino acid sequence of SEQ ID NO: 49, the HC-CDR2 comprising the amino acid sequence of SEQ ID NO: 50, and the HC-CDR3 comprising the amino acid sequence of SEQ ID NO: 51, and the $V_{L-2}$ comprises the LC-CDR1 comprising the amino acid sequence of SEQ ID NO: 52, the LC-CDR2 comprising the amino acid sequence of SEQ ID NO: 53, and the LC-CDR3 comprising the amino acid sequence of SEQ ID NO: 54;

e) the $V_{H-2}$ comprises the HC-CDR1 comprising the amino acid sequence of SEQ ID NO: 65, the HC-CDR2 comprising the amino acid sequence of SEQ ID NO:

66, and the HC-CDR3 comprising the amino acid sequence of SEQ ID NO: 67, and the $V_{L-2}$ comprises the LC-CDR1 comprising the amino acid sequence of SEQ ID NO: 68, the LC-CDR2 comprising the amino acid sequence of SEQ ID NO: 69, and the LC-CDR3 comprising the amino acid sequence of SEQ ID NO: 70;

f) the $V_{H-2}$ comprises the HC-CDR1 comprising the amino acid sequence of SEQ ID NO: 81, the HC-CDR2 comprising the amino acid sequence of SEQ ID NO: 82, and the HC-CDR3 comprising the amino acid sequence of SEQ ID NO: 83, and the $V_{L-2}$ comprises the LC-CDR1 comprising the amino acid sequence of SEQ ID NO: 84, the LC-CDR2 comprising the amino acid sequence of SEQ ID NO: 85, and the LC-CDR3 comprising the amino acid sequence of SEQ ID NO: 86;

g) the $V_{H-2}$ comprises the HC-CDR1 comprising the amino acid sequence of SEQ ID NO: 97, the HC-CDR2 comprising the amino acid sequence of SEQ ID NO: 98, and the HC-CDR3 comprising the amino acid sequence of SEQ ID NO: 99, and the $V_{L-2}$ comprises the LC-CDR1 comprising the amino acid sequence of SEQ ID NO: 100, the LC-CDR2 comprising the amino acid sequence of SEQ ID NO: 101, and the LC-CDR3 comprising the amino acid sequence of SEQ ID NO: 102;

h) the $V_{H-2}$ comprises the HC-CDR1 comprising the amino acid sequence of SEQ ID NO: 113, the HC-CDR2 comprising the amino acid sequence of SEQ ID NO: 114, and the HC-CDR3 comprising the amino acid sequence of SEQ ID NO: 115, and the $V_{L-2}$ comprises the LC-CDR1 comprising the amino acid sequence of SEQ ID NO: 116, the LC-CDR2 comprising the amino acid sequence of SEQ ID NO: 117, and the LC-CDR3 comprising the amino acid sequence of SEQ ID NO: 118;

i) the $V_{H-2}$ comprises the HC-CDR1 comprising the amino acid sequence of SEQ ID NO: 129, the HC-CDR2 comprising the amino acid sequence of SEQ ID NO: 130, and the HC-CDR3 comprising the amino acid sequence of SEQ ID NO: 131, and the $V_{L-2}$ comprises the LC-CDR1 comprising the amino acid sequence of SEQ ID NO: 132, the LC-CDR2 comprising the amino acid sequence of SEQ ID NO: 133, and the LC-CDR3 comprising the amino acid sequence of SEQ ID NO: 134;

j) the $V_{H-2}$ comprises the HC-CDR1 comprising the amino acid sequence of SEQ ID NO: 145, the HC-CDR2 comprising the amino acid sequence of SEQ ID NO: 146, and the HC-CDR3 comprising the amino acid sequence of SEQ ID NO: 147, and the $V_{L-2}$ comprises the LC-CDR1 comprising the amino acid sequence of SEQ ID NO: 148, 355, or 358, the LC-CDR2 comprising the amino acid sequence of SEQ ID NO: 149 or 356, and the LC-CDR3 comprising the amino acid sequence of SEQ ID NO: 150, 357 or 359;

k) the $V_{H-2}$ comprises the HC-CDR1 comprising the amino acid sequence of SEQ ID NO: 161, the HC-CDR2 comprising the amino acid sequence of SEQ ID NO: 162, and the HC-CDR3 comprising the amino acid sequence of SEQ ID NO: 163, and the $V_{L-2}$ comprises the LC-CDR1 comprising the amino acid sequence of SEQ ID NO: 164, the LC-CDR2 comprising the amino acid sequence of SEQ ID NO: 165, and the LC-CDR3 comprising the amino acid sequence of SEQ ID NO: 166;

l) the $V_{H-2}$ comprises the HC-CDR1 comprising the amino acid sequence of SEQ ID NO: 177, the HC-CDR2 comprising the amino acid sequence of SEQ ID NO: 178, and the HC-CDR3 comprising the amino acid sequence of SEQ ID NO: 179, and the $V_{L-2}$ comprises the LC-CDR1 comprising the amino acid sequence of SEQ ID NO: 180 or 353, the LC-CDR2 comprising the amino acid sequence of SEQ ID NO: 181 or 354, and the LC-CDR3 comprising the amino acid sequence of SEQ ID NO: 182;

m) the $V_{H-2}$ comprises the HC-CDR1 comprising the amino acid sequence of SEQ ID NO: 193, the HC-CDR2 comprising the amino acid sequence of SEQ ID NO: 194, and the HC-CDR3 comprising the amino acid sequence of SEQ ID NO: 195, and the $V_{L-2}$ comprises the LC-CDR1 comprising the amino acid sequence of SEQ ID NO: 196, the LC-CDR2 comprising the amino acid sequence of SEQ ID NO: 197, and the LC-CDR3 comprising the amino acid sequence of SEQ ID NO: 198;

n) the $V_{H-2}$ comprises the HC-CDR1 comprising the amino acid sequence of SEQ ID NO: 209, the HC-CDR2 comprising the amino acid sequence of SEQ ID NO: 210, and the HC-CDR3 comprising the amino acid sequence of SEQ ID NO: 211, and the $V_{L-2}$ comprises the LC-CDR1 comprising the amino acid sequence of SEQ ID NO: 212, the LC-CDR2 comprising the amino acid sequence of SEQ ID NO: 213, and the LC-CDR3 comprising the amino acid sequence of SEQ ID NO: 214;

o) the $V_{H-2}$ comprises the HC-CDR1 comprising the amino acid sequence of SEQ ID NO: 289, the HC-CDR2 comprising the amino acid sequence of SEQ ID NO: 290, and the HC-CDR3 comprising the amino acid sequence of SEQ ID NO: 291, and the $V_{L-2}$ comprises the LC-CDR1 comprising the amino acid sequence of SEQ ID NO: 292, the LC-CDR2 comprising the amino acid sequence of SEQ ID NO: 293, and the LC-CDR3 comprising the amino acid sequence of SEQ ID NO: 294; or p) the $V_{H-2}$ comprises the HC-CDR1 comprising the amino acid sequence of SEQ ID NO: 17 or 304, the HC-CDR2 comprising the amino acid sequence of SEQ ID NO: 18 or 305, and the HC-CDR3 comprising the amino acid sequence of SEQ ID NO: 19, and the $V_{L-2}$ comprises the LC-CDR1 comprising the amino acid sequence of SEQ ID NO: 20, 301, 302, 303, or 306, the LC-CDR2 comprising the amino acid sequence of SEQ ID NO: 21, and the LC-CDR3 comprising the amino acid sequence of SEQ ID NO:22.

Embodiment 2. The anti-CD93 construct of embodiment 1, wherein:

a) the $V_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6, or a variant thereof comprising up to 5, 4, 3, 2, or 1 amino acid substitutions in the LC-CDRs, b) the $V_H$ comprises i) the HC-CDR1 comprising the amino acid sequence of SEQ ID NO: 17, ii) the HC-CDR2 comprising the amino acid sequence of SEQ ID NO: 18, and iii) the HC-CDR3 comprising the amino acid sequence of SEQ ID NO: 19, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 20, ii) the LC-CDR2 comprising the amino acid sequence of SEQ ID NO: 21, and iii) the LC-CDR3 comprising the amino acid sequence of SEQ ID NO: 22, or a variant thereof comprising up to 5, 4, 3, 2, or 1 amino acid substitutions in the LC-CDRs, c) the $V_H$ comprises i) the HC-CDR1 comprising the amino acid sequence of SEQ ID NO: 33, ii) the HC-CDR2 comprising the amino acid sequence of SEQ ID NO: 34, and iii) the HC-CDR3 comprising the amino acid sequence of SEQ ID NO: 35, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 36, ii) the LC-CDR2 comprising the amino acid sequence of SEQ ID NO: 37, and iii) the LC-CDR3 comprising the amino acid sequence of SEQ ID NO: 38, or a variant thereof comprising up to 5, 4, 3, 2, or 1 amino acid substitutions in the LC-CDRs, d) the $V_H$ comprises i) the HC-CDR1 comprising the amino acid sequence of SEQ ID NO: 49, ii) the HC-CDR2 comprising the amino acid sequence of SEQ ID NO: 50, and iii) the HC-CDR3 comprising the amino acid sequence of SEQ ID NO: 51, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 52, ii) the LC-CDR2 comprising the amino acid sequence of SEQ ID NO: 53, and iii) the LC-CDR3 comprising the amino acid sequence of SEQ ID NO: 54, or a variant thereof comprising up to 5, 4, 3, 2, or 1 amino acid substitutions in the LC-CDRs, e) the $V_H$ comprises i) the HC-CDR1 comprising the amino acid sequence of SEQ ID NO: 65, ii) the HC-CDR2 comprising the amino acid sequence of SEQ ID NO: 66, and iii) the HC-CDR3 comprising the amino acid sequence of SEQ ID NO: 67, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 68, ii) the LC-CDR2 comprising the amino acid sequence of SEQ ID NO: 69, and iii) the LC-CDR3 comprising the amino acid sequence of SEQ ID NO: 70, or a variant thereof comprising up to 5, 4, 3, 2, or 1 amino acid substitutions in the LC-CDRs, f) the $V_H$ comprises i) the HC-CDR1 comprising the amino acid sequence of SEQ ID NO: 81, ii) the HC-CDR2 comprising the amino acid sequence of SEQ ID NO: 82, and iii) the HC-CDR3 comprising the amino acid sequence of SEQ ID NO: 83, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 84, ii) the LC-CDR2 comprising the amino acid sequence of SEQ ID NO: 85, and iii) the LC-CDR3 comprising the amino acid sequence of SEQ ID NO: 86, or a variant thereof comprising up to 5, 4, 3, 2, or 1 amino acid substitutions in the LC-CDRs, g) the $V_H$ comprises i) the HC-CDR1 comprising the amino acid sequence of SEQ ID NO: 97, ii) the HC-CDR2 comprising the amino acid sequence of SEQ ID NO: 98, and iii) the HC-CDR3 comprising the amino acid sequence of SEQ ID NO: 99, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 100, ii) the LC-CDR2 comprising the amino acid sequence of SEQ ID NO: 101, and iii) the LC-CDR3 comprising the amino acid sequence of SEQ ID NO: 102, or a variant thereof comprising up to 5, 4, 3, 2, or 1 amino acid substitutions in the LC-CDRs, h) the $V_H$ comprises i) the HC-CDR1 comprising the amino acid sequence of SEQ ID NO: 113, ii) the HC-CDR2 comprising the amino acid sequence of SEQ ID NO: 114, and iii) the HC-CDR3 comprising the amino acid sequence of SEQ ID NO: 115, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 116, ii) the LC-CDR2 comprising the amino acid sequence of SEQ ID NO: 117, and iii) the LC-CDR3 comprising the amino acid sequence of SEQ ID NO: 118, or a variant thereof comprising up to 5, 4, 3, 2, or 1 amino acid substitutions in the LC-CDRs, i) the $V_H$ comprises i) the HC-CDR1 comprising the amino acid sequence of SEQ ID NO: 129, ii) the HC-CDR2 comprising the amino acid sequence of SEQ ID NO: 130, and iii) the HC-CDR3 comprising the amino acid sequence of SEQ ID NO: 131, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 132, ii) the LC-CDR2 comprising the amino acid sequence of SEQ ID NO: 133, and iii) the LC-CDR3 comprising the amino acid sequence of SEQ ID NO: 134, or a variant thereof comprising up to 5, 4, 3, 2, or 1 amino acid substitutions in the LC-CDRs, j) the $V_H$ comprises i) the HC-CDR1 comprising the amino acid sequence of SEQ ID NO: 145, ii) the HC-CDR2 comprising the amino acid sequence of SEQ ID NO: 146, and iii) the HC-CDR3 comprising the amino acid sequence of SEQ ID NO: 147, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 148, 355, or 358, ii) the LC-CDR2 comprising the amino acid sequence of SEQ ID NO: 149 or 356, and iii) the LC-CDR3 comprising the amino acid sequence of SEQ ID NO: 150,357 or 359, or a variant thereof comprising up to 5, 4, 3, 2, or 1 amino acid substitutions in the LC-CDRs, k) the $V_H$ comprises i) the HC-CDR1 comprising the amino acid sequence of SEQ ID NO: 161, ii) the HC-CDR2 comprising the amino acid sequence of SEQ ID NO: 162, and iii) the HC-CDR3 comprising the amino acid sequence of SEQ ID NO: 163, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 164, ii) the LC-CDR2 comprising the amino acid sequence of SEQ ID NO: 165, and iii) the LC-CDR3 comprising the amino acid sequence of SEQ ID NO: 166, or a variant thereof comprising up to 5, 4, 3, 2, or 1 amino acid substitutions in the LC-CDRs, l) the $V_H$ comprises i) the HC-CDR1 comprising the amino acid sequence of SEQ ID NO: 177, ii) the HC-CDR2 comprising the amino acid sequence of SEQ ID NO: 178, and iii) the HC-CDR3 comprising the amino acid sequence of SEQ ID NO: 179, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 180 or 353, ii) the LC-CDR2 comprising the amino acid sequence of SEQ ID NO: 181 or 354, and iii) the LC-CDR3 comprising the amino acid sequence of SEQ ID NO: 182, or a variant thereof comprising up to 5, 4, 3, 2, or 1 amino acid substitutions in the LC-CDRs, m) the $V_H$ comprises i) the HC-CDR1 comprising the amino acid sequence of SEQ ID NO: 193, ii) the HC-CDR2 comprising the amino acid sequence of SEQ ID NO: 194, and iii) the HC-CDR3 comprising the amino acid sequence of SEQ ID NO: 195, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 196, ii) the LC-CDR2 comprising the amino acid sequence of SEQ ID NO: 197, and iii) the LC-CDR3 comprising the amino acid sequence of SEQ ID NO: 198, or a variant thereof comprising up to 5, 4, 3, 2, or 1 amino acid substitutions in the LC-CDRs, n) the $V_H$ comprises i) the HC-CDR1 comprising the amino acid sequence of SEQ ID NO: 209, ii) the HC-CDR2 comprising the amino acid sequence of SEQ ID NO: 210, and iii) the HC-CDR3 comprising the amino acid sequence of SEQ ID NO: 211, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 212, ii) the LC-CDR2 comprising the amino acid sequence of SEQ ID NO: 213, and iii) the LC-CDR3 comprising the amino acid sequence of SEQ ID NO: 214, or a variant thereof comprising up to 5, 4, 3, 2, or 1 amino acid substitutions in the LC-CDRs, o) the $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294, or a variant thereof comprising up to 5, 4, 3, 2, or 1 amino acid substitutions in the LC-CDRs, or p) the $V_H$ comprises the HC-CDR1 comprising the amino acid sequence of SEQ ID NO: 17 or 304, the HC-CDR2 comprising the amino acid sequence of SEQ ID NO: 18 or 305, and the HC-CDR3 comprising the amino acid sequence of SEQ ID NO: 19, or a variant thereof comprising up to 5, 4, 3, 2, or 1 amino acid substitutions in the HC-CDRs; and the $V_L$ comprises the LC-CDR1 comprising the amino acid sequence of SEQ ID NO: 20, 301, 302, 303, or 306, the LC-CDR2 comprising the amino acid sequence of SEQ ID NO: 21, and the LC-CDR3 comprising the amino acid sequence of SEQ ID NO:22, or a variant thereof comprising up to 5, 4, 3, 2, or 1 amino acid substitutions in the LC-CDRs.

Embodiment 3. The anti-CD93 construct of embodiment 2, wherein the $V_H$ comprises i) the HC-CDR1 comprising the amino acid sequence of SEQ ID NO: 1, ii) the HC-CDR2 comprising the amino acid sequence of SEQ ID NO: 2, and iii) the HC-CDR3 comprising the amino acid sequence of SEQ ID NO: 3, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 4, ii) the LC-CDR2 comprising the amino acid sequence of SEQ ID NO: 5, and iii) the LC-CDR3 comprising the amino acid sequence of SEQ ID NO: 6, or a variant thereof comprising up to 5, 4, 3, 2, or 1 amino acid substitutions in the LC-CDRs.

Embodiment 4. The anti-CD93 construct of embodiment 2, wherein the $V_H$ comprises i) the HC-CDR1 comprising the amino acid sequence of SEQ ID NO: 17 or 304, ii) the HC-CDR2 comprising the amino acid sequence of SEQ ID NO: 18 or 305, and iii) the HC-CDR3 comprising the amino acid sequence of SEQ ID NO: 19, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 20, 301, 302, 303, or 306, ii) the LC-CDR2 comprising the amino acid sequence of SEQ ID NO: 21, and iii) the LC-CDR3 comprising the amino acid sequence of SEQ ID NO: 22, or a variant thereof comprising up to 5, 4, 3, 2, or 1 amino acid substitutions in the LC-CDRs.

Embodiment 5. The anti-CD93 construct of embodiment 2, wherein the $V_H$ comprises i) the HC-CDR1 comprising the amino acid sequence of SEQ ID NO: 33, ii) the HC-CDR2 comprising the amino acid sequence of SEQ ID NO: 34, and iii) the HC-CDR3 comprising the amino acid sequence of SEQ ID NO: 35, or a variant thereof comprising up to 5, 4, 3, 2, or 1 amino acid substitutions in the HC-CDRs; and the $V_L$ comprises i) the LC-CDR1 comprising the amino acid sequence of SEQ ID NO: 36, ii) the LC-CDR2 comprising the amino acid sequence of SEQ ID NO: 37, and iii) the LC-CDR3 comprising the amino acid sequence of SEQ ID NO: 38, or a variant thereof comprising up to 5, 4, 3, 2, or 1 amino acid substitutions in the LC-CDRs.

Embodiment 6. The anti-CD93 construct of embodiment 2, wherein the $V_H$ comprises i) the HC-CDR1 comprising the amino acid sequence of SEQ ID NO: 49, ii) the HC-CDR2 comprising the amino acid sequence of SEQ ID NO: 50, and iii) the HC-CDR3 comprising the amino acid sequence of SEQ ID NO: 51, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 52, ii) the LC-CDR2 comprising the amino acid sequence of SEQ ID NO: 53, and iii) the LC-CDR3 comprising the amino acid sequence of SEQ ID NO: 54, or a variant thereof comprising up to 5, 4, 3, 2, or 1 amino acid substitutions in the LC-CDRs.

Embodiment 7. The anti-CD93 construct of embodiment 2, wherein the $V_H$ comprises i) the HC-CDR1 comprising the amino acid sequence of SEQ ID NO: 65, ii) the HC-CDR2 comprising the amino acid sequence of SEQ ID NO: 66, and iii) the HC-CDR3 comprising the amino acid sequence of SEQ ID NO: 67, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 68, ii) the LC-CDR2 comprising the amino acid sequence of SEQ ID NO: 69, and iii) the LC-CDR3 comprising the amino acid sequence of SEQ ID NO: 70, or a variant thereof comprising up to 5, 4, 3, 2, or 1 amino acid substitutions in the LC-CDRs.

Embodiment 8. The anti-CD93 construct of embodiment 2, wherein the $V_H$ comprises i) the HC-CDR1 comprising the amino acid sequence of SEQ ID NO: 81, ii) the HC- CDR2 comprising the amino acid sequence of SEQ ID NO: 82, and iii) the HC-CDR3 comprising the amino acid sequence of SEQ ID NO: 83, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 84, ii) the LC-CDR2 comprising the amino acid sequence of SEQ ID NO: 85, and iii) the LC-CDR3 comprising the amino acid sequence of SEQ ID NO: 86, or a variant thereof comprising up to 5, 4, 3, 2, or 1 amino acid substitutions in the LC-CDRs.

Embodiment 9. The anti-CD93 construct of embodiment 2, wherein the $V_H$ comprises i) the HC-CDR1 comprising the amino acid sequence of SEQ ID NO: 97, ii) the HC-CDR2 comprising the amino acid sequence of SEQ ID NO: 98, and iii) the HC-CDR3 comprising the amino acid sequence of SEQ ID NO: 99, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 100, ii) the LC-CDR2 comprising the amino acid sequence of SEQ ID NO: 101, and iii) the LC-CDR3 comprising the amino acid sequence of SEQ ID NO: 102, or a variant thereof comprising up to 5, 4, 3, 2, or 1 amino acid substitutions in the LC-CDRs.

Embodiment 10. The anti-CD93 construct of embodiment 2, wherein the $V_H$ comprises i) the HC-CDR1 comprising the amino acid sequence of SEQ ID NO: 113, ii) the HC-CDR2 comprising the amino acid sequence of SEQ ID NO: 114, and iii) the HC-CDR3 comprising the amino acid sequence of SEQ ID NO: 115, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 116, ii) the LC-CDR2 comprising the amino acid sequence of SEQ ID NO: 117, and iii) the LC-CDR3 comprising the amino acid sequence of SEQ ID NO: 118, or a variant thereof comprising up to 5, 4, 3, 2, or 1 amino acid substitutions in the LC-CDRs.

Embodiment 11. The anti-CD93 construct of embodiment 2, wherein the $V_H$ comprises i) the HC-CDR1 comprising the amino acid sequence of SEQ ID NO: 129, ii) the HC-CDR2 comprising the amino acid sequence of SEQ ID NO: 130, and iii) the HC-CDR3 comprising the amino acid sequence of SEQ ID NO: 131, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 132, ii) the LC-CDR2 comprising the amino acid sequence of SEQ ID NO: 133, and iii) the LC-CDR3 comprising the amino acid sequence of SEQ ID NO: 134, or a variant thereof comprising up to 5, 4, 3, 2, or 1 amino acid substitutions in the LC-CDRs.

Embodiment 12. The anti-CD93 construct of embodiment 2, wherein the $V_H$ comprises i) the HC-CDR1 comprising the amino acid sequence of SEQ ID NO: 145, ii) the HC-CDR2 comprising the amino acid sequence of SEQ ID NO: 146, and iii) the HC-CDR3 comprising the amino acid sequence of SEQ ID NO: 147, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 148, 355, or 358, ii) the LC-CDR2 comprising the amino acid sequence of SEQ ID NO: 149 or 356, and iii) the LC-CDR3 comprising the amino acid sequence of SEQ ID NO: 150, 357 or 359, or a variant thereof comprising up to 5, 4, 3, 2, or 1 amino acid substitutions in the LC-CDRs.

Embodiment 13. The anti-CD93 construct of embodiment 2, wherein the $V_H$ comprises i) the HC-CDR1 comprising the amino acid sequence of SEQ ID NO: 161, ii) the HC-CDR2 comprising the amino acid sequence of SEQ ID NO: 162, and iii) the HC-CDR3 comprising the amino acid sequence of SEQ ID NO: 163, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 164, ii) the LC-CDR2 comprising the amino acid sequence of SEQ ID NO: 165, and iii) the LC-CDR3 comprising the amino acid sequence of SEQ ID NO: 166, or a variant thereof comprising up to 5, 4, 3, 2, or 1 amino acid substitutions in the LC-CDRs.

Embodiment 14. The anti-CD93 construct of embodiment 2, wherein the $V_H$ comprises i) the HC-CDR1 comprising the amino acid sequence of SEQ ID NO: 177, ii) the HC-CDR2 comprising the amino acid sequence of SEQ ID NO: 178, and iii) the HC-CDR3 comprising the amino acid sequence of SEQ ID NO: 179, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 180 or 353, ii) the LC-CDR2 comprising the amino acid sequence of SEQ ID NO: 181 or 354, and iii) the LC-CDR3 comprising the amino acid sequence of SEQ ID NO: 182, or a variant thereof comprising up to 5, 4, 3, 2, or 1 amino acid substitutions in the LC-CDRs.

Embodiment 15. The anti-CD93 construct of embodiment 2, wherein the $V_H$ comprises i) the HC-CDR1 comprising the amino acid sequence of SEQ ID NO: 193, ii) the HC-CDR2 comprising the amino acid sequence of SEQ ID NO: 194, and iii) the HC-CDR3 comprising the amino acid sequence of SEQ ID NO: 195, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 196, ii) the LC-CDR2 comprising the amino acid sequence of SEQ ID NO: 197, and iii) the LC-CDR3 comprising the amino acid sequence of SEQ ID NO: 198, or a variant thereof comprising up to 5, 4, 3, 2, or 1 amino acid substitutions in the LC-CDRs.

Embodiment 16. The anti-CD93 construct of embodiment 2, wherein the $V_H$ comprises i) the HC-CDR1 comprising the amino acid sequence of SEQ ID NO: 209, ii) the HC-CDR2 comprising the amino acid sequence of SEQ ID NO: 210, and iii) the HC-CDR3 comprising the amino acid sequence of SEQ ID NO: 211, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 212, ii) the LC-CDR2 comprising the amino acid sequence of SEQ ID NO: 213, and iii) the LC-CDR3 comprising the amino acid sequence of SEQ ID NO: 214, or a variant thereof comprising up to 5, 4, 3, 2, or 1 amino acid substitutions in the LC-CDRs.

Embodiment 17. The anti-CD93 construct of embodiment 2, wherein the $V_H$ comprises i) the HC-CDR1 comprising the amino acid sequence of SEQ ID NO: 289, ii) the HC-CDR2 comprising the amino acid sequence of SEQ ID NO: 290, and iii) the HC-CDR3 comprising the amino acid sequence of SEQ ID NO: 291, or a variant thereof comprising up to 5, 4, 3, 2, or 1 amino acid substitutions in the HC-CDRs, and the $V_L$ comprises i) the LC-CDR1 comprising the amino acid sequence of SEQ ID NO: 292, ii) the LC-CDR2 comprising the amino acid sequence of SEQ ID NO: 293, and iii) the LC-CDR3 comprising the amino acid sequence of SEQ ID NO: 294, or a variant thereof comprising up to 5, 4, 3, 2, or 1 amino acid substitutions in the LC-CDRs Embodiment 18. An anti-CD93 construct comprising an antibody moiety that specifically binds to CD93, comprising:

a) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 13, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 14;

b) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 29 and 307-312, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 30, and 313-318;

c) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 45, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 46;

d) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 61, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 62;

e) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 77, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 78;

f) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 93, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 94;

g) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 109, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 110;

h) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 125, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 126;

i) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 141, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 142;

j) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 157 and 360-362, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 158, and 363-365;

k) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 173, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 174;

l) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 189 and 347-349, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 190, and 350-352;

m) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 205, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 206;

n) a HC-CDR1, a HC-CDR2, and a HC-CDR3, respectively comprising the amino acid sequences of a CDR1, a CDR2, and a CDR3 within a $V_H$ chain region having the sequence set forth in SEQ ID NO: 221, and a LC-CDR1, a LC-CDR2, and a LC-CDR3, respectively comprising the amino acid sequences of a CDR1, a CDR2, and a CDR3 within a $V_L$ chain region having the sequence set forth in SEQ ID NO: 222;

o) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NO: 287 and 319-321, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NO: 288, and 322-324;

p) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NOs: 307-312, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NOs: 313-318; or q) a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NOs: 319-321, and a LC-CDR1, a LC-CDR2, and a LC-CDR3, respectively comprising the amino acid sequences of a CDR1, a CDR2, and a CDR3 within a $V_L$ chain region having the sequence set forth in any of SEQ ID NOs: 322-324.

Embodiment 19. The anti-CD93 construct of any one of embodiments 1-18, wherein the $V_H$ comprises an amino acid sequence of any one of SEQ ID NOs: 13, 29, 45, 61, 77, 93, 109, 125, 141, 157, 173, 189, 205, 221, 287, 307-312 and 319-321, or a variant comprising an amino acid sequence having at least about 80% sequence identity; and/or wherein the $V_L$ comprises an amino acid sequence of any one of SEQ ID NOs: 14, 30, 46, 62, 78, 94, 110, 126, 142, 158, 174, 190, 206, 222, 288, 313-318 and 322-324 or a variant comprising an amino acid sequence having at least about 80% sequence identity.

Embodiment 20. The anti-CD93 construct of embodiment 19, wherein:

a) the $V_H$ comprises an amino acid sequence of SEQ ID NO: 13, or a variant comprising an amino acid sequence having at least about 80% sequence identity; and the $V_L$ comprises an amino acid sequence of SEQ ID NO: 14, or a variant comprising an amino acid sequence having at least about 80% sequence identity, b) the $V_H$ comprises an amino acid sequence of any of SEQ ID NO: 29 and 307-312, or a variant comprising an amino acid sequence having at least about 80% sequence identity; and the $V_L$ comprises an amino acid sequence of any of SEQ ID NO: 30, and 313-318, or a variant comprising an amino acid sequence having at least about 80% sequence identity, c) the $V_H$ comprises an amino acid sequence of SEQ ID NO: 45, or a variant comprising an amino acid sequence having at least about 80% sequence identity; and the $V_L$ comprises an amino acid sequence of SEQ ID NO: 46, or a variant comprising an amino acid sequence having at least about 80% sequence identity, d) the $V_H$ comprises an amino acid sequence of SEQ ID NO: 61, or a variant comprising an amino acid sequence having at least about 80% sequence identity; and the $V_L$ comprises an amino acid sequence of SEQ ID NO: 62, or a variant comprising an amino acid sequence having at least about 80% sequence identity, e) the $V_H$ comprises an amino acid sequence of SEQ ID NO: 77, or a variant comprising an amino acid sequence having at least about 80% sequence identity; and the $V_L$ comprises an amino acid sequence of SEQ ID NO: 78, or a variant comprising an amino acid sequence having at least about 80% sequence identity, f) the $V_H$ comprises an amino acid sequence of SEQ ID NO: 93, or a variant comprising an amino acid sequence having at least about 80% sequence identity; and the $V_L$ comprises an amino acid sequence of SEQ ID NO: 94, or a variant comprising an amino acid sequence having at least about 80% sequence identity, g) the $V_H$ comprises an amino acid sequence of SEQ ID NO: 109, or a variant comprising an amino acid sequence having at least about 80% sequence identity; and the $V_L$ comprises an amino acid sequence of SEQ ID NO: 110, or a variant comprising an amino acid sequence having at least about 80% sequence identity, h) the $V_H$ comprises an amino acid sequence of SEQ ID NO: 125, or a variant comprising an amino acid sequence having at least about 80% sequence identity; and the $V_L$ comprises an amino acid sequence of SEQ ID NO: 126, or a variant comprising an amino acid sequence having at least about 80% sequence identity, i) the $V_H$ comprises an amino acid sequence of SEQ ID NO: 141, or a variant comprising an amino acid sequence having at least about 80% sequence identity; and the $V_L$ comprises an amino acid sequence of SEQ ID NO: 142, or a variant comprising an amino acid sequence having at least about 80% sequence identity, j) the $V_H$ comprises an amino acid sequence of SEQ ID NO: 157, or a variant comprising an amino acid sequence having at least about 80% sequence identity; and the $V_L$ comprises an amino acid sequence of SEQ ID NO: 158, or a variant comprising an amino acid sequence having at least about 80% sequence identity, k) the $V_H$ comprises an amino acid sequence of SEQ ID NO: 173, or a variant comprising an amino acid sequence having at least about 80% sequence identity; and the $V_L$ comprises an amino acid sequence of SEQ ID NO: 174, or a variant comprising an amino acid sequence having at least about 80% sequence identity, l) the $V_H$ comprises an amino acid sequence of any of SEQ ID NO: 189 and 347-349, or a variant comprising an amino acid sequence having at least about 80% sequence identity; and the $V_L$ comprises an amino acid sequence of any of SEQ ID NO: 190, and 350-352, or a variant comprising an amino acid sequence having at least about 80% sequence identity, m) the $V_H$ comprises an amino acid sequence of SEQ ID NO: 205, or a variant comprising an amino acid sequence having at least about 80% sequence identity; and the $V_L$ comprises an amino acid sequence of SEQ ID NO: 206, or a variant comprising an amino acid sequence having at least about 80% sequence identity, n) the $V_H$ comprises an amino acid sequence of SEQ ID NO: 221, or a variant comprising an amino acid sequence having at least about 80% sequence identity; and the $V_L$ comprises an amino acid sequence of SEQ ID NO: 222, or a variant comprising an amino acid sequence having at least about 80% sequence identity, o) the $V_H$ comprises an amino acid sequence of any of SEQ ID NO: 287 and 319-321, or a variant comprising an amino acid sequence having at least about 80% sequence identity; and the $V_L$ comprises an amino acid sequence of any of SEQ ID NO: 288, and 322-324, or a variant comprising an amino acid sequence having at least about 80% sequence identity, p) the $V_H$ comprises an amino acid sequence of any one of SEQ ID NOs: 307-312, or a variant comprising an amino acid sequence having at least about 80% sequence identity; and the $V_L$ comprises an amino acid sequence of any one of SEQ ID NOs: 313-318, or a variant comprising an amino acid sequence having at least about 80% sequence identity, or q) the $V_H$ comprises an amino acid sequence of any one of SEQ ID NOs: 319-321, or a variant comprising an amino acid sequence having at least about 80% sequence identity; and the $V_L$ comprises an amino acid sequence of any one of SEQ ID NOs: 322-324, or a variant comprising an amino acid sequence having at least about 80% sequence identity.

Embodiment 21. The anti-CD93 construct of any one of embodiments 1-20, wherein the antibody moiety is an antibody or antigen-binding fragment thereof selected from the group consisting of a full-length antibody, a bispecific antibody, a single-chain Fv (scFv) fragment, a Fab fragment, a Fab' fragment, a F(ab')2, an Fv fragment, a disulfide stabilized Fv fragment (dsFv), a (dsFv)2, a Fv-Fc fusion, a scFv-Fc fusion, a scFv-Fv fusion, a diabody, a tribody, and a tetrabody.

Embodiment 22. The anti-CD93 construct of embodiment 21, wherein the antibody moiety is a full-length antibody.

Embodiment 23. The anti-CD93 construct of any one of embodiments 1-22, wherein the antibody moiety has an Fc fragment is selected from the group consisting of Fc fragments form IgG, IgA, IgD, IgE, IgM, and combinations and hybrids thereof.

Embodiment 24. The anti-CD93 construct of embodiment 23, wherein the Fc fragment is selected from the group consisting of Fc fragments from IgG1, IgG2, IgG3, IgG4, and combinations and hybrids thereof.

Embodiment 25. The anti-CD93 construct of embodiment 23 or embodiment 24, wherein the Fc fragment has a reduced effector function as compared to the corresponding wildtype Fc fragment.

Embodiment 26. The anti-CD93 construct of embodiment 23 or embodiment 24, wherein the Fc fragment has an enhanced effector function as compared to the corresponding wildtype Fc fragment.

Embodiment 27. The anti-CD93 construct of any one of embodiments 1-26, wherein the antibody moiety blocks the binding of CD93 to IGFBP7.

Embodiment 28. The anti-CD93 construct of any one of embodiments 1-26, wherein the antibody moiety blocks the binding of CD93 to MMRN2

Embodiment 29. The anti-CD93 construct of any one of embodiments 1-22, wherein the CD93 is a human CD93.

Embodiment 30. A pharmaceutical composition comprising the anti-CD93 construct of any one of embodiments 1-29, and a pharmaceutical acceptable carrier.

Embodiment 31. An isolated nucleic acid encoding the anti-CD93 construct of any one of embodiments 1-28.

Embodiment 32. A vector comprising the isolated nucleic acid of embodiment 31.

Embodiment 33. An isolated host cell comprising the isolated nucleic acid of embodiment 31, or the vector of embodiment 32.

Embodiment 34. An immunoconjugate comprising the anti-CD93 construct of any one of embodiments 1-29, linked to a therapeutic agent or a label.

Embodiment 35. A method of producing an anti-CD93 construct comprising:
 a) culturing the isolated host cell of embodiment 33 under conditions effective to express the anti-CD93 construct; and
 b) obtaining the expressed anti-CD93 construct from the host cell.

Embodiment 36. A method of treating a disease or condition in an individual, comprising administering to the individual an effective mount of the anti-CD93 construct of any one of embodiments 1-29, or the pharmaceutical composition of embodiment 30.

Embodiment 37. The method of embodiment 36, wherein the disease or condition is associated with an abnormal vascular structure.

Embodiment 38. The method of embodiment 36 or embodiment 37, wherein the disease or condition is a cancer.

Embodiment 39. The method of embodiment 38, wherein the cancer is a solid tumor.

Embodiment 40. The method of embodiment 38 or embodiment 39, wherein the cancer comprises CD93+ endothelial cells.

Embodiment 41. The method of any one of embodiments 38-40, wherein the cancer comprises IGFBP7+ blood vessels.

Embodiment 42. The method of any one of embodiments 38-41, wherein the cancer comprises MMRN2+ blood vessels.

Embodiment 43. The method of any one of embodiments 38-42, wherein the cancer is characterized by tumor hypoxia.

Embodiment 44. The method of any one of embodiments 38-43, wherein the cancer is a locally advanced or metastatic cancer.

Embodiment 45. The method of any one of embodiments 38-44, wherein the cancer is selected from the group consisting of a lymphoma, colon cancer, brain cancer, breast cancer, ovarian cancer, endometrial cancer, esophageal cancer, prostate cancer, cervical cancer, renal cancer, bladder cancer, gastric cancer, non-small cell lung cancer, melanoma, and pancreatic cancer.

Embodiment 46. The method of any one of embodiments 36-45, wherein the anti-CD93 construct is administered parenterally into the individual.

Embodiment 47. The method of any one of embodiments 36-46, wherein the method further comprises administering a second therapy.

Embodiment 48. The method of embodiment 47, wherein the second therapy is selected from the group consisting of surgery, radiation, gene therapy, immunotherapy, bone marrow transplantation, stem cell transplantation, hormone therapy, targeted therapy, cryotherapy, ultrasound therapy, photodynamic therapy, and chemotherapy.

Embodiment 49. The method of embodiment 48, wherein the second therapy is an immunotherapy.

Embodiment 50. The method of embodiment 49, wherein the immunotherapy comprises administering an immunomodulatory agent.

Embodiment 51. The method of embodiment 50, wherein the immunomodulatory agent is an immune checkpoint inhibitor.

Embodiment 52. The method of embodiment 51, wherein the immune checkpoint inhibitor comprises an anti-PD-L1 antibody or an anti-PD-1 antibody.

Embodiment 53. The method of any one of embodiments 36-52, wherein the individual is a human.

EXAMPLES

The examples below are intended to be purely exemplary of the application and should therefore not be considered to limit the application in any way. The following examples and detailed description are offered by way of illustration and not by way of limitation.

Example 1. Generation of Mouse Anti-Human CD93 Monoclonal Antibodies

Four NZBWF1 mice were immunized with human CD93 recombinant protein (Sino Biologicals). Mice received one prime immunization with a mixture of 100 ug antigen and 100 μL Complete Freund Adjuvant intraperitoneally, followed by 2 boosts of 100 ug antigen mixed with 100 μL of Incomplete Freund Adjuvant intraperitoneally. The serum titer was tested and confirmed by ELISA and FACS assays. A final IP boost with 80 ug of antigen was delivered to mice 5 days before spleen harvest. Single cell suspension of spleen cells from the immunized mice were fused to the mouse myeloma cell line. Fused hybridoma supernatants were screened for specific binding to human CD93 protein by ELISA assay, followed by FACS screen with CD93 expressing CHO cells. Briefly, for FACS screening, the presence of CD93 binding antibodies in the hybridoma supernatant was revealed by goat anti-mouse polyclonal antibody labeled with PE. FACS-positive CD93 specific hybridomas were subcloned and further confirmed by ELISA and FACS assays. Purified monoclonal antibodies were characterized by functional IGFBP7/CD93 blockade and HUVEC tube formation assays. The resulting hybridoma 16E4, 17B10 and 7F3 were identified as representative antibody clones.

Example 2. Cloning and Sequencing of CD93 Monoclonal Antibodies

Sample Preparation

Total RNA was isolated from the hybridoma cell line culture ($2\times10^6$ cells). RNA was treated to remove aberrant transcripts and reverse transcribed using oligo (dT) primers. Samples of the resulting cDNA were amplified in separate PCRs using framework 1 and constant region primer pairs specific for either the heavy or light chain. Reaction products were separated on an agarose gel, size-evaluated and recovered. In some cases, a second, nested PCR was performed to increase yield of the desired fragment(s). Amplicons were cloned into pCR®4-TOPO vector using the TA cloning strategy. Fifteen colonies were selected and plasmid DNA was amplified using primers specific for vector DNA sequences. PCR product size for each cloned insert was evaluated by gel electrophoresis, and six reactions were prepared for sequencing using a PCR clean up kit and using cycle sequencing with fluorescent dye terminators and capillary-based electrophoresis. Both PCR products and TA cloned multiple plasmid DNA were subjected to Sanger sequencing.

Sequence Analysis

DNA sequence data from all constructs were analyzed and consensus sequences for heavy and light chain were determined. See FIGS. 7A-7B and 8A-8B for alignment of $V_H$ and $V_L$ CDRs according to Kabat numbering or determined based upon VBASE2 tool. Tables 3 and 4 list $V_H$ and $V_L$ CDRs of various antibodies and consensus sequences.

TABLE 3

| $V_H$ CDRs of various antibodies and consensus sequences. | | | |
|---|---|---|---|
| | CDRH1 | CDRH2 | CDRH3 |
| 10B1 | SFGVN (SEQ ID NO: 1) | VIWSGGSTDYNVAFIS (SEQ ID NO: 2) | NWRYDGYFYAMDY (SEQ ID NO: 3) |
| 19B5 | NYYMS (SEQ ID NO: 193) | TISNNGDSTYYLDTV KG (SEQ ID NO: 194) | VGTGFTY (SEQ ID NO: 195) |
| 16G9 | DYYMN (SEQ ID NO: 49) | RVNPNNGGKTYNQKF KG (SEQ ID NO: 50) | WRLRP-VDYGMDY (SEQ ID NO: 51) |
| 16A1 | DHGIH (SEQ ID NO: 145) | NISPGNGDIKYNEKFK G (SEQ ID NO: 146) | YFVD (SEQ ID NO: 147) |
| 20C7 | AYVMH (SEQ ID NO: 113) | YIFPYNDGTEYNEKFK G (SEQ ID NO: 114) | RTDGNPYTMDY (SEQ ID NO: 115) |
| 17E6 | SYVIH (SEQ ID NO: 209) | YINPYSDYTQYNEKF KG (SEQ ID NO: 210) | RADGNPYAMDY (SEQ ID NO: 211) |
| 16E4 | SYWMH (SEQ ID NO: 17) | EIDPSASYTYYNQKFK G (SEQ ID NO: 18) | SVYYGNKYFDV (SEQ ID NO: 19) |
| 12H4 | DYYIH (SEQ ID NO: 129) | EIYPGSDDAYYNEKF KG (SEQ ID NO: 130) | ETTATAY (SEQ ID NO: 131) |
| 5H9 | TYWMN (SEQ ID NO: 33) | RIFPGDGDANYNGKF KG (SEQ ID NO: 34) | TGAAYDFDPFPY (SEQ ID NO: 35) |
| 17A7 | TYWMN (SEQ ID NO: 161) | RIFPGDGDTDYDGKF KG (SEQ ID NO: 162) | TGAAYEFDPFPY (SEQ ID NO: 163) |
| 16B6 | RSWMN (SEQ ID NO: 97) | WIYPGDGDTNYNGKF KG (SEQ ID NO: 98) | SATLPYWYFDV (SEQ ID NO: 99) |

TABLE 3-continued

| V$_H$ CDRs of various antibodies and consensus sequences. | | |
| --- | --- | --- |
| | CDRH1 | CDRH2 | CDRH3 |
| 17B10 | SYWLN (SEQ ID NO: 177) | RIYPGDGDTDYNGKF KG (SEQ ID NO: 178) | GDGYWAMDY (SEQ ID NO: 179) |
| 19E12 | DYEMH (SEQ ID NO: 65) | GIDPETGGTAYNQKF KG (SEQ ID NO: 66) | GAWFAY (SEQ ID NO: 67) |
| 17G11 | SYWMH (SEQ ID NO: 81) | AIYPGNSDTSYNQKF KG (SEQ ID NO: 82) | GGFDYSNYWFAY (SEQ ID NO: 83) |
| 7F3 | DYEMH (SEQ ID NO: 289) | GIDPETGDTAYNQNF KG (SEQ ID NO: 290) | YGNLYYYAMDY (SEQ ID NO: 291) |
| Consensus sequence based upon 5H9/17A7 | TYWMN (SEQ ID NO: 33) | RIFPGDGDX$_1$X$_2$YX$_3$GK FKG X$_1$X$_2$ = AN or TD, X$_3$ = N or D (SEQ ID NO: 233) | TGAAYX$_1$FDPFPY X$_1$ = D or E (SEQ ID NO: 234) |
| Consensus sequence based upon 5H9/17A7/ 17B10 | X$_1$YWX$_2$N X$_1$ = S or T, X$_2$ = L or M (SEQ ID NO: 236) | RIX$_1$PGDGDX$_2$X$_3$YX$_4$G KFKG X$_1$ = Y or F, X$_2$X$_3$ = TD or AN, X$_4$ = N or D (SEQ ID NO: 237) | |
| Consensus sequence based upon 20C7/17E6 | X$_1$YVX$_2$H X$_1$ = A or S, X$_2$ = M or I (SEQ ID NO: 241) | YIX$_1$PYX$_2$DX$_3$TX$_4$YNE KFKG X$_1$ = F or N, X$_2$ = N or S, X$_3$ = G or Y, X$_4$ = E or Q (SEQ ID NO: 242) | RX$_1$DGNPYX$_2$MDY X$_1$ = T or A, X$_2$ = T or A (SEQ ID NO: 243) |

TABLE 4

| V$_L$ CDRs of various antibodies and consensus sequences. | | |
| --- | --- | --- |
| | CDRL1 | CDRL2 | CDRL3 |
| 19E12 | RSSTGAVTTSNSAN (SEQ ID NO: 68) | GTNNRAP (SEQ ID NO: 69) | ALWYNNHFV (SEQ ID NO: 70) |
| 19B5 | RASQSINNYLH (SEQ ID NO: 196) | FASQSIS (SEQ ID NO: 197) | QQSNSWPLT (SEQ ID NO: 198) |
| 5H9 | SSSKSLLHSNGVTYLY (SEQ ID NO: 36) | RMSNLAS (SEQ ID NO: 37) | AQMLERPFT (SEQ ID NO: 38) |
| 17A7 | SSTKSLLHSSGITYLY (SEQ ID NO: 164) | RMSNLAS (SEQ ID NO: 165) | AQMLERPFT (SEQ ID NO: 166) |
| 17B10 | RFSKSLLHSNGITYLY (SEQ ID NO: 180) | QMSNLAS (SEQ ID NO: 181) | AQNLELPWT (SEQ ID NO: 182) |
| 16A1 | KSSQSLLNSNNQKNCLA (SEQ ID NO: 148) | FACTRES (SEQ ID NO: 149) | QQHCNTPLT (SEQ ID NO: 150) |
| 17G11 | KASQSVSNDVA (SEQ ID NO: 84) | YASNRYT (SEQ ID NO: 85) | QQDYSSYT (SEQ ID NO: 86) |
| 10B1 | KASQNVGTNVA (SEQ ID NO: 4) | SASYRFI (SEQ ID NO: 5) | QQYNRNPIT (SEQ ID NO: 6) |
| 20C7 | KASQDVSTAVA (SEQ ID NO: 116) | SASYRYT (SEQ ID NO: 117) | QQHYSTPFT (SEQ ID NO: 118) |
| 17E6 | KASQDVSTAVV (SEQ ID NO: 212) | SASYRYT (SEQ ID NO: 213) | QQHYSTPFT (SEQ ID NO: 214) |
| 16B6 | KASQDIKSYLS (SEQ ID NO: 100) | YATNLAD (SEQ ID NO: 101) | LQHVESPWT (SEQ ID NO: 102) |

TABLE 4-continued

| $V_L$ CDRs of various antibodies and consensus sequences. | | |
| --- | --- | --- |
| CDRL1 | CDRL2 | CDRL3 |
| 12H4 SASSSVSLIY (SEQ ID NO: 132) | STSNLAS (SEQ ID NO: 133) | QQRSGYPPT (SEQ ID NO: 134) |
| 16E4 KASQSVDYAGDSYMN (SEQ ID NO: 20) | AASNLES (SEQ ID NO: 21) | QQTNEDPRT (SEQ ID NO: 22) |
| 16G9 RASQSVSTSSYSYMH (SEQ ID NO: 52) | YASNLES (SEQ ID NO: 53) | QHSWEIPFT (SEQ ID NO: 54) |
| 7F3 RASSSVSSSYLH (SEQ ID NO: 292) | STSNLAF (SEQ ID NO: 293) | QQYSGYPLT (SEQ ID NO: 294) |
| Consensus sequence based upon 5H9/17A7 $SSX_1KSLLHSX_2GX_3TYLY$ $X_1$ = S or T, $X_2$ = N or S, $X_3$ = V or I (SEQ ID NO: 235) | RMSNLAS (SEQ ID NO: 37) | AQMLERPFT (SEQ ID NO: 38) |
| Consensus sequence based upon 5H9/17A7/ 17B10 $X_1X_2X_3KSLLHSX_4GX_5TYLY$ $X_1X_2X_3$ = SSS, SST, or RFS, $X_4$ = N or S, X5 = V or I (SEQ ID NO: 238) | $X_1MSNLAS$ $X_1$ = R or Q (SEQ ID NO: 239) | $AQX_1LEX_2PX_3T$ $X_1$ = M or N, $X_2$ = R or L, $X_3$ = F or W (SEQ ID NO: 240) |
| Consensus sequence based upon 20C7/17E6 $KASQDVSTAVX_1$ $X_1$ = A or V (SEQ ID NO: 244) | SASYRYT (SEQ ID NO: 117) | QQHYSTPFT (SEQ ID NO: 118) |
| Consensus sequence based upon 10B1/20C7/ 17E6 $KASQX_1VX_2TX_3VX_4$ $X_1$ = N or D, $X_2$ = G or S, $X_3$ = N or A, $X_4$ = A or V (SEQ ID NO: 245) | $SASYRX_1X_2$ $X_1$ = F or Y, $X_2$ = I or T $X_1X_2$ = FI or YT (SEQ ID NO: 246) | $QQX_1X_2X_3X_4PX_5T$ $X_1X_2X_3X_4$ = YNRN or HYST, $X_5$ = I or F (SEQ ID NO: 247) |
| Consensus sequence based upon 16E4/16G9 $X_1ASQSVX_2X_3X_4X_5X_6S$ $YMX_7$ $X_1$ = K or R, $X_2X_3X_4X5X_6$ = DYAGD or STSSY, $X_7$ = N or H (SEQ ID NO: 248) | $X_1ASNLES$ $X_1$ = A or Y (SEQ ID NO: 249) | $QX_1X_2X_3X_4X_5PX_6T$ $X_1X_2X_3X_4X_5$ = QTN ED or HSWEI, $X_6$ = R or F (SEQ ID NO: 250) |

The consensus sequences are compared to known variable region sequences to rule out artifacts and/or process contamination. Consensus sequences are then analyzed using an online tool to verify that the sequences could encode a productive immunoglobulin.

Example 3. Binding Affinity of Anti-CD93 Antibodies for Human and Cynomolgus CD93 Measured by Bio-Layer Interferometry (BLI) Assay The binding affinity of anti-CD93 antibodies were determined with bio-layer interferometry using Octet QKe (Fortebio). Human CD93 recombinant protein (Sino Biological Inc, Catalog #12589-H08H) or cynomolgus CD93 protein (made in-house) were biotinylated using EZ-LINK NHS-PEG4 biotin (Thermo Fisher Scientific). Streptavidin biosensors (Fortebio) were used to load biotinylated CD93 protein (300 seconds at 5 μg/ml). The baseline was stabilized for 60 seconds in a 1× kinetics buffer (Fortebio) before serially diluted anti-CD93 antibodies were allowed to associate for 300 seconds with captured protein. The sensors were dissociated in a 1× kinetics buffer for 600 seconds. Data analysis was performed on ForteBio Data Analysis HT 11.1 software.

As shown in FIG. 1 and FIG. 9, 16E4, 10B1, 7F3, and reference antibody MM01 all effectively bind to human CD93. 16E4 and MM01 bind to cynomolgus CD93 as well (FIG. 1). 10B1 and 7F3 also bind to cynomolgus CD93 (data not shown).

Example 4. Binding of Anti-CD93 Antibodies to Cell Surface Expressing Human CD93 CHO Cells Determined by Fluorescence Activated Cell Sorting (FACS) Assay Human CD93 expressing CHO cells were detached by incubation with TrypLE reagents (Thermos Fisher), which preserves the integrity of CD93 on the cell surface. The cells were then incubated with anti-CD93 antibodies and reference antibody MM01 (Sino Biological Inc, Catalog #12589-MMO1) at 10 μg/ml for 30 minutes in 4° C. After washing with FACS buffer, the cells were incubated with Alexa Fluor 488 conjugated anti-human IgG or anti-mouse IgG antibodies (Jackson ImmunoResearch) for 30 minutes at 4° C. After washing with FACS buffer twice, the samples were acquired in NovoCyte Flow Cytometer and analyzed by NovoExpress software. Antibodies 16E4, 10B1, and 7F3 were tested similarly for binding to CHO-K1 cells.

Figure 2:
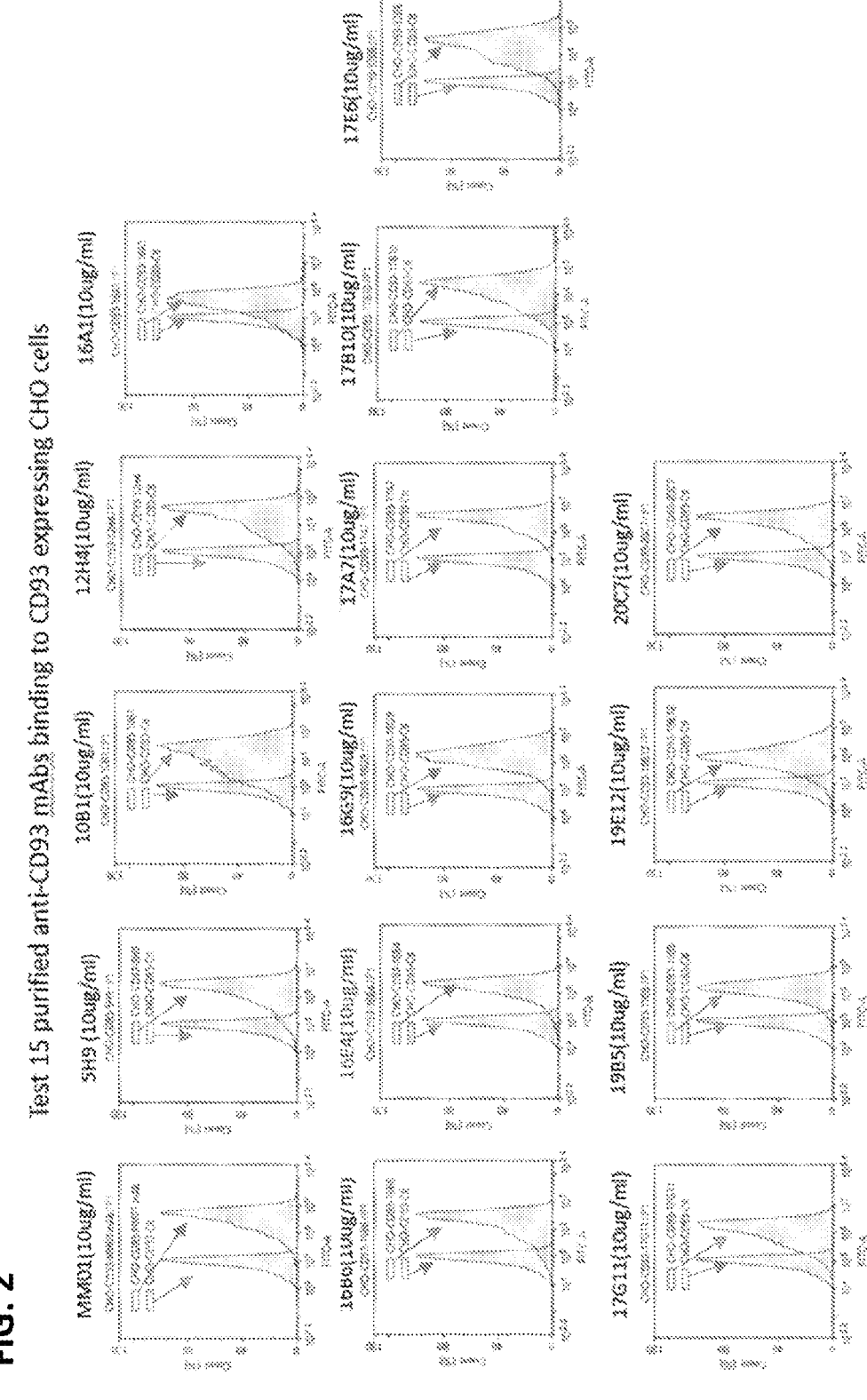
FIG. 2 shows binding of various anti-CD93 antibodies to CD93-expressing CHO cells.
Figures 3A, 3B:
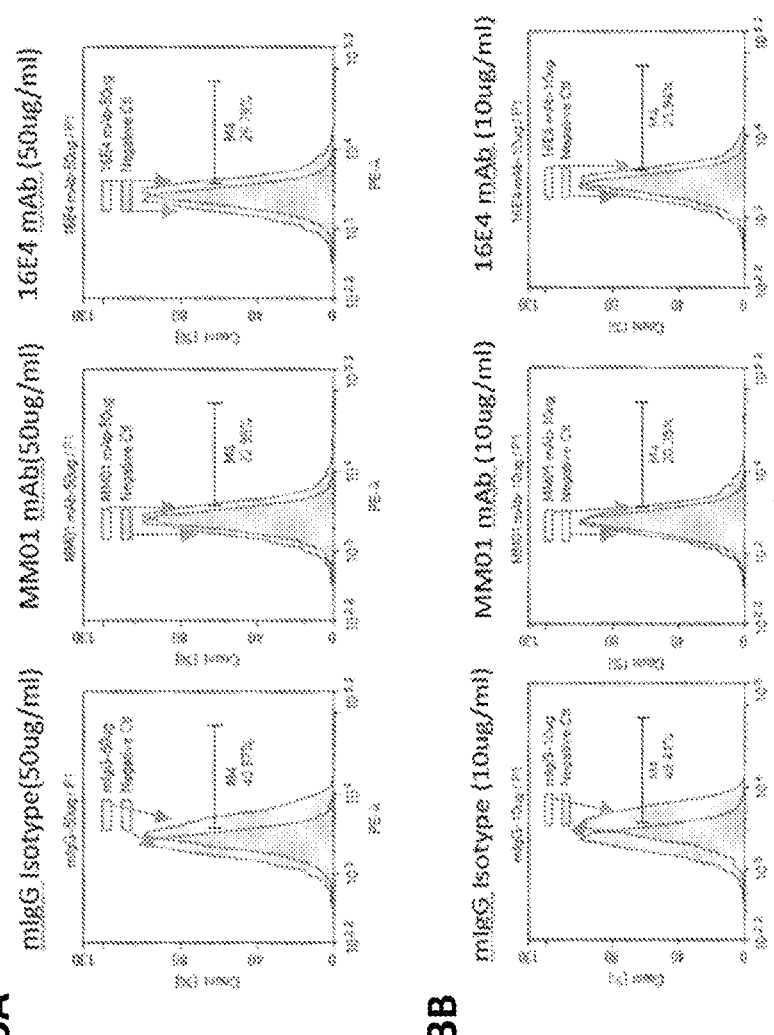
FIGS. 3A-3D show that the inhibition of the interaction between CD93 and IGFBP7 by 16E4 and MM01 as compared to mIgG isotype at various concentrations.
Figure 3C:
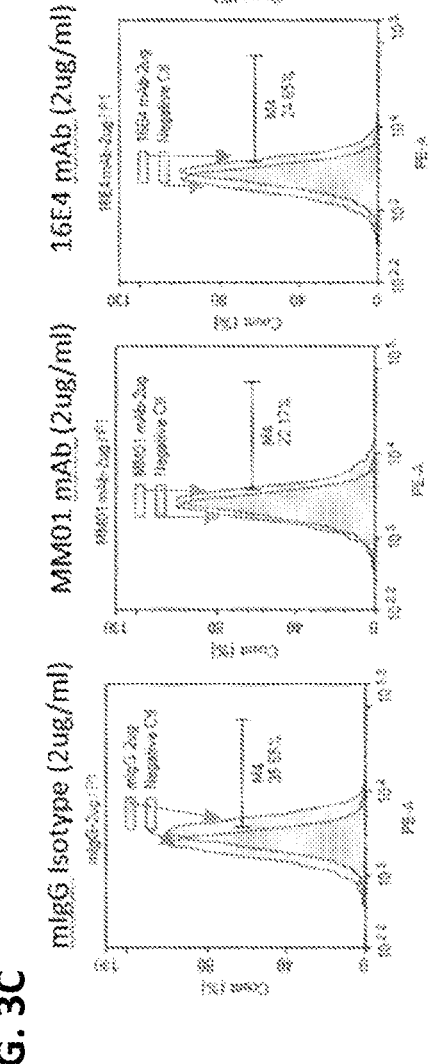
Figure 3D:
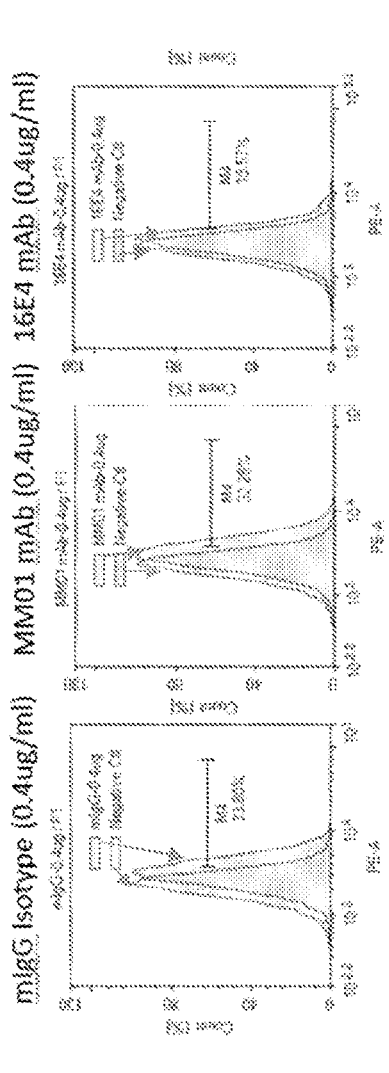
Figures 4A, 4B:
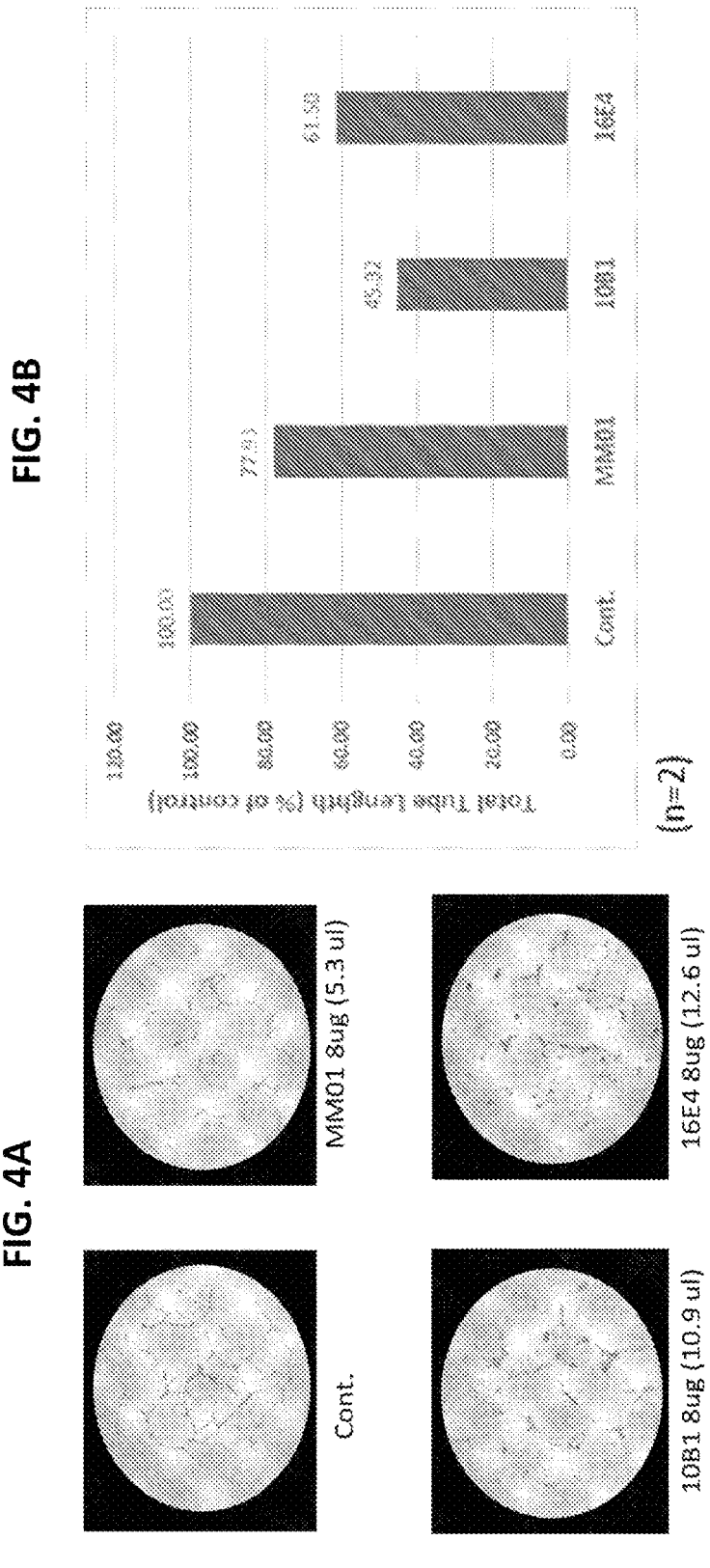
Figure 4D:
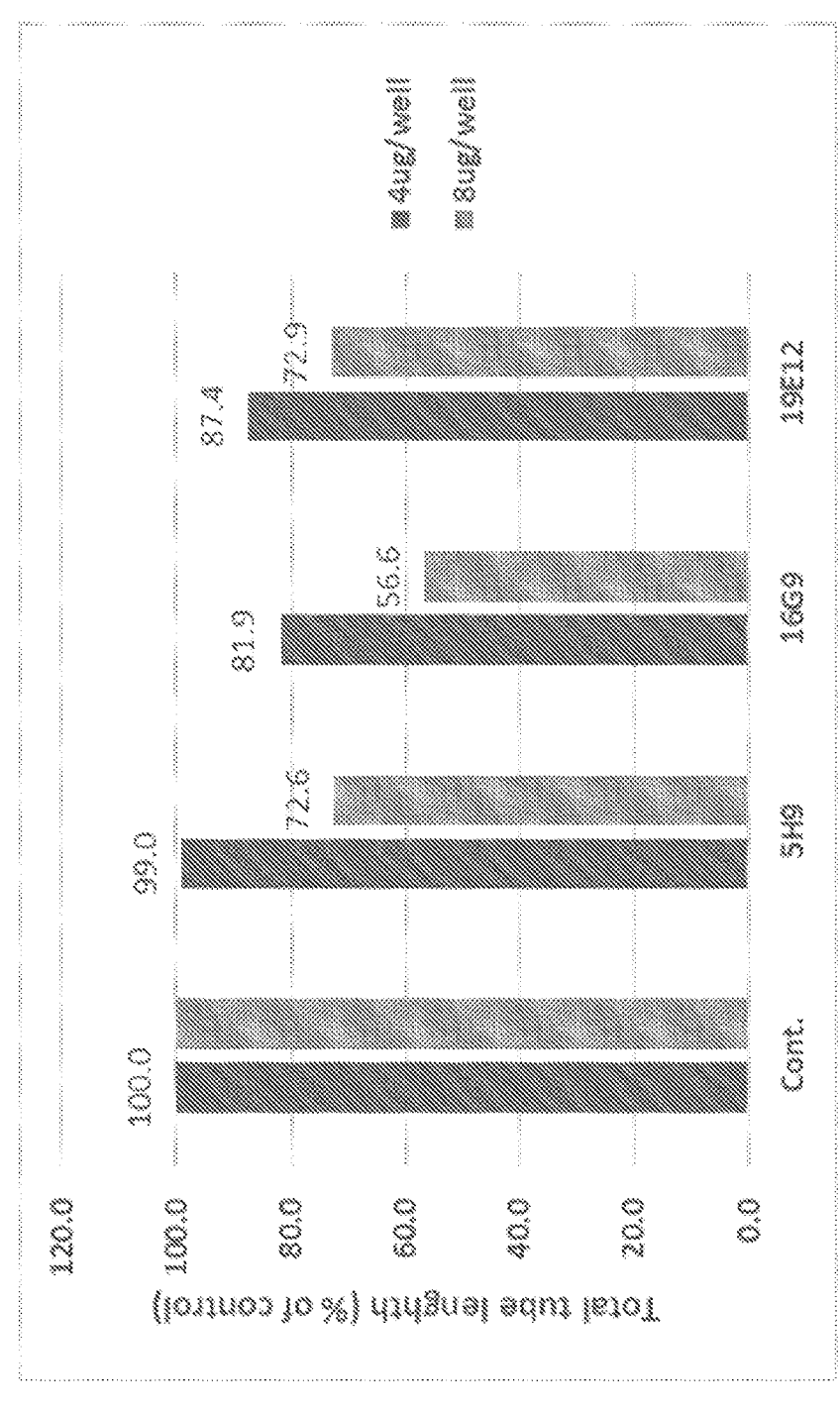
Figure 4F:
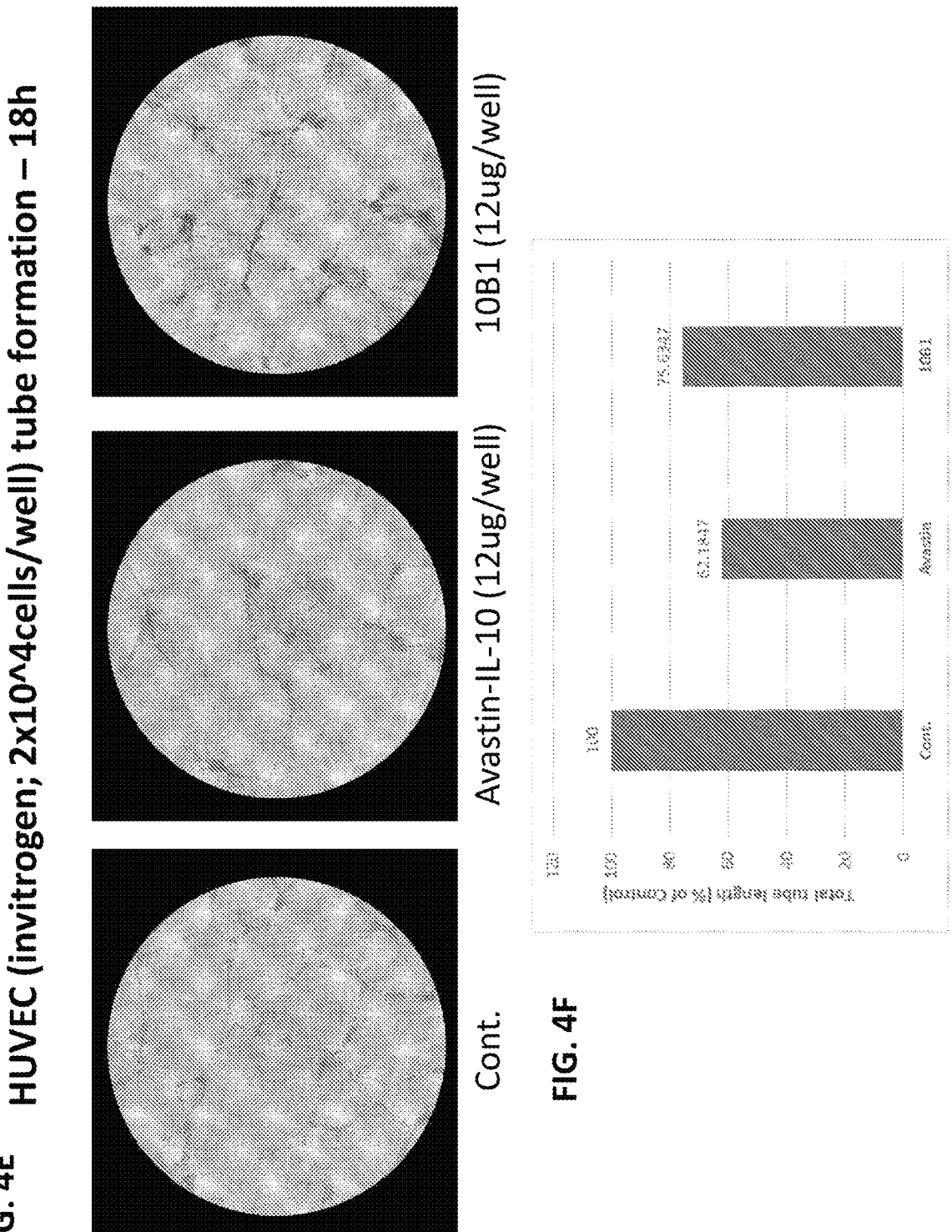
Figure 5A:
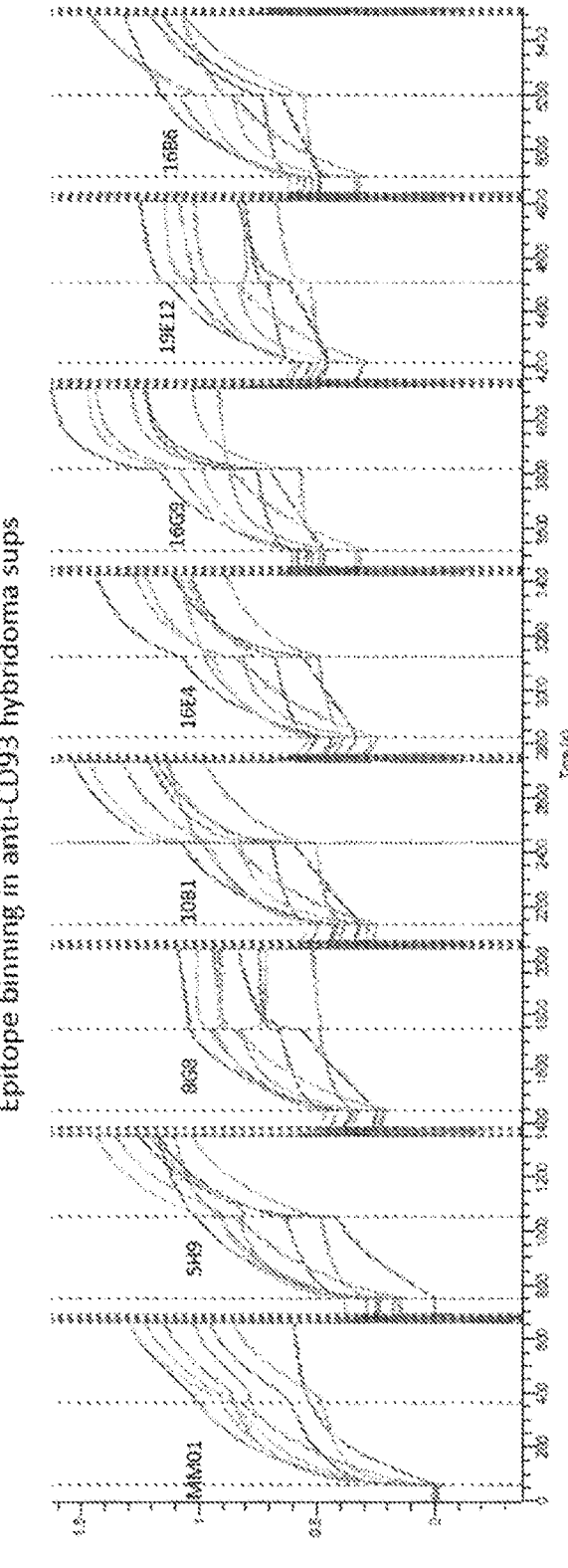
FIGS. 5A-5B show results of epitope binning of various anti-CD93 antibodies by Octet competition.
Figure 5B:
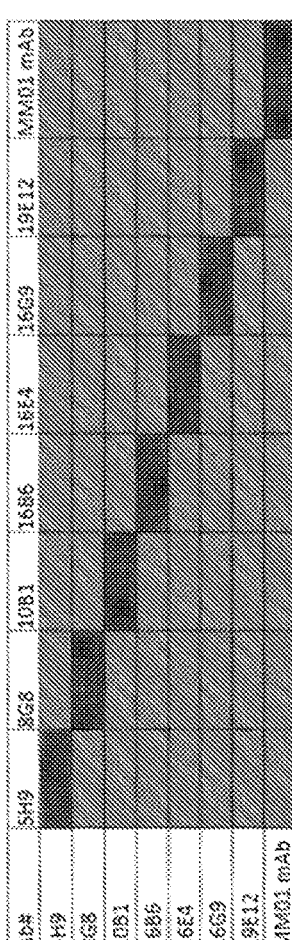
Figure 6A:
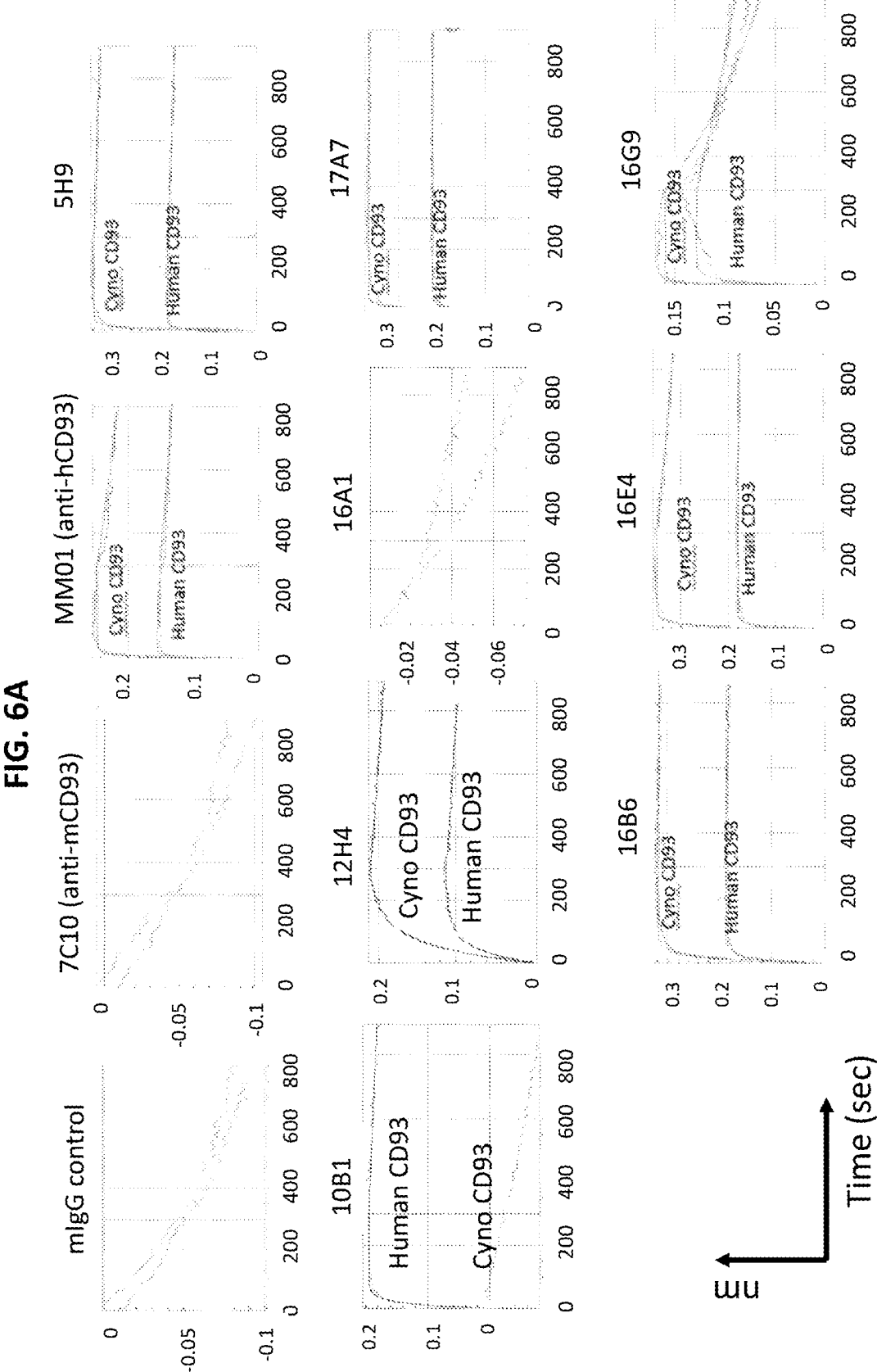
FIGS. 6A-6B show cross-binding activities of various anti-CD93 antibodies against human and cynomolgus CD93 measured by bio-layer interferometry (BLI) assay.
Figure 6B:
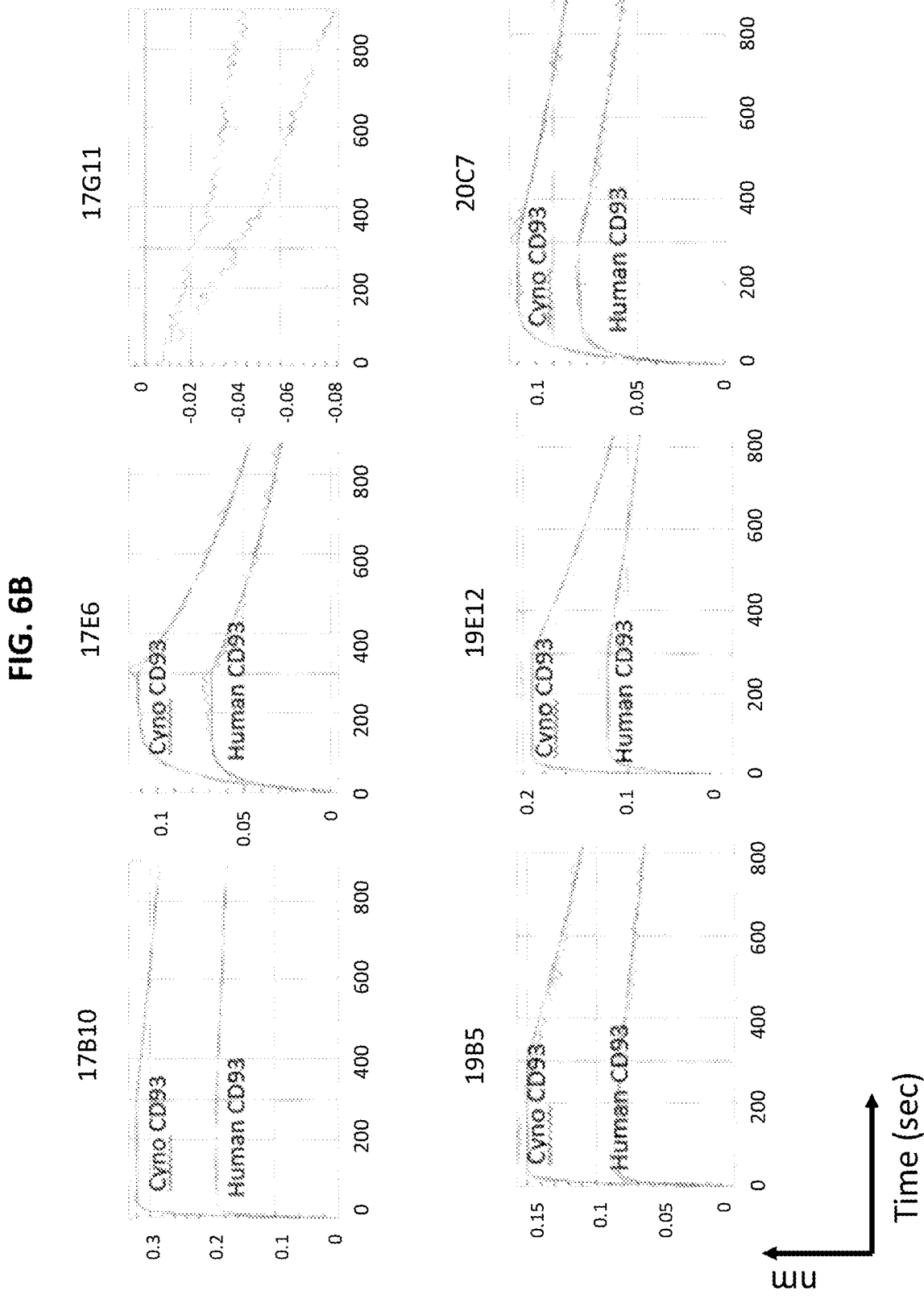
Figure 9:
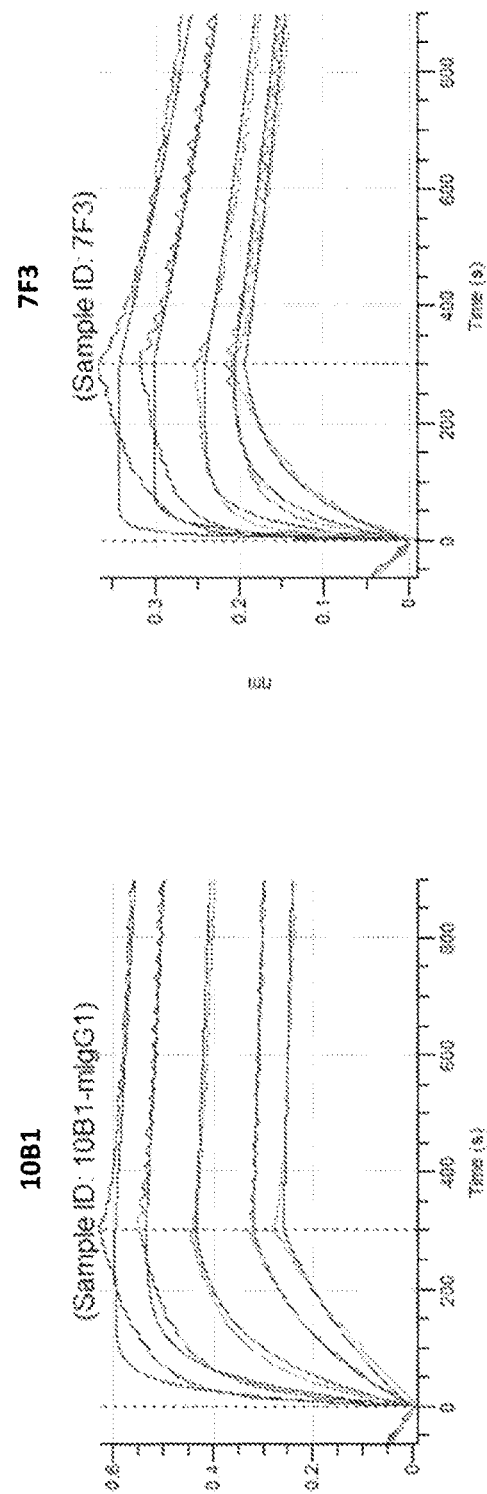
FIG. 9 shows binding affinity of 10B1 and 7F3 to human CD93.
Figure 10:
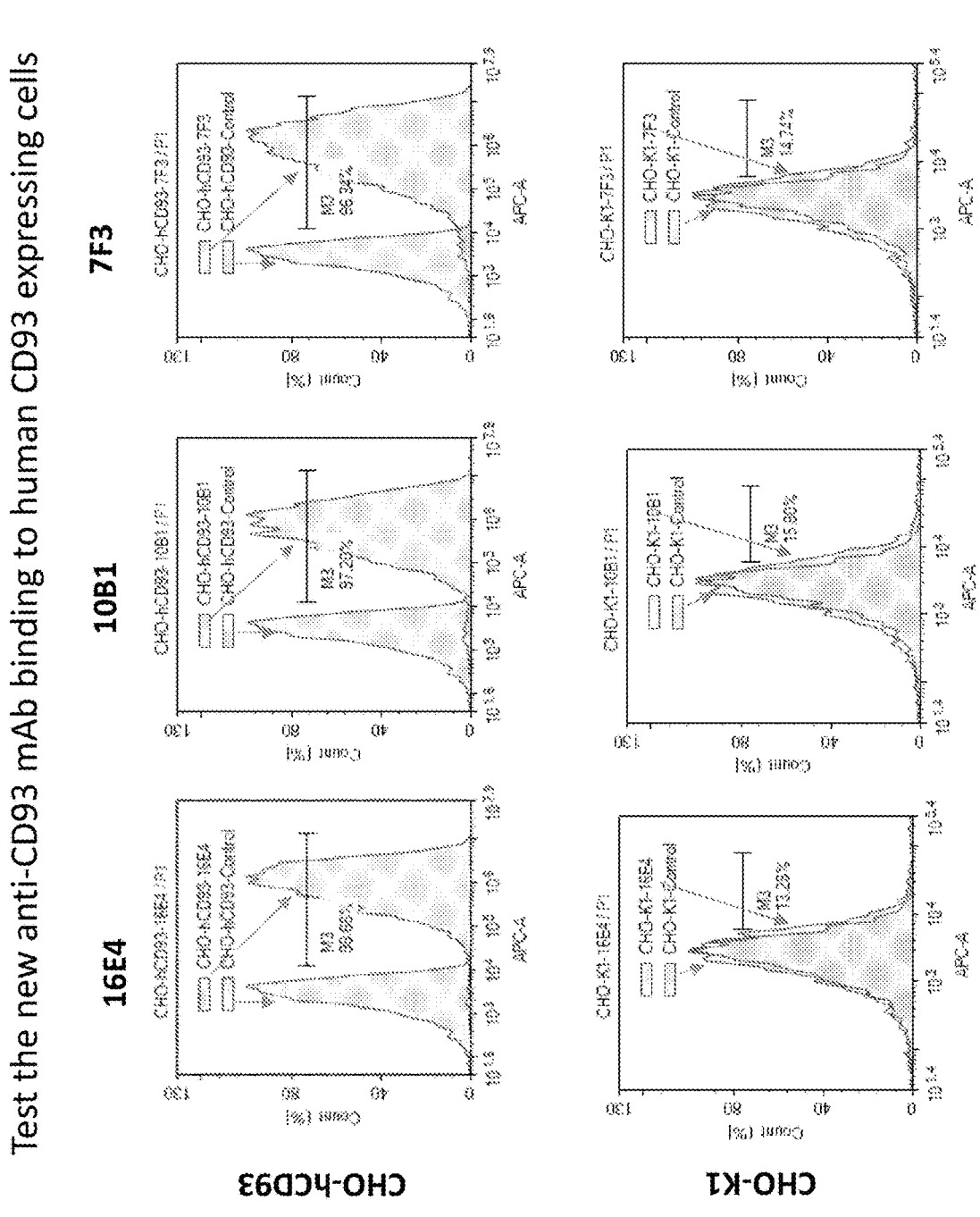
FIG. 10 shows binding of 16E4, 10B1 and 7F3 to human CD93-expressing CHO cells and lack of binding to CHO-K1 cells.

As shown in FIG. 2 and FIG. 10, all fifteen hybridoma clones, as well as commercially available antibody MM01, bind to hCD93 expressing CHO cells (as evidenced by separation of peaks corresponding to anti-CD93 mAbs and control), and there is no binding between CHO-K1 cells and 16E4, 10B1, or 7F3 (as evidenced by no separation of peaks).

Example 5. IGFBP7/CD93 Blockade Assay in Human CD93 Expressing CHO Cells by Anti-CD93 Antibody Treatment Human CD93 expressing CHO cells ($1\times10^5$ per well) were treated with anti-CD93 antibodies or isotype control at a serial concentration for 30 minutes at 4° C. Then the cells were incubated with HIS tagged human IGFBP7 recombinant protein (0.1 µg/ml) for another 30 minutes at 4° C. Then the cells were washed with FACS buffer and incubated with a rabbit anti-IGFBP7 antibody (Sino Biological Inc, Catalog #13100-R003) at 1 µg/ml for 30 minutes at 4° C. After incubation, the cells were washed with FACS buffer and incubated with PE-conjugated anti-rabbit IgG antibody (Biolegend) for 30 minutes in 4° C. After washing by FACS buffer twice, the samples were analyzed and data acquired in NovoCyte Flow.

Figure 14:
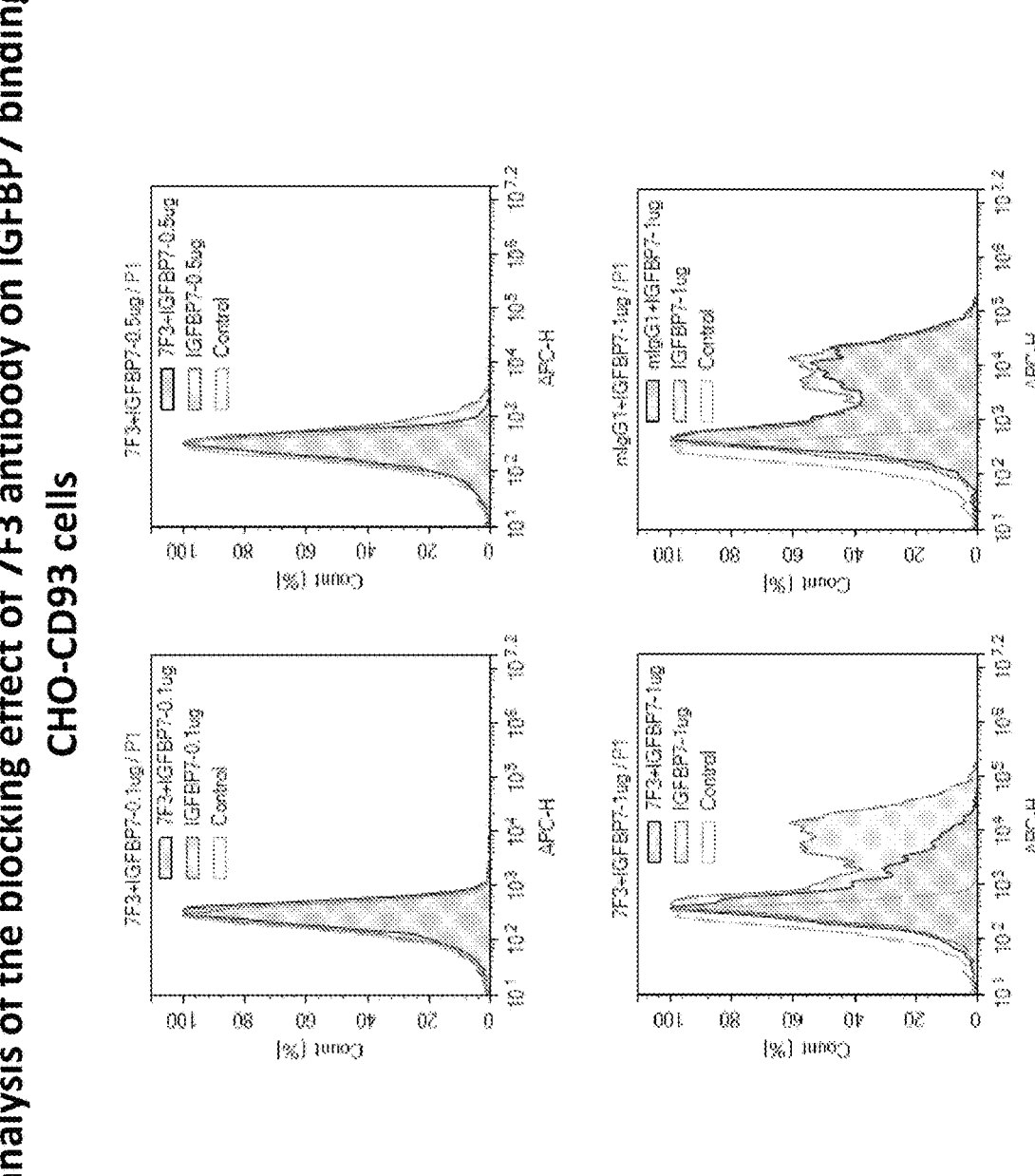
FIG. 14 show that the inhibition of the interaction between CD93 and IGFBP7 by 7F3 as compared to mIgG1 isotype at various concentrations.
Figure 15A:
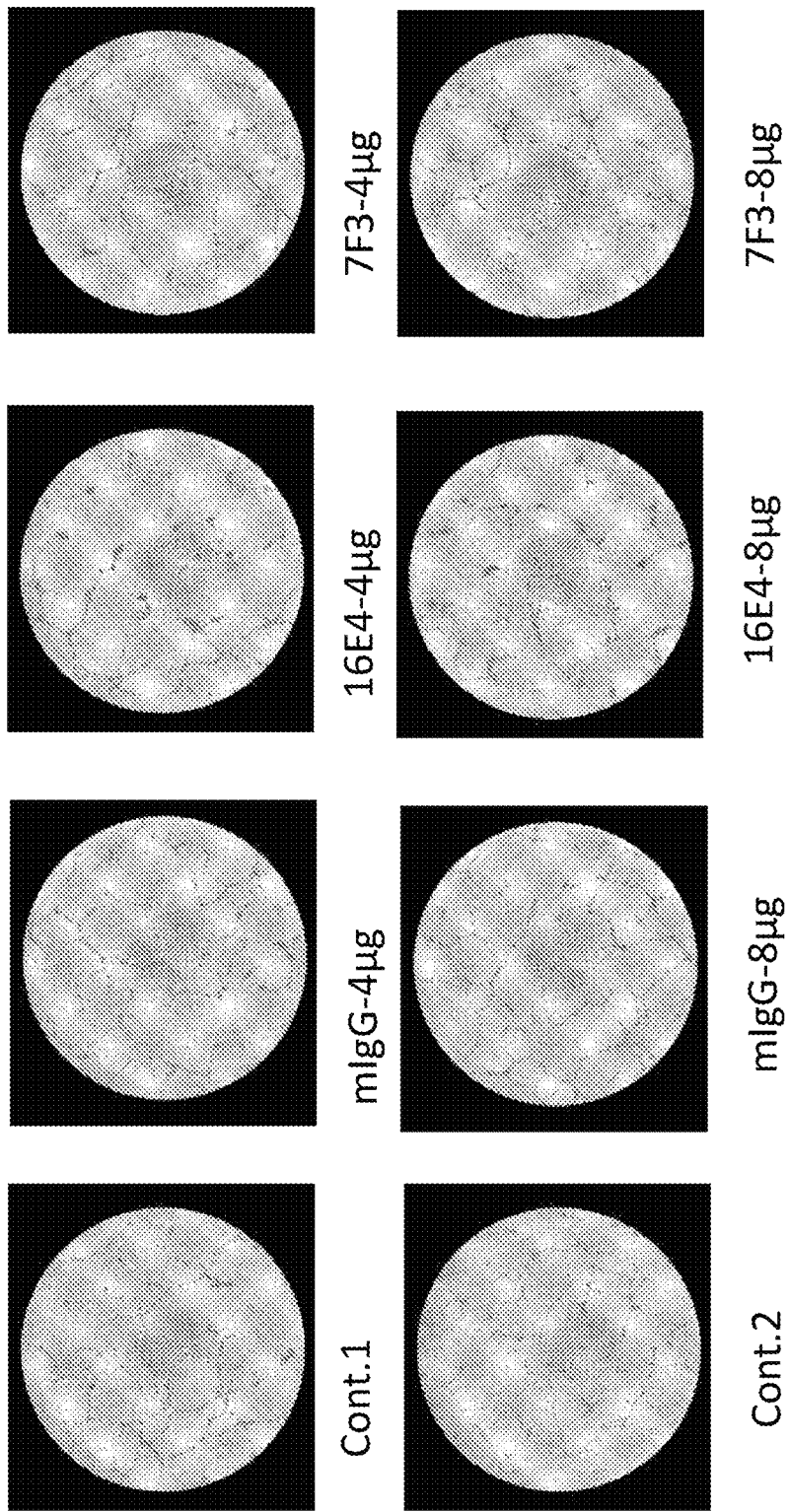
FIGS. 15A-15B shows the inhibition of HUVEC tube formation by 16E4 and 7F3 at two concentrations as compared to control.
Figure 15B:
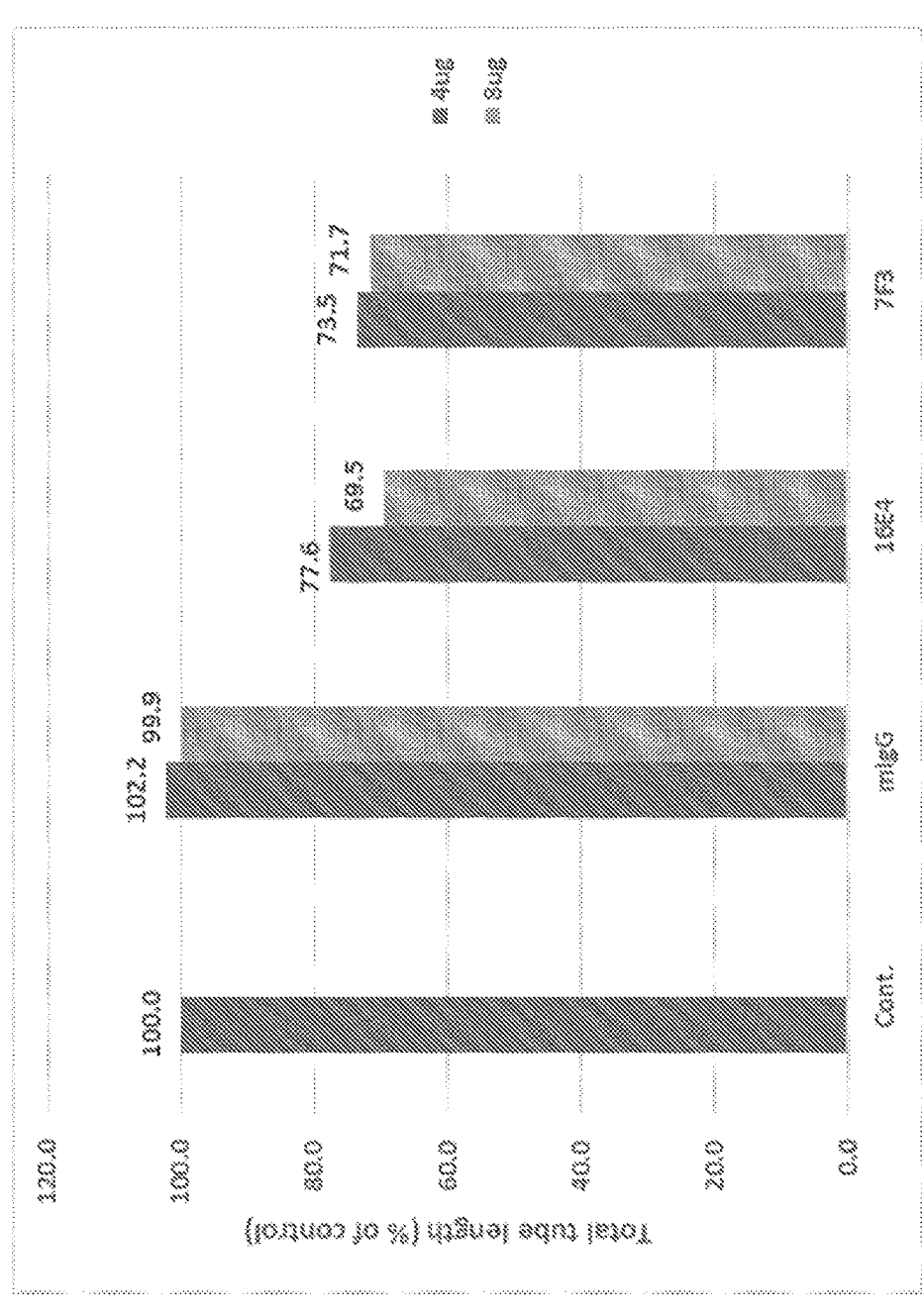
Figure 16:
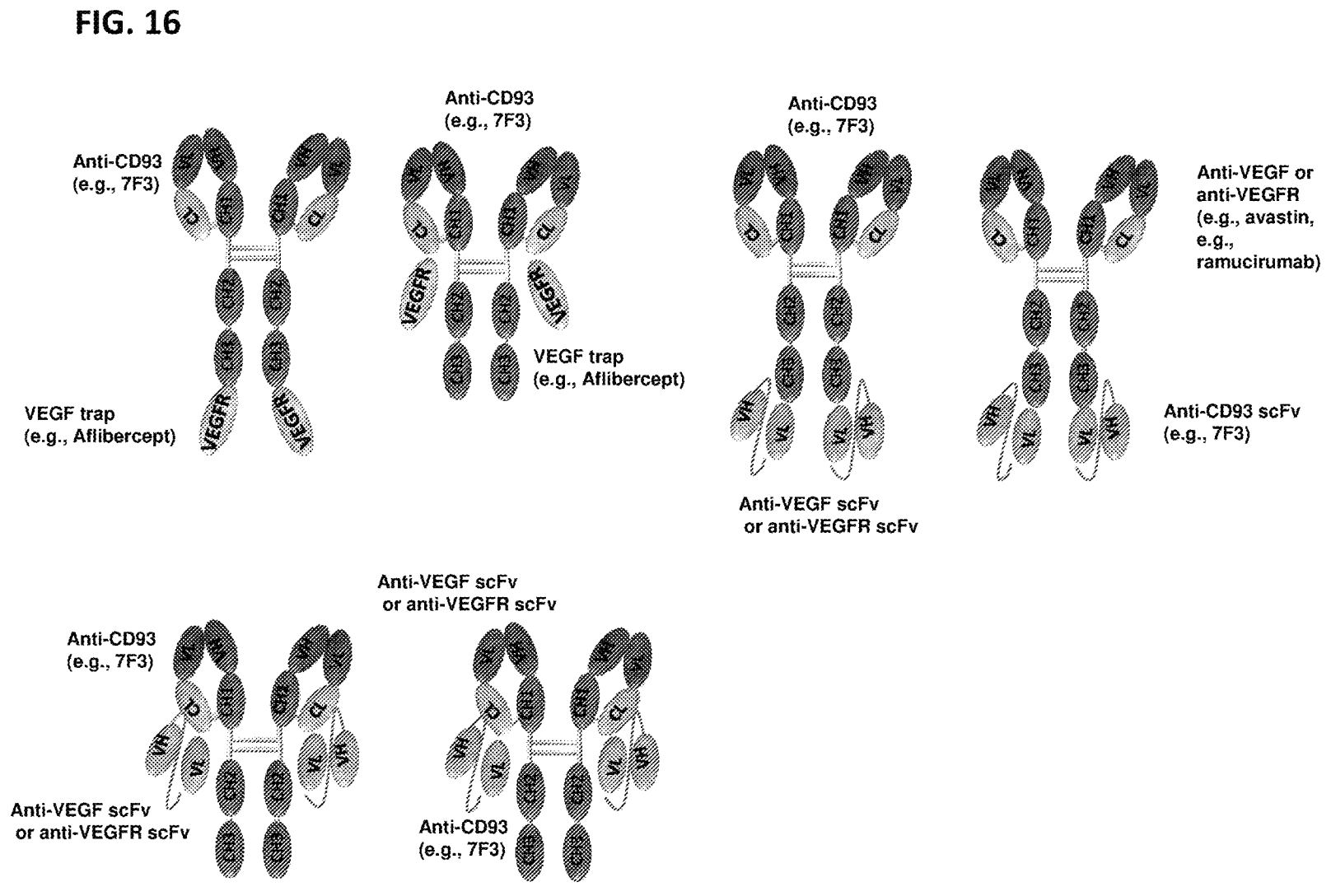

As shown in FIGS. 3A-3D, 16E4 mAb effectively blocks the interaction between CD93 and IGFBP7 at various concentrations, including at the lowest concentration of 0.4 µg/ml (as evidenced by reduction of separation between peaks corresponding to anti-CD93 mAbs and negative controls). FIG. 14 shows that 7F3 effectively blocks the interaction between CD 93 and IGFBP7 at 50 µg/ml (as evidenced by disappearance of the "shoulder" for the control peak).

Example 6. MMRN2/CD93 Blockade Assay in Human CD93 Expressing CHO Cells by Anti-CD93 Antibody Treatment Human CD93 expressing CHO cells ($1\times10^5$ per well) were treated with anti-CD93 antibodies (16E4, 10B1, and 7F3) or isotype control at 50 µg/ml for 30 minutes at 4° C. The cells were then incubated with His-tagged MMRN2 recombinant protein or biotinylated MMRN2 protein (0.1~0.5 µg/ml) for another 30 minutes at 4° C. After incubation, the cells were washed with FACS buffer and incubated with anti-His conjugated APC or streptavidin conjugated APC at a ratio of 1:500 for 30 minutes at 4° C. After washing with FACS buffer twice, the samples were analyzed and data acquired in NovoCyte Flow.

Figures 11A, 11B:
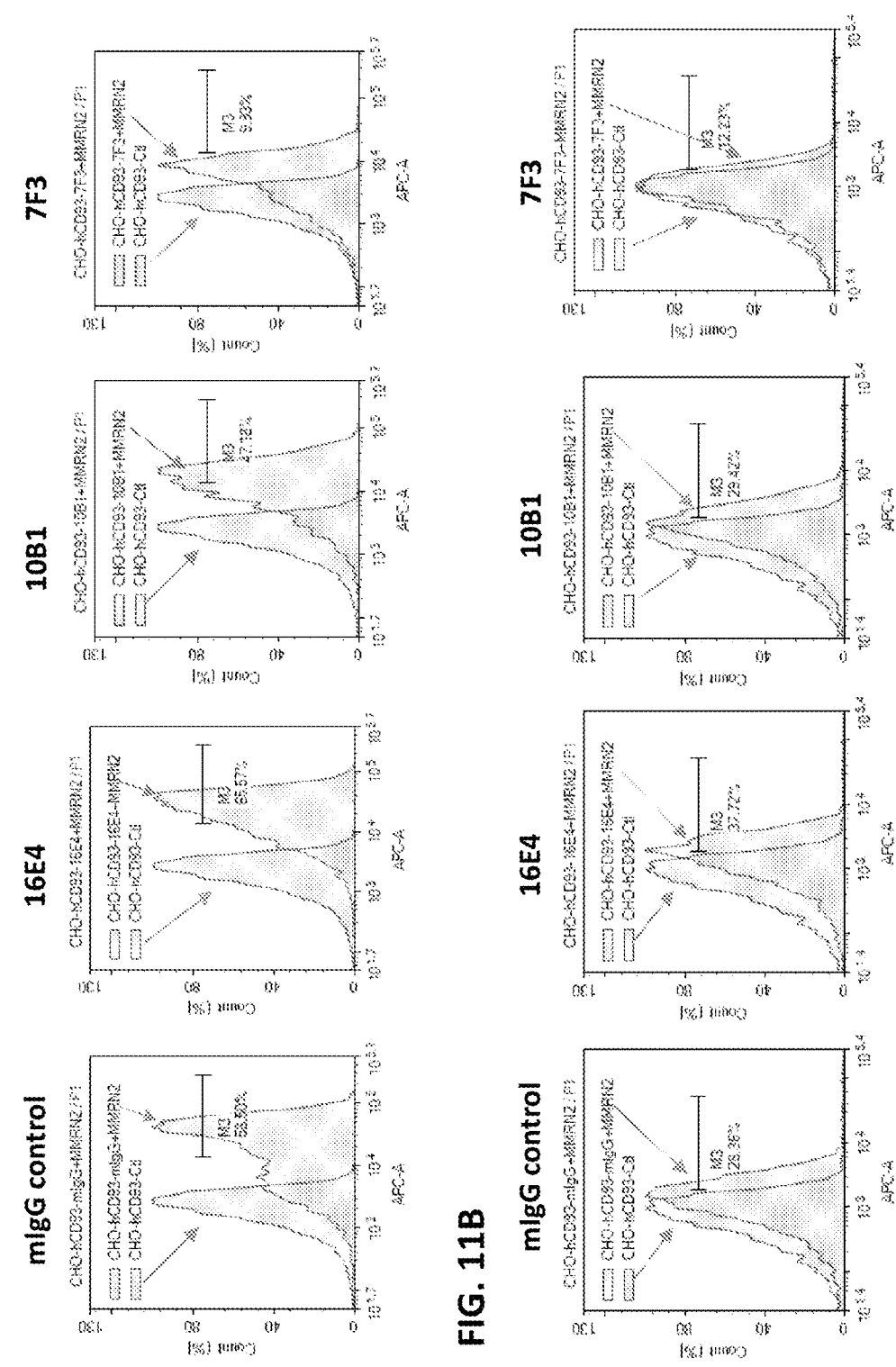
FIGS. 11A-11B show that the inhibition of the interaction between CD93 and MMRN2 by 16E4, 10B1, and 7F3 as compared to mIgG isotype at 50 μg/mL.

As shown in FIG. 11A-11B, 7F3 mAb effectively blocks the interaction between MMRN2 and CD93 (as evidenced by reduction of the separation between peaks corresponding to 7F3 mAb and control; FIG. 11A: 0.5 µg/ml of MMRN2; FIG. 11B: 0.1 µg/ml). 16E4 and 10B1 show no significant blockade of the interactions between MMRN2 and CD93.

The blockade of CD93/MMRN2 by 7F3 mIgG1, 5H9 mIgG2a, and 16E4 mIgG2a was further tested as described above at 0.1 µg/ml MMRN2$^{495-674}$ and 0.5 µg/ml MMRN2$^{495-674}$ (produced in-house), with IgG2a as negative control.

Figure 12:
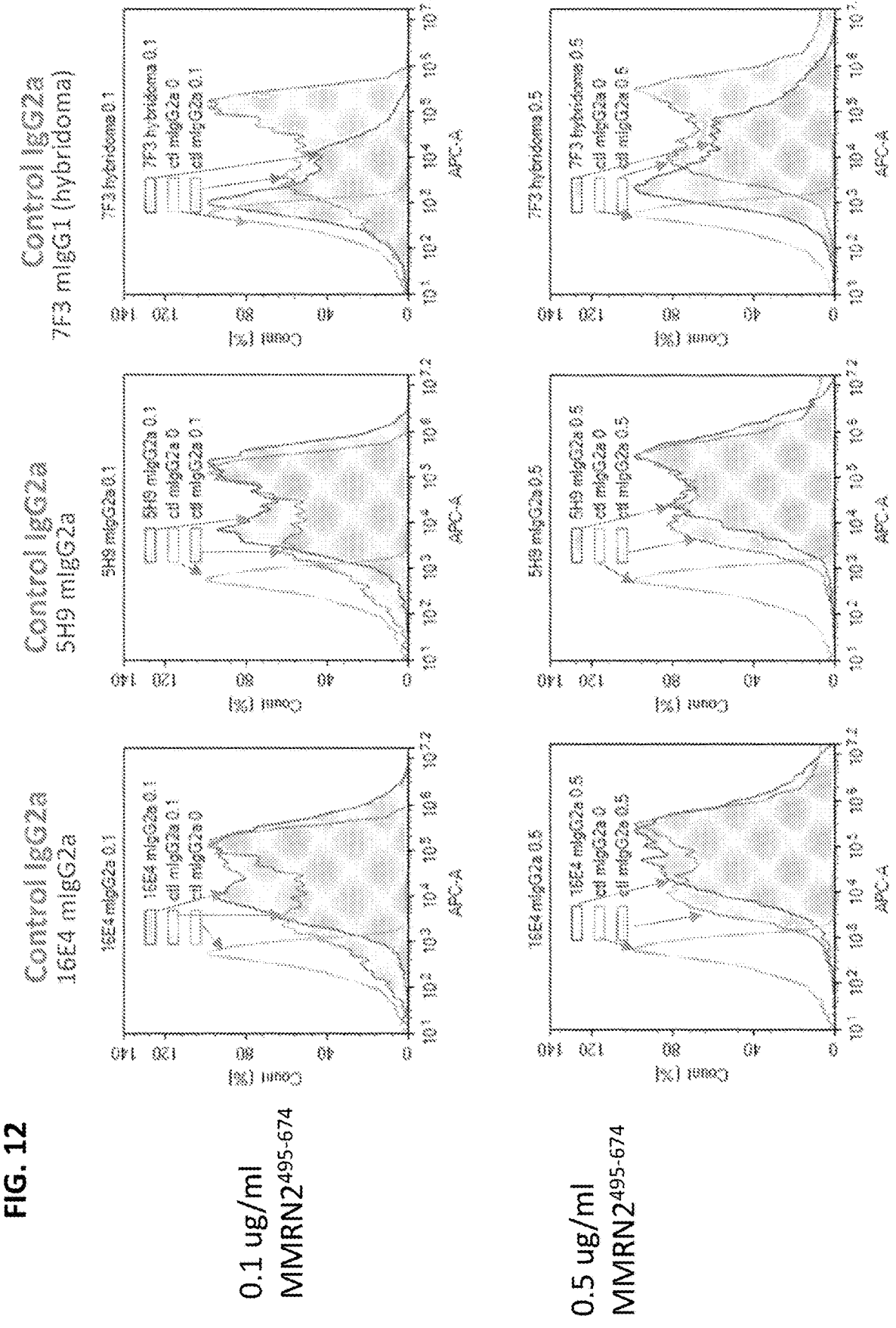
FIG. 12 shows the inhibition of the interaction between CD93 and MMRN2 by 7F3 at different MMRN2 concentrations as compared to control (IgG2a)

As shown in FIG. 12, 7F3 effectively blocks CD93/MMRN2 interaction at 0.1 µg/ml MMRN2$^{495-674}$ and as high as 0.5 µg/ml MMRN2$^{495-674}$ (as evidenced by shift of the 7F3 peak to the left. 7F3 also effectively blocks CD93/

Figure 13:
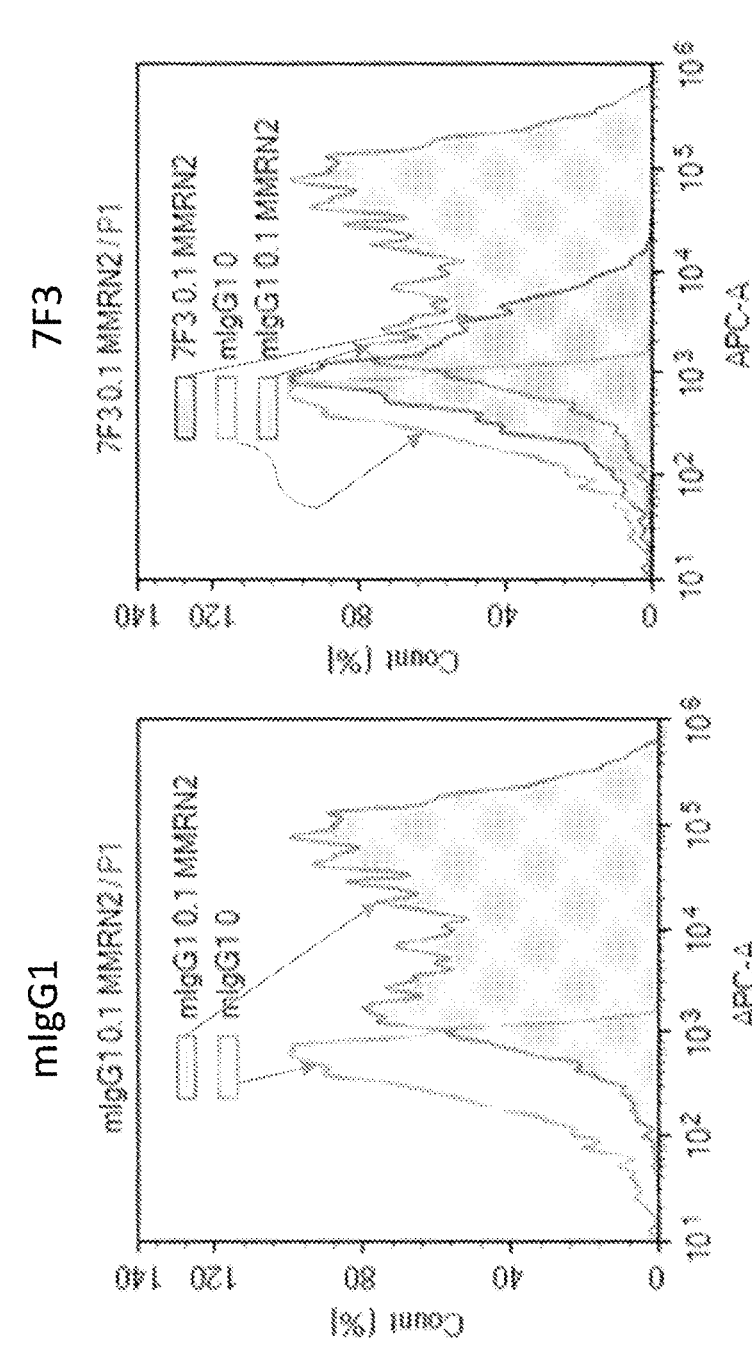
FIG. 13 shows the inhibition of the interaction between CD93 and MMRN2 by 7F3 as compared to control (IgG1).

MMRN2 interaction at 0.1 µg/ml MMRN2, as shown in FIG. 13 (as evidenced by shift of the 7F3 peak to the left).

Example 7. HUVEC Tube Forming Inhibition Assay

Human umbilical vein endothelial cells (HUVECs, Thermo Fisher Scientific, Waltham, MA) were cultured in medium 200 supplemented with low serum growth supplement (LSGS, Thermo Fisher Scientific, Waltham, MA) at 37° C. with 5% $CO_2$. 96 well plates were coated with 50 µl of Geltrex reduced growth factor basement membrane matrix (Thermo Fisher Scientific) and incubated for 30 min at 37° C. To investigate the effects of hybridoma antibodies on tube formation, $2\times10^4$ HUVEC cells were seeded onto Matrix-coated plates and incubated in the presence or absence of purified hybridoma antibodies for 18 hours at 37° C. with 5% $CO_2$. Avastin-IL10 fusion protein was used as a control. Images were obtained using a light microscope.

As shown in FIGS. 4A-4F and FIGS. 15A-15B, hybridoma antibodies including 10B1, 16E4, 5H9, 16G9, 19E12 and 7F3 effectively inhibit tube formation at the concentration of 4 µg/ml and/or 8 µg/ml. Specifically, total tube lengths of HUVECs treated with 10B1 or 16E4 decrease to 45% and 61.5% as compared to that of the negative control. Total tube lengths of HUVECs treated with 7F3 at 8 µg/ml decreases to 71.7% as compared to that of the negative control, and to 73.5% at 4 µg/ml. 10B1 achieved a comparable inhibitory effects as Avastin at the same dose.

Example 8. Epitope Binning Assay of Anti-CD93 Antibodies by Octet Competition Anti-CD93 antibody epitope bins were determined using Octet QKe (Fortebio). Human CD93 recombinant protein (Sino Biological Inc, Catalog #12589-H08H) were biotinylated using EZ-LINK NHS-PEG4 biotin (Thermo Fisher Scientific). Streptavidin biosensors tips (Fortebio) were used to capture biotinylated human CD93 protein (300 seconds in 5 µg/ml). The baseline was stabilized for 60 seconds in 1× kinetics buffer (Fortebio) before primary anti-CD93 antibodies (10 µg/ml) were allowed to associate for 300 seconds with captured protein. A panel of secondary anti-CD93 antibodies (10 µg/ml) were then allowed to associate with the antigen and primary antibody complex for additional 300 seconds. Signals were recorded for each binding event and data analysis was performed on ForteBio Data Analysis HT 11.1 software.

As shown in FIGS. 5A-5B, 5H9, 10B1, 16E4, 16G9, 19E12, 16B6, and MM01 serve as binding pairs among themselves, indicating that they bind to different epitopes on CD93.

Example 9. Human and Cynomolgus CD93 Antigen Cross-Binding Activities of Anti-CD93 mAbs Measured by Bio-Layer Interferometry (BLI) Assay The binding affinity of anti-CD93 antibodies were determined with bio-layer interferometry using Octet QKe (Fortebio). Human CD93 recombinant protein (Sino Biological Inc, Catalog #12589-H08H) or cynomolgus CD93 protein (made in-house) were biotinylated using EZ-LINK NHS-PEG4 biotin (Thermo Fisher Scientific). Streptavidin biosensors (Fortebio) were used to load biotinylated CD93 protein (300 seconds in 5 µg/ml). The baseline was stabilized for 60 seconds in 1× kinetics buffer (Fortebio) before anti-CD93 antibodies at a serial dilution were allowed to associate for 300 seconds with captured protein. Then the sensors were dissociated in 1× kinetics buffer for 600 seconds. Data analysis was performed on ForteBio Data Analysis HT 11.1 software.

As shown in FIGS. 6A-6B, 5H9, 12H4, 16B6, 16E4, 16G9, 17A7, 17B10, 17E6, 19B5, 19E12, 20C7 as well as MM01 cross-reacted with cynomolgus CD93, while 7C10, 16A1, and 17G11 did not cross-react with cynomolgus CD93.

Table 5 is a summary of the properties of various anti-CD93 antibodies.

TABLE 5

Summary of properties of various anti-CD93 antibodies.

| Clone Name | Binding | Blocking between CD93 and IGFBP7 (FACS) | Blocking between CD93 and MNRN2 (FACS) | HUVEC Tube inhibition | Cyno Cross (EEISA) |
|---|---|---|---|---|---|
| 10B1 | +++ | + | – | +++ | + |
| 16E4 | +++ | +++ | – | +++ | + |
| 5H9 | +++ | + | N.D. | + | + |
| 19E12 | ++ | + | N.D. | + | + |
| 16B6 | +++ | – | N.D. | + | + |
| 17G11 | +++ | – | N.D. | ++ | + |
| 20C7 | +++ | – | N.D. | ++ | + |

TABLE 5-continued

Summary of properties of various anti-CD93 antibodies.

| Clone Name | Binding | Blocking between CD93 and IGFBP7 (FACS) | Blocking between CD93 and MNRN2 (FACS) | HUVEC Tube inhibition | Cyno Cross (EEISA) |
|---|---|---|---|---|---|
| 16G9 | ++ | + | N.D. | + | + |
| 12H4 | +++ | + | N.D. | + | + |
| 16A1 | ++ | – | N.D. | + | + |
| 17A7 | +++ | – | N.D. | – | + |
| 17B10 | +++ | + | N.D. | + | + |
| 17E6 | +++ | – | N.D. | ++ | + |
| 19B5 | ++ | – | N.D. | – | + |
| 7F3 | +++ | +++ | +++ | +++ | + |

Example 10. Humanization of Anti-CD93 Antibodies and Generation of Anti-CD93 Constructs that Inhibit VEGF Exemplary humanized anti-CD93 heavy chain variable sequences and light chain variable sequences were generated. See SEQ ID NO: 307-324 and 347-365 in Sequence Table. CDR sequences of 16E4, 17B310, 16A1 and 71F3 humanized heavy chain variable region sequences and light chain variable region sequences were analyzed and shown in Tables 6-7.

TABLE 6

Heavy chain CDRs of anti-CD93 antibodies and humanized sequences.

| | HC-CDR1 | HC-CDR2 | HC-CDR3 | HC variable region sequences |
|---|---|---|---|---|
| 16E4 (parental) | SYWMH (SEQ ID NO: 17) | EIDPSASYTYYNQKFKG (SEQ ID NO: 18) | SVYYGNKYFDV (SEQ ID NO: 19) | SEQ ID NO: 29 |
| 16E4 VH1 | SYWMH (SEQ ID NO: 17) | EIDPSASYTYYNQKFKG (SEQ ID NO: 18) | SVYYGNKYFDV (SEQ ID NO: 19) | SEQ ID NO: 307 |
| 16E4 VH2 | SYWMH (SEQ ID NO: 17) | EIDPSASYTYYNQKFKG (SEQ ID NO: 18) | SVYYGNKYFDV (SEQ ID NO: 19) | SEQ ID NO: 308 |
| 16E4 VH3 | SYWMH (SEQ ID NO: 17) | EIDPSASYTYYNQKFKG (SEQ ID NO: 18) | SVYYGNKYFDV (SEQ ID NO: 19) | SEQ ID NO: 309 |
| 16E4 VH4 | SYWMH (SEQ ID NO: 17) | EIDPSASYTYYNQKFKG (SEQ ID NO: 18) | SVYYGNKYFDV (SEQ ID NO: 19) | SEQ ID NO: 310 |
| 16E4 VH5 | SYWIH (SEQ ID NO: 304) | EIEPSASYTYYNQKFKG (SEQ ID NO: 305) | SVYYGNKYFDV (SEQ ID NO: 19) | SEQ ID NO: 311 |
| 16E4 VH6 | SYWMH (SEQ ID NO: 17) | EIDPSASYTYYNQKFKG (SEQ ID NO: 18) | SVYYGNKYFDV (SEQ ID NO: 19) | SEQ ID NO: 312 |
| 17B10 (parental) | SYWLN (SEQ ID NO: 177) | RIYPGDGDTDYNGKFKG (SEQ ID NO: 178) | GDGYWAMDY (SEQ ID NO: 179) | SEQ ID NO: 189 |
| 17B10 VH1 | SYWLN (SEQ ID NO: 177) | RIYPGDGDTDYNGKFKG (SEQ ID NO: 178) | GDGYWAMDY (SEQ ID NO: 179) | SEQ ID NO: 347 |

TABLE 6-continued

Heavy chain CDRs of anti-CD93 antibodies and humanized sequences.

| | HC-CDR1 | HC-CDR2 | HC-CDR3 | HC variable region sequences |
|---|---|---|---|---|
| 17B10 VH2 | SYWLN (SEQ ID NO: 177) | RIYPGDGDTDYNGKFKG (SEQ ID NO: 178) | GDGYWAMDY (SEQ ID NO: 179) | SEQ ID NO: 348 |
| 17B10 VH3 | SYWLN (SEQ ID NO: 177) | RIYPGDGDTDYNGKFKG (SEQ ID NO: 178) | GDGYWAMDY (SEQ ID NO: 179) | SEQ ID NO: 349 |
| 16A1 (parental) | DHGIH (SEQ ID NO: 145) | NISPGNGDIKYNEKFKG (SEQ ID NO: 146) | YFVD (SEQ ID NO: 147) | SEQ ID NO: 157 |
| 16A1 VH1 | DHGIH (SEQ ID NO: 145) | NISPGNGDIKYNEKFKG (SEQ ID NO: 146) | YFVD (SEQ ID NO: 147) | SEQ ID NO: 360 |
| 16A1 VH2 | DHGIH (SEQ ID NO: 145) | NISPGNGDIKYNEKFKG (SEQ ID NO: 146) | YFVD (SEQ ID NO: 147) | SEQ ID NO: 361 |
| 16A1 VH3 | DHGIH (SEQ ID NO: 145) | NISPGNGDIKYNEKFKG (SEQ ID NO: 146) | YFVD (SEQ ID NO: 147) | SEQ ID NO: 362 |
| 7F3 (parental) | DYEMH (SEQ ID NO: 289) | GIDPETGDTAYNQNFKG (SEQ ID NO: 290) | YGNLYYYAMDY (SEQ ID NO: 291) | SEQ ID NO: 287 |
| 7F3 VH1 | DYEMH (SEQ ID NO: 289) | GIDPETGDTAYNQNFKG (SEQ ID NO: 290) | YGNLYYYAMDY (SEQ ID NO: 291) | SEQ ID NO: 319 |
| 7F3 VH2 | DYEMH (SEQ ID NO: 289) | GIDPETGDTAYNQNFKG (SEQ ID NO: 290) | YGNLYYYAMDY (SEQ ID NO: 291) | SEQ ID NO: 320 |
| 7F3 VH3 | DYEMH (SEQ ID NO: 289) | GIDPETGDTAYNQNFKG (SEQ ID NO: 290) | YGNLYYYAMDY (SEQ ID NO: 291) | SEQ ID NO: 321 |

TABLE 7

Light chain CDRs of anti-CD93 antibodies and humanized sequences.

| | LC-CDR1 | LC-CDR2 | LC-CDR3 | LC variable region sequences |
|---|---|---|---|---|
| 16E4 | KASQSVDYAGDSYMN (SEQ ID NO: 20) | AASNLES (SEQ ID NO: 21) | QQTNEDPRT (SEQ ID NO: 22) | SEQ ID NO: 30 |
| 16E4 VL1 | KASQSVDYAGDSYLN (SEQ ID NO: 301) | AASNLES (SEQ ID NO: 21) | QQTNEDPRT (SEQ ID NO: 22) | SEQ ID NO: 313 |
| 16E4 VL2 | RASQSVDYAGDSYMN (SEQ ID NO: 302) | AASNLES (SEQ ID NO: 21) | QQTNEDPRT (SEQ ID NO: 22) | SEQ ID NO: 314 |
| 16E4 VL3 | RASQSVDYAGDSYLA (SEQ ID NO: 303) | AASNLES (SEQ ID NO: 21) | QQTNEDPRT (SEQ ID NO: 22) | SEQ ID NO: 315 |
| 16E4 VL4 | RASQSVDYAGDSYMN (SEQ ID NO: 302) | AASNLES (SEQ ID NO: 21) | QQTNEDPRT (SEQ ID NO: 22) | SEQ ID NO: 316 |
| 16E4 VL5 | RASQSVDYAGDSYLN (SEQ ID NO: 306) | AASNLES (SEQ ID NO: 21) | QQTNEDPRT (SEQ ID NO: 22) | SEQ ID NO: 317 |
| 16E4 VL6 | KASQSVDYAGDSYMN (SEQ ID NO: 20) | AASNLES (SEQ ID NO: 21) | QQTNEDPRT (SEQ ID NO: 22) | SEQ ID NO: 318 |

TABLE 7-continued

Light chain CDRs of anti-CD93 antibodies and humanized sequences.

| | LC-CDR1 | LC-CDR2 | LC-CDR3 | LC variable region sequences |
|---|---|---|---|---|
| 17B10 (parental) | RFSKSLLHSNGITYLY (SEQ ID NO: 180) | QMSNLAS (SEQ ID No: 181) | AQNLELPWT (SEQ ID NO: 182) | SEQ ID NO: 190 |
| 17B10 VL1 | RFSQSLLHSNGITYLY (SEQ ID NO: 353) | QMSNLAS (SEQ IDNo:181) | AQNLELPWT (SEQ ID NO: 182) | SEQ ID NO: 350 |
| 17B10 VL2 | RFSQSLLHSNGITYLY (SEQ ID NO: 353) | TMSNLAS (SEQ ID No:354) | AQNLELPWT (SEQ ID NO: 182) | SEQ ID NO: 351 |
| 17B10 VL3 | RFSKSLLHSNGITYLY (SEQ ID NO: 180) | QMSNLAS (SEQ IDNo:181) | AQNLELPWT (SEQ ID NO: 182) | SEQ ID NO: 352 |
| 16A1 (parental) | KSSQSLLNSNNQKNCL A (SEQ ID NO: 148) | FACTRES (SEQ ID NO: 149) | QQHCNTPLT (SEQ ID NO: 150) | SEQ ID NO: 158 |
| 16A1 VL1 | KSSQSLLNSNNQKNYL A (SEQ ID NO: 355) | FASTRES (SEQ ID NO: 356) | QQHYNTPLT (SEQ ID NO: 357) | SEQ ID NO: 363 |
| 16A1 VL2 | KSSQSLLNSNNQKNSL A (SEQ ID NO: 358) | FASTRES (SEQ ID NO: 356) | QQHSNTPLT (SEQ ID NO: 359) | SEQ ID NO: 364 |
| 16A1 VL3 | KSSQSLLNSNNQKNCL A (SEQ ID NO: 148) | FASTRES (SEQ ID NO: 356) | QQHCNTPLT (SEQ ID NO: 150) | SEQ ID NO: 365 |
| 7F3 (parental) | RASSSVSSSYLH (SEQ ID NO: 292) | STSNLAF (SEQ ID NO: 293) | QQYSGYPLT (SEQ ID NO: 294) | SEQ ID NO: 288 |
| 7F3 VL1 | RASSSVSSSYLH (SEQ ID NO: 292) | STSNLAF (SEQ ID NO: 293) | QQYSGYPLT (SEQ ID NO: 294) | SEQ ID NO: 322 |
| 7F3 VL2 | RASSSVSSSYLH (SEQ ID NO: 292) | STSNLAF (SEQ ID NO: 293) | QQYSGYPLT (SEQ ID NO: 294) | SEQ ID NO: 323 |
| 7F3 VL3 | RASSSVSSSYLH (SEQ ID NO: 292) | STSNLAF (SEQ ID NO: 293) | QQYSGYPLT (SEQ ID NO: 294) | SEQ ID NO: 324 |

Various humanized 16E4, 17B10, 16A1 and 7F3 were generated by pairing one of the humanized heavy chain variable region sequences with one of the humanized light chain variable region sequences shown in Tables 6 and 7.

Figure 29:
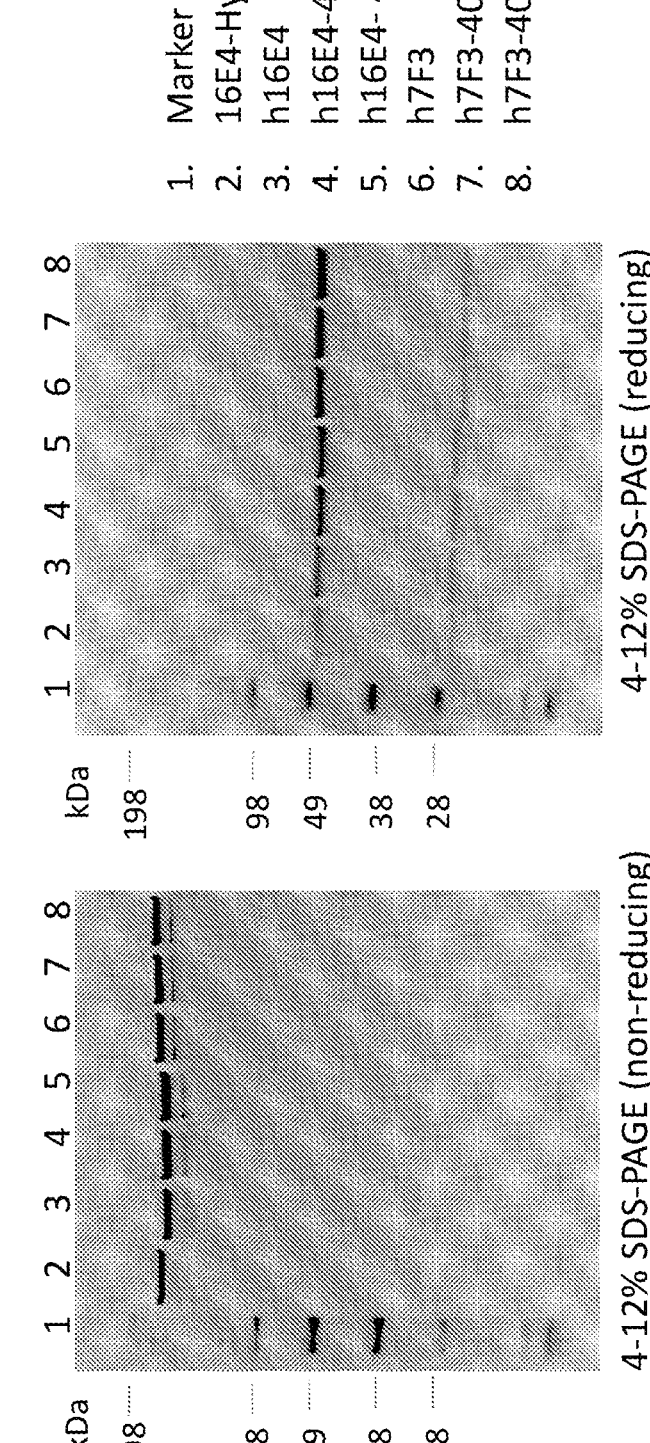
FIG. 29 shows SDS-PAGE analysis of exemplary humanized 16E4 antibody and humanized 7F3 antibody.

SDS-PAGE stability analysis of humanized 16E4 and 7F3 is shown in FIG. 29. SDS-PAGE was performed under reduced and non-reduced conditions to evaluate the stability of humanized 16E4 and 7F3 antibodies. Humanized 16E4 and 7F3 antibodies were incubated in the dark at 40° C. for two and four weeks. The final samples were run on SDS-PAGE and stained with Coomassie Blue to evaluate any visual changes in the antibodies that could have occurred during the incubation. Parental hybridoma 16E4 was run as a positive control. There was no significant change in the recombinant humanized 16E4 and 7F3 observed by this SDS-PAGE analysis at Day 0, 2 weeks or 4 weeks after incubation.

Anti-CD93 constructs that also target VEGF were designed and generated. See FIG. 16. For example, VEGF-trap (Afibercept, e.g., SEQ ID NO: 325) were fused to C-terminus of two heavy chains of full-length human IgG1 antibody that comprises heavy chain variable region and light chain variable region of any of the 7F3 and its humanized sequences (e.g., SEQ ID NOs: 287, 288 and 319-324) via a linker GSDKTHT (SEQ ID NO: 338). See SEQ ID NOs: 342 and 343 for exemplary heavy chain and light chain sequences. In some embodiments, the heavy chain or light chain further has a signal peptide (such as SEQ ID NO: 344, 345, or 346) fused to the N-terminus of the heavy chain or light chain.

Example 11. Animal Studies Using 17B10 Antibodies

1. Syngeneic B16F10 Model

The anti-tumor effect of the anti-CD93 17B10 antibodies was evaluated in a syngeneic mouse model of B16F10 melanoma at Biocytogen. The 17B10 antibody did not strongly cross-react with mouse CD93 based on Octet and FACS analysis, but did show some binding at high protein concentrations to CD93-HEK cells.

Figures 17, 18:
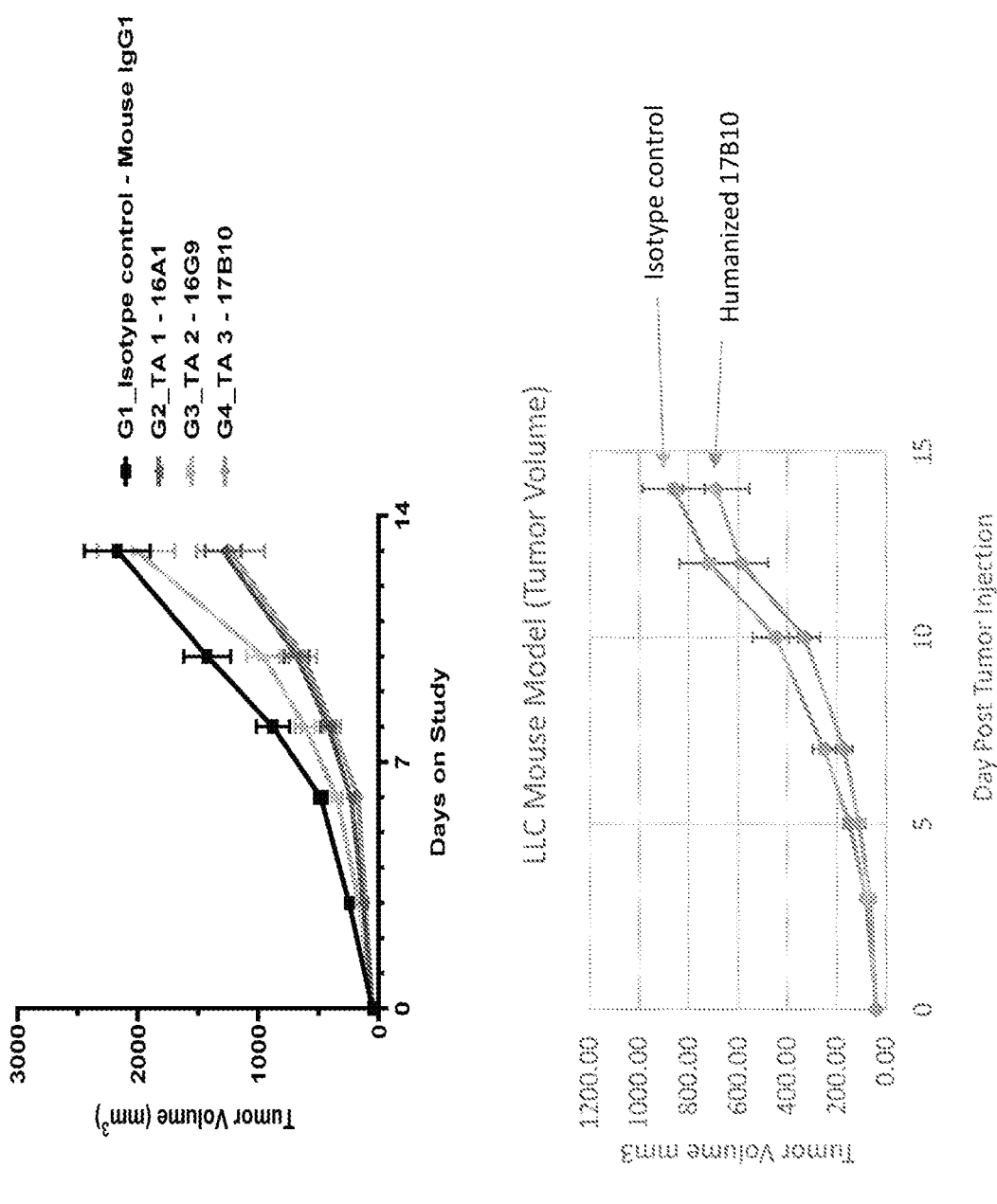
FIG. 17 shows tumor volume in mice treated with exemplary anti-CD93 constructs.
FIG. 18 shows tumor volume in mice treated with humanized 17B10 anti-CD93 antibody.

For the syngeneic mouse model, female C57BL/6J mice were implanted with a murine cell line of B16F10 tumor cells ($0.2 \times 10^6$) in serum-free media. When tumors reach 40-50 mm$^3$, the mice (n=8 per test article) were randomly assigned to groups. Anti-CD93 antibodies (and isotype control) were dosed at 0.3 mg/mouse intraperitoneally on days 0, 3, 7, and 10. Efficacy was evaluated based on overall tumor volume. Body weight was measured to ensure general health of the animals was not affected by test articles. The 17B10 used in this study was expressed in hybridoma cells and purified over a Protein G column. 16G9 and 16A1 were used as comparisons. Tumor volume in each group is shown in FIG. 17. Mice in 17B10 and 16G9 groups exhibited smaller tumor volume compared to mice in 16A1 group and IgG1 control group, suggesting better anti-tumor effects.

2. Lewis Lung Carcinoma

The anti-tumor effect of the humanized anti-CD93 17B10 antibody was evaluated in a syngeneic mouse model of Lewis Lung Carcinoma (LLC). Humanized 17B10 containing a mouse IgG1 Fc was recombinantly produced in ExpiHEK cells. The antibody was purified using a Protein G column, then concentrated and buffer exchanged into 1× PBS. The humanized 17B10 antibody did not strongly cross-react with mouse CD93 based on Octet and FACS analysis, but did show binding at high protein concentrations.

For the syngeneic mouse model, female C57BL/6J mice were implanted with a murine cell line of LLC tumor cells ($0.2 \times 10^6$) in serum-free media. When tumors reach 40-50 mm$^3$, the mice (n=7 per test article) were randomly assigned to groups. Anti-CD93 antibodies (and isotype control) were dosed at 0.3 mg/mouse intraperitoneally on days 0, 3, 7, and 10. Efficacy was evaluated based on overall tumor volume. Body weight was measured to ensure general health of the animals was not affected by test articles.

FIG. 18 shows tumor volume +/− SEM from baseline. FIG. 18 demonstrates that mice in 17B10 group exhibited lower tumor volume compared to mice in the isotype control group.

3. Knock-In Mouse Model Development

Knock-in mouse model was developed using two methods. The knock-in model was designed to replace the mouse CD93 protein with human CD93 protein.

CRISPR/Cas9 was utilized to make two cuts with a guide RNA #1 targeting near the ATG at the 5'UTR of mouse CD93, and the guide RNA #2 targeting near the beginning of the 3'UTR. Homology directed repair used a donor to fuse in-frame the mouse 5'UTR with the CD93 human cDNA and enable expression from the endogenous CD93 promotor. The repair downstream of the STOP codon ensured that the CD93 hybrid transcript contains the mouse 3'UTR. Pure C57BL/6N mice were used as the background for the knock in model. Embryonic stem cell clones were produced and expanded with the knock-in human CD93 gene. Following sequence confirmation, a blastocyst injection was performed to establish the chimeric founders. Breeding proceeded from there with genotyping to identify heterozygote and homozygote pups.

Alternatively, CRISPR/Cas9 was utilized to remove the mouse exon 1 of CD93 corresponding to the extracellular domain of CD93 (S25-N572). In homology directed repair, the donor DNA contained the human sequence of CD93 from T26-K580. The resulting construct expressed a protein containing the humanized extracellular domain of CD93 with the mouse transmembrane and intracellular domains. C57BL/6 mouse embryonic stem cells were utilized for the knock-in model following sequence confirmation. Ozgene used its proprietary Go-Germiline blastocyst for the injections to establish the chimeric founders. Genotyping and phenotyping was performed to ensure heterozygote and homozygote mice.

Figures 19, 20:
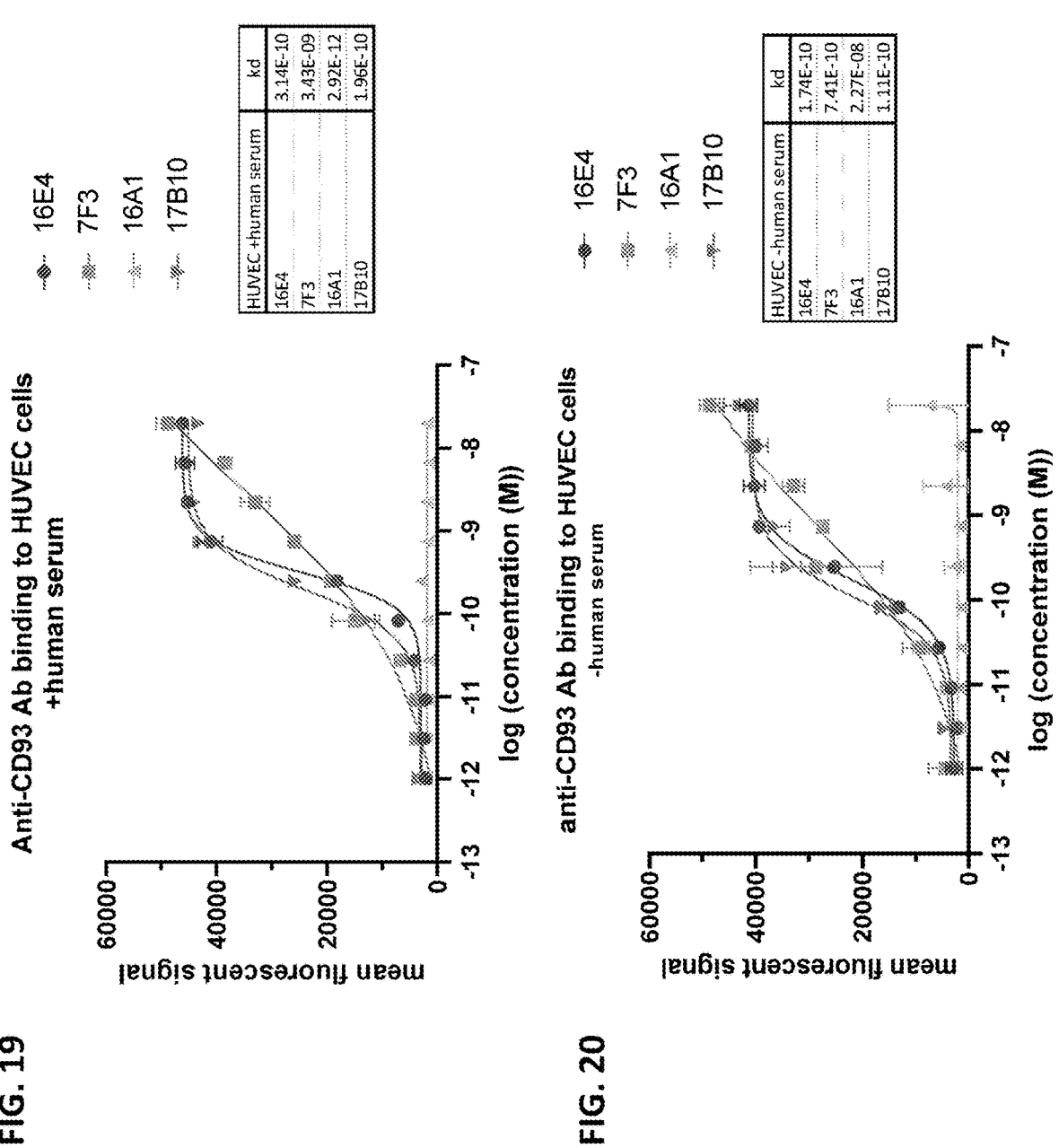
FIG. 19 shows binding of anti-CD93 antibodies to primary HUVEC cells in the presence of human serum determined by flow cytometry.
FIG. 20 shows binding of anti-CD93 antibodies to primary HUVEC cells in the absence of human serum determined by flow cytometry.

Example 12. Anti-CD93 Antibodies Binding to CD93 Expressing Cells Determined by Flow Cytometry Recombinant parental anti-CD93 antibodies were evaluated for their ability to bind to HUVEC cells in the presence or absence of human serum. The 16E4, 7F3, 16A1, and 17B10 sequences obtained from the hybridoma cells were expressed recombinantly with a human CH1 domain and mouse IgG1 CH2 and CH3 Fc domains. Antibodies were purified using Protein G Sepharose. The resulting antibodies were tested for its binding capacity to a variety of cells that express CD93. HUVEC cells were detached by incubation with TrypLE reagent (Gibco cat #12604-013), which preserves the integrity of CD93 on the cell surface. Cells were quenched with media then counted. Cells were resuspended in FACS buffer (ice cold PBS with 0.5% BSA) and human serum was added to 20% (10% final volume) and put on ice for approximately 20 minutes. $5 \times 10^4$ cells were seeded per well in 100 µL media and incubated with serial diluted anti-CD93 antibodies in 100 µL on ice for 2 hours. Cells were then washed by spinning cells at 1200 rpm for 5 min. Media was discarded and cells were resuspended in 200 µL ice cold FACS buffer. The wash step was repeated and cells were resuspended in 100 µL of secondary antibody, AlexaFluor647 conjugated anti-human IgG or anti-mouse IgG antibodies (Jackson ImmunoResearch), diluted 1:500 in FACS buffer. Plates were blocked from light and incubated 1 hour at 4° C. Cells were then washed again then were resuspended in 200 µL ice cold FACS buffer. Cells were washed again and resuspended in 200 µL fixing solution (PBS with 1% formaldehyde). Samples were stored at 4° C. covered in foil, then were acquired in NovoCyte Flow Cytometer and analyzed by NovoExpress software. Results obtained with serum containing samples are shown in FIG. 19. Results from serum-free samples are shown in FIG. 20.

FIGS. 19 and 20 show that 16E4, 7F3, and 17B10 successfully bound to HUVEC cells under experimental conditions. The serum containing samples (FIG. 19) showed similar binding capacities to those run without serum present (FIG. 20), suggesting that there was little effect of Fc binding for these antibodies on HUVEC cells.

CD93 expressing CHO cells were detached by incubation with TrypLE reagents (Gibco cat #12604-013), which preserves the integrity of CD93 on the cell surface. Cells were quenched with media then counted. Cells were resuspended in FACS buffer (ice cold PBS with 0.5% BSA) and human serum was added to 20% (10% final volume) and put on ice for approximately 20 minutes. $5 \times 10^4$ cells were seeded per well in 100 µL and incubated with serial diluted anti-CD93 antibodies in 100 µL on ice for 2 hours. Samples were then washed by spinning samples at 1200 rpm for 5 minutes. Media was discarded and cells were resuspended in 200 µL ice cold FACS buffer. Cells were washed again and resuspended in 100 µL of secondary Antibody, AlexaFluor647 conjugated anti-human IgG or anti-mouse IgG antibodies (Jackson ImmunoResearch), diluted 1:500 in FACS buffer. Plates were covered with foil to protect from like and incubated for 1 hour on ice. Cells were washed again resuspended in 200 µL ice cold FACS buffer. Cells were washed again and were resuspended in 200 µL fixing solution (PBS with 1% formaldehyde). Samples were stored at 4° C. covered in foil, then were acquired in NovoCyte Flow Cytometer and analyzed by NovoExpress software. Results are shown in FIG. 21.

Figures 21, 22:
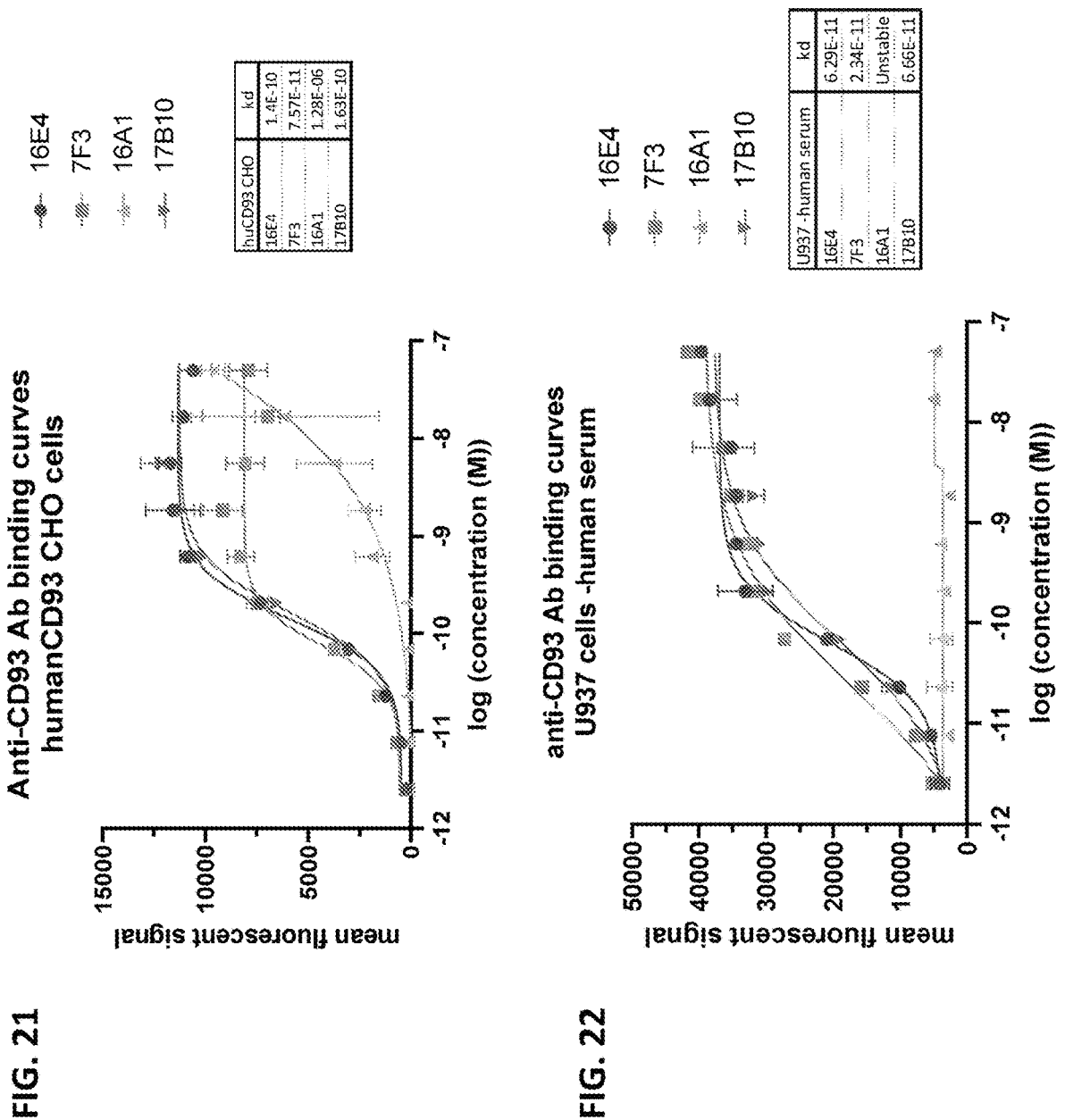
FIG. 21 shows binding of anti-CD93 antibodies to hCD93 CHO cells in the presence of human serum determined by flow cytometry assay.
FIG. 22 shows binding of anti-CD93 antibodies to U937 cells determined by flow cytometry assay.

FIG. 21 shows that 16E4, 7F3, 16A1 and 17B10 successfully bound to human CD93 CHO cells under experimental conditions. 16E4, 7F3, and 17B10 had similar binding affinities to hCD93 CHO cells, while 16A1 had relatively reduced affinity to human CD93 compared to the other antibodies.

U937 cells were detached by incubation with TrypLE reagent (Gibco cat #12604-013), which preserves the integrity of CD93 on the cell surface. Cells were quenched with media then counted. Cells were resuspended in FACS buffer (ice cold PBS with 0.5% BSA) and put on ice ~20 min. $5 \times 10^4$ cells were seeded per well in 100 µL and incubated with serial diluted anti-CD93 antibodies in 100 µL on ice for 2 hours. Samples were then washed by spinning samples at 1200 rpm for 5 minutes. Media was discarded and cells were resuspended in 200 µL ice cold FACS buffer. Cells were washed again and resuspended in 100 µL of secondary Antibody, AlexaFluor647 conjugated anti-human IgG or anti-mouse IgG antibodies (Jackson ImmunoResearch), diluted 1:500 in FACS buffer. Plates were covered with foil to protect from light and were incubated for 1 hour on ice. Samples were then washed again and resuspended in 200 µL ice cold FACS buffer. Cells were washed again and resuspended in 200 µL fixing solution (PBS with 1% formaldehyde). Samples were stored at 4° C. covered in foil, ands were subsequently acquired in NovoCyte Flow Cytometer and analyzed by NovoExpress software.

FIG. 22 shows that 16E4, 7F3, and 17B10 successfully bound to U937 cells under experimental conditions.

Example 13. Cell Based Assay Analysis of 17B10 Antibodies

1. Binding of Humanized 17B10 to Overexpressing Human CD93 CHO Cells

Figure 25A:
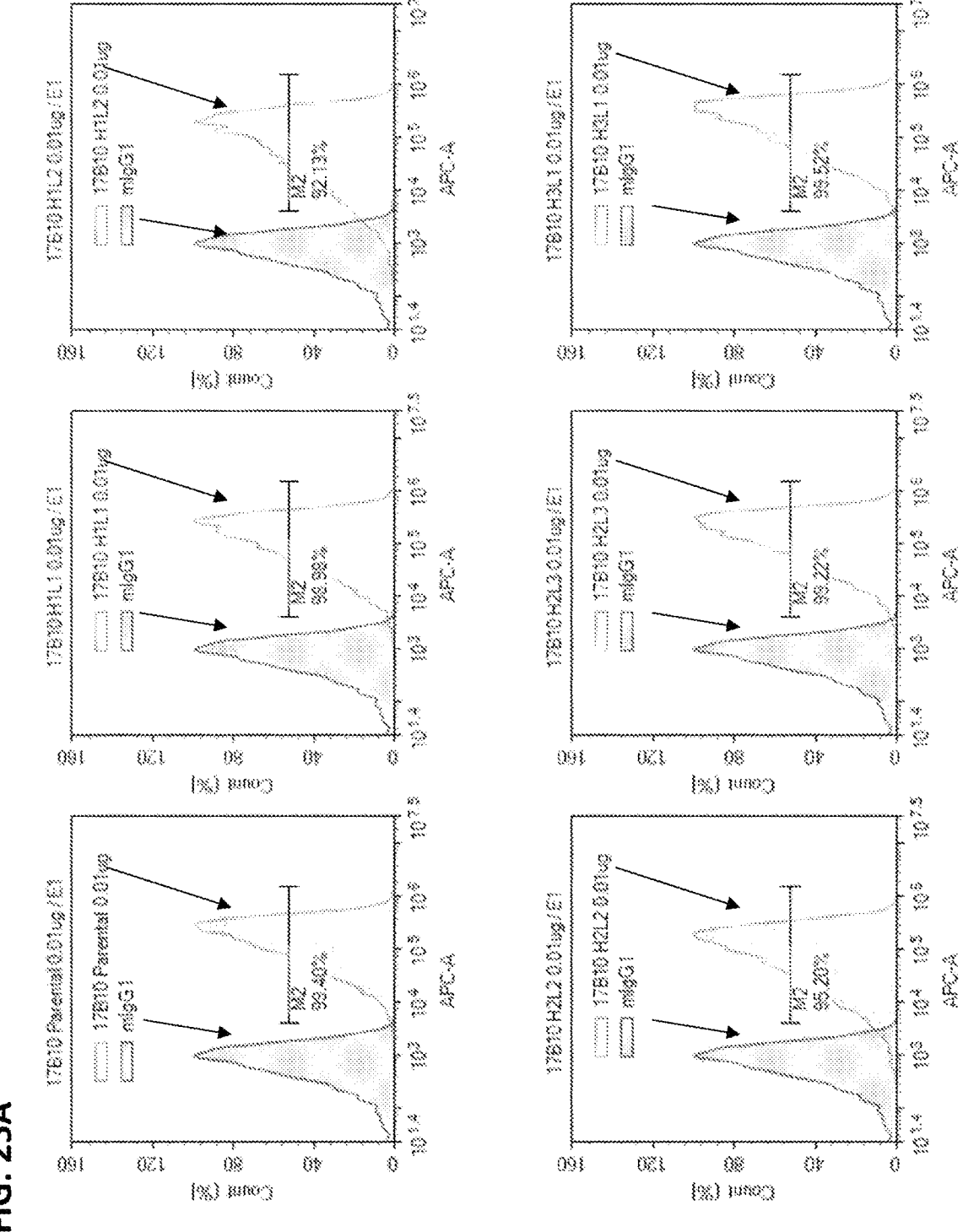
FIGS. 25A-25B show binding of exemplary humanized 17B10 antibodies to overexpressing human CD93 CHO cells.
Figure 25B:
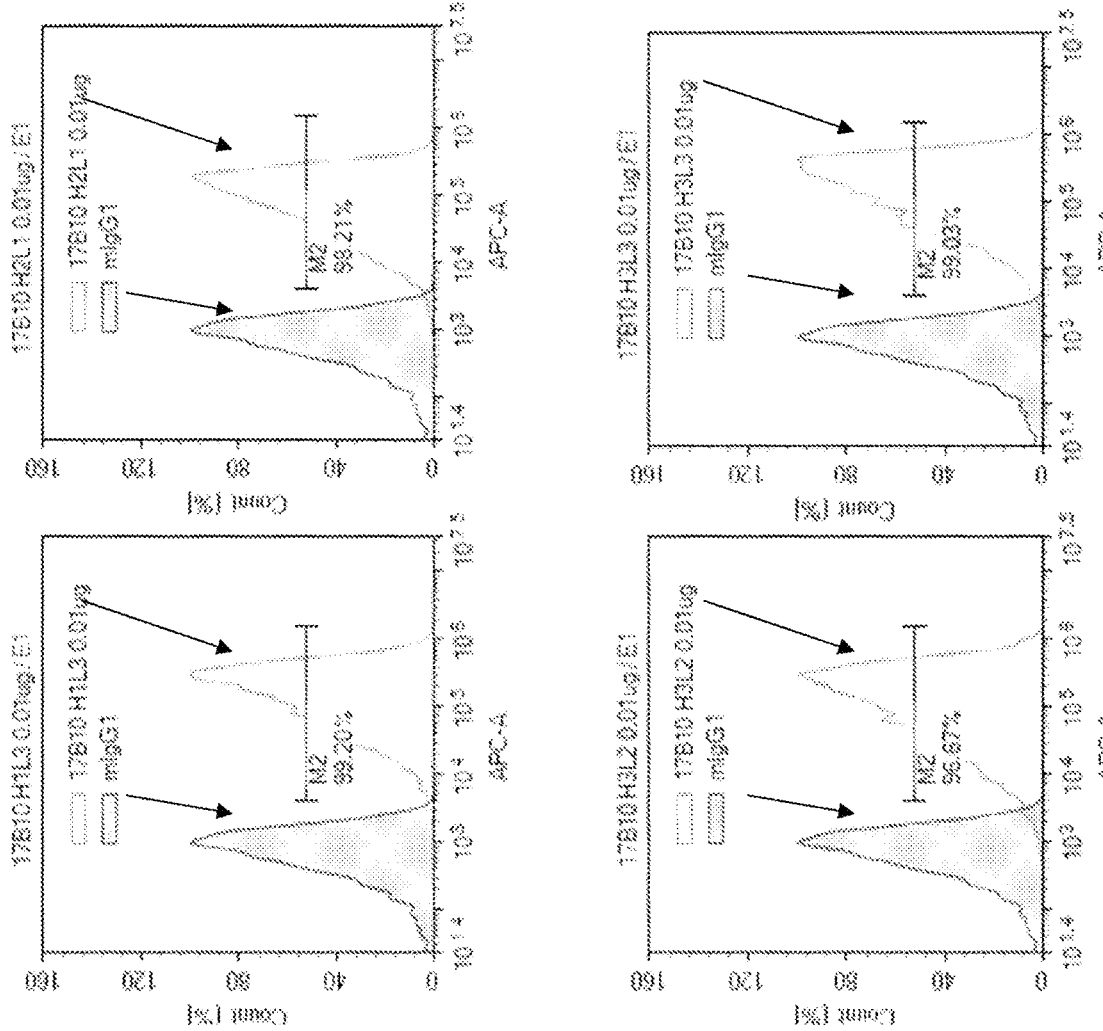

Various humanized 17B10 antibodies comprising a chimeric Fc containing mouse IgG1 CH2 and CH3 domains and human CH1 domains was made in ExpiHEK by combining one of the three humanized heavy chains with one of the three humanized light chains (see Example 10, Tables 6-7). The resulting antibodies were tested for binding to CHO cells overexpressing human CD93 using FACS analysis. The results are shown in FIGS. 25A-25B. As shown, all tested antibodies (i.e., H1L1, H1L2, H1L3, H2L1, H2L2, H2L3, H3L1, H3L2, H3L3) effectively bind to CHO cells overexpressing human CD93.

2. Binding of Humanized 17B10 to KG1a and U937 Cells

Figures 26A, 26B:
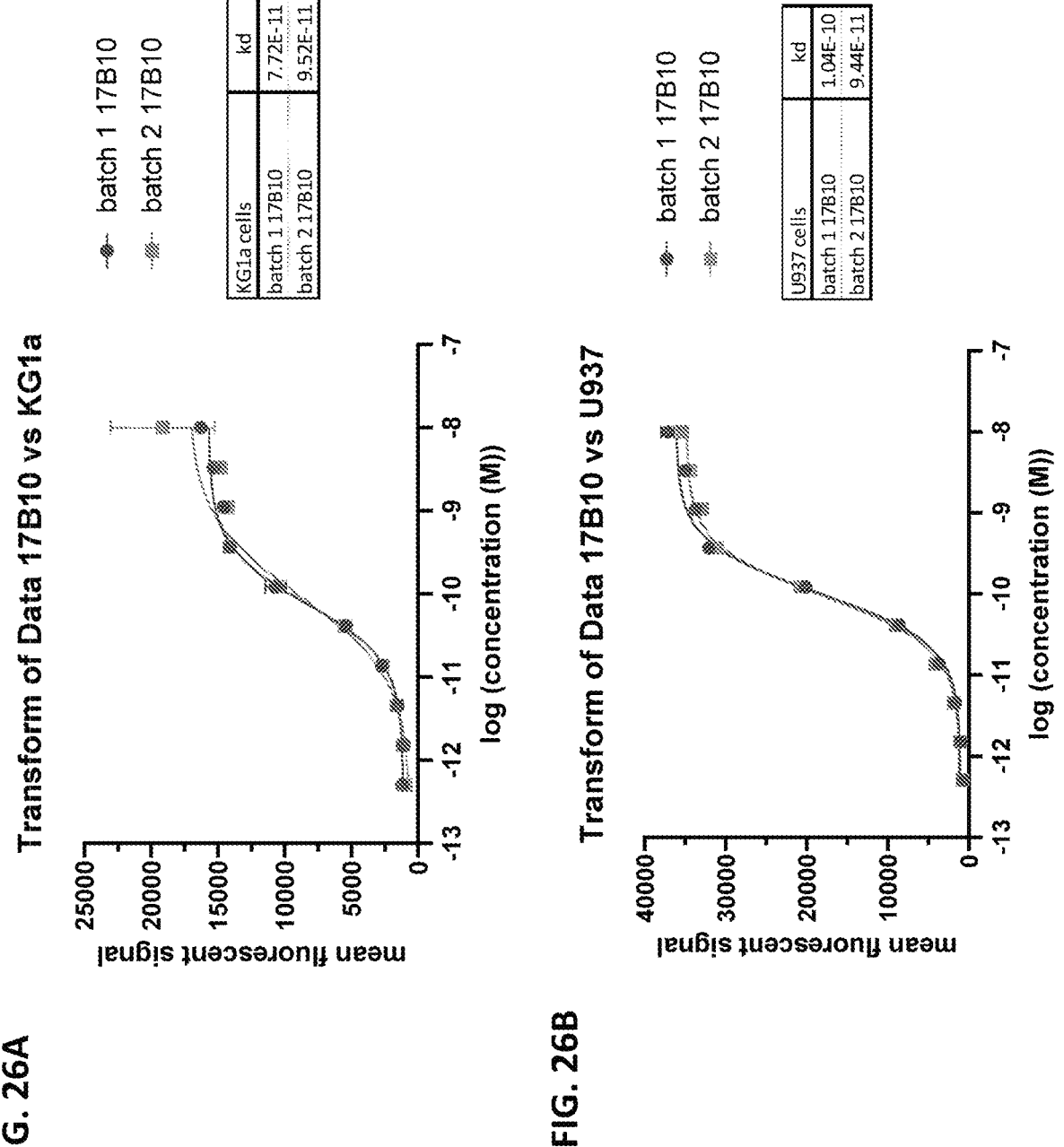
FIGS. 26A-26B show binding of exemplary humanized 17B10 antibodies to KG1a and U937 cells.

Binding of humanized 17B10 ($V_H3V_L3$, i.e., H3L3) to KG1a and U937 cells were tested as described in Example 12. Experiments were repeated using two batches of 17B10 antibody. FIGS. 26A-26B show that 17B10 bound to both KG1a and U937 with high affinity.

3. Binding of Humanized 17B10 (VH3VL3) to Mouse CHO Cells

Parental 17B10 antibody and humanized 17B10 having a VH sequence of SEQ ID NO: 349 and a VL sequence of SEQ ID NO: 352, and a chimeric Fc containing mouse IgG1 CH2 and CH3 domains and human CH1 domains was made in ExpiHEK. Mouse CD93 expressing CHO cells were detached by incubation with TrypLE reagents (Thermo Fisher), which preserved the integrity of CD93 on the cell surface. Then the cells were incubated with parental 17B10 antibody or humanized 17B10 anti-CD93 antibody (50 µg/mL) for 30 minutes at 4° C. After washing with FACS buffer, the cells were incubated with Alexa Fluor 488 conjugated anti-human IgG or anti-mouse IgG antibodies (Jackson ImmunoResearch) for 30 minutes in 4° C. After washing with FACS buffer twice, the samples were acquired in NovoCyte Flow Cytometer and analyzed by NovoExpress software.

Figure 27:
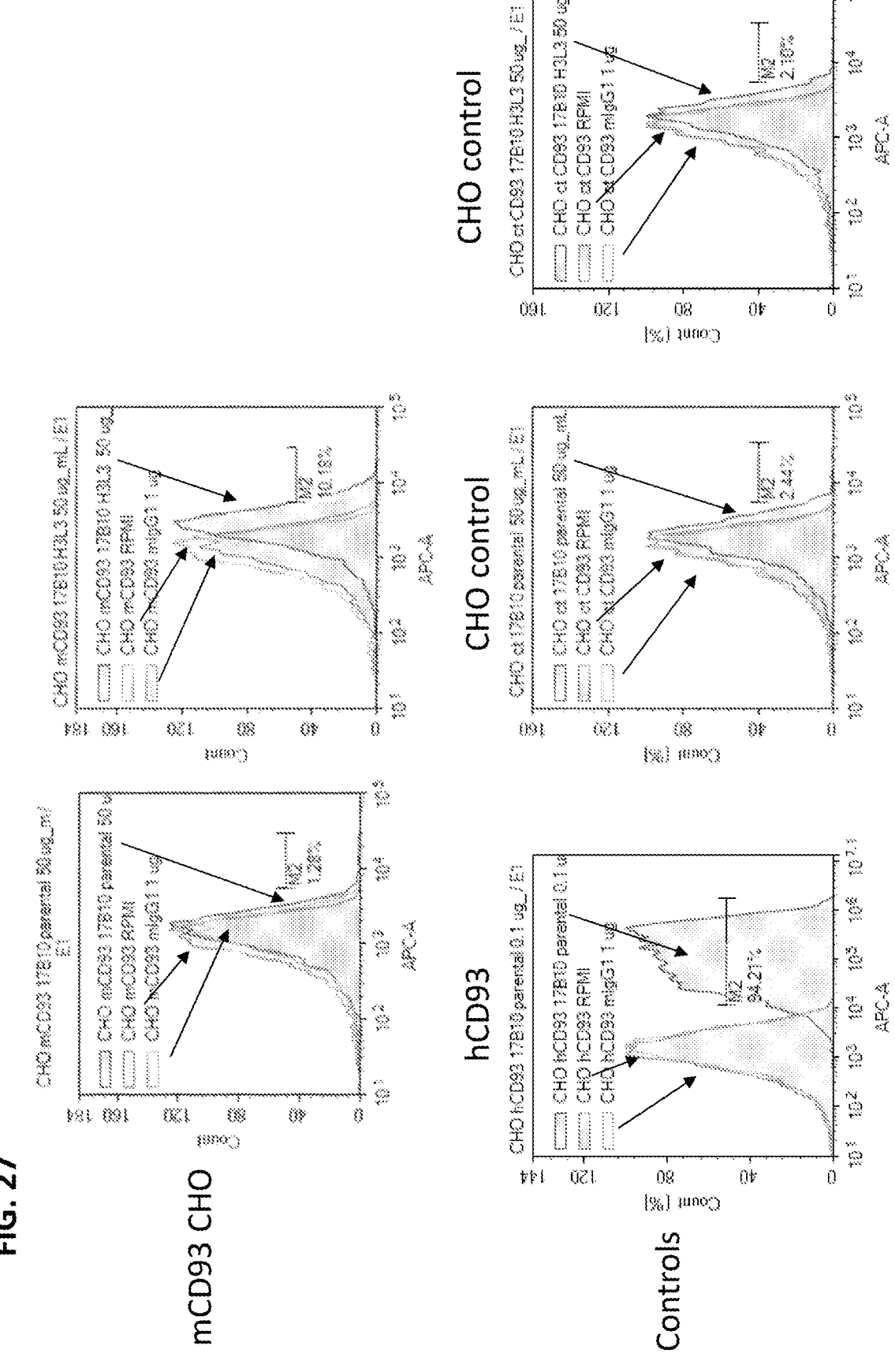
FIG. 27 shows binding of humanized anti-CD93 antibody 17B10 to cell surface expressing mouse CD93 CHO cells determined by fluorescence activated cell sorting (FACS) assay.

FIG. 27 shows that the humanized 17B10 bound to mouse CD93 expressing cells at 50 µg/mL.

4. Binding of Humanized 17B10 (VH3VL3) to mCD93 HEK

Mouse CD93 expressing HEK cells were detached by incubation with TrypLE reagents (Thermo Fisher), which preserves the integrity of CD93 on the cell surface. Then the cells were incubated with serial diluted parental 17B10 and humanized 17B10 ((H3L3) anti-CD93 antibodies for 30 minutes at 4° C. After washing with FACS buffer, the cells were incubated with Alexa Fluor 488 conjugated anti-human IgG or anti-mouse IgG antibodies (Jackson ImmunoResearch) for 30 minutes in 4° C. After washing with FACS buffer twice, the samples were acquired in NovoCyte Flow Cytometer and analyzed by NovoExpress software.

FIG. 28 shows that both parental 17B10 and humanized 17B10 (H3L3) bound to mouse CD93 expressing HEK cells at 50 µg/mL.

4. HUVEC Tube Formation Assay

Figure 23:
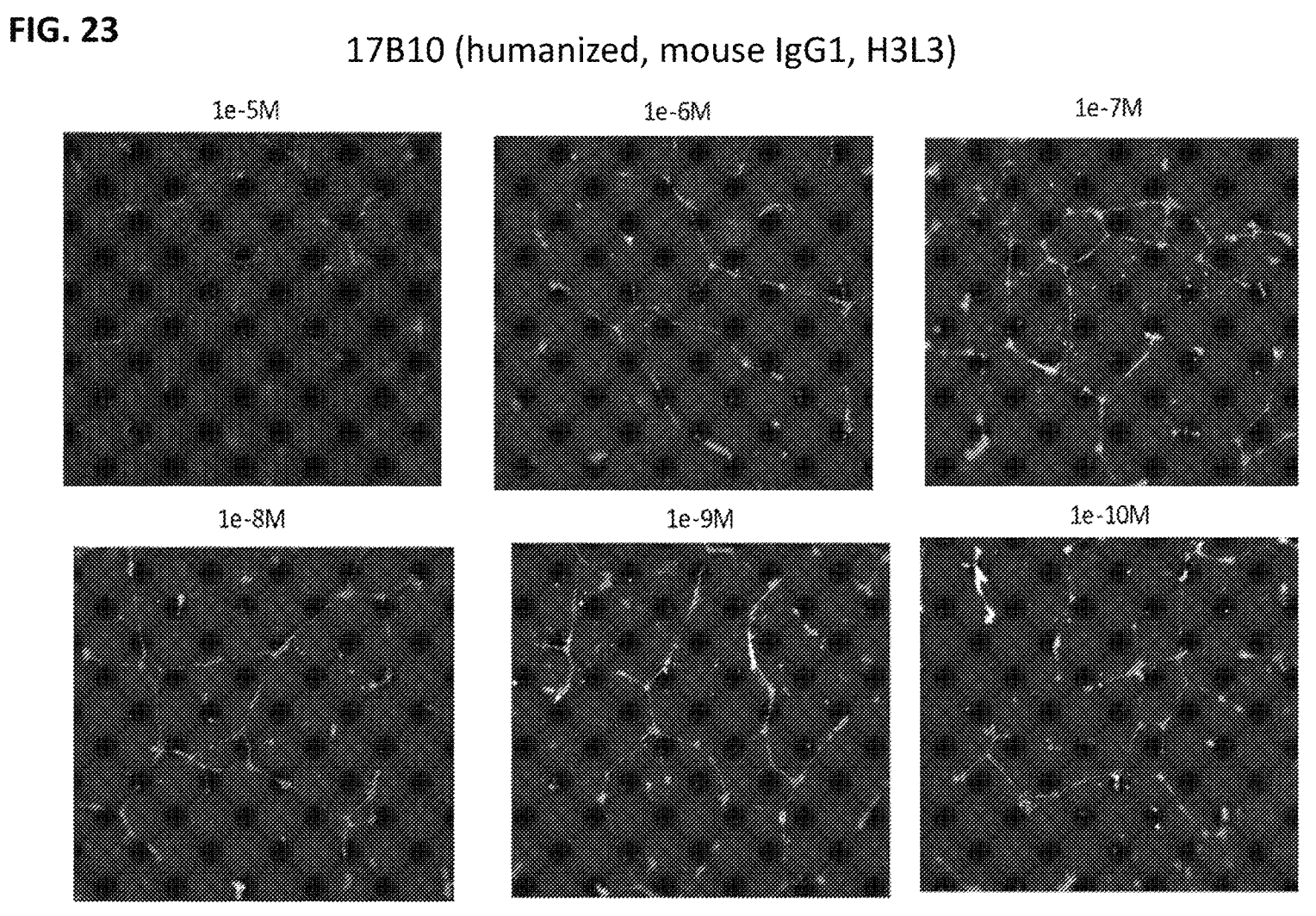
Figure 24:
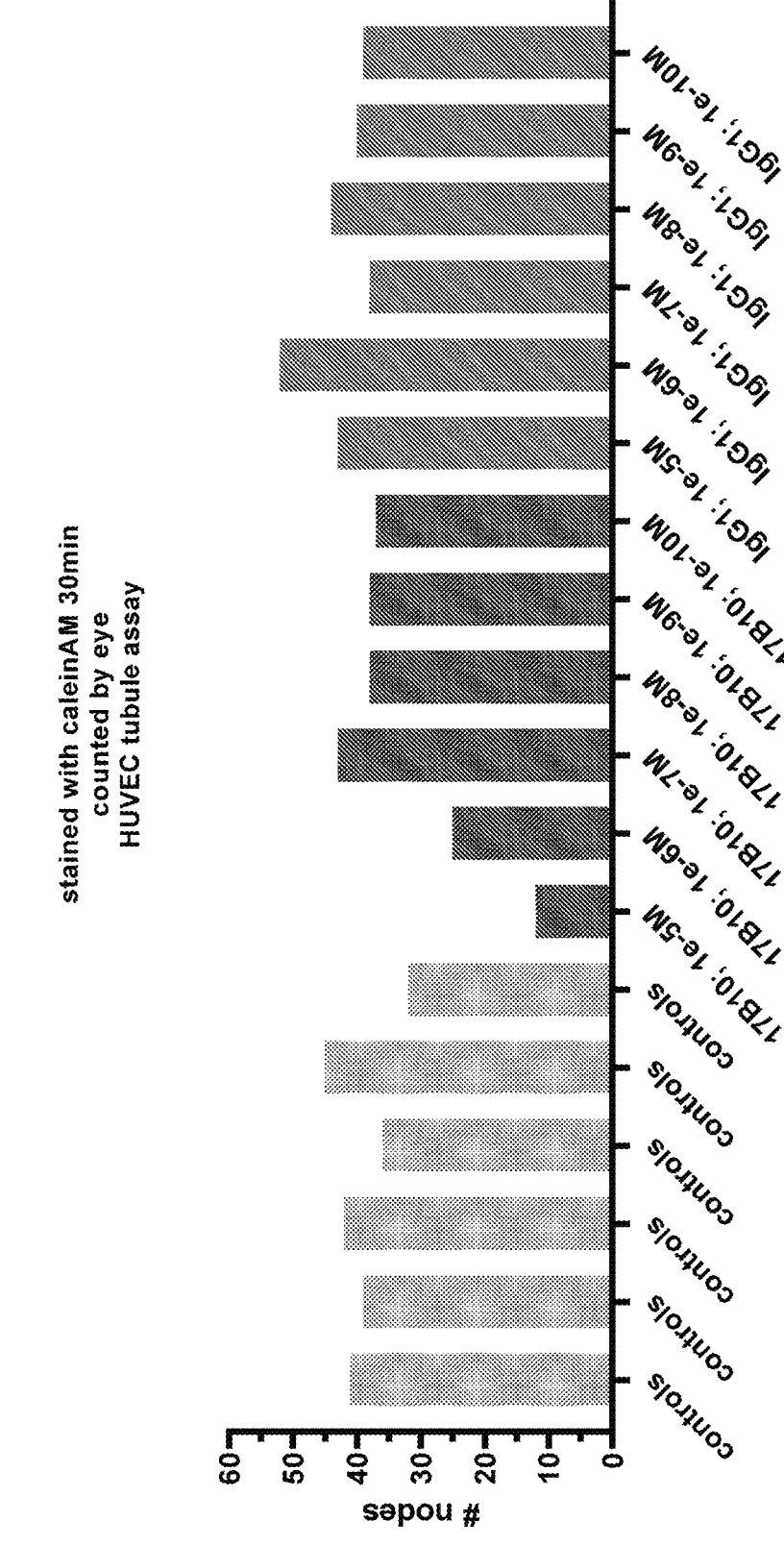

Inhibition of angiogenesis by humanized 17B10 anti-CD93 antibody (H3L3) was tested in a HUVEC tube formation assay. Human umbilical vein endothelial cell (HUVECs, Thermo Fisher Scientific, Waltham, MA) were cultured in medium 200 supplemented with low serum growth supplement (LSGS, Thermo Fisher Scientific, Waltham, MA) at 37° C. with 5% $CO_2$. 96 well plates were coated with 50 µl of Geltrex reduced growth factor basement membrane matrix (Thermo Fisher Scientific) and incubated for 30 min at 37° C. To investigate the effects of humanized 17B10 antibody on tube formation, $1 \times 10^4$ HUVEC cells were seeded onto Matrix-coated plates and incubated in the presence or absence of purified antibodies at various concentrations for 18 hours at 37° C. with 5% $CO_2$. Cells were stained with calcein AM, and images were collected. FIGS. 23-24 show that humanized 17B10 inhibited tube formation at certain concentrations as compared to the controls.

4. Blocking Capacities of 17B10 Antibodies

17B10 antibodies (parental and humanized) were tested in cell based assays.

Parental and humanized 17B10 antibodies did not significantly block IGFBP7 binding to CD93 or MMRN2 binding to CD93 (data not shown).

Example 14. ELISA Binding Analysis of Anti-CD93 Antibodies

Hybridoma produced parental 16E4 and 7F3 were compared to recombinant, chimeric versions of the antibodies. His-tagged human CD93 was coated onto a 96 well plate at 1 µg/mL in 1×PBS overnight at 4° C. The plate was washed with ELISA wash buffer (Boston BioProduct, Inc.) and the wells were blocked with ELISA blocking buffer for 1 hour at 37° C. Purified antibodies were serially diluted in ELISA blocking buffer (Boston BioProduct, Inc.) and incubated on the receptor for 1 hour at 37° C. The plate was washed with ELISA wash Buffer. HRP conjugated Anti-mouse Fc was diluted in ELISA blocking buffer and added to the wells containing the hybridoma produced 16E4 and 7F3 (16E4-

Figures 30, 31:
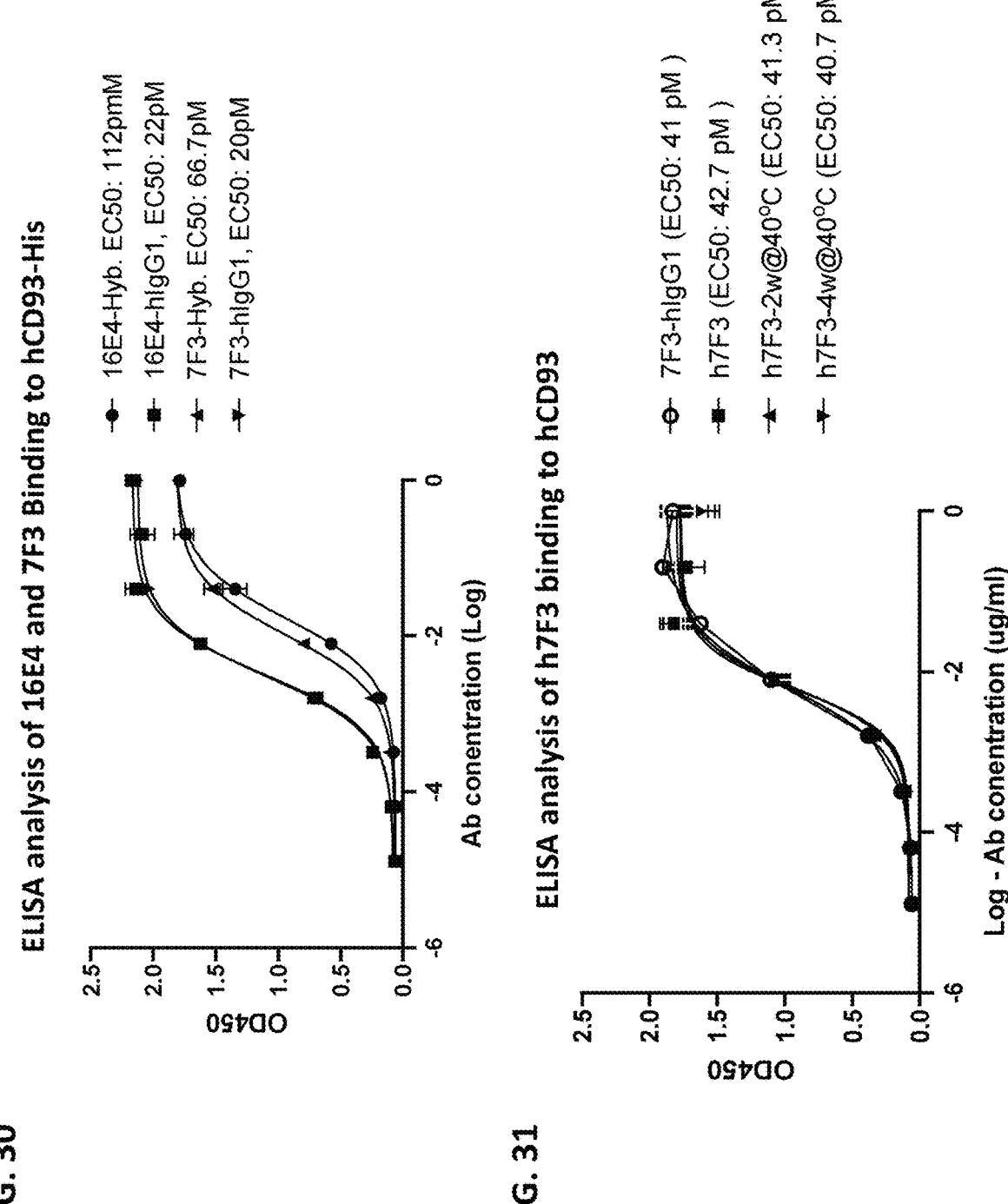
FIG. 30 shows ELISA analysis of the binding of exemplary humanized 16E4 and 7F3 antibodies to human CD93 (hCD93).
FIG. 31 shows ELISA analysis of the binding of exemplary h7F3 (humanized 7F3) antibodies to human CD93 (hCD93).

Hyb and 7F3-Hyb in FIG. 30). HRP conjugated Anti-human Fc was added to the well containing the humanized 16E4 and 7F3 antibodies (16E4-hIgG1 and 7F3-hIgG1 in FIG. 30) for one hour at 37° C. The plate was washed with ELISA wash buffer. HRP substrate was added for indirect detection of the antibodies binding to CD93. FIG. 30 shows that recombinant chimeric antibodies had stronger affinity for the CD93 than the parental antibodies under this method.

Humanized 7F3 antibody was stored in the dark at 40° C. for 2 or 4 weeks. His-tagged human CD93 was coated onto a 96 well plate at 1 µg/mL in 1×PBS overnight at 4° C. The plate was washed with ELISA wash buffer (Boston Bio-Product, Inc.) and the wells were blocked with ELISA blocking buffer for 1 hour at 37° C. Purified 7F3 antibodies were serially diluted in ELISA blocking buffer (Boston BioProduct, Inc.) and incubated on the receptor for 1 hour at 37° C. The plate was washed with ELISA wash Buffer. HRP-conjugated anti-human Fc antibody was incubated for 1 hour at 37° C. The plate was washed with ELISA wash Buffer. HRP substrate was added for indirect detection of the antibodies binding to CD93. FIG. 31 shows that no difference was observed for any of the treated or untreated samples by ELISA.

Figures 32, 33:
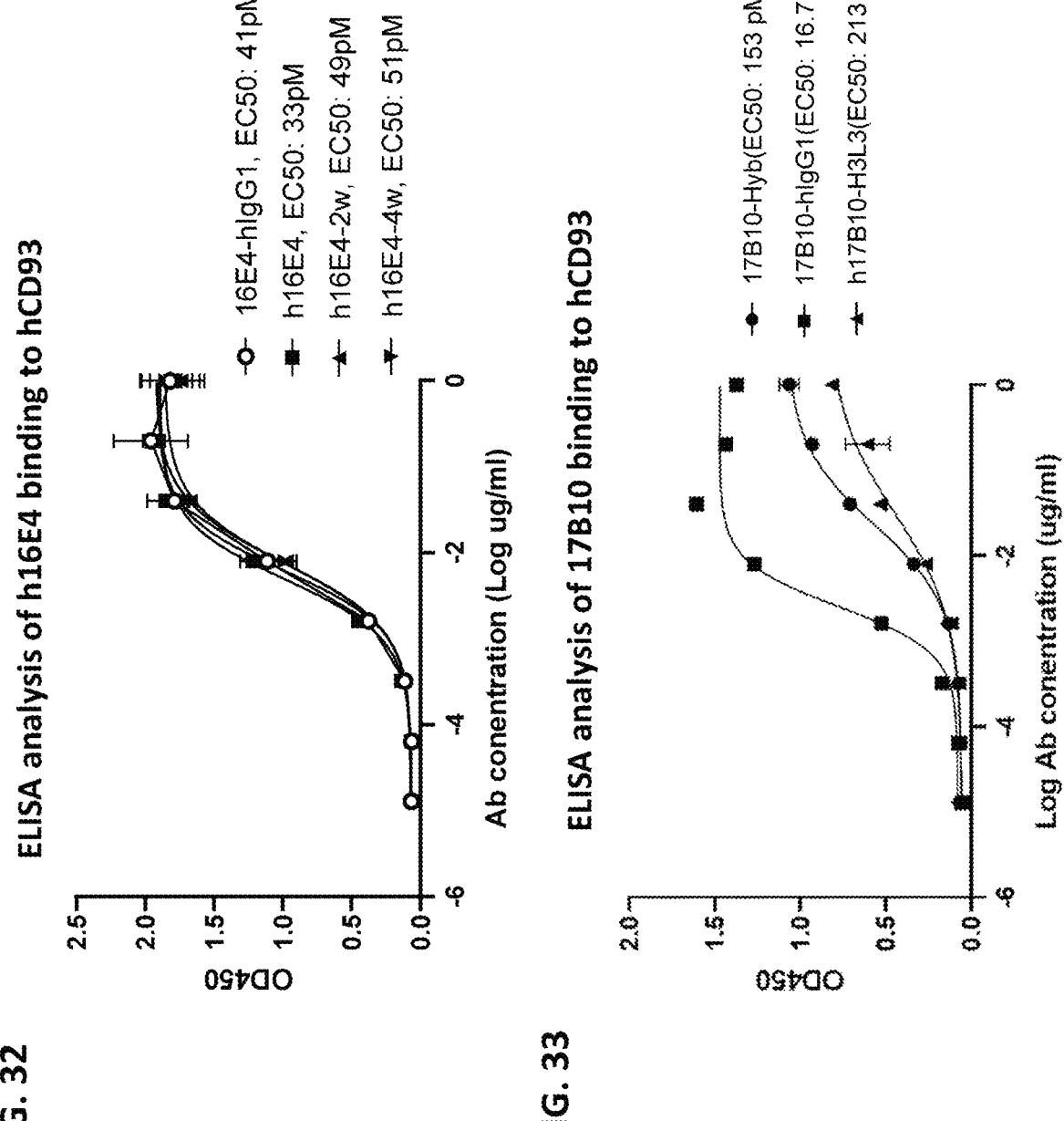
FIG. 32 shows ELISA analysis the binding of exemplary hybridoma or humanized 16E4 antibodies to hCD93.
FIG. 33 shows ELISA analysis of the binding of exemplary hybridoma or humanized 17B10 antibodies to hCD93.

Humanized 16E4 antibody was stored in the dark at 40° C. for 2 or 4 weeks. His-tagged human CD93 was coated onto a 96 well plate at 1 µg/mL in 1×PBS overnight at 4° C. The plate was washed with ELISA wash buffer (Boston BioProduct, Inc.) and the wells were blocked with ELISA blocking buffer for 1 hour at 37° C. Purified 16E4 antibodies were serially diluted in ELISA blocking buffer (Boston BioProduct, Inc.) and incubated on the receptor for 1 hour at 37° C. The plate was washed with ELISA wash Buffer. HRP-conjugated anti-human Fc antibody was incubated for 1 hour at 37° C. The plate was washed with ELISA wash Buffer. HRP substrate was added for indirect detection of the antibodies binding to CD93. FIG. 32 shows that no difference was observed for any of the treated or untreated samples by ELISA.

17B10 antibody produced by hybridoma (17B10-Hyb in FIG. 33) was compared to recombinant parental 17B10-hFc (17B10-hIgG1 in FIG. 33) and humanized 17B10-mFc (h17B10-H3L3 in FIG. 33) to determine the binding to human CD93. His-tagged human CD93 was coated onto a 96 well plate at 1 µg/mL in 1×PBS overnight at 4° C. The plate was washed with ELISA wash buffer (Boston Bio-Product, Inc.) and the wells were blocked with ELISA blocking buffer for 1 hour at 37° C. Purified 17B10 antibodies were serially diluted in ELISA blocking buffer (Boston BioProduct, Inc.) and incubated on the receptor for 1 hour at 37° C. The plate was washed with ELISA wash Buffer. HRP conjugated Anti-mouse Fc was diluted in ELISA blocking buffer and added to the wells containing the hybridoma produced 17B10. HRP conjugated anti-human Fc was added to the well containing the recombinant 17B10 antibodies for 1 hour at 37° C. The plate was washed with ELISA wash Buffer. HRP substrate was added for indirect detection of the antibodies binding to CD93. FIG. 33 shows that the mouse Fc containing molecules had weaker binding to the human CD93 than the recombinant parental 17B10 with the human Fc.

Figures 34, 35:
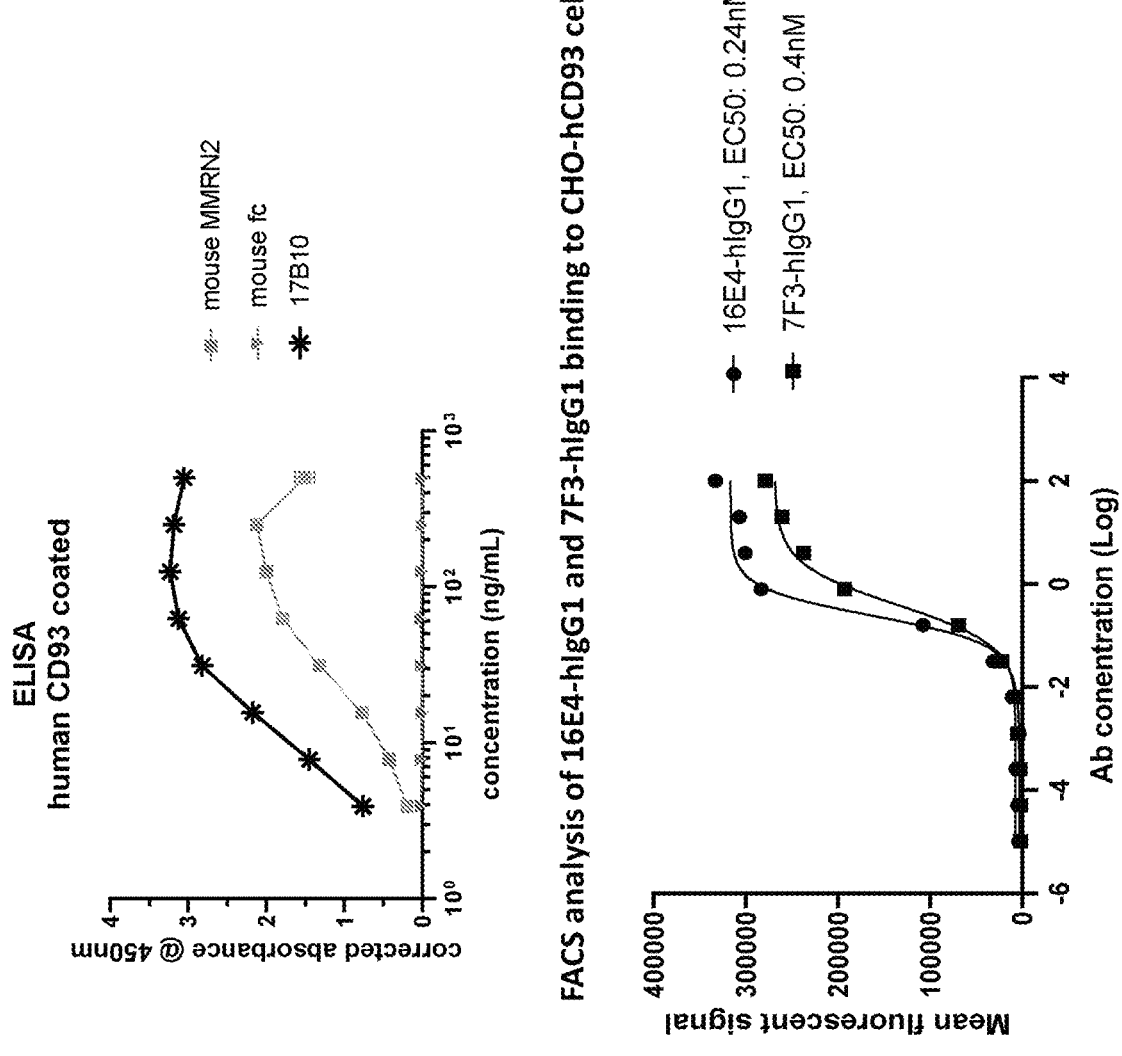
FIG. 34 shows ELISA analysis of the binding of exemplary humanized 17B10 to hCD93.
FIG. 35 shows FACS analysis of the binding of 16E4-hIgG1 and 7F3-hIgG1 antibodies to CHO-hCD93 cells.

A chimeric 17B10 molecule was made with a humanized CDR and human CH1 domain but mouse IgG1 CH2 and CH3 domains. This molecule was compared to mouse MMRN2-mFc for its ability to bind to human CD93. His-tagged human CD93 was coated onto a 96 well plate at 1 µg/mL in 1×PBS overnight at 4° C. The plate was washed with ELISA wash buffer (PBS with tween; Boston Bioproduct cat #BB-171) 3 times then wells were blocked with 200 µL ELISA blocking buffer (5% BSA (VWR cat #0332) in PBS) for 1 hour at room temp. The plates were then washed 3 times with ELISA wash buffer then purified 17B10 anti-body and mouse MMRN2-mFc were serially diluted in ELISA blocking buffer (BSA 5% in PBS) and incubated on the receptor for 2 hours at room temperature on orbital shaker at 100 rpm. The plate was washed 3 times with ELISA wash Buffer then HRP-conjugated anti-mouse Fc antibody (Jackson ImmunoResearch cat #115-035-164) was added to the 17B10 and the mouse MMRN2-mFc for 1 hour at room temperature on orbital shaker at 100 rpm. HRP-conjugated anti-mouse Fc antibody (Jackson ImmunoResearch cat #115-035-164) was added to the wells for 1 hour at room temperature on orbital shaker at 100 rpm. The plates were washed 3 times with ELISA wash Buffer then 100 µL TMB (SeraCare cat #5120-0077) added per well and allowed to mix 1-5 min then stopped by adding 100 µL Sulfuric Acid 1.0N (VWR cat #BDH7232-1). Absorbance measured at 450 nm. Absorbance signals corrected by subtracting averaged background signal from control wells containing secondary HRP Ab only. FIG. 34 shows that 17B10 bound to human CD93-his by ELISA better than mouse MMRN2-mFc.

Example 15. FACS Cell-Based Binding Analysis of Anti-CD93 Antibodies

Binding of anti-CD93 antibodies 7F3 and 16E4 to cell surface expressing human CD93 CHO cells was determined by fluorescence activated cell sorting (FACS) assay. Human CD93 expressing CHO cells were detached by incubation with TrypLE reagents (Thermo Fisher), which preserves the integrity of CD93 on the cell surface. Then the cells were incubated with serially diluted anti-CD93 antibodies for 30 minutes in 4° C. After washing by FACS buffer, the cells were incubated with Alexa Fluor 647 conjugated anti-human IgG (Jackson ImmunoResearch) for 30 minutes in 4° C. After washing by FACS buffer twice, the samples were acquired in NovoCyte Flow Cytometer and analyzed by NovoExpress software. Recombinant 16E4 bound to the cells with an EC50 of 0.24 nM, while recombinant 7F3 antibody bound with an EC50 of 0.4 nM (FIG. 35).

Figure 36:
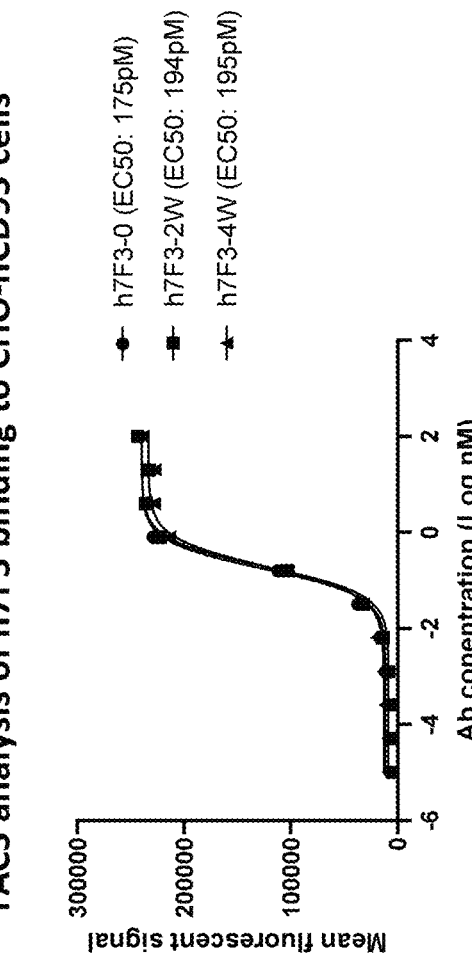
FIG. 36 shows FACS analysis of the binding of humanized 7F3 to CHO-hCD93 cells.

Binding of humanized 7F3 anti-CD93 antibodies to cell surface expressing human CD93 CHO cells was determined by fluorescence activated cell sorting (FACS) assay. Humanized 7F3 antibody was stored in the dark at 40° C. for 2 or 4 weeks. Human CD93 expressing CHO cells were detached by incubation with TrypLE reagents (Thermo Fisher), which preserves the integrity of CD93 on the cell surface. Then the cells were incubated with serial diluted anti-CD93 antibodies for 30 minutes in 4° C. After washing by FACS buffer, the cells were incubated with Alexa Fluor 647 conjugated anti-human IgG (Jackson ImmunoResearch) for 30 minutes at 4° C. After washing by FACS buffer twice, the samples were acquired in NovoCyte Flow Cytometer and analyzed by NovoExpress software. There was no change in the affinity for the 7F3 antibody to CD93 due to the high temperature treatment (FIG. 36).

Figure 37:
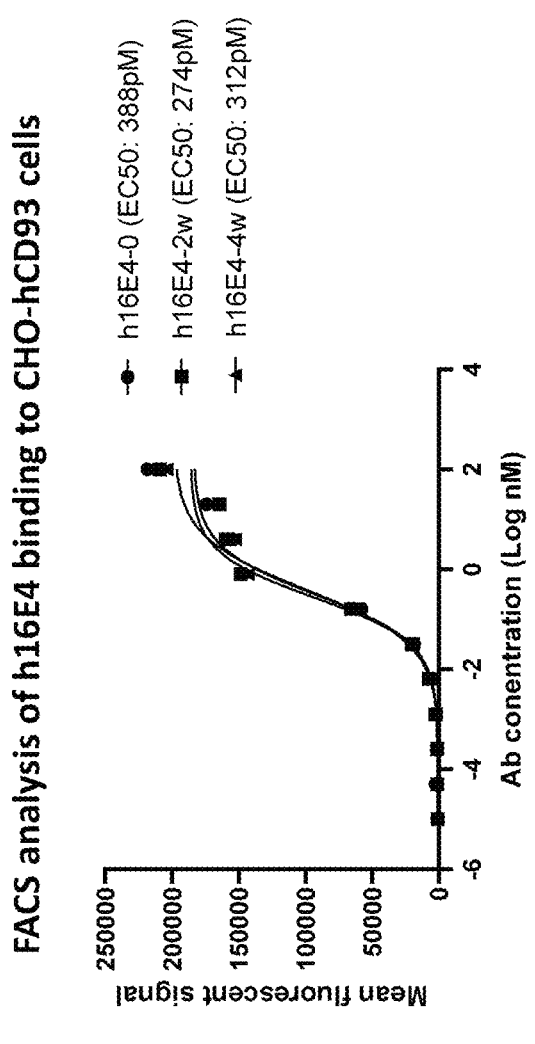
FIG. 37 shows FACS analysis of the binding of h16E4 (humanized 16E4) to CHO-hCD93 cells.

Humanized 16E4 antibody was stored in the dark at 40° C. for 2 or 4 weeks. Human CD93 expressing CHO cells were detached by incubation with TrypLE reagents (Thermo Fisher), which preserves the integrity of CD93 on the cell surface. Then the cells were incubated with serial diluted anti-CD93 antibodies for 30 minutes at 4° C. After washing by FACS buffer, the cells were incubated with Alexa Fluor 647 conjugated anti-human IgG (Jackson ImmunoResearch)

for 30 minutes in 4° C. After washing by FACS buffer twice, the samples were acquired in NovoCyte Flow Cytometer and analyzed by NovoExpress software. Incubation of humanized 16E4 at 40° C. did not reduce the binding of the antibodies to the CD93 expressing cells (FIG. 37).

Figure 38:
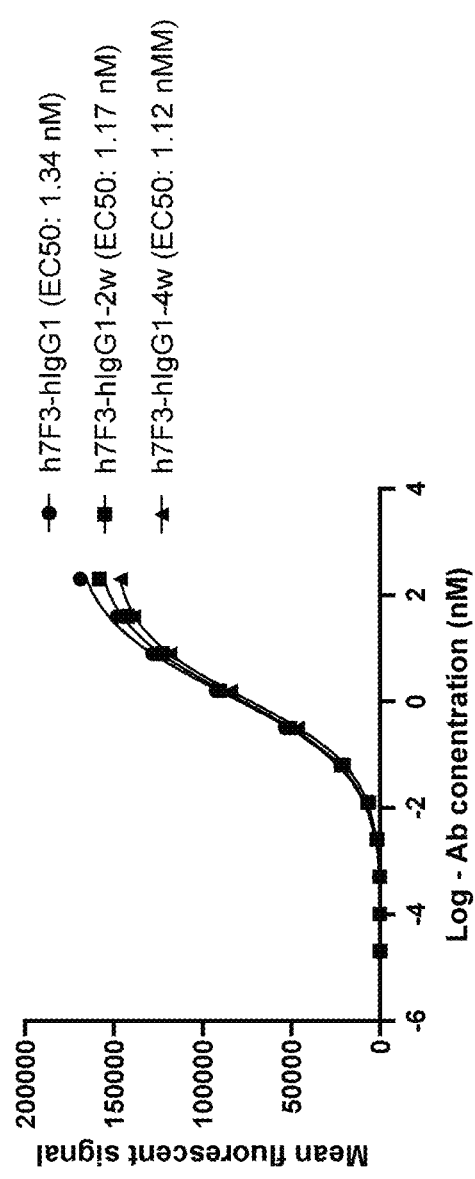
FIG. 38 shows FACS analysis of the binding of humanized 7F3 to HUVEC cells.

Humanized 7F3 antibody was stored in the dark at 40° C. for 2 or 4 weeks. HUVEC cells were detached by incubation with TrypLE reagents (Thermo Fisher), which preserves the integrity of CD93 on the cell surface. Then the cells were incubated with serial diluted anti-CD93 antibodies for 30 minutes at 4° C. After washing by FACS buffer, the cells were incubated with Alexa Fluor 647 conjugated anti-human IgG (Jackson ImmunoResearch) for 30 minutes in 4° C. After washing by FACS buffer twice, the samples were acquired in NovoCyte Flow Cytometer and analyzed by NovoExpress software. Incubation of humanized 7F3 at 40° C. did not reduce the binding of the antibodies to HUVEC cells (FIG. 38).

Figures 39, 40:
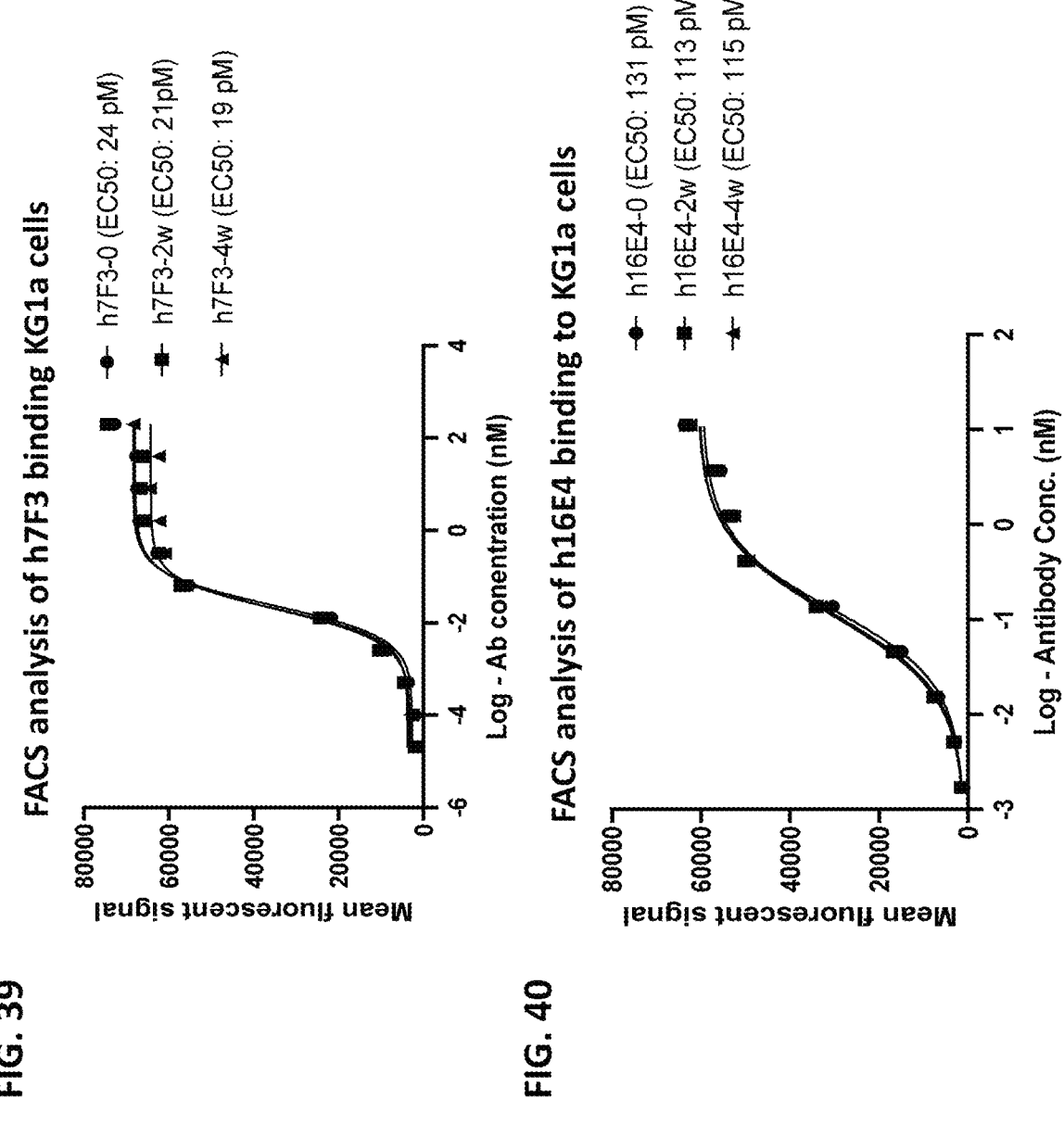
FIG. 39 shows FACS analysis of the binding of humanized 7F3 KG1a cells.
FIG. 40 shows FACS analysis of the binding of humanized 16E4 to KG1a cells.

Binding of 7F3 anti-CD93 antibodies to KG1a cells was determined by fluorescence activated cell sorting (FACS) assay. Humanized 7F3 antibody was stored in the dark at 40° C. for 2 or 4 weeks. KG1a cells were detached by incubation with TrypLE reagents (Thermo Fisher), which preserves the integrity of CD93 on the cell surface. Then the cells were incubated with serial diluted anti-CD93 antibodies for 30 minutes at 4° C. After washing by FACS buffer, the cells were incubated with Alexa Fluor 647 conjugated anti-human IgG (Jackson ImmunoResearch) for 30 minutes in 4° C. After washing by FACS buffer twice, the samples were acquired in NovoCyte Flow Cytometer and analyzed by NovoExpress software. Incubation of 7F3 at 40° C. did not reduce the binding of the antibodies to KG1a cells (FIG. 39).

Humanized 16E4 antibody was stored in the dark at 40° C. for 2 or 4 weeks. KG1a cells were detached by incubation with TrypLE reagents (Thermo Fisher), which preserves the integrity of CD93 on the cell surface. Then the cells were incubated with serial diluted anti-CD93 antibodies for 30 minutes at 4° C. After washing by FACS buffer, the cells were incubated with Alexa Fluor 647 conjugated anti-human IgG (Jackson ImmunoResearch) for 30 minutes in 4° C. After washing by FACS buffer twice, the samples were acquired in NovoCyte Flow Cytometer and analyzed by NovoExpress software. Incubation of 16E4 at 40° C. did not reduce the binding of the antibodies to KG1a cells (FIG. 40).

Example 16. Anti-CD93 Antibody Octet Binding Analysis

Figure 41:
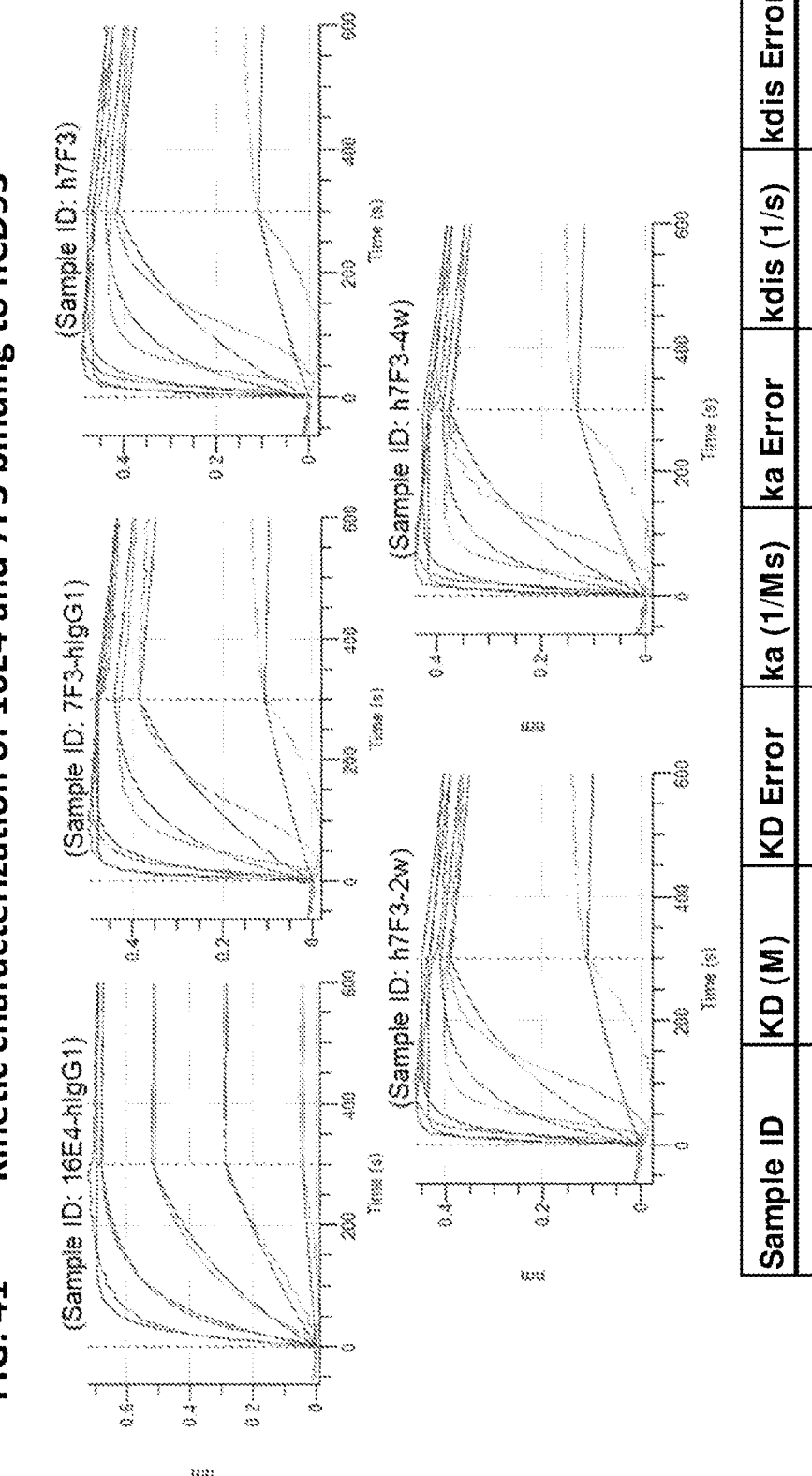
FIG. 41 shows kinetic characterization of the binding of exemplary 16E4 and 7F3 antibodies to hCD93.

The binding affinity of anti-CD93 antibodies was determined with bio-layer interferometry using Octet QKe (Fortebio). Humanized 7F3 antibody was stored in the dark at 40° C. for 2 or 4 weeks. Human CD93 recombinant protein (Sino Biological Inc, Catalog #12589-H08H) was biotinylated using EZ-LINK NHS-PEG4 biotin (Thermo Fisher Scientific). Streptavidin biosensors (Fortebio) were used to load biotinylated CD93 protein (300 seconds in 5 μg/ml). Baseline was stabilized for 60 seconds in 1× kinetics buffer (Fortebio) before anti-CD93 antibodies, at a serial dilution, were allowed to associate for 300 seconds with captured protein. Then the sensors were dissociated in 1× kinetics buffer for 600 seconds. Data analysis was performed on ForteBio Data Analysis HT 11.1 software. The binding affinity of humanized 7F3 antibody against CD93 was not affected by the incubation at 40° C. (FIG. 41).

Figure 42:
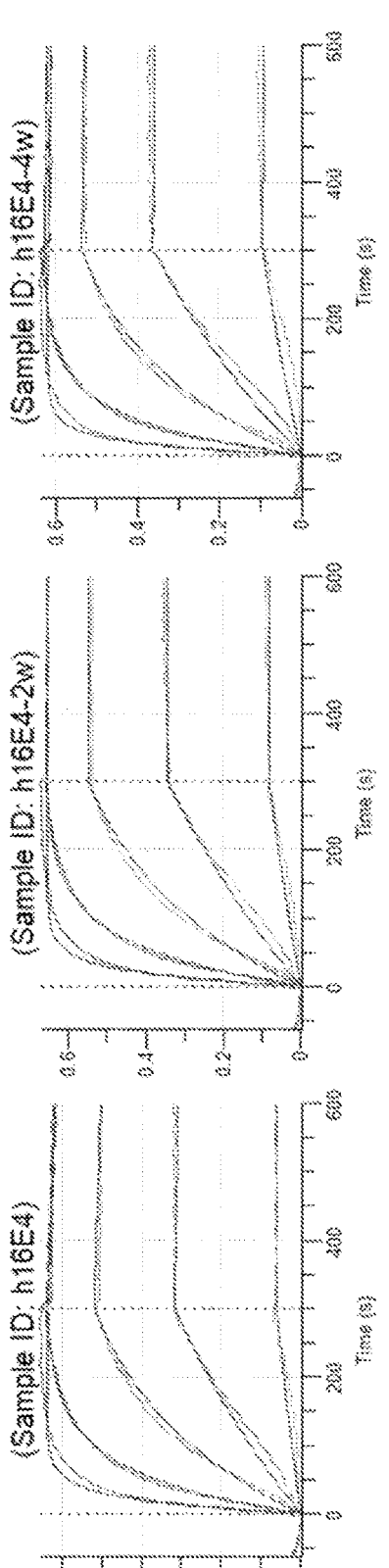
FIG. 42 shows kinetic characterization of the binding of exemplary humanized 16E4 antibodies to hCD93

The binding affinity of anti-CD93 antibodies was determined with bio-layer interferometry using Octet QKe (Fortebio). Humanized 16E4 antibody was stored in the dark at 40° C. for 2 or 4 weeks. Human CD93 recombinant protein (Sino Biological Inc, Catalog #12589-H08H) was biotinylated using EZ-LINK NHS-PEG4 biotin (Thermo Fisher Scientific). Streptavidin biosensors (Fortebio) were used to load biotinylated CD93 protein (300 seconds in 5 μg/ml). Baseline was stabilized for 60 seconds in 1× kinetics buffer (Fortebio) before anti-CD93 antibodies, at a serial dilution, were allowed to associate for 300 seconds with captured protein. Then the sensors were dissociated in 1× kinetics buffer for 600 seconds. Data analysis was performed on ForteBio Data Analysis HT 11.1 software. The binding affinity of humanized 16E4 antibody against CD93 was not affected by the incubation at 40° C. (FIG. 42).

A summary of binding affinity of 16E4 and 7F3 is shown in FIG. 43.

Example 17. Anti-CD93 Antibody Blocking Function Analysis

Figure 44:
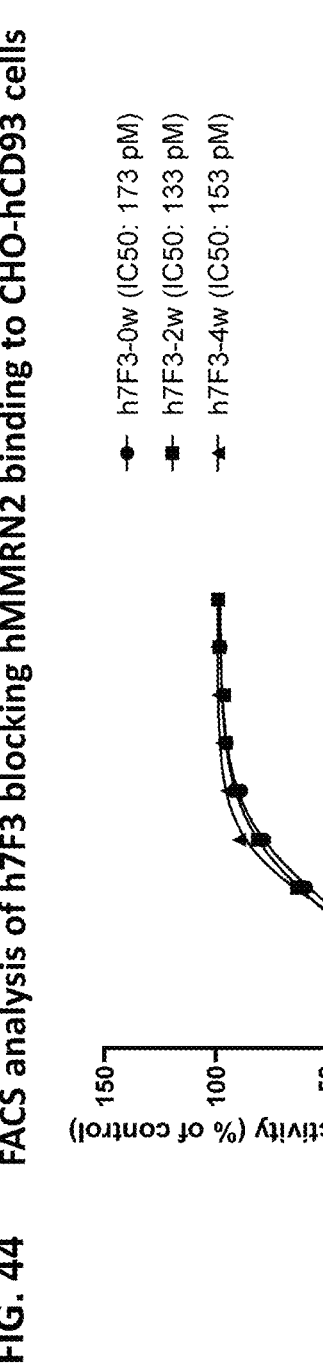
FIG. 44 shows FACS analysis of the blocking effect of humanized 7F3 on the binding of human MMRN2 to CHO-hCD93 cells.

Blocking of MMRN2 binding to cell surface expressed human CD93 CHO cells by the 7F3 anti-CD93 antibody was determined by fluorescence activated cell sorting (FACS) assay. Humanized 7F3 antibody was stored in the dark at 40° C. for 2 or 4 weeks. Human CD93 expressing CHO cells $(1\times10^5$ per well) were treated with serially diluted anti-CD93 7F3 antibodies or isotype control for 30 minutes at 4° C. Then the cells were incubated with hMMRN2$_{495-674}$ at 0.1 μg/ml. After incubation, the cells were washed with FACS buffer and incubated with APC-conjugated anti-His tag (BioLegend) for 30 minutes at 4° C. to detect the MMRN2 binding. After washing with FACS buffer twice, the samples were analyzed, and data acquired in NovoCyte Flow. Recombinant his tagged hMMRN2$_{495-674}$ was produced internally in E. coli following routine procedure. Incubation of 7F3 at 40° C. did not affect the ability of 7F3 to block MMRN2 binding to human CD93 expressing CHO cells (FIG. 44).

Figure 45:
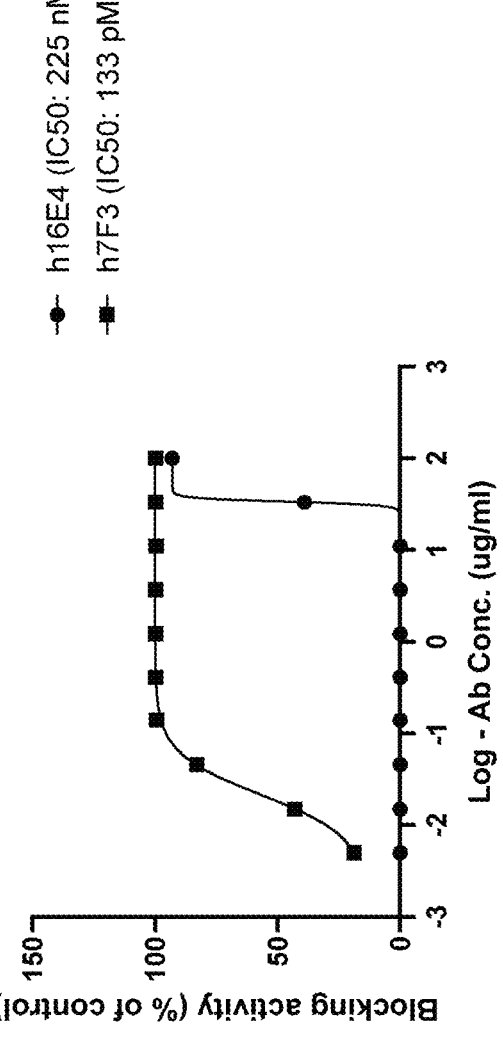
FIG. 45 shows FACS analysis of the blocking effect of humanized 16E4 and 7F3 antibodies on the binding of MMRN2 to CHO-hCD93 cells.

Blocking of MMRN2 binding to cell surface expressed human CD93 CHO cells by the humanized 7F3 and 16E4 anti-CD93 antibody was also determined by fluorescence activated cell sorting (FACS) assay. Human CD93 expressing CHO cells $(1\times10^5$ per well) were treated with serially diluted anti-CD93 7F3 or 16E4 antibodies or isotype control for 30 minutes at 4° C. Then the cells were incubated with hMMRN2$_{495-674}$ at 0.1 μg/ml. APC-conjugated anti-His tag (BioLegend) was used to detect the MMRN2 binding. Then the cells were washed with FACS buffer and incubated with APC-conjugated anti-His tag antibody at 1 μg/ml for 30 minutes at 4° C. After washing with FACS buffer twice, the samples were analyzed and data acquired in NovoCyte Flow. Recombinant his tagged hMMRN2$_{495-674}$ was produced internally in Expi_HEK following routine procedure. Humanized 7F3 was able to block MMRN2 binding to human CD93 expressing CHO cells, but humanized 16E4 was not (FIG. 45).

Figure 46:
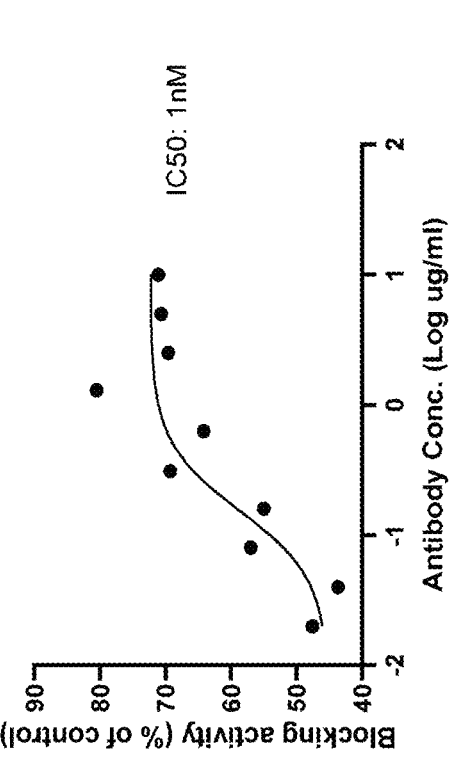
FIG. 46 shows FACS analysis of the blocking effect of an exemplary humanized 7F3 antibody on the binding of human IGFBP7 to HUVEC cells.

Blocking of IGFBP7 binding to the cell surface of HUVEC cells by humanized 7F3 anti-CD93 antibody was determined by FACS. HUVEC cells $(1\times10^5$ per well) were treated with serially diluted humanized anti-CD93 7F3 antibody or isotype control for 30 minutes at 4° C. Then the cells were incubated with His-tagged human IGFBP7 recombinant protein (0.1 μg/ml) for another 30 minutes at 4° C. After incubation, the cells were washed with FACS buffer and incubated with APC-conjugated anti-His tag (BioLegend) for 30 minutes in 4° C. to detect the IGFBP7 binding. After washing with FACS buffer twice, the samples were analyzed and data acquired in NovoCyte Flow. As shown in FIG. 46, 7F3 antibody blocked the binding of IGFBP7 to HUVEC cells.

Blocking of IGFBP7 binding to CD93 by 7F3 and 16E4 was determined using bio-layer interferometry (BLI). The blocking of IGFBP7 binding to hCD93 by anti-CD93 antibodies 7F3 and 16E4 was determined with bio-layer interferometry using Octet QKe (Fortebio). Human CD93 recombinant protein (Sino Biological Inc, Catalog #12589-H08H) was biotinylated using EZ-LINK NHS-PEG4 biotin (Thermo Fisher Scientific). Streptavidin biosensors (Fortebio) were used to load biotinylated CD93 protein (300 seconds in 5 µg/ml). Baseline was stabilized for 60 seconds in 1× kinetics buffer (Fortebio) before anti-CD93 antibodies and a negative control antibody (9F9) (90 µg/mL) were allowed to associate for 300 seconds with captured protein. The IGFBP7 was added to associate for 300 seconds. Then the sensors were dissociated in 1× kinetics buffer for 600 seconds. Data analysis was performed on ForteBio Data Analysis HT 11.1 software. Hybridoma and humanized 7F3 and 16E4 antibodies were able to block IGFBP7 association to human CD93 (FIGS. 47 and 48).

Example 18. Anti-CD93 Antibody Tube Formation Analysis

Figure 49:
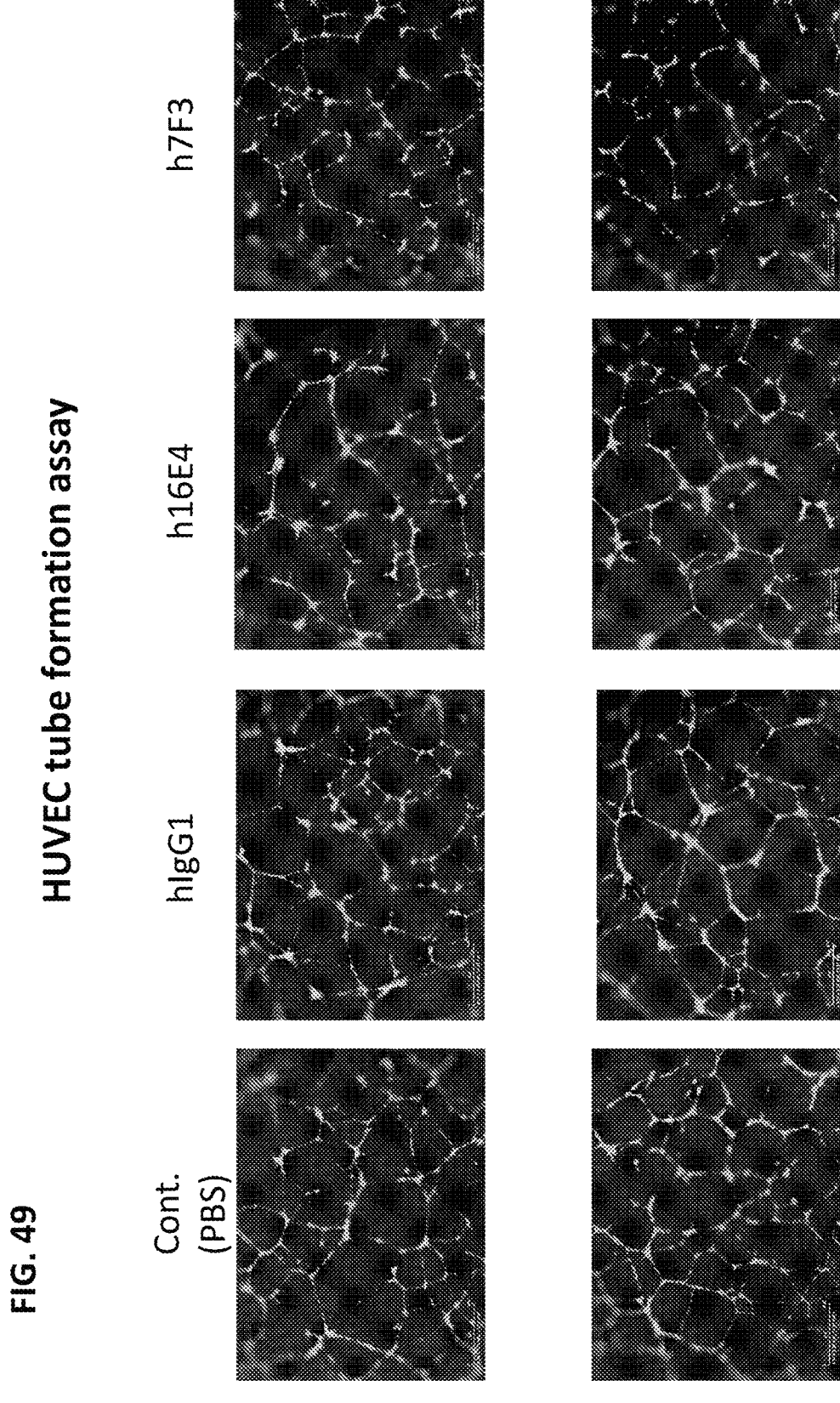
FIGS. 49-50 show the effects of exemplary humanized 7F3 and 16E4 antibodies on HUVEC tube formation.
Figure 50:
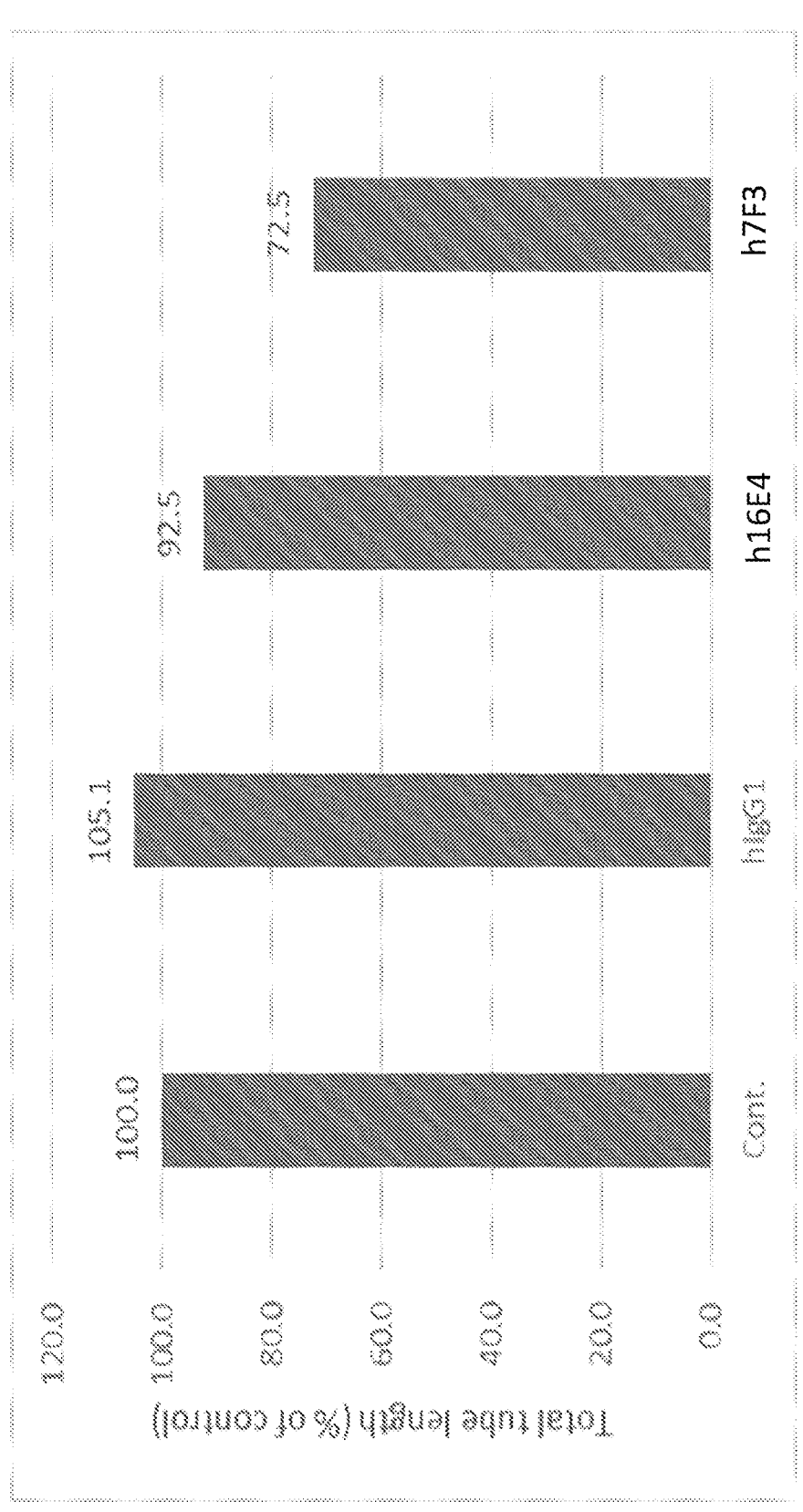

Inhibition of angiogenesis by humanized 7F3 and 16E4 anti-CD93 antibodies was tested in a HUVEC tube formation assay. Human umbilical vein endothelial cell (HUVECs, Thermo Fisher Scientific, Waltham, MA) were cultured in medium 200 supplemented with low serum growth supplement (LSGS, Thermo Fisher Scientific, Waltham, MA) at 37° C. with 5% $CO_2$. 96 well plates were coated with 50 µl of Geltrex reduced growth factor basement membrane matrix (Thermo Fisher Scientific) and incubated for 30 min at 37° C. To investigate the effects of humanized 7F3 and 16E4 antibodies on tube formation, $2\times10^4$ HUVEC cells were seeded onto Matrix-coated plates and incubated in the presence or absence of purified antibodies (40 µg/mL) for 18 hours at 37° C. with 5% $CO_2$. Cells were stained with calcein AM, and images were collected. FIGS. 49 and 50 show that humanized 16E4 showed 92.5% tube formation, while humanized 7F3 showed 72.5% tube formation compared to the controls.

Example 19. Anti-Tumor Effect of the CD93 Antibodies in KI Mouse Model

The anti-tumor effect of the anti-CD93 antibodies is evaluated in a B16F10 melanoma syngeneic hCD93 KI mouse model using conventional technique in the art. The mice used for the study have human CD93 knock-in, such that the mouse CD93 is completely replaced by the human CD93. Alternatively, extracellular portion of the mouse CD93 is replaced by the respective human portion, with intracellular portion of the mouse CD93 intact.

For the syngeneic mouse model, female human CD93 KI-C57BL/6J mice are implanted with a murine cell line of B16F10 tumor cells ($0.2\times10^6$) in serum-free media. When tumors reach 40-50 mm$^3$, the mice (n=8 per test article) are randomly assigned to groups. Anti-CD93 antibodies (and a negative control antibody) are dosed at a pharmaceutically relevant concentration, such as 15 mg/kg mouse intraperitoneally biweekly for 4 weeks. Tumor volume and body weight are measured for each mouse. Upon completion of the study, tumors are surgically removed, weighed, measured, and snap frozen for cell analysis. Anti-tumor efficacy of the anti-CD93 antibodies is evaluated based on overall tumor volume, and levels of T cell infiltrated lymphocytes. Body weight is measured throughout the study to ensure general health of the animals. It is expected that treatment with the anti-CD93 antibodies will inhibit the tumor growth as compared to the negative control antibody. In some cases, the anti-CD93 antibodies may cause shrinkage of the tumor. In some cases, the anti-CD93 antibodies may increase the immune cell infiltration in tumors.

See FIG. 51 for a summary of properties of 16E4, 7F3, 16A1 and 17B10.

|  |  |  |
|---|---|---|
| SEQUENCE TABLE | | |

| SEQ ID NO. | Description | Nucleotide or Amino Acid Sequence |
|---|---|---|
| 1. | 10B1 HC-CDR1 (Kabat) | SFGVN |
| 2. | 10B1 HC-CDR2 (Kabat) | VIWSGGSTDYNVAFIS |
| 3. | 10B1 HC-CDR3 (Kabat) | NWRYDGYFYAMDY |
| 4. | 10B1 LC-CDR1 (Kabat) | KASQNVGTNVA |
| 5. | 10B1 LC-CDR2 (Kabat) | SASYRFI |
| 6. | 10B1 LC-CDR3 (Kabat) | QQYNRNPIT |

-continued

| SEQ ID NO. | Description | Nucleotide or Amino Acid Sequence |
|---|---|---|
| 7. | 10B1 HC-CDR1 (Vbase2) | DFSLSSFG |
| 8. | 10B1 HC-CDR2 (Vbase2) | IWSGGST |
| 9. | 10B1 HC-CDR3 (Vbase2) | ARNWRYDGYFYAMDY |
| 10. | 10B1 LC-CDR1 (Vbase2) | QNVGTN |
| 11. | 10B1 LC-CDR2 (Vbase2) | SAS |
| 12. | 10B1 LC-CDR3 (Vbase2) | QQYNRNPIT |
| 13. | 10B1 VH Amino Acid Sequence | QVQLKQSGPGLVQPSQSLSITCTVSDFSLSSFGVNWV RQPPGKGLEWLGVIWSGGSTDYNVAFISRLSISKDNS KSQVFFKMNNLQADDTAIYYCARNWRYDGYFYAM DYWGQGTSVTVSS |
| 14. | 10B1 VL Amino Acid Sequence | DIVMTQSQKFMSTSTGDRVSVTCKASQNVGTNVAWY QQKPGQSPKALIYSASYRFIGVPDRFTGSGSGTDFT LTITNVQSEDLAEYFCQQYNRNPITFGSGTKLEIK |
| 15. | 10B1 VH DNA Sequence | CAGGTGCAGCTGAAGCAGTCAGGACCTGGCCTAGT GCAGCCCTCACAGAGCCTGTCCATCACCTGCACAG TCTCTGATTTCTCATTATCTAGCTTTGGTGTAAACT GGGTTCGCCAGCCTCCAGGAAAGGGTCTGGAGTGG CTGGGGGTGATATGGAGTGGTGGAAGTACAGACTA TAATGTAGCTTTCATATCCAGACTGAGCATCAGCA AGGACAACTCCAAGAGCCAAGTTTTCTTTAAAATG AACAATCTGCAAGCTGATGACACAGCCATATACTA CTGTGCCAGAAATTGGAGGTATGATGGTTACTTCT ATGCTATGGACTACTGGGGTCAAGGAACCTCAGTC ACCGTCTCCTCAG |
| 16. | 10B1 VL DNA Sequence | GACATTGTGATGACCCAGTCTCAAAAATTCATGTC CACATCAACAGGAGACAGGGTCAGCGTCACCTGCA AGGCCAGTCAGAATGTGGGTACTAATGTAGCCTGG TATCAACAGAAACCAGGACAGTCTCCTAAAGCACT GATTTACTCGGCATCATACCGATTCATTGGAGTCCC TGATCGCTTCACAGGCAGTGGATCTGGGACAGATT TCACTCTCACCATCACCAATGTGCAGTCTGAAGAC TTGGCAGAGTATTTCTGTCAGCAATATAACAGAAA TCCTATCACGTTCGGCTCGGGGACAAAGTTGGAAA TAAAAC |
| 17. | 16E4 HC-CDR1 (Kabat) | SYWMH |
| 18. | 16E4 HC-CDR2 (Kabat) | EIDPSASYTYYNQKFKG |
| 19. | 16E4 HC-CDR3 (Kabat) | SVYYGNKYFDV |
| 20. | 16E4 LC-CDR1 (Kabat) | KASQSVDYAGDSYMN |

| SEQUENCE TABLE | | |
|---|---|---|

| SEQ ID NO. | Description | Nucleotide or Amino Acid Sequence |
|---|---|---|
| 21. | 16E4 LC-CDR2 (Kabat) | AASNLES |
| 22. | 16E4 LC-CDR3 (Kabat) | QQTNEDPRT |
| 23. | 16E4 HC-CDR1 (Vbase2) | GYTFTSYW |
| 24. | 16E4 HC-CDR2 (Vbase2) | IDPSASYT |
| 25. | 16E4 HC-CDR3 (Vbase2) | ARSVYYGNKYFDV |
| 26. | 16E4 LC-CDR1 (Vbase2) | QSVDYAGDSY |
| 27. | 16E4 LC-CDR2 (Vbase2) | AAS |
| 28. | 16E4 LC-CDR3 (Vbase2) | QQTNEDPRT |
| 29. | 16E4 VH Amino Acid Sequence | QVQLQQPGAELVKPGASVKLSCKASGYTFTSYWMH WVKQRPGQGLEWIGEIDPSASYTYNQKFKGKATLT VDKSSSTAYMQLSSLTSEDSAVYYCARSVYYGNKYF DVWGAGTTVTVSS |
| 30. | 16E4 VL Amino Acid Sequence | DIVLTQSPASLAVSLGQRATISCKASQSVDYAGDSYM NWYQQKPGQPPKLLIYAASNLESGIPARFSGSGSGTD FTLNIHPVEEEDAATYYCQQTNEDPRTFGGGTKLEIK |
| 31. | 16E4 VH DNA Sequence | CAGGTCCAGCTTCAGCAGCCTGGGGCTGAACTGGT GAAGCCTGGGGCTTCAGTGAAGCTGTCCTGCAAGG CTTCTGGATACACCTTCACTAGCTACTGGATGCACT GGGTGAAGCAGAGGCCTGGACAAGGCCTTGAGTG GATCGGAGAGATTGATCCTTCTGCTAGTTATACTTA CTACAATCAAAAGTTCAAGGGCAAGGCCACATTGA CTGTAGACAAATCCTCCAGCACAGCCTACATGCAA CTCAGCAGCCTGACATCTGAGGACTCTGCGGTCTA TTACTGTGCAAGATCGGTCTACTATGGTAACAAGT ATTTCGATGTCTGGGGCGCAGGGACCACGGTCACC GTCTCCTCA |
| 32. | 16E4 VL DNA Sequence | GACATTGTGCTGACCCAATCTCCAGCTTCTTTGGCT GTGTCTCTAGGGCAGAGGGCCACCATCTCCTGCAA GGCCAGCCAAAGTGTTGATTATGCCGGTGATAGTT ATATGAACTGGTACCAACAGAAACCAGGACAGCC ACCCAAACTCCTCATCTATGCTGCATCCAATCTAGA ATCTGGGATCCCAGCCAGGTTTAGTGGCAGTGGGT CTGGGACAGACTTCACCCTCAACATCCATCCTGTG GAGGAGGAGGATGCTGCAACCTATTACTGTCAGCA AACTAATGAGGATCCTCGGACGTTCGGTGGAGGCA CCAAGCTGGAAATCAAAC |
| 33. | 5H9 HC-CDR1 (Kabat) | TYWMN |
| 34. | 5H9 HC-CDR2 (Kabat) | RIFPGDGDANYNGKFKG |

-continued

| SEQUENCE TABLE | | |
|---|---|---|
| SEQ ID NO. | Description | Nucleotide or Amino Acid Sequence |
| 35. | 5H9 HC-CDR3 (Kabat) | TGAAYDFDPFPY |
| 36. | 5H9 LC-CDR1 (Kabat) | SSSKSLLHSNGVTYLY |
| 37. | 5H9 LC-CDR2 (Kabat) | RMSNLAS |
| 38. | 5H9 LC-CDR3 (Kabat) | AQMLERPFT |
| 39. | 5H9 HC-CDR1 (Vbase2) | GYAFSTYW |
| 40. | 5H9 HC-CDR2 (Vbase2) | IFPGDGDA |
| 41. | 5H9 HC-CDR3 (Vbase2) | TRTGAAYDFDPFPY |
| 42. | 5H9 LC-CDR1 (Vbase2) | KSLLHSNGVTY |
| 43. | 5H9 LC-CDR2 (Vbase2) | RMS |
| 44. | 5H9 LC-CDR3 (Vbase2) | AQMLERPFT |
| 45. | 5H9 VH Amino Acid Sequence | QVQLQQSGPDLVKPGASVKISCKASGYAFSTYWMN WVKQRPGKGLEWIGRIFPGDGDANYNGKFKGKATL TADKSSSTAYMQLSSLTSEDSAVYFCTRTGAAYDFDP FPYWGQGTLVTVSA |
| 46. | 5H9 VL Amino Acid Sequence | DIVMTQAAFSNPVTLGTSASISCSSSKSLLHSNGVTYL YWYLQRPGQSPQLLIYRMSNLASGVPDRFSGSGSGT DFTLRISRVEAEDVGIYYCAQMLERPFTFGSGTKLEIK |
| 47. | 5H9 VH DNA Sequence | CAGGTTCAGCTGCAGCAGTCTGGACCTGACCTGGT GAAGCCTGGGGCCTCAGTGAAGATTTCCTGCAAAG CTTCTGGCTACGCATTCAGTACCTACTGGATGAACT GGGTGAAGCAGAGGCCTGGAAAGGGTCTTGAGTG GATTGGACGGATTTTTCCTGGAGATGGAGATGCTA ACTACAATGGGAAGTTCAAGGGCAAGGCCACACTG ACTGCAGACAAATCCTCCAGCACAGCCTACATGCA ACTCAGCAGCCTGACATCTGAGGACTCTGCGGTCT ACTTCTGTACAAGAACTGGGGCCGCCTATGATTTC GACCCTTTTCCTTACTGGGGCCAAGGGACTCTGGTC ACTGTCTCTGCAG |
| 48. | 5H9 VL DNA Sequence | GATATTGTGATGACGCAGGCTGCATTCTCCAATCC AGTCACTCTTGGAACATCAGCTTCCATCTCTTGCAG TTCTAGTAAGAGTCTCCTACATAGTAATGGCGTCA CTTATTTGTATTGGTATCTGCAGAGGCCAGGCCAGT CTCCTCAGCTCCTGATATATCGGATGTCCAACCTTG CCTCAGGAGTCCCAGACAGGTTCAGTGGCAGTGGG TCAGGAACTGATTTCACACTGAGAATCAGCAGAGT GGAGGCTGAGGATGTGGGTATTTATTACTGTGCTC AAATGCTAGAACGCCCATTCACGTTCGGCTCGGGG ACAAAGTTGGAAATAAAAC |

-continued

| SEQUENCE TABLE | | |
|---|---|---|
| SEQ ID NO. | Description | Nucleotide or Amino Acid Sequence |
| 49. | 16G9 HC-CDR1 (Kabat) | DYYMN |
| 50. | 16G9 HC-CDR2 (Kabat) | RVNPNNGGKTYNQKFKG |
| 51. | 16G9 HC-CDR3 (Kabat) | WRLRPVDYGMDY |
| 52. | 16G9 LC-CDR1 (Kabat) | RASQSVSTSSYSYMH |
| 53. | 16G9 LC-CDR2 (Kabat) | YASNLES |
| 54. | 16G9 LC-CDR3 (Kabat) | QHSWEIPFT |
| 55. | 16G9 HC-CDR1 (Vbase2) | GYTFTDYY |
| 56. | 16G9 HC-CDR2 (Vbase2) | VNPNNGGK |
| 57. | 16G9 HC-CDR3 (Vbase2) | ARWRLRPVDYGMDY |
| 58. | 16G9 LC-CDR1 (Vbase2) | QSVSTSSYSY |
| 59. | 16G9 LC-CDR2 (Vbase2) | YAS |
| 60. | 16G9 LC-CDR3 (Vbase2) | QHSWEIPFT |
| 61. | 16G9 VH Amino Acid Sequence | EVQLQQSGPELVKPGASVKMSCKASGYTFTDYYMN WVKQSHGKSLEWIGRVNPNNGGKTYNQKFKGKATL TVDKSLSTAYMQLNSLTSEDSAVYYCARWRLRPVDY GMDYWGQGTSVTVSS |
| 62. | 16G9 VL Amino Acid Sequence | DIVLTQSPASLAVSLGQRATISCRASQSVSTSSYSYMH WYQQKPGQPPKLLIKYASNLESGVPARFSGSGSGTDF TLNIHPVEEEDTATYYCQHSWEIPFTFGSGTKLEIK |
| 63. | 16G9 VH DNA Sequence | GAGGTCCAGCTGCAACAGTCTGGACCTGAGCTGGT GAAGCCTGGGGCTTCAGTGAAGATGTCCTGTAAGG CTTCTGGATACACATTCACTGACTACTACATGAACT GGGTGAAGCAGAGTCATGGAAAGAGTCTTGAGTG GATTGGACGTGTTAATCCTAACAATGGTGGTAAAA CCTACAACCAGAAGTTCAAGGGCAAGGCCACATTG ACAGTAGACAAATCCCTCAGCACAGCCTACATGCA GCTCAACAGCCTGACATCTGAGGACTCTGCGGTCT ATTACTGTGCAAGATGGAGGCTACGGCCCGTTGAC TATGGTATGGACTACTGGGGTCAAGGAACCTCAGT CACCGTCTCCTCAG |
| 64. | 16G9 VL DNA Sequence | GACATTGTGCTGACACAGTCTCCTGCTTCCTTGGCT GTATCTCTGGGGCAGAGGGCCACCATCTCATGCAG GGCCAGCCAAAGTGTCAGTACATCTAGCTATAGTT ATATGCACTGGTACCAACAGAAACCAGGACAGCCA |

-continued

| SEQ ID NO. | Description | Nucleotide or Amino Acid Sequence |
|---|---|---|
| | | CCCAAACTCCTCATCAAGTATGCATCCAACCTAGA<br>ATCTGGGGTCCCTGCCAGGTTCAGTGGCAGTGGGT<br>CTGGGACAGACTTCACCCTCAACATCCATCCTGTG<br>GAGGAGGAGGATACTGCAACATATTACTGTCAGCA<br>CAGTTGGGAGATTCCATTCACGTTCGGCTCGGGGA<br>CAAAGTTGGAAATAAAAC |
| 65. | 19E12HC-CDR1 (Kabat) | DYEMH |
| 66. | 19E12HC-CDR2 (Kabat) | GIDPETGGTAYNQKFKG |
| 67. | 19E12HC-CDR3 (Kabat) | GAWFAY |
| 68. | 19E12 LC-CDR1 (Kabat) | RSSTGAVTTSNSAN |
| 69. | 19E12 LC-CDR2 (Kabat) | GTNNRAP |
| 70. | 19E12 LC-CDR3 (Kabat) | ALWYNNHFV |
| 71. | 19E12HC-CDR1 (Vbase2) | GYTFTDYE |
| 72. | 19E12HC-CDR2 (Vbase2) | IDPETGGT |
| 73. | 19E12HC-CDR3 (Vbase2) | TRGAWFAY |
| 74. | 19E12 LC-CDR1 (Vbase2) | TGAVTTSNS |
| 75. | 19E12 LC-CDR2 (Vbase2) | GTN |
| 76. | 19E12 LC-CDR3 (Vbase2) | ALWYNNHFV |
| 77. | 19E12 VH Amino Acid Sequence | QVQLQQSGAELVRPGASVKLSCKASGYTFTDYEMH<br>WVRQTPVHGLEWIGGIDPETGGTAYNQKFKGKATLT<br>ADKSSSTAYMELRSLTSEDSAVYYCTRGAWFAYWG<br>QGTLVTVSA |
| 78. | 19E12 VL Amino Acid Sequence | QAVVTQESALTTSPGETVTLTCRSSTGAVTTSNSANW<br>VQEKPDHLFTGLIGGTNNRAPGVPARFSGSLIGDKAA<br>LTITGAQTEDEAIYFCALWYNNHFVFGGGTKLTVL |
| 79. | 19E12 VH DNA Sequence | CAGGTTCAATTGCAGCAGTCTGGGGCTGAGCTGGT<br>GAGGCCTGGGGCTTCAGTGAAGCTGTCCTGCAAGG<br>CTTCGGGCTATACATTTACTGACTATGAAATGCACT<br>GGGTGAGGCAGACACCTGTGCATGGCCTGGAATGG<br>ATTGGAGGTATTGATCCTGAAACTGGTGGTACTGC<br>CTACAATCAGAAGTTCAAGGGCAAGGCCACACTGA<br>CTGCAGACAAATCCTCCAGCACAGCCTACATGGAG<br>CTCCGCAGCCTGACATCTGAGGACTCTGCCGTCTAT<br>TACTGTACACGAGGGGCCTGGTTTGCTTACTGGGG<br>CCAAGGGACTCTGGTCACTGTCTCTGCAG |

-continued

| SEQUENCE TABLE | | |
|---|---|---|
| SEQ ID NO. | Description | Nucleotide or Amino Acid Sequence |
| 80. | 19E12 VL DNA Sequence | CAGGCTGTTGTGACTCAGGAATCTGCACTCACCAC ATCACCTGGTGAAACAGTCACACTCACTTGTCGCT CAAGTACTGGGGCTGTTACAACTAGTAACTCTGCC AACTGGGTCCAAGAAAAACCAGATCATTTATTCAC TGGTCTAATCGGTGGTACCAACAACCGAGCTCCAG GTGTTCCTGCCAGATTCTCAGGCTCCCTGATTGGAG ACAAGGCTGCCCTCACCATCACAGGGGCACAGACT GAGGATGAGGCAATATATTTCTGTGCTCTATGGTA CAACAACCATTTCGTGTTCGGTGGAGGCACCAAAC TGACTGTCCTAG |
| 81. | 17G11 HC-CDR1 (Kabat) | SYWMH |
| 82. | 17G11 HC-CDR2 (Kabat) | AIYPGNSDTSYNQKFKG |
| 83. | 17G11 HC-CDR3 (Kabat) | GGFDYSNYWFAY |
| 84. | 17G11 LC-CDR1 (Kabat) | KASQSVSNDVA |
| 85. | 17G11 LC-CDR2 (Kabat) | YASNRYT |
| 86. | 17G11 LC-CDR3 (Kabat) | QQDYSSYT |
| 87. | 17G11 HC-CDR1 (Vbase2) | GYTFTSYW |
| 88. | 17G11 HC-CDR2 (Vbase2) | IYPGNSDT |
| 89. | 17G11 HC-CDR3 (Vbase2) | TRGGFDYSNYWFAY |
| 90. | 17G11 LC-CDR1 (Vbase2) | QSVSND |
| 91. | 17G11 LC-CDR2 (Vbase2) | YAS |
| 92. | 17G11 LC-CDR3 (Vbase2) | QQDYSSYT |
| 93. | 17G11 VH Amino Acid Sequence | EVQLQQSGTVLARPGASVKMSCKASGYTFTSYWMH WVKQRPGQGLEWIGAIYPGNSDTSYNQKFKGKAKLT AVTSASTAYMELSSLTNEDSAVYYCTRGGFDYSNYW FAYWGQGTLVTVSA |
| 94. | 17G11 VL Amino Acid Sequence | SIVMTQTPKFLLVSAGDRVTITCKASQSVSNDVAWY QQKPGQSPKLLIYYASNRYTGVPDRFTGSGYGTDFTF TISTVQAEDLAVYFCQQDYSSYTFGGGTKLEIK |
| 95. | 17G11 VH DNA Sequence | GAGGTTCAGCTCCAGCAGTCTGGGACTGTGCTGGC AAGGCCTGGGGCTTCAGTGAAGATGTCCTGCAAGG CTTCTGGCTACACCTTTACCAGCTACTGGATGCACT GGGTAAAACAGAGGCCTGGACAGGGTCTGGAATG GATTGGCGCTATTTATCCTGGAAATAGTGATACTA |

-continued

| SEQUENCE TABLE | | |
|---|---|---|
| SEQ ID NO. | Description | Nucleotide or Amino Acid Sequence |
| | | GCTACAACCAGAAGTTCAAGGGCAAGGCCAAACT GACTGCAGTCACATCTGCCAGCACTGCCTACATGG AGCTCAGCAGCCTGACAAATGAGGACTCTGCGGTC TATTACTGTACAAGAGGAGGATTTGACTATAGTAA CTACTGGTTTGCTTACTGGGGCCAAGGGACTCTGG TCACTGTCTCTGCA |
| 96. | 17G11 VL DNA Sequence | AGTATTGTGATGACCCAGACTCCCAAATTCCTGCTT GTATCAGCAGGAGACAGGGTTACCATAACCTGCAA GGCCAGTCAGAGTGTGAGTAATGATGTAGCTTGGT ACCAACAGAAGCCAGGGCAGTCTCCTAAACTGCTG ATATACTATGCATCCAATCGCTACACTGGAGTCCCT GATCGCTTCACTGGCAGTGGATATGGGACGGATTT CACTTTCACCATCAGCACTGTGCAGGCTGAAGACC TGGCAGTTTATTTCTGTCAGCAGGATTATAGCTCGT ACACGTTCGGAGGGGGGACCAAGCTGGAAATAAA AC |
| 97. | 16B6 HC-CDR1 (Kabat) | RSWMN |
| 98. | 16B6 HC-CDR2 (Kabat) | WIYPGDGDTNYNGKFKG |
| 99. | 16B6 HC-CDR3 (Kabat) | SATLPYWYFDV |
| 100. | 16B6 LC-CDR1 (Kabat) | KASQDIKSYLS |
| 101. | 16B6 LC-CDR2 (Kabat) | YATNLAD |
| 102. | 16B6 LC-CDR3 (Kabat) | LQHVESPWT |
| 103. | 16B6 HC-CDR1 (Vbase2) | GYAFSRSW |
| 104. | 16B6 HC-CDR2 (Vbase2) | IYPGDGDT |
| 105. | 16B6 HC-CDR3 (Vbase2) | ARSATLPYWYFDV |
| 106. | 16B6 LC-CDR1 (Vbase2) | QDIKSY |
| 107. | 16B6 LC-CDR2 (Vbase2) | YAT |
| 108. | 16B6 LC-CDR3 (Vbase2) | LQHVESPWT |
| 109. | 16B6 VH Amino Acid Sequence | QVQLQQSGPELVKPGASVKISCKASGYAFSRSWMNW VKQRPGKGLEWIGWIYPGDGDTNYNGKFKGKATLT ADKSSSTAYMQLSSLTSEDSAAYFCARSATLPYWYF DVWGAGTTVTVSS |
| 110. | 16B6 VL Amino Acid Sequence | DIKMTQSPSSMYASLGERVTITCKASQDIKSYLSWYQ QKPWKSPKTLIYYATNLADGVPSRFSGSGSGQDYSLT ISSLGSDDTATYYCLQHVESPWTFGGGTKLEIK |

-continued

| SEQUENCE TABLE | | |
|---|---|---|
| SEQ ID NO. | Description | Nucleotide or Amino Acid Sequence |
| 111. | 16B6 VH DNA Sequence | CAGGTCCAGCTGCAGCAGTCTGGACCTGAGCTGGT GAAGCCTGGGGCCTCAGTGAAGATTTCCTGCAAAG CTTCTGGCTATGCATTCAGTCGCTCCTGGATGAACT GGGTAAAGCAGAGGCCTGGAAAGGGTCTTGAGTG GATTGGATGGATTTATCCTGGAGATGGTGATACTA ACTACAATGGAAAGTTCAAGGGCAAGGCCACACTG ACTGCAGACAAATCCTCAAGCACAGCCTACATGCA GCTCAGCAGCCTGACATCTGAGGACTCTGCGGCCT ATTTCTGTGCAAGGTCGGCTACCCTACCTTACTGGT ACTTCGATGTCTGGGGCGCAGGGACCACGGTCACC GTCTCCTCAG |
| 112. | 16B6 VL DNA Sequence | GACATCAAGATGACCCAGTCTCCATCCTCCATGTA TGCATCGCTGGGAGAGAGAGTCACTATCACTTGCA AGGCGAGTCAGGACATTAAAAGCTATTTAAGTTGG TACCAGCAGAAACCATGGAAATCTCCTAAGACCCT GATCTATTATGCAACAAACTTGGCAGATGGGGTCC CATCAAGATTCAGTGGCAGTGGATCTGGGCAGGAT TATTCTCTAACCATCAGCAGCCTGGGGTCTGACGA TACAGCAACTTATTACTGTCTACAGCATGTTGAGA GCCCGTGGACGTTCGGTGGAGGCACCAAGCTGGAA ATCAAAC |
| 113. | 20C7 HC-CDR1 (Kabat) | AYVMH |
| 114. | 20C7 HC-CDR2 (Kabat) | YIFPYNDGTEYNEKFKG |
| 115. | 20C7 HC-CDR3 (Kabat) | RTDGNPYTMDY |
| 116. | 20C7 LC-CDR1 (Kabat) | KASQDVSTAVA |
| 117. | 20C7 LC-CDR2 (Kabat) | SASYRYT |
| 118. | 20C7 LC-CDR3 (Kabat) | QQHYSTPFT |
| 119. | 20C7 HC-CDR1 (Vbase2) | GYTFTAYV |
| 120. | 20C7 HC-CDR2 (Vbase2) | IFPYNDGT |
| 121. | 20C7 HC-CDR3 (Vbase2) | ARRTDGNPYTMDY |
| 122. | 20C7 LC-CDR1 (Vbase2) | QDVSTA |
| 123. | 20C7 LC-CDR2 (Vbase2) | SAS |
| 124. | 20C7 LC-CDR3 (Vbase2) | QQHYSSPFT |

| SEQ ID NO. | Description | Nucleotide or Amino Acid Sequence |
|---|---|---|
| 125. | 20C7 VH Amino Acid Sequence | EVQLQQSGPELVNPGASVKMSCKASGYTFTAYVMH WVKQKPGQGLEWIGYIFPYNDGTEYNEKFKGKATLT SDKSSSTAYMELSSLTSEDSAVYYCARRTDGNPYTM DYWGQGTSVTVSS |
| 126. | 20C7 VL Amino Acid Sequence | DIVMTQSHKFMSTSVGDRVSITCKASQDVSTAVAWY QQKPGQSPKLLIHSASYRYTGVPDRFTGRGSGTDFTF TISSVQAEDLAVYYCQQHYSTPFTFGSGTKLEIK |
| 127. | 20C7 VH DNA Sequence | GAGGTCCAGCTGCAGCAGTCTGGACCTGAGTTGGT AAATCCTGGGGCTTCAGTGAAGATGTCCTGCAAGG CTTCTGGATACACATTCACTGCCTATGTTATGCACT GGGTGAAACAGAAGCCTGGGCAGGGCCTTGAGTG GATTGGATATATTTTTCCTTACAATGATGGTACTGA GTACAATGAGAAGTTCAAAGGCAAGGCCACACTG ACTTCAGACAAATCCTCCAGCACAGCCTACATGGA GCTCAGCAGCCTGACCTCTGAGGACTCTGCGGTCT ATTACTGTGCAAGGAGGACAGATGGTAACCCCTAT ACTATGGACTATTGGGGTCAAGGAACCTCAGTCAC CGTCTCCTCAG |
| 128. | 20C7 VL DNA Sequence | GACATTGTGATGACCCAGTCTCACAAATTCATGTC CACATCAGTAGGAGACAGGGTCAGCATCACCTGCA AGGCCAGTCAGGATGTGAGTACTGCTGTAGCCTGG TATCAACAGAAACCAGGACAATCTCCTAAACTACT GATTCATTCGGCATCCTACCGGTACACTGGAGTCC CTGATCGCTTCACTGGCAGAGGATCTGGGACGGAT TTCACTTTCACCATCAGCAGTGTGCAGGCTGAAGA CCTGGCAGTTTATTACTGTCAGCAACATTATAGTAC TCCATTCACGTTCGGCTCGGGGACAAAGTTGGAAA TAAAAC |
| 129. | 12H4 HC-CDR1 (Kabat) | DYYIH |
| 130. | 12H4 HC-CDR2 (Kabat) | EIYPGSDDAYYNEKFKG |
| 131. | 12H4 HC-CDR3 (Kabat) | ETTATAY |
| 132. | 12H4 LC-CDR1 (Kabat) | SASSSVSLIY |
| 133. | 12H4 LC-CDR2 (Kabat) | STSNLAS |
| 134. | 12H4 LC-CDR3 (Kabat) | QQRSGYPPT |
| 135. | 12H4 HC-CDR1 (Vbase2) | GYTFTDYY |
| 136. | 12H4 HC-CDR2 (Vbase2) | IYPGSDDA |
| 137. | 12H4 HC-CDR3 (Vbase2) | TRETTATAY |
| 138. | 12H4 LC-CDR1 (Vbase2) | SSVSL |

-continued

| SEQ ID NO. | Description | Nucleotide or Amino Acid Sequence |
|---|---|---|
| 139. | 12H4 LC-CDR2 (Vbase2) | STS |
| 140. | 12H4 LC-CDR3 (Vbase2) | QQRSGYPPT |
| 141. | 12H4 VH Amino Acid Sequence | EVQLQQSGPELVKPGASVKVSCKASGYTFTDYYIHW VKQRPGQGLEWIGEIYPGSDDAYYNEKFKGKATLTA DKSSSTAYMQLSSLTSEDSAVYFCTRETTATAYWGQ GTLVTVSA |
| 142. | 12H4 VL Amino Acid Sequence | QIVLTQSPAIMSASPGEKVTITCSASSSVSLIYWFQQKP GTSPKLWIYSTSNLASGVPARFSGSGSGTSYSLTISRM EAEDAATYYCQQRSGYPPTFGGGTKLEIK |
| 143. | 12H4 VH DNA Sequence | CTGAGGTCCAGCTGCAGCAGTCTGGACCTGAGCTG GTTAAGCCTGGGGCTTCAGTGAAGGTATCCTGCAA GGCCTCTGGATACACATTCACTGACTACTATATAC ACTGGGTGAAGCAGAGGCCTGGGCAGGGCCTTGA GTGGATTGGAGAGATTTATCCTGGAAGTGATGATG CTTACTACAATGAGAAATTCAAGGGCAAGGCCACA CTGACTGCAGACAAATCCTCCAGCACAGCCTACAT GCAGCTCAGCAGCCTGACATCTGAGGACTCTGCAG TCTATTTCTGTACAAGAGAGACTACGGCTACGGCT TACTGGGGCCAAGGGACTCTGGTCACTGTCTCTGC AG |
| 144. | 12H4 VL DNA Sequence | CAAATTGTTCTCACCCAGTCTCCAGCAATCATGTCT GCATCTCCAGGGGAGAAGGTCACCATAACCTGCAG TGCCAGCTCAAGTGTAAGTCTCATTTACTGGTTCCA GCAGAAGCCAGGCACTTCTCCCAAACTCTGGATTT ATAGCACATCCAACCTGGCTTCTGGAGTCCCTGCTC GCTTCAGTGGCAGTGGATCTGGGACCTCTTACTCTC TCACAATCAGCCGAATGGAGGCTGAAGATGCTGCC ACTTATTACTGCCAGCAAAGGAGTGGTTACCCACC CACGTTCGGAGGGGGGACCAAGCTGGAAATAAAA C |
| 145. | 16A1 HC-CDR1 (Kabat) | DHGIH |
| 146. | 16A1 HC-CDR2 (Kabat) | NISPGNGDIKYNEKFKG |
| 147. | 16A1 HC-CDR3 (Kabat) | YFVD |
| 148. | 16A1 LC-CDR1 (Kabat) | KSSQSLLNSNNQKNCLA |
| 149. | 16A1 LC-CDR2 (Kabat) | FACTRES |
| 150. | 16A1 LC-CDR3 (Kabat) | QQHCNTPLT |
| 151. | 16A1 HC-CDR1 (Vbase2) | GYTFTDHG |
| 152. | 16A1 HC-CDR2 (Vbase2) | ISPGNGDI |

-continued

| SEQ ID NO. | Description | Nucleotide or Amino Acid Sequence |
|---|---|---|
| 153. | 16A1 HC-CDR3 (Vbase2) | TTYFVD |
| 154. | 16A1 LC-CDR1 (Vbase2) | QSLLNSNNQKNC |
| 155. | 16A1 LC-CDR2 (Vbase2) | FAC |
| 156. | 16A1 LC-CDR3 (Vbase2) | QQHCNTPLT |
| 157. | 16A1 VH Amino Acid Sequence | QVQLQQSDAELVKPGTSVKISCKASGYTFTDHGIHW VKQRPERGLEWIGNISPGNGDIKYNEKFKGKATLTAD KSSSTVYMQVNSLTSEDSAVYFCTTYFVDWGRGTLV TVSA |
| 158. | 16A1 VL Amino Acid Sequence | DIVMTQSPSSLAMSIGQRVTMSCKSSQSLLNSNNQKN CLAWYQQKPGQSPRLLIYFACTRESGVPDRFIGSGSG TDFTLTISSVQAEDLAYYFCQQHCNTPLTFGAGTKLE LK |
| 159. | 16A1 VH DNA Sequence | CAGGTTCAGCTGCAACAGTCTGACGCTGAGTTGGT GAAACCTGGGACTTCAGTGAAGATATCCTGCAAGG CTTCTGGCTACACCTTCACTGACCATGGTATTCACT GGGTGAAACAGAGGCCTGAACGGGGCCTGGAATG GATTGGAAATATTTCTCCCGGAAATGGTGATATTA AGTATAATGAGAAGTTCAAGGGCAAGGCCACGCTG ACTGCAGACAAATCCTCCAGCACTGTCTACATGCA GGTCAACAGCCTGACATCTGAGGATTCTGCAGTGT ATTTCTGTACAACCTATTTTGTTGACTGGGGCCGGG GGACTCTGGTCACTGTCTCTGCAG |
| 160. | 16A1 VL DNA Sequence | GACATTGTGATGACACAGTCTCCATCCTCCCTGGCT ATGTCAATTGGACAGAGGGTCACTATGAGCTGCAA GTCCAGTCAGAGCCTTTTAAATAGTAACAATCAAA AGAACTGTTTGGCCTGGTACCAGCAGAAACCAGGA CAGTCTCCTAGACTTCTGATTTACTTTGCATGTACT AGGGAATCGGGGGTCCCTGATCGCTTCATTGGCAG TGGATCTGGGACAGATTTCACCCTTACCATCAGCA GTGTGCAGGCTGAAGACCTGGCATATTACTTCTGT CAGCAACATTGTAACACTCCGCTCACGTTCGGTGC TGGGACCAAGCTGGAGCTGAAAC |
| 161. | 17A7 HC-CDR1 (Kabat) | TYWMN |
| 162. | 17A7 HC-CDR2 (Kabat) | RIFPGDGDTDYDGKFKG |
| 163. | 17A7 HC-CDR3 (Kabat) | TGAAYEFDPFPY |
| 164. | 17A7 LC-CDR1 (Kabat) | SSTKSLLHSSGITYLY |
| 165. | 17A7 LC-CDR2 (Kabat) | RMSNLAS |
| 166. | 17A7 LC-CDR3 (Kabat) | AQMLERPFT |

-continued

| SEQUENCE TABLE | | |
|---|---|---|
| SEQ ID NO. | Description | Nucleotide or Amino Acid Sequence |
| 167. | 17A7 HC-CDR1 (Vbase2) | GYAFSTYW |
| 168. | 17A7 HC-CDR2 (Vbase2) | IFPGDGDT |
| 169. | 17A7 HC-CDR3 (Vbase2) | ARTGAAYEFDPFPY |
| 170. | 17A7 LC-CDR1 (Vbase2) | KSLLHSSGITY |
| 171. | 17A7 LC-CDR2 (Vbase2) | RMS |
| 172. | 17A7 LC-CDR3 (Vbase2) | AQMLERPFT |
| 173. | 17A7 VH Amino Acid Sequence | QVQLQQSGPELVKPGASVKISCKGSGYAFSTYWMN WVKQRPGKGLEWIGRIFPGDGDTDYDGKFKGKATLT ADKSSNTAYMQLSSLTSEDSAVYFCARTGAAYEFDP FPYWGQGTLVTVSA |
| 174. | 17A7 VL Amino Acid Sequence | DIVMTQAAFSNPVTLGTSASISCSSTKSLLHSSGITYLY WYLQRPGQSPQLLIYRMSNLASGVPDRFSGSGSGTDF TLRISRVEAEDVGVYYCAQMLERPFTFGSGTKLEIK |
| 175. | 17A7 VH DNA Sequence | CAGGTTCAGCTGCAGCAGTCTGGACCTGAGCTGGT GAAGCCTGGGGCCTCAGTGAAGATTTCCTGCAAAG GTTCTGGCTACGCATTCAGTACCTACTGGATGAACT GGGTGAAGCAGAGGCCTGGAAAGGGTCTTGAGTG GATTGGACGGATTTTTCCTGGAGATGGAGATACAG ATTACGATGGGAAGTTCAAGGGCAAGGCCACACTG ACTGCAGACAAATCCTCCAACACAGCCTACATGCA ACTCAGCAGCCTGACATCTGAAGACTCTGCGGTCT ACTTCTGTGCAAGAACTGGGGCCGCCTATGAATTC GACCCTTTTCCTTACTGGGGCCAAGGGACTCTGGTC ACTGTCTCTGCAG |
| 176. | 17A7 VL DNA Sequence | GATATTGTGATGACGCAGGCTGCATTCTCCAATCC AGTCACTCTTGGAACATCAGCTTCCATCTCTTGCAG TTCTACTAAGAGTCTCCTACATAGTAGCGGCATCA CTTATCTGTATTGGTATCTGCAGAGGCCAGGCCAG TCTCCTCAGCTCCTGATATATCGGATGTCCAACCTT GCCTCAGGAGTCCCAGACAGGTTCAGTGGCAGTGG GTCAGGAACTGATTTCACACTGAGAATCAGCAGAG TGGAGGCTGAGGATGTGGGTGTTTATTACTGTGCT CAAATGCTAGAACGCCCATTCACGTTCGGCTCGGG GACAAAGTTGGAAATAAAAC |
| 177. | 17B10HC-CDR1 (Kabat) | SYWLN |
| 178. | 17B10HC-CDR2 (Kabat) | RIYPGDGDTDYNGKFKG |
| 179. | 17B10HC-CDR3 (Kabat) | GDGYWAMDY |
| 180. | 17B10LC-CDR1 (Kabat) | RFSKSLLHSNGITYLY |

| SEQUENCE TABLE |||
|---|---|---|
| SEQ ID NO. | Description | Nucleotide or Amino Acid Sequence |
| 181. | 17B10LC-<br>CDR2<br>(Kabat) | QMSNLAS |
| 182. | 17B10LC-<br>CDR3<br>(Kabat) | AQNLELPWT |
| 183. | 17B10HC-<br>CDR1<br>(Vbase2) | GYAFSSYW |
| 184. | 17B10HC-<br>CDR2<br>(Vbase2) | IYPGDGDT |
| 185. | 17B10HC-<br>CDR3<br>(Vbase2) | VRGDGYWAMDY |
| 186. | 17B10LC-<br>CDR1<br>(Vbase2) | KSLLHSNGITY |
| 187. | 17B10LC-<br>CDR2<br>(Vbase2) | QMS |
| 188. | 17B10LC-<br>CDR3<br>(Vbase2) | AQNLELPWT |
| 189. | 17B10 VH<br>Amino Acid<br>Sequence | QVQLQQSGPELVKPGASVKISCKASGYAFSSYWLNW<br>VKQRPGKGLEWFGRIYPGDGDTDYNGKFKGKATLT<br>ADKSSSTAYMQLRSLTSEDSAVYFCVRGDGYWAMD<br>YWGQGTSVTVSS |
| 190. | 17B10 VL<br>Amino Acid<br>Sequence | DIVMTQAAFSNPVTLGTSASISCRFSKSLLHSNGITYL<br>YWYLQKPGQSPQLLIYQMSNLASGVPDRFSSSGSGTD<br>FTLRISRVEAEDVGVYYCAQNLELPWTFGGGTKLEIK |
| 191. | 17B10 VH<br>DNA<br>Sequence | CAGGTTCAGCTGCAGCAGTCTGGACCTGAGCTGGT<br>GAAGCCTGGGGCCTCGGTGAAGATTTCCTGCAAAG<br>CTTCTGGCTACGCATTCAGTAGCTACTGGCTGAACT<br>GGGTGAAGCAGAGGCCTGGAAAGGGTCTTGAGTG<br>GTTTGGACGGATTTATCCTGGAGATGGAGATACTG<br>ACTACAATGGGAAGTTCAAGGGCAAGGCCACACTG<br>ACTGCAGACAAATCCTCCAGCACAGCCTACATGCA<br>ACTCAGAAGCCTGACATCTGAGGACTCTGCGGTCT<br>ACTTCTGTGTAAGAGGTGATGGTTACTGGGCTATG<br>GACTACTGGGGTCAAGGAACCTCAGTCACCGTCTC<br>CTCAG |
| 192. | 17B10 VL<br>DNA<br>Sequence | GATATTGTGATGACGCAGGCTGCATTCTCCAATCC<br>AGTCACTCTTGGAACATCAGCTTCCATCTCCTGCAG<br>GTTTAGTAAGAGTCTCCTACATAGTAATGGCATCA<br>CTTATTTGTATTGGTATCTGCAGAAGCCAGGCCAGT<br>CTCCTCAGCTCCTGATTTATCAGATGTCCAACCTTG<br>CCTCAGGAGTCCCAGACAGGTTCAGTAGCAGTGGG<br>TCAGGAACTGATTTCACACTGAGAATCAGCAGAGT<br>GGAGGCTGAGGATGTGGGTGTTTATTACTGTGCTC<br>AAAATCTAGAACTTCCGTGGACGTTCGGTGGAGGC<br>ACCAAGCTGGAAATCAAAC |
| 193. | 19B5 HC-<br>CDR1<br>(Kabat) | NYYMS |
| 194. | 19B5 HC-<br>CDR2<br>(Kabat) | TISNNGDSTYYLDTVKG |

-continued

| SEQ ID NO. | Description | Nucleotide or Amino Acid Sequence |
|---|---|---|
| 195. | 19B5 HC-CDR3 (Kabat) | VGTGFTY |
| 196. | 19B5 LC-CDR1 (Kabat) | RASQSINNYLH |
| 197. | 19B5 LC-CDR2 (Kabat) | FASQSIS |
| 198. | 19B5 LC-CDR3 (Kabat) | QQSNSWPLT |
| 199. | 19B5 HC-CDR1 (Vbase2) | GFTFSNYY |
| 200. | 19B5 HC-CDR2 (Vbase2) | ISNNGDST |
| 201. | 19B5 HC-CDR3 (Vbase2) | TRVGTGFTY |
| 202. | 19B5 LC-CDR1 (Vbase2) | QSINNY |
| 203. | 19B5 LC-CDR2 (Vbase2) | FAS |
| 204. | 19B5 LC-CDR3 (Vbase2) | QQSNSWPLT |
| 205. | 19B5 VH Amino Acid Sequence | DVNLVESGGGLVKLGGSLKLSCAASGFTFSNYYMSW VRQSPEKRLEWVATISNNGDSTYYLDTVKGRFTISRD SAENTLYLQMSSLISEDTAVYYCTRVGTGFTYWGQG TLVTVSA |
| 206. | 19B5 VL Amino Acid Sequence | DIVLTQSPATLSVTPGDSVSLSCRASQSINNYLHWYQ QRSHESPRLLIKFASQSISDIPSRFSGSGSGTDFTLS INSIETEDFGMYFCQQSNSWPLTFGAGTKLELK |
| 207. | 19B5 VH DNA Sequence | GACGTGAACCTCGTGGAGTCTGGGGGAGGCTTAGT GAAGCTTGGAGGGTCCCTGAAACTCTCCTGTGCAG CCTCTGGATTCACTTTCAGTAACTACTACATGTCTT GGGTTCGCCAGAGTCCGGAGAAGAGGCTGGAGTG GGTCGCAACCATTAGTAATAATGGTGATAGCACCT ACTATCTAGACACTGTGAAGGGCCGATTCACCATC TCCAGAGACAGTGCCGAGAACACCCTGTACCTGCA AATGAGCAGTCTGATTTCTGAGGACACAGCCGTGT ATTACTGTACAAGAGTTGGGACGGGGTTTACTTAC TGGGGCCAAGGGACTCTGGTCACTGTCTCTGCAG |
| 208. | 19B5 VL DNA Sequence | GATATTGTGCTAACTCAGTCTCCAGCCACCCTGTCT GTGACTCCAGGAGATAGCGTCAGTCTTTCCTGCAG GGCCAGCCAAAGTATTAACAACTACCTACACTGGT ATCAACAAAGATCACATGAGTCTCCAAGGCTTCTC ATCAAGTTTGCTTCCCAGTCCATCTCTGACATCCCC TCCAGGTTCAGTGGCAGTGGATCAGGGACAGATTT CACTCTCAGTATCAACAGTATAGAGACTGAAGATT TTGGAATGTATTTCTGTCAACAGAGTAACAGCTGG CCGCTCACGTTCGGTGCTGGGACCAAGCTGGAGCT GAAAC |

-continued

| SEQUENCE TABLE | | |
| --- | --- | --- |

SEQ ID
NO.   Description        Nucleotide or Amino Acid Sequence 209. 17E6 HC-           SYVIH
     CDR1
     (Kabat)

210. 17E6 HC-           YINPYSDYTQYNEKFKG
     CDR2
     (Kabat)

211. 17E6 HC-           RADGNPYAMDY
     CDR3
     (Kabat)

212. 17E6 LC-           KASQDVSTAVV
     CDR1
     (Kabat)

213. 17E6 LC-           SASYRYT
     CDR2
     (Kabat)

214. 17E6 LC-           QQHYSTPFT
     CDR3
     (Kabat)

215. 17E6 HC-           GYTFTSYV
     CDR1
     (Vbase2)

216. 17E6 HC-           INPYSDYT
     CDR2
     (Vbase2)

217. 17E6 HC-           ARRADGNPYAMDY
     CDR3
     (Vbase2)

218. 17E6 LC-           QDVSTA
     CDR1
     (Vbase2)

219. 17E6 LC-           SAS
     CDR2
     (Vbase2)

220. 17E6 LC-           QQHYSTPFT
     CDR3
     (Vbase2)

221. 17E6 VH            EVQLQQSGPELVKPGASVKMSCKASGYTFTSYVIHW
     Amino Acid         VKQKPGQGLEWIGYINPYSDYTQYNEKFKGKATLTS
     Sequence           DKSSSTAYMELSSLTSEDSAVYSCARRADGNPYAMD
                        YWGQGTSVTVSS 222. 17E6 VL            DIVMTQSHKFMSTSVGDRVSTTCKASQDVSTAVVWY
     Amino Acid         QQKPGQSPKLLIYSASYRYTGVPDRFTGSGSGTDFT
     Sequence           FTITSVQAEDLAVYYCQQHYSTPFTFGSGTKLEIK 223. 17E6 VH            GAGGTCCAGCTACAGCAGTCTGGACCTGAGCTGGT
     DNA                AAAGCCTGGGGCTTCAGTGAAGATGTCCTGCAAGG
     Sequence           CTTCTGGATACACATTCACTAGCTATGTTATTCAC
                        TGGGTAAAGCAGAAGCCTGGGCAGGGCCTTGAGTG
                        GATTGGATATATTAATCCTTACAGTGATTATACTC
                        AGTACAATGAGAAGTTCAAAGGCAAGGCCACACTG
                        ACTTCAGACAAATCCTCCAGCACAGCCTACATGGA
                        GCTCAGCAGCCTGACCTCTGAGGACTCTGCGGTCT
                        ATTCCTGTGCAAGGAGGGCAGATGGTAACCCCTAT
                        GCTATGGACTACTGGGGTCAAGGAACCTCAGTCAC
                        CGTCTCCTCAG 224. 17E6 VL            GACATTGTGATGACCCAGTCTCACAAATTCATGTC
     DNA                CACATCAGTAGGAGACAGGGTCAGCACCACCTGCA
     Sequence           AGGCCAGTCAGGATGTGAGTACTGCTGTAGTCTGG
                        TATCAACAGAAACCAGGACAATCTCCTAAACTACT

| SEQUENCE TABLE | | |
|---|---|---|

| SEQ ID NO. | Description | Nucleotide or Amino Acid Sequence |
|---|---|---|
| | | GATTTACTCGGCATCCTACCGGTACACTGGAGTCC CTGATCGCTTCACTGGCAGTGGATCTGGGACGGAT TTCACTTTCACCATCACCAGTGTGCAGGCTGAAGA CCTGGCAGTTTATTACTGTCAGCAACATTATAGTA CTCCATTCACGTTCGGCTCGGGGACAAAGTTGGAA ATAAAAC |

Exemplary linkers

| 225. | Linker | (G)$_n$, n >= 1 |
|---|---|---|
| 226. | Linker | (GS)$_n$, 8 >= n >= 1 |
| 227. | Linker | (GSGGS)$_n$, 8 >= n >= 1 |
| 228. | Linker | (GGGGS)$_n$, 8 >= n >= 1 |
| 229. | Linker | (GGGS)$_n$, 8 >= n >= 1 |
| 230. | Linker | (GGGGS)$_3$ |
| 231. | Linker | (GGGGS)$_6$ |
| 232. | Linker | (GSTSGSGKPGSGEGS)n<br>3 >= n >= 1 |

Exemplary consensus sequence of anti-CD93 antibodies

| 233. | CDRH2 (5H9/17A7) | RIFPGDGDX$_1$X$_2$YX$_3$GKFKG<br>X$_1$X$_2$ = AN or TD, X$_3$ = N or D |
|---|---|---|
| 234. | CDRH3 (5H9/17A7) | TGAAYX$_1$FDPFPY<br>X$_1$ = D or E |
| 235. | CDRL1 (5H9/17A7) | SSX$_1$KSLLHSX$_2$GX$_3$TYLY<br>X$_1$ = S or T, X$_2$ = N or S, X$_3$ = V or I |
| 236. | CDRH1 (5H9/17A7/ 17B10) | X$_1$YWX$_2$N<br>X$_1$ = S or T, X$_2$ = L or M |
| 237. | CDRH2 (5H9/17A7/ 17B10) | RIX$_1$PGDGDX$_2$X$_3$YX$_4$GKFKG<br>X$_1$ = Y or F, X$_2$X$_3$ = TD or AN, X$_4$ = N or D |
| 238. | CDRL1 (5H9/17A7/ 17B10) | X$_1$X$_2$X$_3$KSLLHSX$_4$GX$_5$TYLY<br>X$_1$X$_2$X$_3$ = SSS, SST, or RFS, X$_4$ = N or S, X$_5$ = V or I |
| 239. | CDRL2 (5H9/17A7/ 17B10) | X$_1$MSNLAS<br>X$_1$ = R or Q |
| 240. | CDRL3 (5H9/17A7/ 17B10) | AQX$_1$LEX$_2$PX$_3$T<br>X$_1$ = M or N, X$_2$ = R or L, X$_3$ = F or W |
| 241. | CDRH1 (20C7/17E6) | X$_1$YVX$_2$H<br>X$_1$ = A or S, X$_2$ = M or I |
| 242. | CDRH2 (20C7/17E6) | YIX$_1$PYX$_2$DX$_3$TX$_4$YNEKFKG<br>X$_1$ = F or N, X$_2$ = N or S, X$_3$ = G or Y, X$_4$ = E or Q |
| 243. | CDRH3 (20C7/17E6) | RX$_1$DGNPYX$_2$MDY<br>X$_1$ = T or A, X$_2$ = T or A |
| 244. | CDRL1 (20C7/17E6) | KASQDVSTAVX$_1$<br>X$_1$ = A or V |
| 245. | CDRL1 (10B1/20C7/1 7E6) | KASQX$_1$VX$_2$TX$_3$VX$_4$<br>X$_1$ = N or D, X$_2$ = G or S, X$_3$ = N or A, X$_4$ = A or V |

-continued

| SEQUENCE TABLE | | |
|---|---|---|
| SEQ ID NO. | Description | Nucleotide or Amino Acid Sequence |
| 246. | CDRL2 (10B1/20C7/1 7E6) | SASYRX$_1$X$_2$ <br> X$_1$X$_2$ = FI or YT |
| 247. | CDRL3 (10B1/20C7/1 7E6) | QQXX$_2$X$_3$X$_4$PX$_5$T <br> X$_1$X$_2$X$_3$X$_4$ = YNRN or HYST, X$_5$ = I or F |
| 248. | CDRL1 (16E4/16G9) | X$_1$ASQSVX$_2$X$_3$X$_4$X$_5$X$_6$SYMX$_7$ <br> X$_1$ = K or R, X$_2$X$_3$X$_4$X$_5$X$_6$ = DYAGD or STSSY, X$_7$ = N or H |
| 249. | CDRL2 (16E4/16G9) | X$_1$ASNLES <br> X$_1$ = A or Y |
| 250. | CDRL3 (16E4/16G9) | QX$_1$X$_2$X$_3$X$_4$X$_5$PX$_6$T <br> X$_1$X$_2$X$_3$X$_4$X$_5$ = QTNED or HSWEI, X$_6$ = R or F |
| Exemplary anti-PD-L1 antibody moiety sequences | | |
| 251. | HC-CDR1 | DTYMY |
| 252. | HC-CDR2 | RIDPANDNTKYAQKFQG |
| 253. | HC-CDR3 | AKNLLNYFDY |
| 254. | LC-CDR1 | RASQEISGYLS |
| 255. | LC-CDR2 | ATSTLQS |
| 256. | LC-CDR3 | LQYAIYPLT |
| Exemplary anti-PD-1 antibody moiety sequences | | |
| 257. | Ab1 HC-CDR1 (Vbase2) | GFTFSSYT |
| 258. | Ab1 HC-CDR2 (Vbase2) | ISHGGGDT |
| 259. | Ab1 HC-CDR3 (Vbase2) | ARHSGYERGYYYVMDY |
| 260. | Ab1 LC-CDR1 (Vbase2) | ESVDYYGFSF |
| 261. | Ab1 LC-CDR2 (Vbase2) | AAS |
| 262. | Ab1 LC-CDR3 (Vbase2) | QQSKEVPW |
| 263. | Ab2 HC-CDR1 (Vbase2) | GYTFTSYT |
| 264. | Ab2 HC-CDR2 (Vbase2) | INPTTGYT |
| 265. | Ab2 HC-CDR3 (Vbase2) | ARDDAYYSGY |
| 266. | Ab2 LC-CDR1 (Vbase2) | ENIYSNL |

-continued

| SEQUENCE TABLE | | |
| --- | --- | --- |

| SEQ ID NO. | Description | Nucleotide or Amino Acid Sequence |
| --- | --- | --- |
| 267. | Ab2 LC-CDR2 (Vbase2) | AAK |
| 268. | Ab2 LC-CDR3 (Vbase2) | QHFWGTPWT |
| 269. | Ab3 HC-CDR1 (Vbase2) | GFAFSSYD |
| 270. | Ab3 HC-CDR2 (Vbase2) | ITIGGGTT |
| 271. | Ab3 HC-CDR3 (Vbase2) | ARHRYDYFAMDN |
| 272. | Ab3 LC-CDR1 (Vbase2) | ENVDNYGINF |
| 273. | Ab3 LC-CDR2 (Vbase2) | VSS |
| 274. | Ab3 LC-CDR3 (Vbase2) | QQSKDVPW |
| 275. | Murine Ab1 VH | SQVQLQQSGAELARPGASVKMSCKASGYTFTSYTMH WVKQRPGQGLEWIGYINPTTGYTNYNQKFKDKANPT TGYTNYNQKFKDKATLTADKSSSTAYMQLSSLTSED SAVYYCARDDAYYSGYWGQGTTLTVSS |
| 276. | Murine Ab1 VL | DIQMTQSPASLSVSVGETVTITCRASENIYSNLAWYR QKQGKSPQLLVYAAKNLADGVPSRFSGSGSGTQYSL KINSLQSEDFGSYYCQHFWGTPWTFGGGTKLEIKR |
| 277. | Murine Ab2 VH | VQLVESGGGLVKPGGSLKLSCAASGFAFSSYDMSWV RQTPEKRLVWVAYITIGGGTTYYSDTVKRLVWVAYI TIGGGTTYYSDTVKGRFTISRDNAKNTLYLQMSSLKS EDTAMYYCARHRYDYFAMDNWGHGTSVTVSS |
| 278. | Murine Ab2 VL | DIVLTQSPASLAVSLEHRATISCQASENVDNYGINFM NWFQHKPAQPPQLLIYVSSNLGSGVPAKFSGSGSGTD FSLNIHPMEEDDTAMYFCQQSKDVPWTFSGGTKLEIK R |
| 279. | Murine Ab3 VH | EVKLVESGGGLVQPGGSLKLSCAASGFTFSSYTMSWI RQTPEKRLEWVAYISHGGGDTYYPDTVKGRFTISRD NAKNTLYLQMSSLKSEDTAMYYCARHSGYERGYYY VMDYWGQGTSVTVSS |
| 280. | Murine Ab3 VL | DIVLTQFPTSLAVSLGQRATISCRASESVDYYGFSFIN WFQQKPGQPPKLLIYAASNQGSGVPARFGGSGSGTD FSLNIHPMEEDDTAMYFCQQSKEVPWTFGGGTKLEIK |

| Additional Exemplary anti-PD-L1 antibody moiety sequences | | |
| --- | --- | --- |

| 281. | Humanized VH 1 | QVQLVQSGAEVKKPGASVKVSCKASGFNIKDTYMY WVRQAPGQGLEWMGRIDPANDNTKYAQKFQGRVTI TADTSTSTAYMELSSLRSEDTAVYYCARAKNLLNYF DYWGQGTLVTVSS |
| 282. | Humanized VH2 | QVQLVQSGAEVKKPGASVKVSCKASGFNIKDTYMY WVRQAPGQGLEWIGRIDPANDNTKYAPKFQGRVTIT ADTSTNTAYMELSSLRSEDTAVYYCARAKNLLNYFD YWGQGTLVTVSS |

SEQUENCE TABLE

| SEQ ID NO. | Description | Nucleotide or Amino Acid Sequence |
|---|---|---|
| 283. | Humanized VH3 | EVQLVQSGAEVKKPGASVKVSCKASGFNIKDTYMY WVRQAPGQGLEWMGRIDPANDNTKYAQKFQGRVTI TADTSTNTAYMELSSLRSEDTAVYYCARAKNLLNYF DYWGQGTLVTVSS |
| 284. | Humanized VL 1 | DIQMTQSPSSLSASVGDRVTITCRASQEISGYLSWYQ QKPGKAPKRLIYATSTLDSGVPSRFSGSGSGTDFTLTI SSLQPEDFATYYCLQYAIYPLTFGQGTKLEIKR |
| 285. | Humanized VL2 | DIQMTQSPSSLSASVGDRVTITCRASQEISGYLSWLQQ KPGKAPKRLIYATSTLQSGVPSRFSGSRSGTDYTLTIS SLQPEDFATYYCLQYAIYPLTFGQGTKLEIKR |
| 286. | Humanized VL3 | DIQMTQSPSSLSASVGDRVTITCRASQEISGYLSWYQ QKPGKAPKRLIYATSTLDSGVPSRFSGSRSGSDYTLTI SSLQPEDFATYYCLQYAIYPLTFGQGTKLEIKR |

Additional exemplary anti-CD93 antibody sequences

| SEQ ID NO. | Description | Nucleotide or Amino Acid Sequence |
|---|---|---|
| 287. | 7F3 Heavy chain | QVQLQQSGADLVRPGASVKLSCKASGYTFTDYEMH WVKQTPVYGLEWIGGIDPETGDTAYNQNFKGKATLT ADKSSSAAYMELRSLTSEDSAVYYCTNYGNLYYYA MDYWGQGTSVTVSS |
| 288. | 7F3 Light chain | ENVLTQSPAIMSASPGEKVTMTCRASSSVSSSYLHWY QQKSGASPKLWIYSTSNLAFGVPARFSGSGSGTSYSL TISSVEAEDAATYYCQQYSGYPLTFGSGTKLEIK |
| 289. | 7F3 HC-CDR1 (Kabat) | DYEMH |
| 290. | 7F3 HC-CDR2 (Kabat) | GIDPETGDTAYNQNFKG |
| 291. | 7F3 HC-CDR3 (Kabat) | YGNLYYYAMDY |
| 292. | 7F3 LC-CDR1 (Kabat) | RASSSVSSSYLH |
| 293. | 7F3 LC-CDR2 (Kabat) | STSNLAF |
| 294. | 7F3 LC-CDR3 (Kabat) | QQYSGYPLT |
| 295. | 7F3 HC-CDR1 (Vbase2) | GYTFTDYE |
| 296. | 7F3 HC-CDR2 (Vbase2) | IDPETGDT |
| 297. | 7F3 HC-CDR3 (Vbase2) | TNYGNLYYYAMDY |
| 298. | 7F3 LC-CDR1 (Vbase2) | SSVSSSY |
| 299. | 7F3 LC-CDR2 (Vbase2) | STS |

-continued

| SEQ ID NO. | Description | Nucleotide or Amino Acid Sequence |
|---|---|---|
| 300. | 7F3 LC-CDR3 (Vbase2) | QQYSGYPLT |
| 301. | 16E4 VL1 LC-CDR1 (Kabat) | KASQSVDYAGDSYLN |
| 302. | 16E4 VL2/16E4 VL4 LC-CDR1 (Kabat) | RASQSVDYAGDSYMN |
| 303. | 16E4 VL3 LC-CDR1 (Kabat) | RASQSVDYAGDSYLA |
| 304. | 16E4 VH5 HC-CDR1 (Kabat) | SYWIH |
| 305. | 16E4 VH5 HC-CDR2 (Kabat) | EIEPSASYTYYNQKFKG |
| 306. | 16E4 VL5 LC-CDR1 (Kabat) | RASQSVDYAGDSYLN |
| 307. | 16E4 VH-1 | QVQLVESGAEVKKPGASVKLSCKASGYTFTSYWMH<br>WVRQAPGQRLEWMGEIDPSASYTYYNQKFKGRVTIT<br>VDKSASTAYMELSSLRSEDTAVYYCARSVYYGNKYF<br>DVWGPGTTVTVSS |
| 308. | 16E4 VH-2 | QVQLVQSGAEVKKPGASVKVSCKASGYTFTSYWMH<br>WVRQAPGQGLEWMGEIDPSASYTYYNQKFKGRVTM<br>TRDKSISTAYMELNSLTSDDSAVYYCARSVYYGNKY<br>FDVWGAGTTVTVSS |
| 309. | 16E4 VH-3 | QVQLVQSGAEVRKPGASVKVSCKASGYTFTSYWMH<br>WVRQAPGQGLEWVGEIDPSASYTYYNQKFKGRVTIT<br>ADKSTSTAYMELSSLRSEDTDVYYCARSVYYGNKYF<br>DVWGQGTTVTVSS |
| 310. | 16E4 VH-4 | QVQLVQSGAEVKKPGASVKVSCKASGYTFTSYWMH<br>WVRQAPGQGLEWMGEIDPSASYTYYNQKFKGRVTM<br>TRDKSSSTVYMELSSLTSEDSAVYYCARSVYYGNKY<br>FDVWGAGTTVTVSS |
| 311. | 16E4 VH-5 | QVQLVQSGAEVKKPGASVKVSCRASGYTFTSYWIH<br>WVRQAPGQGLEWIGEIEPSASYTYYNQKFKGRVTMT<br>RDKSSSTVYMELSSLTSEDSAVYYCARSVYYGNKYF<br>DVWGAGTTVTVSS |
| 312. | 16E4 VH-6 | QVQLQQSGAEVKKPGASVKVSCKASGYTFTSYWMH<br>WVRQAPGQGLEWIGEIDPSASYTYYNQKFKGRVTMT<br>RDKSTSTVYMQLSSLTSEDTAVYYCARSVYYGNKYF<br>DVWGAGTTVTVSS |
| 313. | 16E4 VL-1 | DIVMTQSPDSLAVSLGERATINCKASQSVDYAGDSYL<br>NWYQQKPGQPPKLLIYAASNLESGVPDRFSGSGSGTD<br>FTLTISSLQAEDVAVYYCQQTNEDPRTFGGGTKVEIK |
| 314. | 16E4 VL-2 | DIVLTQSPSSLSASVGQRVTITCRASQSVDYAGDSYM<br>NWYQQKPGKAPKLLIYAASNLESGVPSRFSGSGSGTD<br>FTLTVSSLEDEDFATYYCQQTNEDPRTFGGGTKVEIK |
| 315. | 16E4 VL-3 | EIVLTQSPATLSLSPGQRATLSCRASQSVDYAGDSYL<br>AWYQQKPGQAPRLLIYAASNLESGIPARFSGSGSGTD<br>FTLTIRPLEEEDAAVYYCQQTNEDPRTFGGGTKLEIK |

SEQUENCE TABLE

| SEQ ID NO. | Description | Nucleotide or Amino Acid Sequence |
|---|---|---|
| 316. | 16E4 VL-4 | DIQMTQSPSSLSASVGDRVTITCRASQSVDYAGDSYM<br>NWYQQKPGKAPKLLIYAASNLESGVPSRFSGSGSGTD<br>FTLTISSLEDEDFATYYCQQTNEDPRTFGGGTKLEIK |
| 317. | 16E4 VL-5 | DIVLTQSPSSLSASVGQRVTITCRASQSVDYAGDSYL<br>NWYQQKPGKAPKLLIYAASNLESGIPSRFSGSGSGTD<br>FTLTISSLEDEDFATYYCQQTNEDPRTFGGGTKLEIK |
| 318. | 16E4 VL-6 | DIQMTQSPSTLSASVGDRVTITCKASQSVDYAGDSYM<br>NWYQQKPGKAPKLLIYAASNLESGVPSRFSGSGSGTE<br>FTLTISSLQPDDFATYYCQQTNEDPRTFGGGTKLEIK |
| 319. | 7F3 VH-1 | QVQLVQSGAEMVKPGASVKISCKASGYTFTDYEMH<br>WVRQTPVYGLEWIGGIDPETGDTAYNQNFKGRVTM<br>TRDTSISTAYMELSRLTSDDTAVYYCTNYGNLYYYA<br>MDYWGQGTLVTVSS |
| 320. | 7F3 VH-2 | QVQLQQSGAEVKKPGSSVKVSCKASGYTFTDYEMH<br>WVRQTPVYGLEWMGGIDPETGDTAYNQNFKGRVTI<br>TADKSTSTAYMELSSLRSEDTAVYYCTNYGNLYYYA<br>MDYWGQGTTVTVSS |
| 321. | 7F3 VH-3 | QVQLVQSGAEVKKPGASVKVSCKASGYTFTDYEMH<br>WVRQAPGQGLEWMGGIDPETGDTAYNQNFKGRVT<br>MTTDTSTSTAYMELRSLTSDDTAVYYCTNYGNLYYY<br>AMDYWGQGTSVTVSS |
| 322. | 7F3 VL-1 | EIVLTQSPATLSLSPGERATLSCRASSSVSSSYLHWYQ<br>QKSGASPRLLIYSTSNLAFGIPARFSGSGSGTDYTLTIS<br>SLEAEDVAVYYCQQYSGYPLTFGGGTKVEIK |
| 323. | 7F3 VL-2 | EIVMTQSPATLSVSPGERATLSCRASSSVSSSYLHWY<br>QQKSGASPRLWIYSTSNLAFGIPARFSGSGSGTEYTLT<br>ISSLQSEDFAAYYCQQYSGYPLTFGGGTKVEIK |
| 324. | 7F3 VL-3 | EIVLTQSPSSLSASVGDRVTITCRASSSVSSSYLHWYQ<br>QKPGKAPKLLIYSTSNLAFGVPSRFSGSGSGTSYTFTIS<br>SLQPEDIATYYCQQYSGYPLTFGSGTKLEIK |
| | Exemplary anti-VEGF sequences | |
| 325. | Afibercept | SDTGRPFVEMYSEIPEIIHMTEGRELVIPCRVTSPNITV<br>TLKKFPLDTLIPDGKRIIWDSRKGFIISNATYKEIGLLT<br>CEATVNGHLYKTNYLTHRQTNTIIDVVLSPSHGIELSV<br>GEKLVLNCTARTELNVGIDFNWEYPSSKHQHKKLVN<br>RDLKTQSGSEMKKFLSTLTIDGVTRSDQGLYTCAASS<br>GLMTKKNSTFVRVH |
| 326. | Avastin HC-<br>CDR1<br>(Kabat) | GYTFTNYGMN |
| 327. | Avastin HC-<br>CDR2<br>(Kabat) | WINTYTGEPTYAADFKR |
| 328. | Avastin HC-<br>CDR3<br>(Kabat) | YPHYYGSSHWYFDV |
| 329. | Avastin LC-<br>CDR1<br>(Kabat) | SASQDISNYLN |
| 330. | Avastin LC-<br>CDR2<br>(Kabat) | FTSSLHS |
| 331. | Avastin LC-<br>CDR3<br>(Kabat) | QQYSTVPWT |

-continued

| SEQUENCE TABLE | | |
|---|---|---|

| SEQ ID NO. | Description | Nucleotide or Amino Acid Sequence |
|---|---|---|
| 332. | Ramucirumab HC-CDR1 (Kabat) | SYSMN |
| 333. | Ramucirumab HC-CDR2 (Kabat) | SISSSSSYIYYADSVKG |
| 334. | Ramucirumab HC-CDR3 (Kabat) | VTDAFDI |
| 335. | Ramucirumab LC-CDR1 (Kabat) | RASQGIDNWLG |
| 336. | Ramucirumab LC-CDR2 (Kabat) | DASNLDT |
| 337. | Ramucirumab LC-CDR3 (Kabat) | QQAKAFPPT |

| Additional sequences | | |
|---|---|---|

| SEQ ID NO. | Description | Nucleotide or Amino Acid Sequence |
|---|---|---|
| 338. | Exemplary Linker | GSDKTHT |
| 339. | hIgG1 CH1 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV |
| 340. | hIgG1 Fc | EPKSCDKTHTCPPCPAPELLGGPSVFLFPPKPKDTLMI SRTPEVTCVVVDVSHEDPEVKFNWYVDGVEVHNAK TKPREEQYNSTYRVVSVLTVLHQDWLNGKEYKCKV SNKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALHN HYTQKSLSLSPGK |
| 341. | Human kappa CL | RTVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 342. | 7F3-HC-Aflibercept fusion (without signal peptide) | QVQLQQSGADLVRPGASVKLSCKASGYTFTDYEMH WVKQTPVYGLEWIGGIDPETGDTAYNQNFKGKATLT ADKSSSAAYMELRSLTSEDSAVYYCTNYGNLYYYA MDYWGQGTSVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK KVEPKSCDKTHTCPPCPAPELLGGPSVFLFPPKPKDTL MISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSRDELT KNQVSLTCLVKGFYPSDIAVEWESNGQPENNYKTTPP VLDSDGSFFLYSKLTVDKSRWQQGNVFSCSVMHEAL HNHYTQKSLSLSPGKGSDKTHTSDTGRPFVEMYSEIP EIIHMTEGRELVIPCRVTSPNITVTLKKFPLDTLIPDGK RIIWDSRKGFIISNATYKEIGLLTCEATVNGHLYKTNY LTHRQTNTIIDVVLSPSHGIELSVGEKLVLNCTARTEL NVGIDFNWEYPSSKHQHKKLVNRDLKTQSGSEMKKF LSTLTIDGVTRSDQGLYTCAASSGLMTKKNSTFVRVH |
| 343. | 7F3 LC (without signal peptide) | ENVLTQSPAIMSASPGEKVTMTCRASSSVSSSYLHWY QQKSGASPKLWIYSTSNLAFGVPARFSGSGSGTSYSL TISSVEAEDAATYYCQQYSGYPLTFGSGTKLEIKRTV AAPSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |

-continued

| SEQUENCE TABLE | | |
|---|---|---|
| SEQ ID NO. | Description | Nucleotide or Amino Acid Sequence |

| | | Exemplary signaling peptides |
|---|---|---|
| 344. | Signaling peptide | MGWTLVFLFLLSVTAGVHS |
| 345. | Signaling peptide | MVSSAQFLGLLLLCFQGTRC |
| 346. | Signaling peptide | MGWSCIILFLVATATGVHS |

| | | Additional humanized anti-CD93 antibody sequence |
|---|---|---|
| 347. | 17B10 VH1 | QVQLVQSGAEVKKPGSSVKVSCKASGYAFSSYWLN WVRQAPGQGLEWFGRIYPGDGDTDYNGKFKGRVTL TADKSTSTAYMELSSLRSEDTAVYFCVRGDGYWAM DYWGQGTTVTVSS |
| 348. | 17B10 VH2 | QVQLVQSGAEVVKSGASVKVSCKASGYAFSSYWLN WVRQAPGQGLEWFGRIYPGDGDTDYNGKFKGRVTLI RDTSTSTVYMELTSLTSEDTAVYYCVRGDGYWAMD YWGQGTLVTVSS |
| 349. | 17B10 VH3 | QVQLVQSGPEVKKPGESLKISCKASGYAFSSYWLNW VRQMPGKGLEWMGRIYPGDGDTDYNGKFKGQVTIS ADKSSGTAYLQLSSLKASDTAVYFCVRGDGYWAMD YWGQGTLVTVSS |
| 350. | 17B10 VL1 | DIVMTQSPLSLPVTPGEPASISCRFSQSLLHSNGITYLY WYLQKPGQSPQLLIYQMSNLASGVPDRFSGSGSGTDF TLKISRVEAEDVGVYYCAQNLELPWTFGGGTKLEIK |
| 351. | 17B10 VL2 | DIVMTQTPLSLPVTPGEPASISCRFSQSLLHSNGITYLY WYLQKPGQSPQLLIYTMSNLASGVPDRFSGSGSGTDF TLKISRVEAEDVGVYYCAQNLELPWTFGGGTKLEIK |
| 352. | 17B10 VL3 | DIVMTQSPDSLAVSLGERATINCRFSKSLLHSNGITYL YWYQQKPGQPPKLLIYQMSNLASGVPDRFSGSGSGT DFTLTISSLQAEDVAVYYCAQNLELPWTFGGGTKLEI K |
| 353. | 17B10 VL1 and VL2 LC-CDR1 (Kabat) | RFSQSLLHSNGITYLY |
| 354. | 17B10 and VL2 LC-CDR2 (Kabat) | TMSNLAS |
| 355. | 16A1 VL1 LC-CDR1 (Kabat) | KSSQSLLNSNNQKNYLA |
| 356. | 16A1 VL1 LC-CDR2 (Kabat) | FASTRES |
| 357. | 16A1 VL1 LC-CDR3 (Kabat) | QQHYNTPLT |
| 358. | 16A1 VL2 LC-CDR1 (Kabat) | KSSQSLLNSNNQKNSLA |
| 359. | 16A1 VL2 LC-CDR3 (Kabat) | QQHSNTPLT |

| SEQUENCE TABLE | | |
|---|---|---|
| SEQ ID NO. | Description | Nucleotide or Amino Acid Sequence |
| 360. | 16A1_VH1 | EVQLVQSGAEVKKPGTTVKIACKVSGYTFTDHGIHW VQQAPGKGLEWMGNISPGNGDIKYNEKFKGRVTLTA DKSSDTAYMELNTLRSEDTAIYFCTTYFVDWGRGTL VTVSS |
| 361. | 16A1_VH2 | QVQLQQSGAEVKKPGASVKVSCKASGYTFTDHGIH WVRQAPGRGLEWLGNISPGNGDIKYNEKFKGRVTM TRDTSTSTVYMELSSLTSEDTAVYFCTTYFVDWGRG TLVTVSS |
| 362. | 16A1_VH3 | QVQLLESGAEAKKPGASVKLSCKASGYTFTDHGIHW VHQAPGQRLEWIGNISPGNGDIKYNEKFKGRVTITVD KSASTAYMEVSSLRSEDTAVYFCTTYFVDWGRGTLV TVSS |
| 363. | 16A1_VL1 | DIVMTQSPSSLAVSLGERATLNCKSSQSLLNSNNQKN YLAWYQQKPGQPPKLLIYFASTRESGVPDRFSGSGSG TDFTLTISSVQAEDVAYYFCQQHYNTPLTFGQGTKLE IK |
| 364. | 16A1_VL2 | DIVMTQSPDSLAVSLGERATINCKSSQSLLNSNNQKN SLAWYQQKPGQSPKLLIYFASTRESGVPDRFSGSGSG TDFTLTISSLQAEDVAYYFCQQHSNTPLTFGGGTKVEI K |
| 365. | 16A1_VL3 | EIVMTQSPATLSVSPGERATLSCKSSQSLLNSNNQKN CLAWYQQKPGQAPRLLIYFASTRESGIPARFSGSGSG TEFTLTISSLQSEDFAYYFCQQHCNTPLTFGGGTKVEI K |

The invention claimed is:

1. An anti-CD93 construct comprising an antibody moiety comprising a heavy chain variable region ($V_H$) and a light chain variable region ($V_L$), wherein:

a) the $V_H$ comprises an HC-CDR1 comprising the amino acid sequence of SEQ ID NO: 17, an HC-CDR2 comprising the amino acid sequence of SEQ ID NO: 18, and an HC-CDR3 comprising the amino acid sequence of SEQ ID NO: 19, and the $V_L$ comprises an LC-CDR1 comprising the amino acid sequence of SEQ ID NO: 20, an LC-CDR2 comprising the amino acid sequence of SEQ ID NO: 21, and an LC-CDR3 comprising the amino acid sequence of SEQ ID NO: 22;

b) the $V_H$ comprises an HC-CDR1 comprising the amino acid sequence of SEQ ID NO: 304, an HC-CDR2 comprising the amino acid sequence of SEQ ID NO: 305, and an HC-CDR3 comprising the amino acid sequence of SEQ ID NO: 19, and the $V_L$ comprises an LC-CDR1 comprising the amino acid sequence of SEQ ID NO: 20, an LC-CDR2 comprising the amino acid sequence of SEQ ID NO: 21, and an LC-CDR3 comprising the amino acid sequence of SEQ ID NO: 22;

c) the $V_H$ comprises an HC-CDR1 comprising the amino acid sequence of SEQ ID NO: 17, an HC-CDR2 comprising the amino acid sequence of SEQ ID NO: 18, and an HC-CDR3 comprising the amino acid sequence of SEQ ID NO: 19, and the $V_L$ comprises an LC-CDR1 comprising the amino acid sequence of SEQ ID NO: 301, an LC-CDR2 comprising the amino acid sequence of SEQ ID NO: 21, and an LC-CDR3 comprising the amino acid sequence of SEQ ID NO: 22;

d) the $V_H$ comprises an HC-CDR1 comprising the amino acid sequence of SEQ ID NO: 304, an HC-CDR2 comprising the amino acid sequence of SEQ ID NO: 305, and an HC-CDR3 comprising the amino acid sequence of SEQ ID NO: 19, and the $V_L$ comprises an LC-CDR1 comprising the amino acid sequence of SEQ ID NO: 301, an LC-CDR2 comprising the amino acid sequence of SEQ ID NO: 21, and an LC-CDR3 comprising the amino acid sequence of SEQ ID NO: 22;

e) the $V_H$ comprises an HC-CDR1 comprising the amino acid sequence of SEQ ID NO: 17, an HC-CDR2 comprising the amino acid sequence of SEQ ID NO: 18, and an HC-CDR3 comprising the amino acid sequence of SEQ ID NO: 19, and the $V_L$ comprises an LC-CDR1 comprising the amino acid sequence of SEQ ID NO: 302, an LC-CDR2 comprising the amino acid sequence of SEQ ID NO: 21, and an LC-CDR3 comprising the amino acid sequence of SEQ ID NO: 22;

f) the $V_H$ comprises an HC-CDR1 comprising the amino acid sequence of SEQ ID NO: 304, an HC-CDR2 comprising the amino acid sequence of SEQ ID NO: 305, and an HC-CDR3 comprising the amino acid sequence of SEQ ID NO: 19, and the $V_L$ comprises an LC-CDR1 comprising the amino acid sequence of SEQ ID NO: 302, an LC-CDR2 comprising the amino acid sequence of SEQ ID NO: 21, and an LC-CDR3 comprising the amino acid sequence of SEQ ID NO: 22;

g) the $V_H$ comprises an HC-CDR1 comprising the amino acid sequence of SEQ ID NO: 17, an HC-CDR2 comprising the amino acid sequence of SEQ ID NO: 18, and an HC-CDR3 comprising the amino acid sequence of SEQ ID NO: 19, and the $V_L$ comprises an LC-CDR1 comprising the amino acid sequence of SEQ ID NO: 303, an LC-CDR2 comprising the amino acid sequence of SEQ ID NO: 21, and an LC-CDR3 comprising the amino acid sequence of SEQ ID NO: 22;

h) the $V_H$ comprises an HC-CDR1 comprising the amino acid sequence of SEQ ID NO: 304, an HC-CDR2 comprising the amino acid sequence of SEQ ID NO: 305, and an HC-CDR3 comprising the amino acid sequence of SEQ ID NO: 19, and the $V_L$ comprises an LC-CDR1 comprising the amino acid sequence of SEQ ID NO: 303, an LC-CDR2 comprising the amino acid sequence of SEQ ID NO: 21, and an LC-CDR3 comprising the amino acid sequence of SEQ ID NO: 22;

i) the $V_H$ comprises an HC-CDR1 comprising the amino acid sequence of SEQ ID NO: 17, an HC-CDR2 comprising the amino acid sequence of SEQ ID NO: 18, and an HC-CDR3 comprising the amino acid sequence of SEQ ID NO: 19, and the $V_L$ comprises an LC-CDR1 comprising the amino acid sequence of SEQ ID NO: 306, an LC-CDR2 comprising the amino acid sequence of SEQ ID NO: 21, and an LC-CDR3 comprising the amino acid sequence of SEQ ID NO: 22;

j) the $V_H$ comprises an HC-CDR1 comprising the amino acid sequence of SEQ ID NO: 304, an HC-CDR2 comprising the amino acid sequence of SEQ ID NO: 305, and an HC-CDR3 comprising the amino acid sequence of SEQ ID NO: 19, and the $V_L$ comprises an LC-CDR1 comprising the amino acid sequence of SEQ ID NO: 306, an LC-CDR2 comprising the amino acid sequence of SEQ ID NO: 21, and an LC-CDR3 comprising the amino acid sequence of SEQ ID NO: 22;

k) the $V_H$ comprises an HC-CDR1 comprising the amino acid sequence of SEQ ID NO: 177, an HC-CDR2 comprising the amino acid sequence of SEQ ID NO: 178, and an HC-CDR3 comprising the amino acid sequence of SEQ ID NO: 179, and the $V_L$ comprises an LC-CDR1 comprising the amino acid sequence of SEQ ID NO: 353, an LC-CDR2 comprising the amino acid sequence of SEQ ID NO: 181, and an LC-CDR3 comprising the amino acid sequence of SEQ ID NO: 182;

l. The $V_H$ comprises an HC-CDR1 comprising the amino acid sequence of SEQ ID NO: 177, an HC-CDR2 comprising the amino acid sequence of SEQ ID NO: 178, and an HC-CDR3 comprising the amino acid sequence of SEQ ID NO: 179, and the $V_L$ comprises an LC-CDR1 comprising the amino acid sequence of SEQ ID NO: 353, an LC-CDR2 comprising the amino acid sequence of SEQ ID NO: 354, and an LC-CDR3 comprising the amino acid sequence of SEQ ID NO: 182;

m) the $V_H$ comprises an HC-CDR1 comprising the amino acid sequence of SEQ ID NO: 177, an HC-CDR2 comprising the amino acid sequence of SEQ ID NO: 178, and an HC-CDR3 comprising the amino acid sequence of SEQ ID NO: 179, and the $V_L$ comprises an LC-CDR1 comprising the amino acid sequence of SEQ ID NO: 180, an LC-CDR2 comprising the amino acid sequence of SEQ ID NO: 181, and an LC-CDR3 comprising the amino acid sequence of SEQ ID NO: 182; or n) the $V_H$ comprises an HC-CDR1 comprising the amino acid sequence of SEQ ID NO: 177, an HC-CDR2 comprising the amino acid sequence of SEQ ID NO: 178, and an HC-CDR3 comprising the amino acid sequence of SEQ ID NO: 179, and the $V_L$ comprises an LC-CDR1 comprising the amino acid sequence of SEQ ID NO: 180, an LC-CDR2 comprising the amino acid sequence of SEQ ID NO: 354, and an LC-CDR3 comprising the amino acid sequence of SEQ ID NO: 182.

2. The anti-CD93 construct of claim 1, wherein:

a) the $V_H$ comprises an amino acid sequence of any of SEQ ID NOs: 29 and 307-312, or a variant comprising an amino acid sequence having at least about 80% sequence identity; and the $V_L$ comprises an amino acid sequence of any of SEQ ID NOs: 30 and 313-318, or a variant comprising an amino acid sequence having at least about 80% sequence identity, or b) the $V_H$ comprises an amino acid sequence of any of SEQ ID NOs: 189 and 347-349, or a variant comprising an amino acid sequence having at least about 80% sequence identity; and the $V_L$ comprises an amino acid sequence of any of SEQ ID NOs: 190 and 350-352, or a variant comprising an amino acid sequence having at least about 80% sequence identity.

3. The anti-CD93 construct of claim 1, wherein the $V_H$ comprises the HC-CDR1 comprising the amino acid sequence of SEQ ID NO: 17, the HC-CDR2 comprising the amino acid sequence of SEQ ID NO: 18, and the HC-CDR3 comprising the amino acid sequence of SEQ ID NO: 19, and the $V_L$ comprises the LC-CDR1 comprising the amino acid sequence of SEQ ID NO: 20, the LC-CDR2 comprising the amino acid sequence of SEQ ID NO: 21, and the LC-CDR3 comprising the amino acid sequence of SEQ ID NO: 22.

4. The anti-CD93 construct of claim 2, wherein the $V_H$ comprises the amino acid sequence of SEQ ID NO: 310, and the $V_L$ comprises the amino acid sequence of SEQ ID NO: 318.

5. The anti-CD93 construct of claim 1, wherein the antibody moiety is an antibody or antigen-binding fragment thereof selected from the group consisting of a full-length antibody, a bispecific antibody, a single-chain Fv (scFv) fragment, a Fab fragment, a Fab' fragment, a F(ab')2, an Fv fragment, a disulfide stabilized Fv fragment (dsFv), a (dsFv)$_2$, a Fv-Fc fusion, a scFv-Fc fusion, a scFv-Fv fusion, a diabody, a tribody, and a tetrabody.

6. The anti-CD93 construct of claim 1, wherein the antibody moiety is a full-length antibody.

7. The anti-CD93 construct of claim 5, wherein the antibody moiety comprises the $V_H$ comprising the amino acid sequence of SEQ ID NO: 310, and the $V_L$ comprising the amino acid sequence of SEQ ID NO: 318, wherein the anti-CD93 construct is a bispecific antibody comprising an IgG1 Fc fragment.

8. The anti-CD93 construct of claim 6, wherein the antibody moiety comprises the $V_H$ comprising the amino acid sequence of SEQ ID NO: 310, and the $V_L$ comprising the amino acid sequence of SEQ ID NO: 318, wherein the anti-CD93 construct is a full-length antibody comprising an IgG1 Fc fragment.

9. The anti-CD93 construct of claim 1, wherein the antibody moiety has an Fc fragment selected from the group consisting of Fc fragments from IgG, IgA, IgD, IgE, IgM, and combinations and hybrids thereof.

10. The anti-CD93 construct of claim 9, wherein the Fc fragment is selected from the group consisting of Fc fragments from IgG1, IgG2, IgG3, IgG4, and combinations and hybrids thereof.

11. The anti-CD93 construct of claim 9, wherein the Fc fragment has a reduced effector function as compared to the corresponding wildtype Fc fragment.

12. The anti-CD93 construct of claim 9, wherein the Fc fragment has an enhanced effector function as compared to the corresponding wildtype Fc fragment.

13. The anti-CD93 construct of claim 1, wherein the antibody moiety blocks the binding of CD93 to IGFBP7.

14. The anti-CD93 construct of claim 1, wherein the antibody moiety blocks the binding of CD93 to MMRN2.

15. The anti-CD93 construct of claim 1, wherein the CD93 is a human CD93.

16. An immunoconjugate comprising the anti-CD93 construct of claim 1, linked to a therapeutic agent or a label.

17. A pharmaceutical composition comprising the anti-CD93 construct of claim 1, and a pharmaceutical acceptable carrier.

18. An isolated nucleic acid encoding the anti-CD93 construct of claim 1.

19. A vector comprising the isolated nucleic acid of claim 18.

20. An isolated host cell comprising the isolated nucleic acid of claim 18.

21. A method of treating a CD93-positive cancer in an individual, comprising administering to the individual an effective amount of the pharmaceutical composition of claim 17.

22. The method of claim 21, wherein the CD93-positive cancer is associated with an abnormal vascular structure.

23. The method of claim 21, wherein the CD93-positive cancer is a solid tumor.

24. The method of claim 21, wherein the antibody moiety comprises the $V_H$ comprising the amino acid sequence of SEQ ID NO: 310, and the $V_L$ comprising the amino acid sequence of SEQ ID NO: 318.

25. The method of claim 21, wherein the antibody moiety comprises the $V_H$ comprising the amino acid sequence of SEQ ID NO: 310, and the $V_L$ comprising the amino acid sequence of SEQ ID NO: 318, wherein the anti-CD93 construct is a full-length antibody comprising an IgG1 Fc fragment.

* * * * *